(12) United States Patent
Lacrampe et al.

(10) Patent No.: US 7,834,016 B2
(45) Date of Patent: Nov. 16, 2010

(54) INHIBITORS OF THE INTERACTION BETWEEN MDM2 AND P53

(75) Inventors: Jean Fernand Armand Lacrampe, Le Mesnil-Esnard (FR); Christophe Meyer, Les Authieux sur le Port Saint Ouen (FR); Yannick Aimé Eddy Ligny, Sotteville-lès-Rouen (FR); Imre Christian Francis Csoka, Louviers (FR); Luc Van Hijfte, Belbeuf (FR); Janine Arts, Breda (NL); Bruno Schoentjes, Bois-Guillaume (FR); Camille Georges Wermuth, Strasbourg (FR); Bruno Giethlen, Altorf (FR); Jean-Marie Contreras, Benfeld (FR); Muriel Joubert, Illkirch (FR)

(73) Assignee: Janssen Pharmaceutica NV, Beerse (BE)

( * ) Notice: Subject to any disclaimer, the term of this patent is extended or adjusted under 35 U.S.C. 154(b) by 672 days.

(21) Appl. No.: 11/575,552

(22) PCT Filed: Sep. 16, 2005

(86) PCT No.: PCT/EP2005/054604

§ 371 (c)(1),
(2), (4) Date: Mar. 19, 2007

(87) PCT Pub. No.: WO2006/032631

PCT Pub. Date: Mar. 30, 2006

(65) Prior Publication Data

US 2008/0039472 A1 Feb. 14, 2008

Related U.S. Application Data

(60) Provisional application No. 60/613,902, filed on Sep. 28, 2004.

(30) Foreign Application Priority Data

Sep. 22, 2004 (EP) .................. 04077630

(51) Int. Cl.
A61K 31/47 (2006.01)
A61K 31/443 (2006.01)
A61K 31/497 (2006.01)
A61P 35/00 (2006.01)
C07D 215/38 (2006.01)
C07D 401/12 (2006.01)
C07D 403/12 (2006.01)
C07D 413/04 (2006.01)
C07D 221/04 (2006.01)

(52) U.S. Cl. .................. 514/252.06; 514/253.09; 514/265.1; 514/299; 514/314; 514/340; 544/238; 544/280; 544/364; 546/160; 546/183; 546/269.4; 546/277.4

(58) Field of Classification Search .................. None
See application file for complete search history.

(56) References Cited

U.S. PATENT DOCUMENTS

| | | | |
|---|---|---|---|
| 6,448,277 B2 | 9/2002 | Altmann et al. |
| 6,861,448 B2 | 3/2005 | Brouillette et al. |
| 6,878,720 B2 | 4/2005 | Altmann et al. |
| 7,002,022 B2 | 2/2006 | Altmann et al. |
| 7,122,547 B1 | 10/2006 | Huth et al. |

FOREIGN PATENT DOCUMENTS

| | | |
|---|---|---|
| EP | 1129074 | 9/2001 |
| EP | 1317443 | 6/2003 |
| EP | 1379239 | 9/2007 |
| JP | 11130750 | 5/1999 |
| WO | WO 93/15047 | 8/1993 |
| WO | WO 00/15357 | 3/2000 |
| WO | WO 01/42224 | 6/2001 |
| WO | WO 02/078693 | 10/2002 |
| WO | WO 03/040402 | 5/2003 |
| WO | WO 03/041715 | 5/2003 |
| WO | WO 03/051359 | 6/2003 |
| WO | WO 2004/005278 | 1/2004 |
| WO | WO 2006/067465 | 6/2006 |
| WO | WO 2007/115289 | 10/2007 |

OTHER PUBLICATIONS

Sausville et al. (Cancer Research, 2006, vol. 66, pp. 3351-3354).*
Finney, D.J., Probit Analyses, 2nd Ed. Chapter 10, Graded Responses, Cambridge University Press, Cambridge 1962.
Vousden K.H., Cell, vol. 103, 691-694, 2000.

* cited by examiner

*Primary Examiner*—Kamal A Saeed

(57) ABSTRACT

The present invention provides compounds of formula (I), their use as an inhibitor of a p53-MDM2 interaction as well as pharmaceutical compositions comprising said compounds of formula (I)

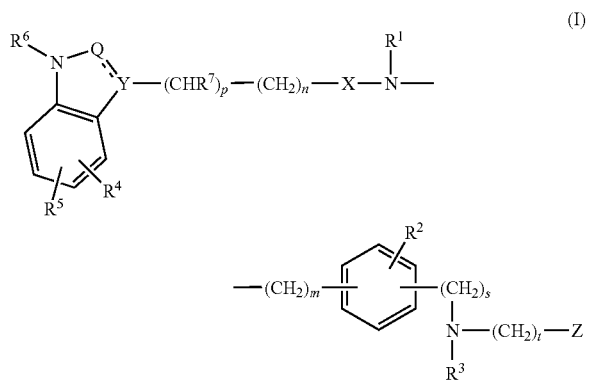

wherein n, m, p, s, t, $R^1$, $R^2$, $R^3$, $R^4$, $R^5$, $R^6$, $R^7$, X, Y, Q and Z have defined meanings.

36 Claims, No Drawings

INHIBITORS OF THE INTERACTION BETWEEN MDM2 AND P53

CROSS REFERENCE TO RELATED APPLICATIONS

This application is the national stage of Application No. PCT/EP2005/054604, filed Sep. 16, 2005, which claims priority from EPO Patent Application No. 04077630.4, filed Sep. 22, 2004, and U.S. provisional Application No. 60/613,902, filed Sep. 28, 2004, the entire disclosures of which are hereby incorporated in their entirely.

FIELD OF THE INVENTION

The present invention relates to compounds and compositions containing said compounds acting as inhibitors of the interaction between MDM2 and p53. Moreover, the present invention provides processes for the preparation of the disclosed inhibitors, compositions comprising them and methods of using them, for instance as a medicine.

p53 is a tumour suppressor protein which plays a pivotal role in the regulation of the balance between cell proliferation and cell growth arrest/apoptosis. Under normal conditions the half life of p53 is very short and consequently the level of p53 in cells is low. However, in response to cellular DNA damage or cellular stress (e.g. oncogene activation, telomere erosion, hypoxia), levels of p53 increase. This increase in p53 levels leads to the activation of the transcription of a number of genes which drives the cell into either growth arrest or into the processes of apoptosis. Thus, an important function of p53 is to prevent the uncontrolled proliferation of damaged cells and thus protect the organism from the development of cancer.

MDM2 is a key negative regulator of p53 function. It forms a negative autoregulatory loop by binding to the amino terminal transactivation domain of p53 and thus MDM2 both inhibits the ability of p53 to activate transcription and targets p53 for proteolytic degradation. Under normal conditions this regulatory loop is responsible for maintaining the low levels of p53. However, in tumours with wild-type p53, the equilibrium concentration of active p53 can be increased by antagonising the interaction between MDM2 and p53. This will result in restoration of the p53-mediated pro-apoptotic and anti-proliferative effects in such tumour cells.

MDM2 is a cellular proto-oncogene. Over-expression of MDM2 has been observed in a range of cancers. MDM2 is over-expressed in a variety of tumours due to gene amplification or increased transcription or translation. The mechanism by which MDM2 amplification promotes tumourigenesis is at least in part related to its interaction with p53. In cells over-expressing MDM2 the protective function of p53 is blocked and thus cells are unable to respond to DNA damage or cellular stress by increasing p53 levels, leading to cell growth arrest and/or apoptosis. Thus after DNA damage and/or cellular stress, cells over-expressing MDM2 are free to continue to proliferate and assume a tumorigenic phenotype. Under these conditions disruption of the interaction of p53 and MDM2 would release the p53 and thus allow normal signals of growth arrest and/or apoptosis to function.

MDM2 may also have separate functions in addition to inhibition of p53. For example, it has been shown that MDM2 interacts directly with the pRb-regulated transcription factor E2F1/DP1. This interaction could be crucial for the p53-independent oncogenic activities of MDM2. A domain of E2F1 shows striking similarity to the MDM2-binding domain of p53. Since the interactions of MDM2 with both p53 and E2F1 locate to the same binding site on MDM2, it can be expected that MDM2/p53 antagonists will not only activate cellular p53 but also modulate E2F1 activities, which are commonly deregulated in tumour cells.

Also the therapeutic effectiveness of DNA damaging agents currently used (chemotherapy and radiotherapy), may be limited through the negative regulation of p53 by MDM2. Thus if the MDM2 feed-back inhibition of p53 is interrupted, an increase in functional p53 levels will increase the therapeutic effectiveness of such agents by restoring the wild-type p53 function that leads to apoptosis and/or reversing of p53-associated drug resistance. It was demonstrated that combining MDM2 inhibition and DNA-damaging treatments in vivo led to synergistic anti-tumour effects (Vousden K. H., Cell, Vol. 103, 691-694, 2000).

Thus disruption of the interaction of MDM2 and p53 offers an approach for therapeutic intervention in tumours with wild-type p53, might even exhibit anti-proliferative effects in tumour cells that are devoid of functional p53 and furthermore can sensitise tumorigenic cells for chemotherapy and radiotherapy.

BACKGROUND OF THE INVENTION

JP 11130750, published on 18 May 1999, describes amongst others, substituted phenylaminocarbonylindolyl derivatives as 5-HT receptor antagonists.

EP1129074, published on 18 May 2000, describes anthranilic acid amides as inhibitors of vascular endothelial growth factor receptors (VEGFR) and useful in the treatment of angiogenic disorders.

EP1317443, published on 21 Mar. 2002, discloses tricyclic tert-amine derivatives, useful as chemokine receptor CXCR4 or CCR5 modulators for treating human immunodeficiency virus and feline immunodeficiency virus.

EP1379239, published on 10 Oct. 2002, discloses N-(2-arylethyl)benzylamines as antagonists of the 5-HT$_6$ receptor. More in particular
6-chloro-N-[[3-(4-pyridinylamino)phenyl]methyl]-1H-indole-3-ethanamine,

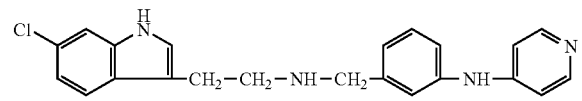

N-[[3-(4-pyridinylamino)phenyl]methyl]-1H-indole-3-ethanamine, and

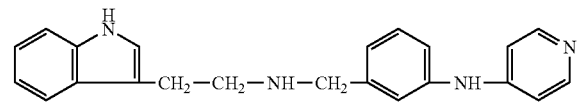

5-methoxy-N-[[3-(4-pyridinylamino)phenyl]methyl]-1H-indole-3-ethanamine,

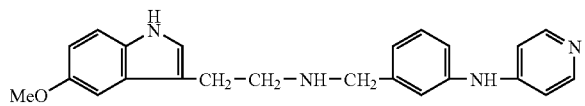

are described.

WO00/15357, published on 23 Mar. 2000, provides piperazine-4-phenyl derivatives as inhibitors of the interaction between MDM2 and p53. EP1137418, published on 8 Jun. 2000, provides tricyclic compounds for restoring conformational stability of a protein of the p53 family.

WO03/041715, published on 22 May 2003, describes substituted 1,4-benzodiazepines and the uses thereof as inhibitors of the MDM2-p53 interactions.

WO03/51359, published on 26 Jun. 2003, provides cis-2, 4,5-triphenyl-imidazolones that inhibit the interaction of MDM2 protein with p53-like peptides and have antiproliferative activity.

WO04/05278, published on 15 Jan. 2004, discloses bisarylsulfonamide compounds that bind to MDM2 and can be used in cancer therapy.

There continues to be a need for effective and potent small molecules that inhibit the interactions between MDM2 and p53.

The compounds of the present invention differs from the prior art in structure, in their pharmacological activity and/or in pharmacological potency.

DESCRIPTION OF THE INVENTION

The present invention provides compounds, compositions for, and methods of, inhibiting the interactions between MDM2 and p53 for treating cancer. Furthermore the compounds and compositions of the present invention are useful in enhancing the effectiveness of chemotherapy and radiotherapy.

This invention concerns compounds of formula (I)
A compound of formula (I),

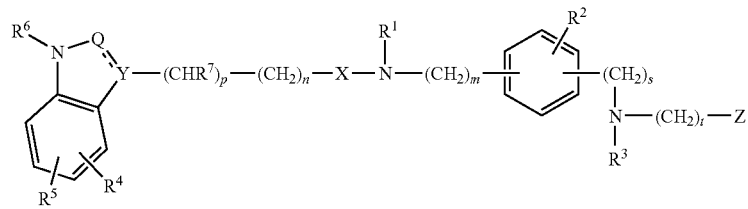

(I)

a N-oxide form, an addition salt or a stereochemically isomeric form thereof, wherein m is 0, 1, or 2 and when m is 0 then a direct bond is intended;
n is 0, 1, 2, or 3 and when n is 0 then a direct bond is intended;
p is 0, or 1 and when p is 0 then a direct bond is intended;
s is 0, or 1 and when s is 0 then a direct bond is intended;
t is 0 or 1 and when t is 0 then a direct bond is intended;
X is C(=O) or CHR$^8$; wherein $R^8$ is hydrogen, $C_{1-6}$alkyl, $C_{3-7}$cycloalkyl, —C(=O)—NR$^{17}$R$^{18}$, hydroxycarbonyl, arylC$_{1-6}$alkyloxycarbonyl, heteroaryl, heteroarylcarbonyl, heteroarylC$_{1-6}$alkyloxycarbonyl, piperazinylcarbonyl, pyrrolidinyl, piperidinylcarbonyl, C$_{1-6}$alkyloxycarbonyl, C$_{1-6}$alkyl substituted with a substituent selected from hydroxy, amino, aryl, and heteroaryl; C$_{3-7}$cycloalkyl substituted with a substituent selected from hydroxy, amino, aryl, and heteroaryl; piperazinylcarbonyl substituted with hydroxy, hydroxyC$_{1-6}$alkyl, hydroxyC$_{1-6}$alkyloxyC$_{1-6}$alkyl; pyrrolidinyl substituted with hydroxyC$_{1-6}$alkyl; or piperidinylcarbonyl substituted with one or two substituents selected from hydroxy, C$_{1-6}$alkyl, hydroxyC$_{1-6}$alkyl, C$_{1-6}$alkyloxyC$_{1-6}$alkyl, C$_{1-6}$alkyl(dihydroxy)C$_{1-6}$alkyl or C$_{1-6}$alkyloxy(hydroxy)C$_{1-6}$alkyl;

R$^{17}$ and R$^{18}$ are each independently selected from hydrogen, C$_{1-6}$alkyl, di(C$_{1-6}$alkyl)aminoC$_{1-6}$alkyl, arylC$_{1-6}$alkyl, C$_{1-6}$alkyloxyC$_{1-6}$alkyl, hydroxyC$_{1-6}$alkyl, hydroxyC$_{1-6}$alkyl(C$_{1-6}$alkyl) or hydroxyC$_{1-6}$alkyl(arylC$_{1-6}$alkyl);

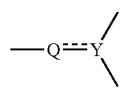

is —CR$^9$=C< and then the dotted line is a bond, —C(=O)—CH<, —C(=O)—N<, —CHR$^9$—CH< or —CHR$^9$—N<; wherein
each R$^9$ is independently hydrogen or C$_{1-6}$alkyl;

R$^1$ is hydrogen, aryl, heteroaryl, C$_{1-6}$alkyloxycarbonyl, C$_{1-12}$alkyl, or C$_{1-12}$alkyl substituted with one or two substituents independently selected from hydroxy, aryl, heteroaryl, amino, C$_{1-6}$alkyloxy, mono- or di(C$_{1-6}$alkyl)amino, morpholinyl, piperidinyl, pyrrolidinyl, piperazinyl, C$_{1-6}$alkylpiperazinyl, arylC$_{1-6}$alkylpiperazinyl, heteroarylC$_{1-6}$alkylpiperazinyl, C$_{3-7}$cycloalkylpiperazinyl and C$_{3-7}$cycloalkylC$_{1-6}$alkylpiperazinyl;

R$^2$ is hydrogen, halo, C$_{1-6}$alkyl, C$_{1-6}$alkyloxy, arylC$_{1-6}$alkyloxy, heteroarylC$_{1-6}$alkyloxy, phenylthio, hydroxyC$_{1-6}$alkylcarbonyl, C$_{1-6}$alkyl substituted with a substituent selected from amino, aryl and heteroaryl; or C$_{3-7}$cycloalkyl substituted with a substituent selected from amino, aryl and heteroaryl;

R$^3$ is hydrogen, C$_{1-6}$alkyl, heteroaryl, C$_{3-7}$cycloalkyl, C$_{1-6}$alkyl substituted with a substituent selected from hydroxy, amino, aryl and heteroaryl; or C$_{3-7}$cycloalkyl substituted with a substituent selected from hydroxy, amino, aryl and heteroaryl;

R$^4$ and R$^5$ are each independently hydrogen, halo, C$_{1-6}$alkyl, polyhaloC$_{1-6}$alkyl, cyano, cyanoC$_{1-6}$alkyl, hydroxy, amino or C$_{1-6}$alkyloxy; or
R$^4$ and R$^5$ together can optionally form a bivalent radical selected from methylenedioxy or ethylenedioxy;

R$^6$ is hydrogen, C$_{1-6}$alkyloxycarbonyl or C$_{1-6}$alkyl;
when p is 1 then R$^7$ is hydrogen, arylC$_{1-6}$alkyl, hydroxy or heteroarylC$_{1-6}$alkyl;
Z is a radical selected from

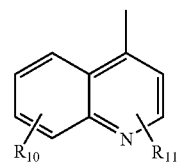

(a-1)

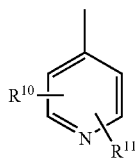
(a-2)

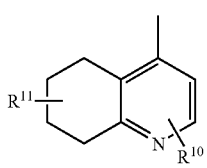
(a-3)

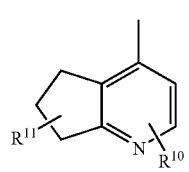
(a-4)

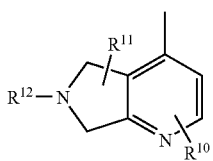
(a-5)

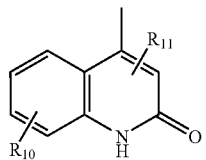
(a-6)

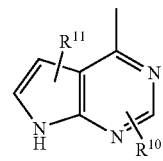
(a-7)

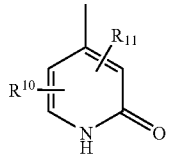
(a-8)

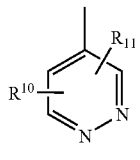
(a-9)

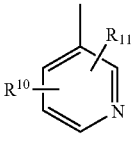
(a-10)

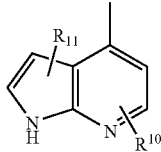
(a-11)

wherein
each $R^{10}$ or $R^{11}$ are each independently selected from hydrogen, halo, hydroxy, amino, $C_{1-6}$alkyl, nitro, polyhalo$C_{1-6}$alkyl, cyano, cyano$C_{1-6}$alkyl, tetrazolo$C_{1-6}$alkyl, aryl, heteroaryl, aryl$C_{1-6}$alkyl, heteroaryl$C_{1-6}$alkyl, aryl(hydroxy)$C_{1-6}$alkyl, heteroaryl(hydroxy)$C_{1-6}$alkyl, arylcarbonyl, heteroarylcarbonyl, $C_{1-6}$alkylcarbonyl, aryl$C_{1-6}$alkylcarbonyl, heteroaryl$C_{1-6}$alkylcarbonyl, $C_{1-6}$alkyloxy, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy$C_{1-6}$alkyl, hydroxy$C_{1-6}$alkyloxy$C_{1-6}$alkyl, $C_{1-6}$alkyloxycarbonyl$C_{2-6}$alkenyl $C_{1-6}$alkyloxy$C_{1-6}$alkyl, $C_{1-6}$alkyloxycarbonyl, $C_{1-6}$alkylcarbonyloxy, aminocarbonyl, hydroxy$C_{1-6}$alkyl, amino$C_{1-6}$alkyl, hydroxycarbonyl, hydroxycarbonyl$C_{1-6}$alkyl and —$(CH_2)_v$—$(C(=O)_r)$—$(CHR^{19})_u$—$NR^{13}R^{14}$; wherein
v is 0, 1, 2, 3, 4, 5, or 6 and when v is 0 then a direct bond is intended;
r is 0, or 1 and when r is 0 then a direct bond is intended;
u is 0, 1, 2, 3, 4, 5, or 6 and when u is 0 then a direct bond is intended;
$R^{19}$ is hydrogen or $C_{1-6}$alkyl;
$R^{12}$ is hydrogen, $C_{1-6}$alkyl, $C_{3-7}$cycloalkyl, $C_{1-6}$alkyl substituted with a substituent selected from hydroxy, amino, $C_{1-6}$alkyloxy and aryl; or $C_{3-7}$cycloalkyl substituted with a substituent selected from hydroxy, amino, aryl and $C_{1-6}$alkyloxy;
$R^{13}$ and $R^{14}$ are each independently selected from hydrogen, $C_{1-12}$alkyl, $C_{1-6}$alkylcarbonyl, $C_{1-6}$alkylsulfonyl, aryl$C_{1-6}$alkylcarbonyl, $C_{3-7}$cycloalkyl, $C_{3-7}$cycloalkylcarbonyl, —$(CH_2)_k$—$NR^{15}R^{16}$, $C_{1-12}$alkyl substituted with a substituent selected from hydroxy, hydroxycarbonyl, cyano, $C_{1-6}$alkyloxycarbonyl, $C_{1-6}$alkyloxy, aryl or heteroaryl; or $C_{3-7}$cycloalkyl substituted with a substituent selected from hydroxy, $C_{1-6}$alkyloxy, aryl, amino, aryl$C_{1-6}$alkyl, heteroaryl or heteroaryl$C_{1-6}$alkyl; or
$R^{13}$ and $R^{14}$ together with the nitrogen to which they are attached can optionally form a morpholinyl, piperidinyl, pyrrolidinyl, piperazinyl, or piperazinyl substituted with a substituent selected from $C_{1-6}$alkyl, aryl$C_{1-6}$alkyl, aryl$C_{1-6}$alkyloxycarbonyl, heteroaryl$C_{1-6}$alkyl, $C_{3-7}$cycloalkyl and $C_{3-7}$cycloalkyl$C_{1-6}$alkyl; wherein
k is 0, 1, 2, 3, 4, 5, or 6 and when k is 0 then a direct bond is intended;
$R^{15}$ and $R^{16}$ are each independently selected from hydrogen, $C_{1-6}$alkyl, aryl$C_{1-6}$alkyloxycarbonyl, $C_{3-7}$cycloalkyl, $C_{1-12}$alkyl substituted with a substituent selected from hydroxy, $C_{1-6}$alkyloxy, aryl, and heteroaryl; and $C_{3-7}$cycloalkyl substituted with a substituent selected from hydroxy, $C_{1-6}$alkyloxy, aryl, aryl$C_{1-6}$alkyl, heteroaryl, and heteroaryl$C_{1-6}$alkyl; or $R^{15}$ and $R^{16}$ together with the nitrogen to which they are attached can optionally form a morpholinyl, a piperazinyl or a piperazinyl substituted with $C_{1-6}$alkyloxycarbonyl;

aryl is phenyl or naphthalenyl;

each phenyl or naphthalenyl can optionally be substituted with one, two or three substituents each independently selected from halo, hydroxy, $C_{1-6}$alkyl, amino, polyhalo$C_{1-6}$alkyl and $C_{1-6}$alkyloxy; and each phenyl or naphthalenyl can optionally be substituted with a bivalent radical selected from methylenedioxy and ethylenedioxy;

heteroaryl is pyridinyl, indolyl, quinolinyl, imidazolyl, furanyl, thienyl, oxadiazolyl, tetrazolyl, benzofuranyl or tetrahydrofuranyl;

each pyridinyl, indolyl, quinolinyl, imidazolyl, furanyl, thienyl, oxadiazolyl, tetrazolyl, benzofuranyl, or tetrahydrofuranyl can optionally be substituted with one, two or three substituents each independently selected from halo, hydroxy, $C_{1-6}$alkyl, amino, polyhalo$C_{1-6}$alkyl, aryl, aryl$C_{1-6}$alkyl or $C_{1-6}$alkyloxy; and each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy;

with the proviso that when m is 1; the substituents on the phenyl ring other than $R^2$ are in the meta position; s is 0; and t is 0; then Z is a radical selected from (a-1), (a-3), (a-4), (a-5), (a-6), (a-7), (a-8) or (a-9).

The compounds of formula (I) may also exist in their tautomeric forms. Such forms although not explicitly indicated in the above formula are intended to be included within the scope of the present invention.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; $C_{1-6}$alkyl defines straight and branched chain saturated hydrocarbon radicals having from 1 to 6 carbon atoms such as, e.g. methyl, ethyl, propyl, butyl, pentyl, hexyl, 1-methylethyl, 2-methylpropyl, 2-methyl-butyl, 2-methylpentyl and the like; $C_{1-6}$alkanediyl defines bivalent straight and branched chained saturated hydrocarbon radicals having from 1 to 6 carbon atoms such as, for example, methylene, 1,2-ethanediyl, 1,3-propanediyl 1,4-butanediyl, 1,5-pentanediyl, 1,6-hexanediyl and the branched isomers thereof such as, 2-methylpentanediyl, 3-methylpentanediyl, 2,2-dimethylbutanediyl, 2,3-dimethylbutanediyl and the like; $C_{1-12}$ alkyl includes $C_{1-6}$alkyl and the higher homologues thereof having 7 to 12 carbon atoms such as, for example heptyl, octyl, nonyl, decyl, undecyl and dodecyl; hydroxy$C_{1-6}$alkyl defines a hydroxy substituent on straight and branched chain saturated hydrocarbon radicals having from 1 to 6 carbon atoms; trihalomethyl defines methyl containing three identical or different halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{3-7}$alkynyl defines straight and branched chained hydrocarbon radicals containing one triple bond and having from 3 to 6 carbon atoms, such as, for example, 2-propynyl, 3-butynyl, 2-butynyl, 2-pentynyl, 3-pentynyl, 3-hexynyl, and the like; $C_{3-7}$cycloalkyl includes cyclic hydrocarbon groups having from 3 to 10 carbons, such as cyclopropyl, cyclobutyl, cyclopentyl, cyclopentenyl, cyclohexyl, cyclohexenyl, cycloheptyl, and the like.

The term "addition salt" comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

The term "addition salt" further comprises pharmaceutically acceptable salts, metal complexes and solvates and the salts thereof, that the compounds of formula (I) are able to form.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

The term "metal complexes" means a complex formed between a compound of formula (I) and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system, e.g. the magnesium or calcium salts, of the third or fourth main group, e.g. aluminium, tin, lead as well as the first to the eighth transition groups of the periodical system such as, for example, chromium, manganese, iron, cobalt, nickel, copper, zinc and the like.

The term "stereochemically isomeric forms of compounds of formula (I)", as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Whenever used hereinafter, the term "compounds of formula (I)" is meant to include also the N-oxide forms, the pharmaceutically acceptable acid or base addition salts and all stereoisomeric forms.

A first group of interesting compounds consists of those compounds of formula (I) wherein one or more of the following restrictions apply:

a) X is C(=O) or CHR$^8$; wherein
R$^8$ is hydrogen, C$_{1-6}$alkyl, C$_{3-7}$cycloalkyl, aminocarbonyl, mono- or di(C$_{1-6}$alkyl)aminocarbonyl, hydroxycarbonyl, arylC$_{1-6}$alkyloxycarbonyl, heteroarylC$_{1-6}$alkyloxycarbonyl, C$_{1-6}$alkyloxycarbonyl, C$_{1-6}$alkyl substituted with a substituent selected from hydroxy, amino, aryl, and heteroaryl or C$_{3-7}$cycloalkyl substituted with a substituent selected from hydroxy, amino, aryl and heteroaryl;

b) R$^1$ is hydrogen, aryl, heteroaryl, C$_{1-12}$alkyl, or C$_{1-12}$alkyl substituted with one or two substituents independently selected from hydroxy, aryl, heteroaryl, amino, C$_{1-6}$alkyloxy, mono- or di(C$_{1-6}$alkyl)amino, morpholinyl, piperidinyl, pyrrolidinyl, piperazinyl, C$_{1-6}$alkylpiperazinyl, arylC$_{1-6}$alkylpiperazinyl, heteroarylC$_{1-6}$alkylpiperazinyl, C$_{3-7}$cycloalkylpiperazinyl and C$_{3-7}$cycloalkylC$_{1-6}$alkylpiperazinyl;

c) R$^3$ is hydrogen, C$_{1-6}$alkyl, C$_{3-7}$cycloalkyl, C$_{1-6}$alkyl substituted with a substituent selected from hydroxy, amino, aryl, and heteroaryl; or C$_{3-7}$cycloalkyl substituted with a substituent selected from hydroxy, amino, aryl and heteroaryl;

d) R$^4$ and R$^5$ are each independently hydrogen, halo, C$_{1-6}$alkyl, polyhaloC$_{1-6}$alkyl, hydroxy, amino or C$_{1-6}$alkyloxy;

e) R$^4$ and R$^5$ together can optionally form a bivalent radical selected from methylenedioxy or ethylenedioxy;

f) R$^6$ is hydrogen or C$_{1-6}$alkyl;

g) when p is 1 then R$^7$ is hydrogen, arylC$_{1-6}$alkyl or heteroarylC$_{1-6}$alkyl;

h) Z is a radical selected from (a-1), (a-2), (a-3), (a-4), (a-5) and (a-6);

i) each R$^{10}$ or R$^{11}$ are each independently selected from hydrogen, hydroxy, amino, C$_{1-6}$alkyl, nitro, polyhaloC$_{1-6}$alkyl, cyano, cyanoC$_{1-6}$alkyl, tetrazoloC$_{1-6}$alkyl, aryl, heteroaryl, arylC$_{1-6}$alkyl, heteroarylC$_{1-6}$alkyl, aryl(hydroxy)C$_{1-6}$alkyl, heteroaryl(hydroxy)C$_{1-6}$alkyl, arylcarbonyl, heteroarylcarbonyl, arylC$_{1-6}$alkylcarbonyl, heteroarylC$_{1-6}$alkylcarbonyl, C$_{1-6}$alkyloxy, C$_{1-6}$alkyloxyC$_{1-6}$alkyl, C$_{1-6}$alkyloxycarbonyl, C$_{1-6}$alkylcarbonyloxy, aminocarbonyl, hydroxyC$_{1-6}$alkyl, aminoC$_{1-6}$alkyl, hydroxycarbonyl, hydroxycarbonylC$_{1-6}$alkyl and —(CH$_2$)$_v$—(C(=O)$_r$)—(CH$_2$)$_u$—NR$^{13}$R$^{14}$;

j) R$^{13}$ and R$^{14}$ are each independently selected from hydrogen, C$_{1-12}$alkyl, C$_{3-7}$cycloalkyl, —(CH$_2$)$_k$—NR$^{15}$R$^{16}$, C$_{1-12}$alkyl substituted with a substituent selected from hydroxy, C$_{1-6}$alkyloxy, aryl, and heteroaryl; or C$_{3-7}$cycloalkyl substituted with a substituent selected from hydroxy, C$_{1-6}$alkyloxy, aryl, arylC$_{1-6}$alkyl, heteroaryl and heteroarylC$_{1-6}$alkyl;

k) R$^{13}$ and R$^{14}$ together with the nitrogen to which they are attached can optionally form a morpholinyl, piperidinyl, pyrrolidinyl, piperazinyl, or piperazinyl substituted with a substituent selected from C$_{1-6}$alkyl, arylC$_{1-6}$alkyl, heteroarylC$_{1-6}$alkyl, C$_{3-7}$cycloalkyl, and C$_{3-7}$cycloalkylC$_{1-6}$alkyl;

l) R$^{15}$ and R$^{16}$ are each independently selected from hydrogen, C$_{1-6}$alkyl, C$_{3-7}$cycloalkyl, C$_{1-12}$alkyl substituted with a substituent selected from hydroxy, C$_{1-6}$alkyloxy, aryl, and heteroaryl; and C$_{3-7}$cycloalkyl substituted with a substituent selected from hydroxy, C$_{1-6}$alkyloxy, aryl, arylC$_{1-6}$alkyl, heteroaryl and heteroarylC$_{1-6}$alkyl;

m) heteroaryl is pyridinyl, indolyl, quinolinyl, imidazolyl, furanyl, thienyl, benzofuranyl, or tetrahydrofuranyl; and each pyridinyl, indolyl, quinolinyl, imidazolyl, furanyl, thienyl, benzofuranyl, or tetrahydrofuranyl can optionally be substituted with one, two or three substituents each independently selected from halo, hydroxy, C$_{1-6}$alkyl, amino, polyhaloC$_{1-6}$alkyl and C$_{1-6}$alkyloxy; and n) each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy;

A second group of interesting compounds consists of those compounds of formula (I) wherein one or more of the following restrictions apply:

a) n is 0, 1 or 2;

b) p is 0;

c) R$^9$ is hydrogen, aminocarbonyl, arylC$_{1-6}$alkyloxycarbonyl or C$_{1-6}$alkyl substituted with hydroxy;

d)

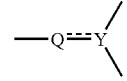

is —CR$^9$=C< or —CHR$^9$—CH<;

e) R$^1$ is hydrogen, C$_{1-12}$alkyl, or C$_{1-12}$alkyl substituted with heteroaryl;

f) R$^2$ is hydrogen, halo, C$_{1-6}$alkyl, C$_{1-6}$alkyloxy, arylC$_{1-6}$alkyloxy or phenylthio;

g) R$^3$ is hydrogen or C$_{1-6}$alkyl;

h) R$^4$ and R$^5$ are each independently hydrogen, halo or C$_{1-6}$alkyloxy;

i) Z is a radical selected from (a-1), (a-2), (a-3), (a-4) or (a-6);

j) each R$^{10}$ or R$^{11}$ are independently selected from hydrogen, hydroxy, amino, C$_{1-6}$alkyl, nitro, polyhaloC$_{1-6}$alkyl, cyano, aryl, arylC$_{1-6}$alkyl, aryl(hydroxy)C$_{1-6}$alkyl, arylcarbonyl, C$_{1-6}$alkyloxy, C$_{1-6}$alkyloxyC$_{1-6}$alkyl, C$_{1-6}$alkyloxycarbonyl, aminocarbonyl, hydroxyC$_{1-6}$alkyl, aminoC$_{1-6}$alkyl, hydroxycarbonyl and —(CH$_2$)$_v$—(C(=O)$_r$)—(CH$_2$)$_u$—NR$^{13}$R$^{14}$;

k) v is 0, or 1;

l) r is o or 1;

m) u is 0;

n) R$^{13}$ and R$^{14}$ are each independently selected from hydrogen, C$_{1-6}$alkyl, —(CH$_2$)$_k$—NR$^{15}$R$^{16}$ and C$_{1-12}$alkyl substituted with hydroxy;

o) R$^{13}$ and R$^{14}$ together with the nitrogen to which they are attached can form a pyrrolidinyl;

p) k is 2;

q) R$^{15}$ and R$^{16}$ are each independently C$_{1-6}$alkyl;

r) aryl is phenyl or phenyl substituted with halo; and s) heteroaryl is pyridinyl or indolyl.

A third group of interesting compounds consists of those compounds of formula (I) wherein one or more of the following restrictions apply:
a) m is 0 or 2;
b) n is 0, 2 or 3;
c) p is 1;
d) s is 1;
e) t is 1;
f) X is C(=O);
g)

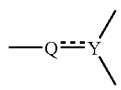

is —C(=O)—CH<, —C(=O)—N<, —CHR$^9$—CH<, or —CHR$^9$—N<;
h) R$^1$ is aryl, heteroaryl, C$_{1-6}$alkyloxycarbonyl, C$_{1-12}$alkyl, or C$_{1-12}$alkyl substituted with one or two substituents independently selected from hydroxy, aryl, heteroaryl, amino, C$_{1-6}$alkyloxy, mono- or di(C$_{1-6}$alkyl)amino, morpholinyl, piperidinyl, pyrrolidinyl, piperazinyl, C$_{1-6}$alkylpiperazinyl, arylC$_{1-6}$alkylpiperazinyl, heteroarylC$_{1-6}$alkylpiperazinyl, C$_{3-7}$cycloalkylpiperazinyl and C$_{3-7}$cycloalkylC$_{1-6}$alkylpiperazinyl;
i) R$^2$ is halo, C$_{1-6}$alkyl, C$_{1-6}$alkyloxy, arylC$_{1-6}$alkyloxy, heteroarylC$_{1-6}$alkyloxy, phenylthio, hydroxyC$_{1-6}$alkylcarbonyl, C$_{1-6}$alkyl substituted with a substituent selected from amino, aryl and heteroaryl; or C$_{3-7}$cycloalkyl substituted with a substituent selected from amino, aryl and heteroaryl;
j) R$^3$ is C$_{1-6}$alkyl, C$_{3-7}$cycloalkyl, C$_{1-6}$alkyl substituted with a substituent selected from hydroxy, amino, aryl, and heteroaryl; or C$_{3-7}$cycloalkyl substituted with a substituent selected from hydroxy, amino, aryl and heteroaryl;
k) R$^4$ and R$^5$ are each independently C$_{1-6}$alkyl, polyhaloC$_{1-6}$alkyl, cyano, cyanoC$_{1-6}$alkyl, hydroxy or amino;
l) R$^4$ and R$^5$ together can optionally form a bivalent radical selected from methylenedioxy or ethylenedioxy;
m) R$^6$ is C$_{1-6}$alkyloxycarbonyl or C$_{1-6}$alkyl;
n) R$^7$ is hydrogen, arylC$_{1-6}$alkyl, hydroxy or heteroarylC$_{1-6}$alkyl; and
o) Z is a radical selected from (a-1), (a-3), (a-4), (a-5), (a-6), (a-7), (a-8) or (a-9).

A fourth group of interesting compounds consists of those compounds of formula (I) wherein one or more of the following restrictions apply:
a) R$^8$ is hydrogen, —C(=O)—NR$^{17}$R$^{18}$, arylC$_{1-6}$alkyloxycarbonyl, C$_{1-6}$alkyl substituted with hydroxy, piperazinylcarbonyl substituted with hydroxy, hydroxyC$_{1-6}$alkyl, hydroxyC$_{1-6}$alkyloxyC$_{1-6}$alkyl, pyrrolidinyl substituted with hydroxyC$_{1-6}$alkyl or piperidinylcarbonyl substituted with one or two substituents selected from hydroxy, C$_{1-6}$alkyl, hydroxyC$_{1-6}$alkyl, C$_{1-6}$alkyloxyC$_{1-6}$alkyl, C$_{1-6}$alkyl(dihydroxy)C$_{1-6}$alkyl or C$_{1-6}$alkyloxy(hydroxy)C$_{1-6}$alkyl;
b) R$^{17}$ and R$^{18}$ are each independently selected from hydrogen, C$_{1-6}$alkyl, di(C$_{1-6}$alkyl)aminoC$_{1-6}$alkyl, arylC$_{1-6}$alkyl, C$_{1-6}$alkyloxyC$_{1-6}$alkyl or hydroxyC$_{1-6}$alkyl;
c)

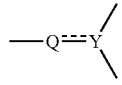

is —CR$^9$=C< and then the dotted line is a bond, —CHR$^9$—CH< or —CHR$^9$—N<;
d) R$^1$ is hydrogen, heteroaryl, C$_{1-6}$alkyloxycarbonyl, C$_{1-12}$alkyl or C$_{1-12}$alkyl substituted with heteroaryl;
e) R$^2$ is hydrogen, halo, C$_{1-6}$alkyl, C$_{1-6}$alkyloxy, arylC$_{1-6}$alkyloxy or phenylthio;
f) R$^3$ is hydrogen, C$_{1-6}$alkyl or heteroaryl;
g) R$^4$ and R$^5$ are each independently hydrogen, halo, C$_{1-6}$alkyl, cyano, cyanoC$_{1-6}$alkyl, hydroxy or C$_{1-6}$alkyloxy;
h) when p is 1 then R$^7$ is arylC$_{1-6}$alkyl or hydroxy;
i) Z is a radical selected from (a-1), (a-2), (a-3), (a-4), (a-5), (a-6), (a-8), (a-9), (a-10) and (a-11);
j) each R$^{10}$ or R$^{11}$ are each independently selected from hydrogen, halo, hydroxy, amino, C$_{1-6}$alkyl, nitro, polyhaloC$_{1-6}$alkyl, cyano, cyanoC$_{1-6}$alkyl, tetrazoloC$_{1-6}$alkyl, aryl, heteroaryl, heteroarylC$_{1-6}$alkyl, aryl(hydroxy)C$_{1-6}$alkyl, arylcarbonyl, C$_{1-6}$alkylcarbonyl, C$_{3-7}$cycloalkylcarbonyl, C$_{3-7}$cycloalkyl(hydroxy)C$_{1-6}$alkyl, arylC$_{1-6}$alkyloxyC$_{1-6}$alkyl, C$_{1-6}$alkyloxyC$_{1-6}$alkyloxyC$_{1-6}$alkyl, C$_{1-6}$alkylcarbonyloxyC$_{1-6}$alkyl, C$_{1-6}$alkyloxycarbonylC$_{1-6}$alkyloxyC$_{1-6}$alkyl, hydroxyC$_{1-6}$alkyloxyC$_{1-6}$alkyl, C$_{1-6}$alkyloxycarbonylC$_{2-6}$alkenyl, C$_{1-6}$alkyloxyC$_{1-6}$alkyl, C$_{1-6}$alkyloxycarbonyl, aminocarbonyl, hydroxyC$_{1-6}$alkyl, aminoC$_{1-6}$alkyl, hydroxycarbonyl, hydroxycarbonylC$_{1-6}$alkyl and —(CH$_2$)$_v$—(C(=O)$_r$)—(CHR$^{19}$)$_u$—NR$^{13}$R$^{14}$;
k) v is 0 or 1;
l) u is 0 or 1;
m) R$^{12}$ is hydrogen or C$_{1-6}$alkyl;
n) R$^{13}$ and R$^{14}$ are each independently selected from hydrogen, C$_{1-12}$alkyl, C$_{1-6}$alkylcarbonyl, C$_{1-6}$alkylsulfonyl, arylC$_{1-6}$alkylcarbonyl, C$_{3-7}$cycloalkylcarbonyl, —(CH$_2$)$_k$—NR$^{15}$R$^{16}$, C$_{1-12}$alkyl substituted with a substituent selected from hydroxy, hydroxycarbonyl, cyano, C$_{1-6}$alkyloxycarbonyl or aryl;
o) R$^{13}$ and R$^{14}$ together with the nitrogen to which they are attached can optionally form a morpholinyl, pyrrolidinyl, piperazinyl, or piperazinyl substituted with a substituent selected from C$_{1-6}$alkyl or arylC$_{1-6}$alkyloxycarbonyl;
p) k is 2;
q) R$^{15}$ and R$^{16}$ are each independently selected from hydrogen, C$_{1-6}$alkyl or arylC$_{1-6}$alkyloxycarbonyl;
r) R$^{15}$ and R$^{16}$ together with the nitrogen to which they are attached can optionally form a morpholinyl, a piperazinyl or a piperazinyl substituted with C$_{1-6}$alkyloxycarbonyl;
s) aryl is phenyl or phenyl substituted with halo;
t) heteroaryl is pyridinyl, indolyl, oxadiazolyl or tetrazolyl; and
u) each pyridinyl, indolyl, oxadiazolyl or tetrazolyl can optionally be substituted with one substituents selected from C$_{1-6}$alkyl, aryl or arylC$_{1-6}$alkyl.

A fifth group of interesting compounds consists of those compounds of formula (I) wherein one or more of the following restrictions apply:
a) m is 0;
b) n is 1;
c) p is 0;
d) s is 0;

e) t is 0;
f) X is CHR$^8$;
g) R$^8$ is hydrogen;
h)

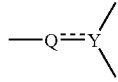

is —CR$^9$=C<;
i) each R$^9$ is hydrogen;
j) R$^1$ is hydrogen;
k) R$^2$ is hydrogen or C$_{1-6}$alkyloxy;
l) R$^3$ is hydrogen;
m) R$^4$ and R$^5$ are each independently hydrogen, C$_{1-6}$alkyl or C$_{1-6}$alkyloxy;
n) R$^6$ is hydrogen;
o) Z is a radical selected from (a-1), (a-2), (a-3) or (a-4);
p) R$^{10}$ or R$^{11}$ are each independently selected from hydrogen, hydroxy or hydroxyC$_{1-6}$alkyl.

A group of preferred compounds consists of those compounds of formula (I) or any subgroup thereof, wherein R$^8$ is hydrogen, —C(=O)—NR$^{17}$R$^{18}$, arylC$_{1-6}$alkyloxycarbonyl, C$_{1-6}$alkyl substituted with hydroxy, piperazinylcarbonyl substituted with hydroxy, hydroxyC$_{1-6}$alkyl, hydroxyC$_{1-6}$alkyloxyC$_{1-6}$alkyl, pyrrolidinyl substituted with hydroxyC$_{1-6}$alkyl or piperidinylcarbonyl substituted with one or two substituents selected from hydroxy, C$_{1-6}$alkyl, hydroxyC$_{1-6}$alkyl, C$_{1-6}$alkyloxyC$_{1-6}$alkyl, C$_{1-6}$alkyl(dihydroxy)C$_{1-6}$alkyl or C$_{1-6}$alkyloxy(hydroxy)C$_{1-6}$alkyl; R$^{17}$ and R$^{18}$ are each independently selected from hydrogen, C$_{1-6}$alkyl, di(C$_{1-6}$alkyl)aminoC$_{1-6}$alkyl, arylC$_{1-6}$alkyl, C$_{1-6}$alkyloxyC$_{1-6}$alkyl or hydroxyC$_{1-6}$alkyl;

is —CR$^9$=C< and then the dotted line is a bond, —CHR$^9$—CH< or —CHR$^9$—N<; R$^1$ is hydrogen, heteroaryl, C$_{1-6}$alkyloxycarbonyl, C$_{1-12}$alkyl or C$_{1-12}$alkyl substituted with heteroaryl; R$^2$ is hydrogen, halo, C$_{1-6}$alkyl, C$_{1-6}$alkyloxy, arylC$_{1-6}$alkyloxy or phenylthio; R$^3$ is hydrogen, C$_{1-6}$alkyl or heteroaryl; R$^4$ and R$^5$ are each independently hydrogen, halo, C$_{1-6}$alkyl, cyano, cyanoC$_{1-6}$alkyl, hydroxy or C$_{1-6}$alkyloxy; when p is 1 then R$^7$ is arylC$_{1-6}$alkyl or hydroxy; Z is a radical selected from (a-1), (a-2), (a-3), (a-4), (a-5), (a-6), (a-8), (a-9), (a-10) and (a-11); each R$^{10}$ or R$^{11}$ are each independently selected from hydrogen, halo, hydroxy, amino, C$_{1-6}$alkyl, nitro, polyhaloC$_{1-6}$alkyl, cyano, cyanoC$_{1-6}$alkyl, tetrazoloC$_{1-6}$alkyl, aryl, heteroaryl, heteroarylC$_{1-6}$alkyl, aryl(hydroxy)C$_{1-6}$alkyl, arylcarbonyl, C$_{1-6}$alkylcarbonyl, C$_{3-7}$cycloalkylcarbonyl, C$_{3-7}$cycloalkyl(hydroxy)C$_{1-6}$alkyl, arylC$_{1-6}$alkyloxyC$_{1-6}$alkyl, C$_{1-6}$alkyloxyC$_{1-6}$alkyloxyC$_{1-6}$alkyl, C$_{1-6}$alkylcarbonyloxyC$_{1-6}$alkyl, C$_{1-6}$alkyloxycarbonylC$_{1-6}$alkyloxyC$_{1-6}$alkyl, hydroxyC$_{1-6}$alkyloxyC$_{1-6}$alkyl, C$_{1-6}$alkyloxycarbonylC$_{2-6}$alkenyl, C$_{1-6}$alkyloxyC$_{1-6}$alkyl, C$_{1-6}$alkyloxycarbonyl, aminocarbonyl, hydroxyC$_{1-6}$alkyl, aminoC$_{1-6}$alkyl, hydroxycarbonyl, hydroxycarbonylC$_{1-6}$alkyl and —(CH$_2$)$_v$—(C(=O)$_r$)—(CHR$^{19}$)$_u$—NR$^{13}$R$^{14}$; v is 0 or 1; u is 0 or 1; R$^{12}$ is hydrogen or C$_{1-6}$alkyl; R$^{13}$ and R$^{14}$ are each independently selected from hydrogen, C$_{1-2}$alkyl, C$_{1-6}$alkylcarbonyl, C$_{1-6}$alkylsulfonyl, arylC$_{1-6}$alkylcarbonyl, C$_{3-7}$cycloalkylcarbonyl, —(CH$_2$)$_k$—NR$^{15}$R$^{16}$, C$_{1-12}$alkyl substituted with a substituent selected from hydroxy, hydroxycarbonyl, cyano, C$_{1-6}$alkyloxycarbonyl or aryl; R$^{13}$ and R$^4$ together with the nitrogen to which they are attached can optionally form a morpholinyl, pyrrolidinyl, piperazinyl or piperazinyl substituted with a substituent selected from C$_{1-6}$alkyl or arylC$_{1-6}$alkyloxycarbonyl; k is 2; R$^{15}$ and R$^{16}$ are each independently selected from hydrogen, C$_{1-6}$alkyl or arylC$_{1-6}$alkyloxycarbonyl; k is 2; R$^{15}$ and R$^{16}$ are each independently selected from hydrogen, C$_{1-6}$alkyl or arylC$_{1-6}$alkyloxycarbonyl; R$^{15}$ and R$^{16}$ together with the nitrogen to which they are attached can optionally form a morpholinyl or piperazinyl, or piperazinyl substituted with C$_{1-6}$alkyloxycarbonyl; aryl is phenyl or phenyl substituted with halo; heteroaryl is pyridinyl, indolyl, oxadiazolyl or tetrazolyl; and each pyridinyl, indolyl, oxadiazolyl or tetrazolyl can optionally be substituted with one substituent selected from C$_{1-6}$alkyl, aryl or arylC$_{1-6}$alkyl.

A group of more preferred compounds consists of those compounds of formula (I) or any subgroup thereof wherein m is 0; n is 1; p is 0; s is 0; t is 0; X is CHR$^8$; R$^9$ is hydrogen;

is —CR$^9$=C<; each R$^9$ is hydrogen; R$^1$ is hydrogen; R$^2$ is hydrogen or C$_{1-6}$alkyloxy; R$^9$ is hydrogen or C$_{1-6}$alkyloxy; R$^3$ is hydrogen; R$^4$ and R$^5$ are each independently hydrogen, C$_{1-6}$alkyl or C$_{1-6}$alkyloxy; R$^6$ is hydrogen; Z is a radical selected from (a-1), (a-2), (a-3) or (a-4); and R$^{10}$ or R$^{11}$ are each independently selected from hydrogen, hydroxy or hydroxyC$_{1-6}$alkyl.

The most preferred compounds are compound No. 1, compound No. 21, compound No. 4, compound No. 5, compound No. 36, compound No. 69, compound No. 110, compound No. 111, compound No. 112, compound No. 229 and compound No. 37.

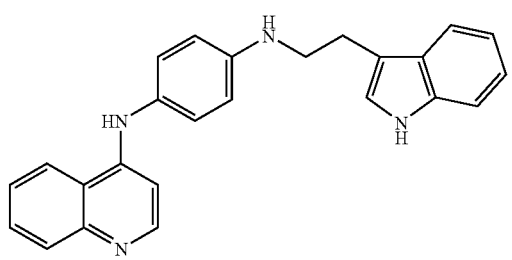

Co. No. 1; •1.58 HCl

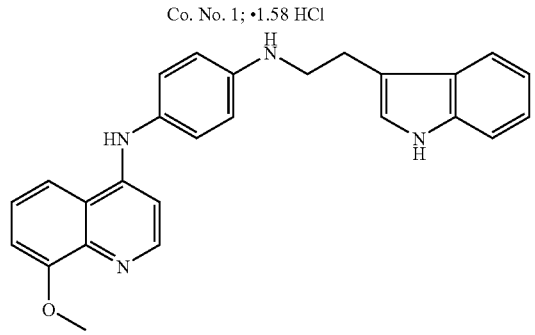

Co. No. 21

-continued

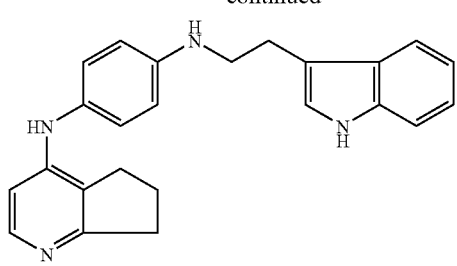
Co. No. 4

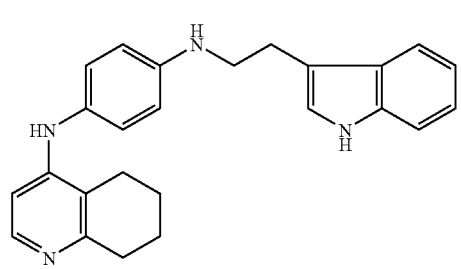
Co. No. 5

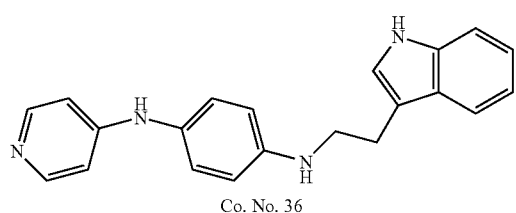
Co. No. 36

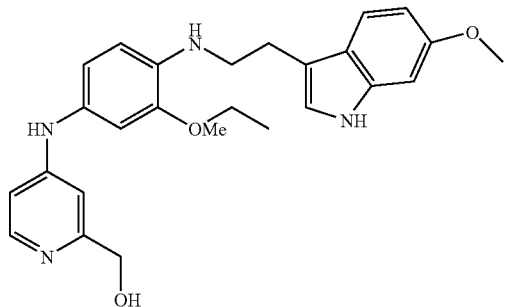
Co. No. 69

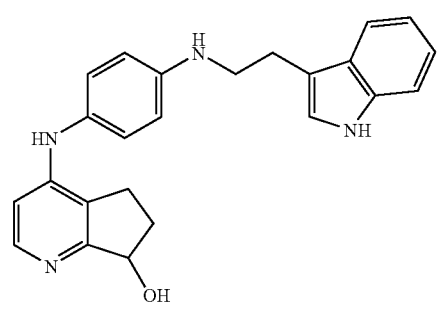
Co. No. 110

-continued

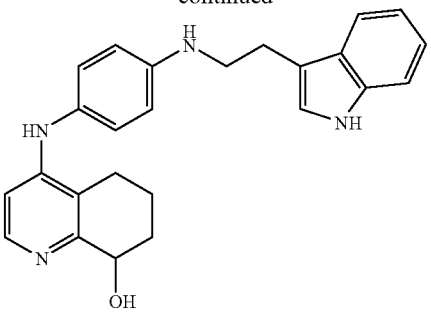
Co. No. 111

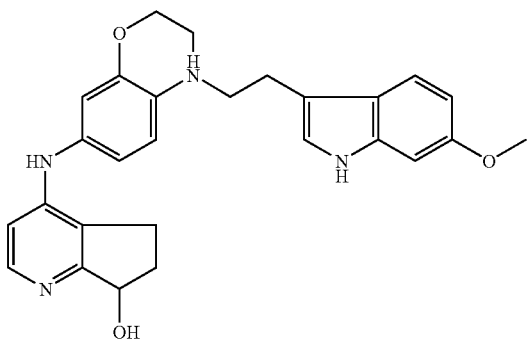
Co. No. 112

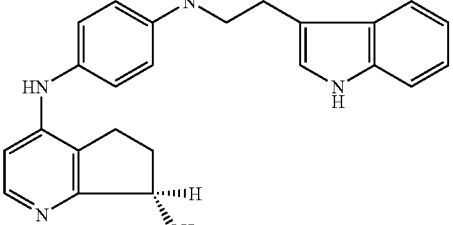
Co. No. 229; (B)

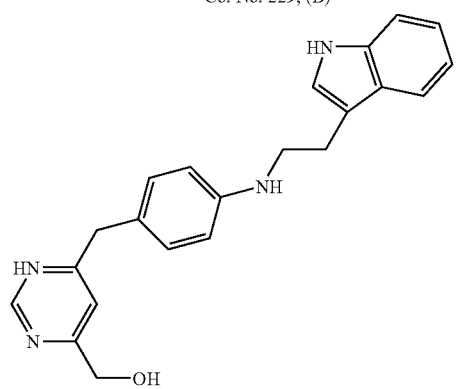
Co. No. 37

The compounds of formula (I), their pharmaceutically acceptable salts and N-oxides and stereochemically isomeric forms thereof may be prepared in conventional manner. The starting materials and some of the intermediates are known compounds and are commercially available or may be prepared according to conventional reaction procedures as generally known in the art.

A number of such preparation methods will be described hereinafter in more detail. Other methods for obtaining final compounds of formula (I) are described in the examples.

The compounds of formula (I) can be prepared by reacting an intermediate of formula (II) with an intermediate of formula (III) wherein W is an appropriate leaving group such as, for example, halo, e.g. fluoro, chloro, bromo or iodo, or a sulfonyloxy radical such as methylsulfonyloxy, 4-methylphenylsulfonyloxy and the like. The reaction can be performed in a reaction-inert solvent such as, for example, an alcohol, e.g. methanol, ethanol, 2-methoxy-ethanol, propanol, butanol and the like; an ether, e.g. 4,4-dioxane, 1,1'-oxybispropane and the like; a ketone, e.g. 4-methyl-2-pentanone; or N,N-dimethylformamide, nitrobenzene, acetonitrile, acetic acid and the like. The addition of an appropriate base such as, for example, an alkali or earth alkaline metal carbonate or hydrogen carbonate, e.g. triethylamine or sodium carbonate, may be utilized to pick up the acid which is liberated during the course of the reaction. A small amount of an appropriate metal iodide, e.g., sodium or potassium iodide may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

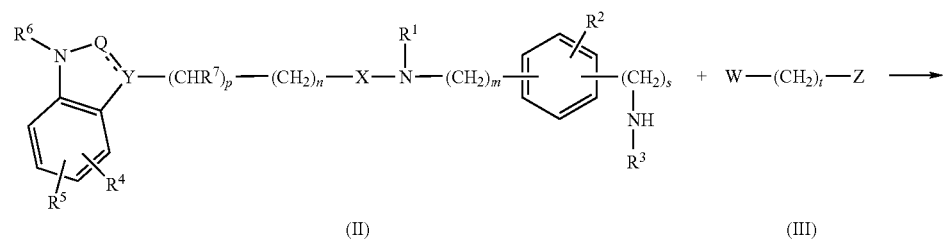

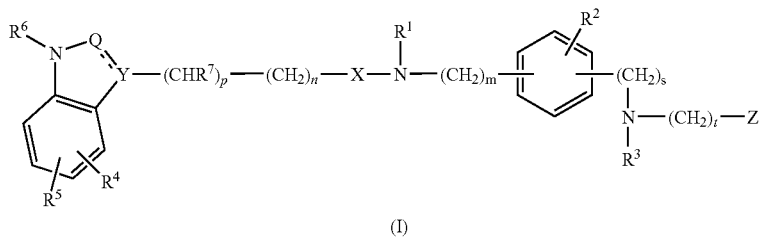

The compounds of formula (I), wherein X is $CH_2$, herein referred to as compounds of formula (I-a), can be prepared by converting compounds of formula (I) wherein X is $C(=O)$, herein referred to as compounds of formula (I-b), by reacting the compound of formula (I-b) with lithium aluminium hydride in a suitable solvent such as tetrahydrofuran.

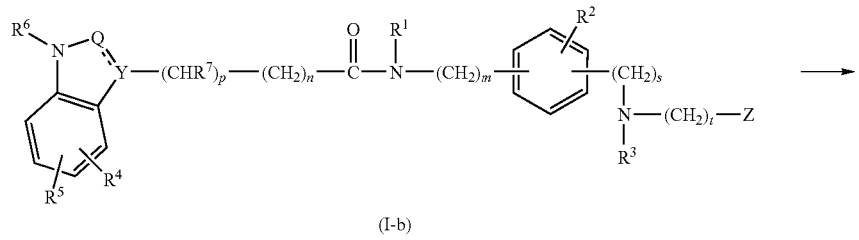

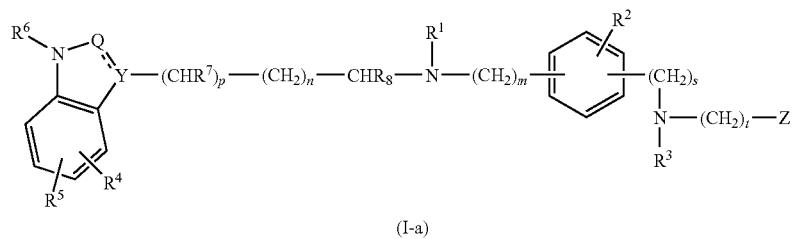

The compounds of formula (I-a) can also be prepared by reacting an appropriate carboxaldehyde of formula (IV), with an intermediate of formula (V), in the presence of an appropriate reagent, such as a sodium borohydride e.g. sodium tetrahydroborate or polymer supported cyanotrihydroborate, in a suitable solvent, such as an alcohol e.g. methanol.

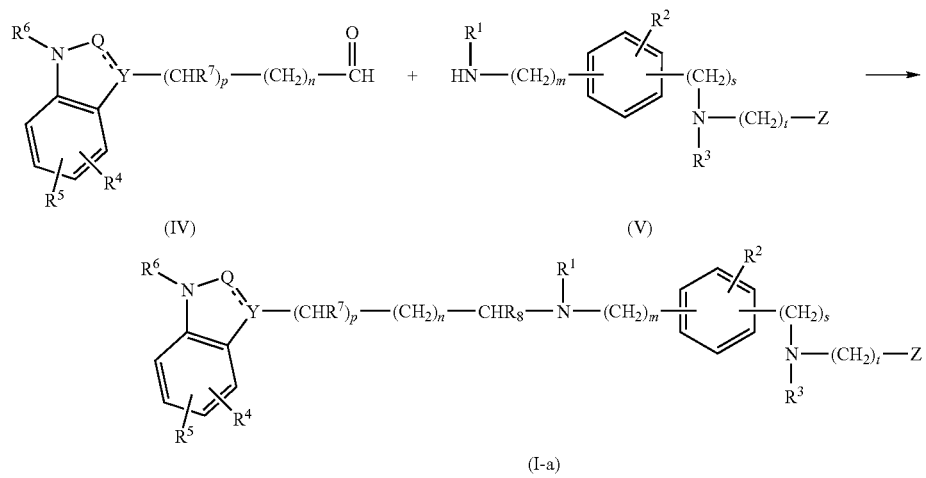

In an identical way the compounds of formula (I), wherein t is 1, herein referred to as compounds of formula (I-c), can be prepared by reacting an intermediate of formula (II) with an appropriate carboxaldehyde of formula (VI).

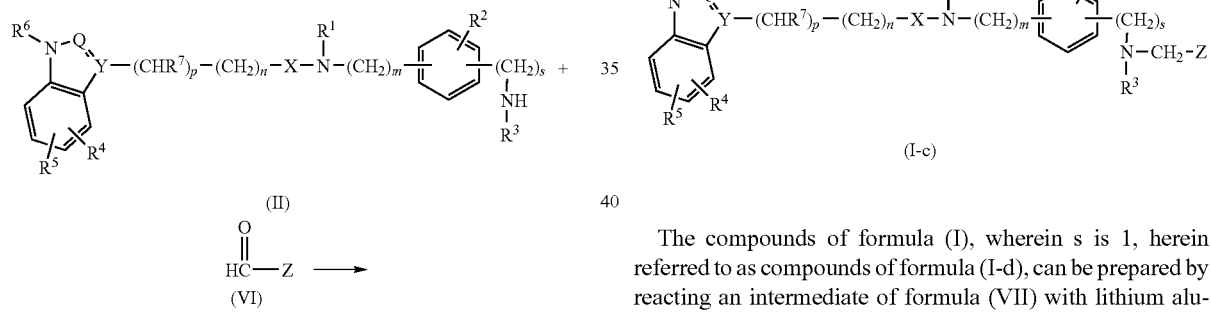

The compounds of formula (I), wherein s is 1, herein referred to as compounds of formula (I-d), can be prepared by reacting an intermediate of formula (VII) with lithium aluminium hydride in a suitable solvent such as tetrahydrofuran.

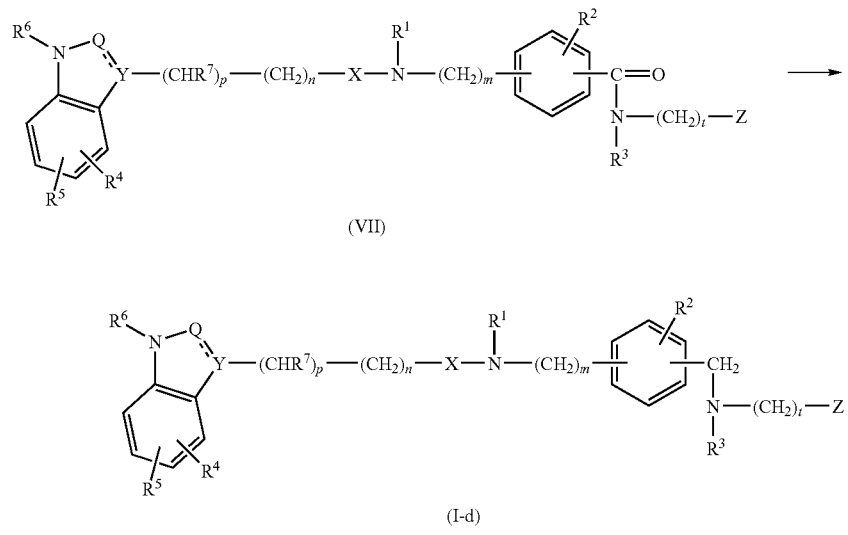

The compounds of formula (I) and the intermediates of formula (III) may also be converted into each other via art-known reactions or functional group transformations. A number of such transformations are already described herein-above. Other examples are hydrolysis of carboxylic esters to the corresponding carboxylic acid or alcohol; hydrolysis of amides to the corresponding carboxylic acids or amines; hydrolysis of nitrites to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

Intermediates of formula (II), wherein X is $CH_2$, m is 0, s is 0 and $R^3$ is hydrogen, herein referred to as intermediates of formula (II-a), can be prepared by a nitro to amine reduction reaction starting with an intermediate of formula (VIII), in the presence of a metal catalyst such as Raney Nickel and an appropriate reductant such as hydrogen, in a suitable solvent such as methanol or ethanol.

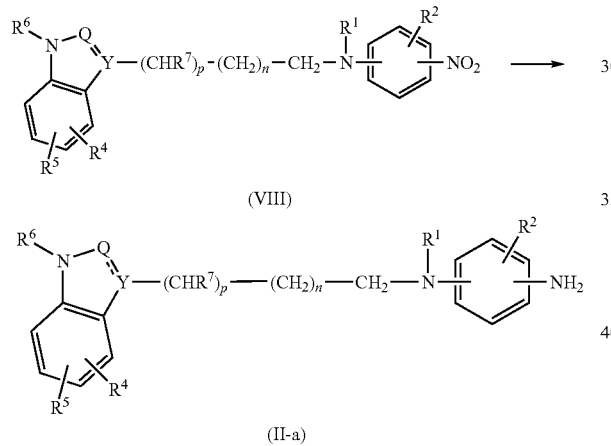

Intermediates of formula (II), wherein X is C(=O), s is 0 and $R^3$ is hydrogen, herein referred to as intermediates of formula (II-b), can be prepared by reacting an intermediate of formula (IX) with an intermediate of formula (X) in the presence of appropriate reagents such as N'-(ethylcarbonimi-doyl)-N,N-dimethyl-1,3-propanediamine, monohydrochloride (EDC) and 1-hydroxy-1H-benzotriazole (HOBT). The reaction may be performed in the presence of a base such as triethylamine, in a suitable solvent, such as, a mixture of dichloromethane and tetrahydrofuran.

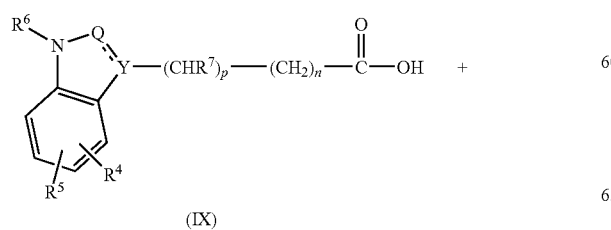

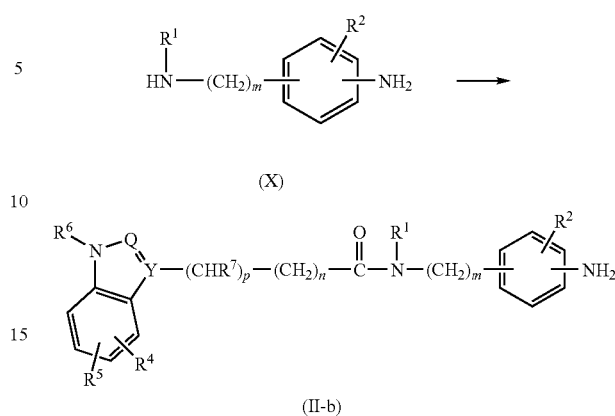

The intermediates of formula (IV) can be prepared by reacting intermediates of formula (XI) with lithium aluminium hydride in a suitable solvent such as tetrahydrofuran.

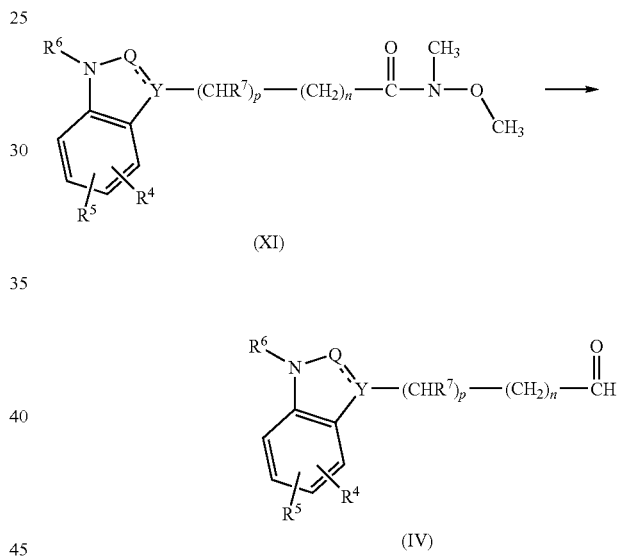

The intermediates of formula (VII) can be prepared by reacting an intermediate of formula (XII) with an intermediate of formula (XIII) in the presence of 2-Chloro-1-methylpyridinium iodide and triethylamine in a suitable solvent such as acetonitrile.

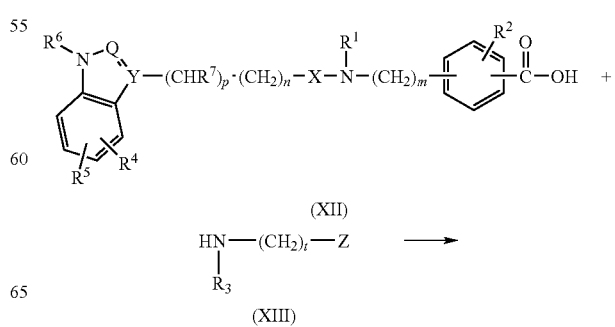

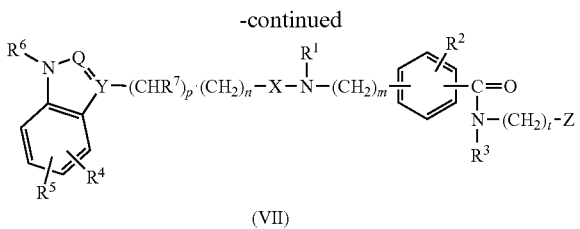

(VII)

The intermediates of formula (VIII) can be prepared by reacting an intermediate of formula (XIV) with an intermediate of formula (XV), wherein A is an appropriate leaving group such as, for example, halo, e.g. fluoro, chloro, bromo or iodo, or

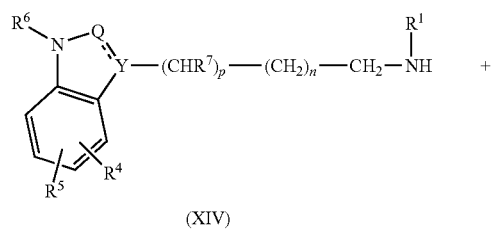

(XIV)

(XV)

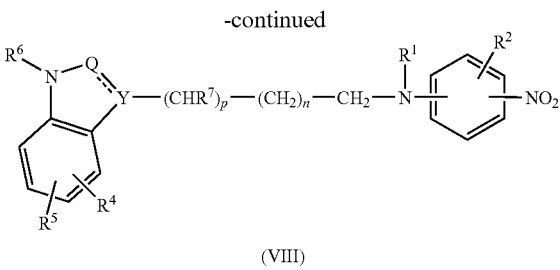

(VIII)

The intermediates of formula (XII) can be prepared by converting an intermediate of formula (XVI) in the presence of sodium hydroxide and water, in a suitable solvent, such as ethanol.

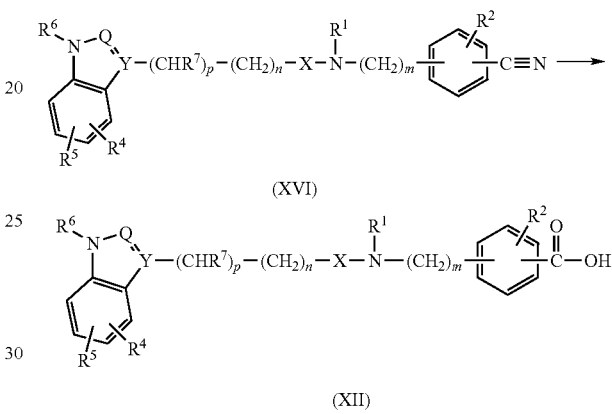

(XVI)

(XII)

The intermediates of formula (XVI) can be prepared by reacting an intermediate of formula (XVIII), wherein A is as defined above, with an intermediate of formula (XIV), in a suitable solvent such as diisopropylethyl amine.

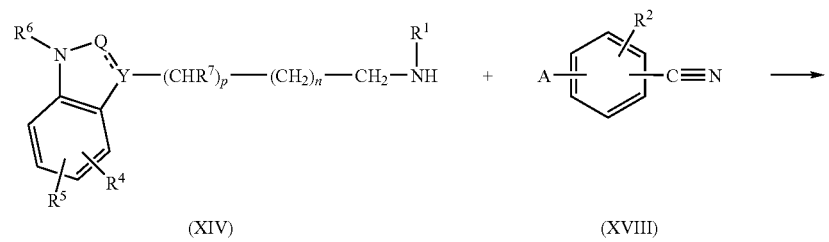

(XIV)            (XVIII)

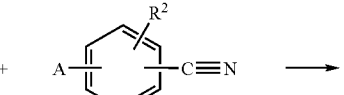

(XVI)

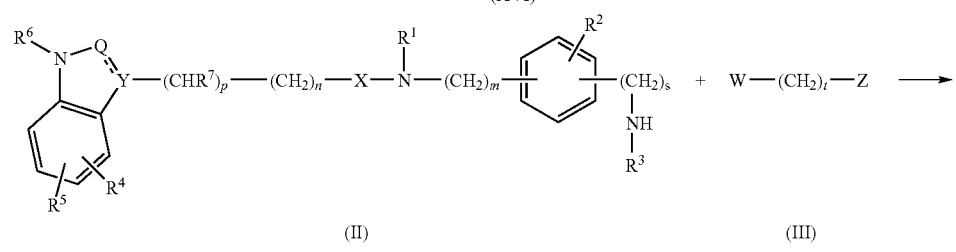

(II)            (III)

-continued

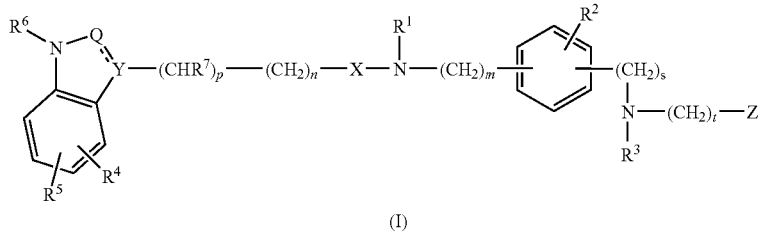

(I)

The compounds of formula (I) and some of the intermediates may have at least one stereogenic centre in their structure. Such stereogenic centre may be present in an R or an S configuration.

The compounds of formula (I) as prepared in the hereinabove described processes are generally racemic mixtures of enantiomers, which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they inhibit the interaction between p53 and MDM2.

The term "MDM2" is used herein to mean a protein obtained as a result of expression of the mdm2 gene. Within the meaning of this term, MDM2 encompass all proteins encoded by mdm2, mutants thereof, alternative slice proteins thereof, and phosphorylated proteins thereof. Additionally, as used herein, the term "MDM2" includes MDM2 analogues, e.g. MDMX, also known as MDM4, and MDM2 homologues and analogues of other animals, e.g. the human homologue HDM2 or the human analogue HDMX.

The term "inhibiting the interaction" or "inhibitor of the interaction" is used herein to mean preventing or reducing the direct of indirect association of one or more molecules, peptides, proteins, enzymes or receptors; or preventing or reducing the normal activity of one or more molecules, peptides, proteins, enzymes, or receptors.

The term "inhibitor of the interaction of p53 with MDM2" or "p53-MDM2 inhibitor" is used herein to describe an agent which increases the expression of p53 in the assay described in C.1. This increase may be caused by, but is not limited to, one or more of the following mechanisms of action:

inhibiting the interaction between p53 and MDM2,
direct association with either the MDM2 or the p53 protein,
interactions with upstream or downstream targets, e.g. kinases, or enzyme activities involved in ubiquitination or SUMO modification,
sequestering or transportation of MDM2 and p53 into different cellular compartments,
modulation of proteins associating with MDM2, for example (but not limited to), p73, E2F-1, Rb, p21waf1 or cip1,
downregulating or interference with MDM2 expression and/or MDM2 activity, for example by (but not limited to), impacting on its cellular localisation, post-translational modification, nuclear export or ubiquitin ligase activity
direct or indirect stabilization of the p53 protein, e.g. by keeping it in its functional structural form, or by preventing misfolding,
enhancing p53 expression or expression of p53 family members, e.g. p63 and p73.
increasing p53 activity, for example by (but not limited to), enhancing its transcriptional activity and/or
increasing expression of genes and proteins of the p53-signalling pathway, for example (but not limited to) p21waf1, cip1, MIC-1 (GDF-15), PIG-3 and ATF-3.

Hence, the present invention discloses the compounds of formula (I) for use as a medicine.

Furthermore, the invention also concerns the use of a compound for the manufacture of a medicament for the treatment of a disorder mediated through a p53-MDM2 interaction, wherein said compound is a compound of formula (I)

The term "treating" or "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

With the term "a disorder mediated through a p53-MDM2 interaction" is meant any undesired or detrimental condition that results in or from the inhibition of the interaction between the MDM2 protein and p53 or other cellular proteins that induce apoptosis, induce cellular death, or regulate the cell cycle.

This invention also provides a method for treating a disorder mediated through a p53-MDM2 interaction by administering an effective amount of a compound of the present invention, to a subject, e.g. a mammal (and more particularly a human) in need of such treatment.

The compounds of the invention can have antiproliferative effects in tumour cells, even if such cells are devoid of functional p53. More in particular, the compounds of the invention can have antiproliferative effects in tumours with wild-type p53 and/or in tumours overexpressing MDM2.

Thus, this invention also provides a method for inhibiting tumour growth by administering an effective amount of a compound of the present invention, to a subject, e.g. a mammal (and more particularly a human) in need of such treatment.

Examples of tumours which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), oesophageal cancer, oral squamous carcinoma, tongue carcinoma, gastric carcinoma, nasopharyngeal cancer, hematopoietic tumours of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, brain tumors, gliomas, benign tumour of the skin (e.g. keratoacanthomas), breast carcinoma (e.g. advanced breast cancer), kidney carcinoma, ovary carcinoma, cervical carcinoma, endometrial carcinoma, bladder carcinoma, prostate cancer including the advanced disease, testicular cancers, osteosarcoma, head and neck cancer and epidermal carcinoma.

The compounds of the present invention can also be used for the treatment and prevention of inflammatory conditions.

Thus, this invention also provides a method for the treatment and prevention of inflammatory conditions by administering an effective amount of a compound of the present invention, to a subject, e.g. a mammal (and more particularly a human) in need of such treatment.

The compounds of the present invention can also be used for the treatment of autoimmune diseases and conditions. With the term "autoimmune diseases" is meant any disease in which an animal's immune system reacts adversely to a self-antigen. With the term "self-antigen" is meant any antigen that is normally found in the animal's body. Representative autoimmune diseases include but are not limited to: Hashimoto's thyroiditis, Grave's disease, multiple sclerosis, pernicious anemia, Addison's disease, insulin-dependent diabetes mellitus, rheumatoid arthritis, systemic lupus erythematosus (SLE or lupus), dermatomyositis, Crohn's disease, Wegener's granulomatosis, Anti Glomerular Basement Membrane Disease, Antiphospholipid Syndrome, Dermatitis Herpetiformis, Allergic Encephalomyelitis, Glomerulonephritis, Membranous Glomerulonephritis, Goodpasture Syndrome, Lambert-Eaton, Myasthenic Syndrome, Myasthenia Gravis, Bullous Pemphigoid, Polyendocrinopathies, Reiter's Disease, and Stiff-Man Syndrome.

Thus, this invention also provides a method for the treatment of autoimmune diseases and conditions and the treatment of diseases associated with conformational unstable or misfolded proteins by administering an effective amount of a compound of the present invention, to a subject, e.g. a mammal (and more particularly a human) in need of such treatment.

The compounds of the present invention can also be useful for the treatment of diseases associated with conformational unstable or misfolded proteins.

Examples of diseases associated with conformational unstable or misfolded proteins include but are not limited to: cystic fibrosis (CFTR), Marfan syndrom (fibrillin), Amyotrophic lateral sclerosis (superoxide dismutase), scurvy (collagen), maple syrup urine disease (alpha-ketoacid dehydrogenase complex), osteogenesis imperfecta (typeI procollagen pro-alpha), Creutzfeldt-Jakob disease (prion), Alzheimer's disease (beta-amyloid), familial amyloidosis (lysozyme), cataracts (crystallins), familial hypercholesterolemia (LDL receptor), αI-antitrypsin deficiency, Tay-Sachs disease (beta-hexosaminidase), retinitis pigmentosa (rhodopsin), and leprechaunism (insulin receptor).

Thus, this invention also provides a method for the treatment of diseases associated with conformational unstable or misfolded proteins by administering an effective amount of a compound of the present invention, to a subject, e.g. a mammal (and more particularly a human) in need of such treatment.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to inhibit the interaction between MDM2 and p53 or other cellular proteins that induce apoptosis, induce cellular death, or regulate the cell cycle.

The oncogenic potential of MDM2 is not only determined by its ability to suppress p53, but also by its ability to regulate other tumour suppressor proteins, e.g. the retinoblastoma protein pRb and the closely associated E2F1 transcription factor.

Thus, the compound of the invention is administered in an amount sufficient to modulate the interaction between MDM2 and the E2F transcription factors.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

As another aspect of the present invention, a combination of a p53-MDM2 inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents. Examples of anti-cancer agents are:
  platinum coordination compounds for example cisplatin, carboplatin or oxalyplatin;
  taxane compounds for example paclitaxel or docetaxel;
  topoisomerase I inhibitors such as camptothecin compounds for example irinotecan or topotecan;
  topoisomerase II inhibitors such as anti-tumour podophyllotoxin derivatives for example etoposide or teniposide;
  anti-tumour vinca alkaloids for example vinblastine, vincristine or vinorelbine;
  anti-tumour nucleoside derivatives for example 5-fluorouracil, gemcitabine or capecitabine;
  alkylating agents such as nitrogen mustard or nitrosourea for example cyclophosphamide, chlorambucil, carmustine or lomustine;
  anti-tumour anthracycline derivatives for example daunorubicin, doxorubicin, idarubicin or mitoxantrone;
  HER2 antibodies for example trastuzumab;
  estrogen receptor antagonists or selective estrogen receptor modulators for example tamoxifen, toremifene, droloxifene, faslodex or raloxifene;
  aromatase inhibitors such as exemestane, anastrozole, letrazole and vorozole;
  differentiating agents such as retinoids, vitamin D and retinoic acid metabolism blocking agents (RAMBA) for example accutane;
  DNA methyl transferase inhibitors for example azacytidine;
  kinase inhibitors for example flavoperidol, imatinib mesylate or gefitinib;
  farnesyltransferase inhibitors;
  HDAC inhibitors;
  other inhibitors of the ubiquitin-proteasome pathway for example Velcade; or
  Yondelis.

The term "platinum coordination compound" is used herein to denote any tumour cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree Camptothecin acuminata and the Indian tree Nothapodytes foetida.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (Vinca rosea).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus *Strep. peuticus var. caesius* and their derivatives, characterised by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumours can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone.

The term "other inhibitors of the ubiquitin-proteasome pathway" is used to identify compounds that inhibit the targeted destruction of cellular proteins in the proteasome, including cell cycle regulatory proteins.

As stated above, the compounds of the present invention also have therapeutic applications in sensitising tumour cells for chemotherapy and radiotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other disease.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease.

In view of their useful pharmacological properties, the components of the combinations according to the invention, i.e. the other medicinal agent and the p53-MDM inhibitor may be formulated into various pharmaceutical forms for administration purposes. The components may be formulated separately in individual pharmaceutical compositions or in a unitary pharmaceutical composition containing both components.

The present invention therefore also relates to a pharmaceutical composition comprising the other medicinal agent and the p53-MDM inhibitor together with one or more pharmaceutical carriers.

The present invention further relates to the use of a combination according to the invention in the manufacture of a pharmaceutical composition for inhibiting the growth of tumour cells.

The present invention further relates to a product containing as first active ingredient a p53-MDM2 inhibitor according to the invention and as second active ingredient an anticancer agent, as a combined preparation for simultaneous, separate or sequential use in the treatment of patients suffering from cancer.

The other medicinal agent and p53-MDM2 inhibitor may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and p53-MDM2 inhibitor being administered, their route of administration, the particular tumour being treated and the particular host being treated. The optimum method and order of administration and the dosage amounts and regime can be readily determined by those skilled in the art using conventional methods and in view of the information set out herein.

The platinum coordination compound is advantageously administered in a dosage of 1 to 500 mg per square meter (mg/m²) of body surface area, for example 50 to 400 mg/m², particularly for cisplatin in a dosage of about 75 mg/m² and for carboplatin in about 300 mg/m² per course of treatment.

The taxane compound is advantageously administered in a dosage of 50 to 400 mg per square meter (mg/m²) of body surface area, for example 75 to 250 mg/m², particularly for paclitaxel in a dosage of about 175 to 250 mg/m² and for docetaxel in about 75 to 150 mg/m² per course of treatment.

The camptothecin compound is advantageously administered in a dosage of 0.1 to 400 mg per square meter (mg/m²) of body surface area, for example 1 to 300 mg/m², particularly for irinotecan in a dosage of about 100 to 350 mg/m² and for topotecan in about 1 to 2 mg/m² per course of treatment.

The anti-tumour podophyllotoxin derivative is advantageously administered in a dosage of 30 to 300 mg per square meter (mg/m²) of body surface area, for example 50 to 250 mg/m², particularly for etoposide in a dosage of about 35 to 100 mg/m² and for teniposide in about 50 to 250 mg/m² per course of treatment.

The anti-tumour vinca alkaloid is advantageously administered in a dosage of 2 to 30 mg per square meter (mg/m²) of body surface area, particularly for vinblastine in a dosage of about 3 to 12 mg/m², for vincristine in a dosage of about 1 to 2 mg/m², and for vinorelbine in dosage of about 10 to 30 mg/m² per course of treatment.

The anti-tumour nucleoside derivative is advantageously administered in a dosage of 200 to 2500 mg per square meter (mg/m²) of body surface area, for example 700 to 1500 mg/m², particularly for 5-FU in a dosage of 200 to 500 mg/m², for gemcitabine in a dosage of about 800 to 1200 mg/m² and for capecitabine in about 1000 to 2500 mg/m² per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

Trastuzumab is advantageously administered in a dosage of 1 to 5 mg per square meter (mg/m²) of body surface area, particularly 2 to 4 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

These dosages may be administered for example once, twice or more per course of treatment, which may be repeated for example every 7, 14, 21 or 28 days.

The compounds of formula (I), the pharmaceutically acceptable acid addition salts and stereoisomeric forms thereof can have valuable diagnostic properties in that they can be used for detecting or identifying an p53-MDM2 interaction in a biological sample comprising detecting or measuring the formation of a complex between a labelled compound and/or p53 and/or MDM2 and or other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase. Biological samples can be defined as body tissue or body fluids. Examples of body fluids are cerebrospinal fluid, blood, plasma, serum, urine, sputum, saliva and the like.

The following examples illustrate the present invention.

EXPERIMENTAL PART

Hereinafter, "DMF" is defined as N,N-dimethylformamide, "DCM" is defined as dichloromethane, "DIPE" is defined as diisopropyl ether, "EtOAc" is defined as ethyl acetate, "EtOH" is defined as ethanol, "EDC" is defined as N'-(ethylcarbonimidoyl)-N,N-dimethyl-1,3-propanediamine, monohydrochloride, "MeOH" is defined as methanol, "THF" is defined as tetrahydrofuran., "HOBT" is defined as 1-hydroxybenzotriazole.

A. Preparation of the Intermediate Compounds

Example A1 a) Preparation of Intermediate 1

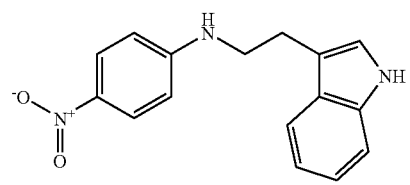

A mixture of 1-fluoro-4-nitro-benzene (0.0142 mol), 1H-indole-3-ethanamine (0.0129 mol) and N-ethyl-N-(1-methylethyl)-2-propanamine (0.032 mol) was stirred at 210° C. for 18 hours, then brought to room temperature, and decanted. The residue was taken up in acetonitrile/water. The precipitate was filtered, washed with diethyl ether and dried, yielding 2.3 g (64%) of intermediate 1.

b) Preparation of Intermediate 2

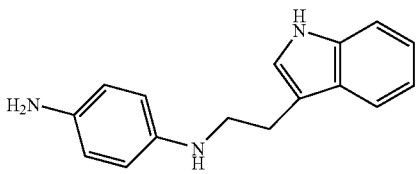

A mixture of intermediate 1 (0.0078 mol) and Raney Nickel (2.2 g) in EtOH (50 ml) was hydrogenated at room temperature for 3 hours under a 3 bar pressure, then filtered over celite. Celite was washed with DCM/MeOH. The filtrate was evaporated. The residue was taken up in DCM, dried ($MgSO_4$), filtered, and the solvent was evaporated, yielding 1.88 g (95%) of intermediate 2.

Example A2 a) Preparation of Intermediate 3

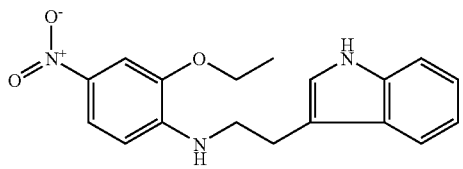

A mixture of 2-ethoxy-1-methoxy-4-nitro-benzene (0.009 mol), 1H-indole-3-ethanamine (0.009 mol) and N-ethyl-N-(1-methylethyl)-2-propanamine (0.0228 mol) was stirred at 210° C. for 24 hours, then brought to room temperature, taken up in DCM/MeOH and dried. The residue was taken up in DCM (few) and purified by column chromatography over silica gel (35-70 µm) (eluent: cyclohexane/DCM 30/70). The pure fractions were collected and the solvent was evaporated, yielding 0.6 g (20%) of intermediate 3.

b) Preparation of Intermediate 4

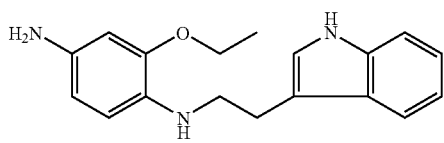

A mixture of intermediate 3 (0.002 mol) and $H_2$/Raney Nickel (0.6 g) in MeOH (100 ml) was hydrogenated at room temperature for 1 hour and 30 minutes under a 3 bar pressure, then filtered over celite. Celite was washed with DCM/MeOH. The filtrate was evaporated. The residue was taken up in DCM/MeOH (few), dried ($MgSO_4$), filtered and the solvent was evaporated, yielding 0.45 g (83%) of intermediate 4.

Example A3 a) Preparation of Intermediate 5

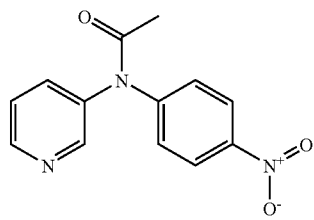

A mixture of N-3-pyridinyl-acetamide (0.038 mol), 1-fluoro-4-nitro-benzene (0.05 mol), copper(I) chloride (0.0038 mol) and potassium carbonate (0.076 mol) in xylene (60 ml) was stirred and refluxed for 18 hours, then brought to room temperature. Water was added. The mixture was filtered over celite. Celite was washed with DCM. The filtrate was evaporated. The residue was purified by column chromatography over silica gel (35-70 µm) (eluent: DCM/MeOH/$NH_4OH$ 97/3/0.1). The pure fractions were collected and the solvent was evaporated, yielding 6.4 g (65%) of intermediate 5.

b) Preparation of Intermediate 6

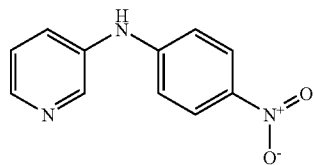

Sodium hydroxide (concentrated) (10 ml) was added to a mixture of intermediate 5 (0.025 mol) in EtOH (80 ml). The mixture was stirred and refluxed for 2 hours, then brought to room temperature. Water was added. The mixture was stirred for 15 minutes then filtered. The residue was purified by column chromatography over silica gel (70-200 µm) (eluent: DCM/MeOH 100/0 to 95/5). The pure fractions were collected and the solvent was evaporated, yielding 1.5 g (28%) of intermediate 6.

c) Preparation of Intermediate 7

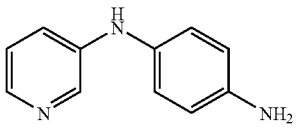

A mixture of intermediate 6 (0.007 mol) and Raney Nickel (1.5 g) in MeOH (30 ml) and THF (10 ml) was hydrogenated at room temperature for 1 hour under a 3 bar pressure, then filtered over celite. Celite was washed with DCM/MeOH. The filtrate was evaporated. The residue was taken up in DCM. The organic layer was separated, dried ($MgSO_4$), filtered, and the solvent was evaporated, yielding 1.2 g (92%) of intermediate 7.

Example A4

Preparation of Intermediate 8

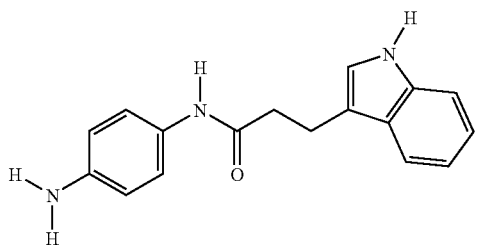

1H-indole-3-propanoic acid (0.0264 mol) then 1-hydroxy-benzotriazole (0.0344 mol) then N'-(ethylcarbonimidoyl)-N,N-dimethyl-1,3-propanediamine, monohydrochloride (=EDCI) (0.0344 mol) were added to a mixture of 1,4-benzenediamine (0.137 mol) in THF (200 ml) and DCM (200 ml) under $N_2$ flow. The mixture was stirred at room temperature for 24 hours, poured out into water and extracted with DCM. The organic layer was separated, dried ($MgSO_4$), filtered, and the solvent was evaporated. The residue was purified by column chromatography over silica gel (20-45 μm) (eluent: DCM/MeOH/$NH_4OH$ 97/3/0.5). The pure fractions were collected and the solvent was evaporated, yielding 1.75 g (24%) of intermediate 8.

Example A5 a) Preparation of Intermediate 9

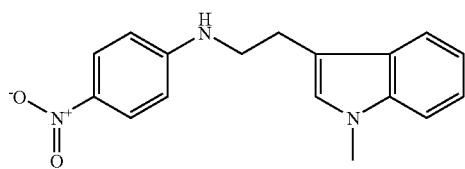

A mixture of 1-fluoro-4-nitro-benzene (0.0025 mol), 1-methyl-1H-indole-3-ethanamine (0.0023 mol) and N-ethyl-N-(1-methylethyl)-2-propanamine (0.0057 mol) was stirred at 200° C. for 2 hours, then brought to room temperature. Water and DCM were added. The organic layer was separated, dried ($MgSO_4$), filtered, and the solvent was evaporated. The residue (0.8 g) was purified by column chromatography over silica gel (35-70 cm) (eluent: DCM 100). The pure fractions were collected and the solvent was evaporated. The residue (0.45 g) was taken up in DIPE. The precipitate was filtered off and dried, yielding 0.33 g (66%) of intermediate 9.

b) Preparation of Intermediate 10

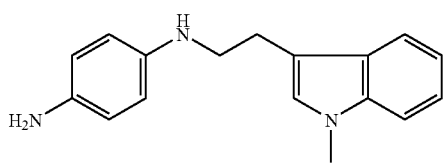

A mixture of intermediate 9 (0.0011 mol) and Raney Nickel (0.4 g) in MeOH (20 ml) was hydrogenated at room temperature for 1 hour under a 3 bar pressure, then filtered over celite. Celite was washed with DCM/MeOH. The filtrate was evaporated. The residue was taken up in DCM. The organic layer was separated, dried ($MgSO_4$), filtered, and the solvent was evaporated, yielding 0.305 g (97%) of intermediate 10.

Example A6 a) Preparation of Intermediate 11

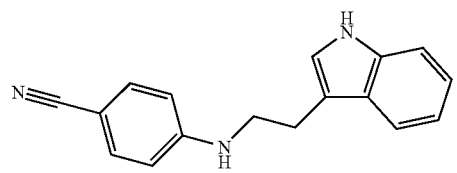

A mixture of 4-fluoro-benzonitrile (0.071 mol), 1H-indole-3-ethanamine (0.071 mol) and N-ethyl-N-(1-methylethyl)-2-propanamine (0.1775 mol) was stirred at 210° C. for 16 hours, then brought to room temperature and taken up in DCM/MeOH. The organic layer was washed with HCl 3N, dried ($MgSO_4$), filtered and the solvent was evaporated. The residue was taken up in diethyl ether/acetonitrile. The precipitate was filtered off and dried, yielding 8.07 g (43%) of intermediate 11, melting point 144° C.

b) Preparation of Intermediate 12

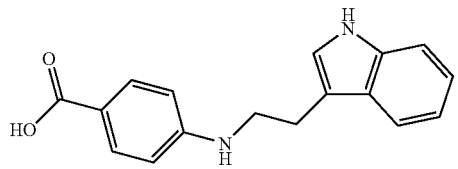

A mixture of intermediate 11 (0.0115 mol) and sodium hydroxide (0.17 mol) in EtOH (50 ml) and water (50 ml) was stirred and refluxed for 18 hours, then brought to room temperature. The solvent was evaporated. The residue was taken up in sodium hydroxide 3N. The aqueous layer was washed with DCM and acidified till pH 5 was obtained. The precipitate was filtered off and dried, yielding 1.06 g (35%) of intermediate 12, melting point 225° C.

c) Preparation of Intermediate 13

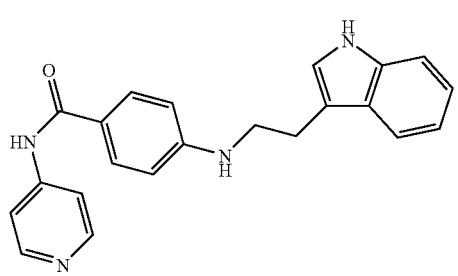

A mixture of intermediate 12 (0.0037 mol), 4-pyridinamine (0.0037 mol), 2-chloro-1-methyl-pyridinium, iodide (0.0113 mol) and triethylamine (0.015 mol) in acetonitrile (100 ml) was stirred and refluxed for 90 minutes, then brought to room temperature. The solvent was evaporated. The residue was taken up in DCM/MeOH. The organic layer was washed with potassium carbonate 10%, dried (MgSO$_4$), filtered and the solvent was evaporated till dryness. The residue was purified by flash column chromatography over silica gel (35-70 cm) (eluent: DCM/MeOH/NH$_4$OH 95/5/0.1). Two fractions were collected and the solvent was evaporated, yielding 0.06 g F1 and 0.08 g F2. F1 was crystallized from diethyl ether/acetonitrile. The precipitate was filtered off and dried, yielding a first batch of 0.032 g (2.4%) of intermediate 13. F2 and the mother layer were combined and crystallized from diethyl ether/acetonitrile. The precipitate was filtered off and dried, yielding a second batch of 0.105 g (10%) of intermediate 13, melting point 200° C.

Example A7

Preparation of Intermediate 14

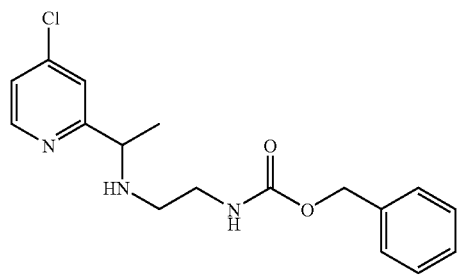

Similar procedure as method 6 (see Example A13) was followed, starting from 1-(4-chloro-2-pyridinyl)-ethanone (227 mg, 0.0015 mol) and with addition of triethylamine (0.22 ml). After workup, the residue was purified by column chromatography over silica gel (40-63 μm) (eluent: EtOAc). The pure fractions were collected and the solvent was evaporated, yielding 256 mg (52%) of intermediate 14 as a pale yellow oil.

Example A8

Preparation of Intermediate 15

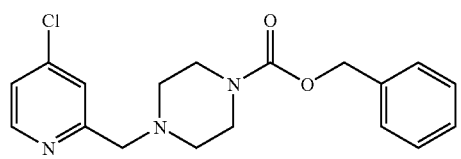

Similar procedure as method 4 (see Example A22/22) was followed, starting from benzyl 1-piperazinecarboxylate (1.3 ml, 0.0069 mol) and 4-chloro-2-pyridinemethanol (500 mg, 0.0034 mol). After workup, the residue was purified by column chromatography over silica gel (40-63 μm) (eluent: DCM/MeOH 95/5). The pure fractions were collected and the solvent was evaporated, yielding 840 mg (70%) of intermediate 15 as an orange oil.

Example A9

Preparation of Intermediate 16

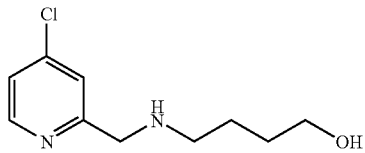

Similar procedure as method 4 (see Example A22/22) was followed, starting from 4-amino-butan-1-ol (310 mg, 0.0021 mol) and 4-chloro-2-pyridinemethanol (300 mg, 0.0021 mol). After workup, the residue was purified by column chromatography over silica gel (40-63 μm) (eluent: DCM/MeOH 85/15). The pure fractions were collected and the solvent was evaporated, yielding 55 mg (17%) of intermediate 16 as a yellow oil.

Example A10

Preparation of Intermediate 17

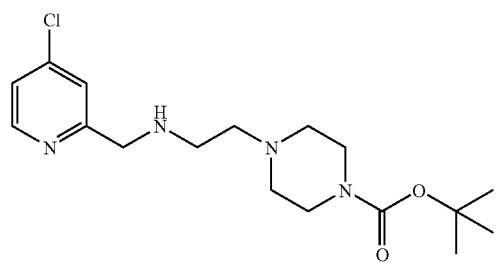

Similar procedure as method 5 (see Example A22/34) was followed, starting from 4-(2-amino-ethyl)-piperazine-1-carboxylic acid tert-butyl ester (579 mg, 0.0025 mol) and 4-chloro-2-pyridinecarboxaldehyde (325 mg, 0.0023 mol). After workup, the residue was purified by column chromatography over silica gel (40-63 μm) (eluent: DCM/MeOH 90/10). The pure fractions were collected and the solvent was evaporated, yielding 425 mg (53%) of intermediate 17 as a yellow oil.

Example A11

Preparation of Intermediate 18

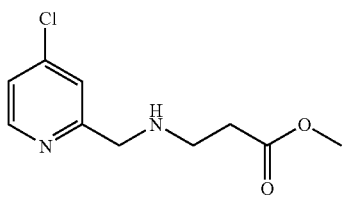

Similar procedure as method 5 (see Example A22/34) was followed, starting from 3-amino-propionic acid methyl ester hydrochloride (351 mg, 0.0025 mol) and 4-chloro-2-pyridinecarboxaldehyde (325 mg, 0.0023 mol) and with addition of triethylamine (0.35 ml, 0.0025 mol). After workup, the residue was purified by column chromatography over silica gel (40-63 μm) (eluent: DCM/MeOH 95/5). The pure fractions were collected and the solvent was evaporated, yielding 160 mg (30%) of intermediate 18 as a yellow oil.

Example A12

Preparation of Intermediate 19

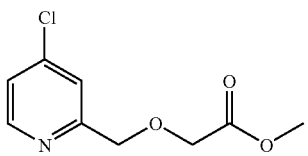

Similar procedure as method 3 (see Example A22/20) was followed, starting from bromo-acetic acid methyl ester (0.26 ml, 0.0021 mol) and 4-chloro-2-pyridinemethanol (300 mg, 0.0021 mol). After workup, the residue was purified by column chromatography over silica gel (40-63 μm) (eluent: AcOEt/cyclohexane 60/40). The pure fractions were collected and the solvent was evaporated, yielding 170 mg (38%) of intermediate 19 as a yellow oil.

Example A13

Preparation of Intermediate 20

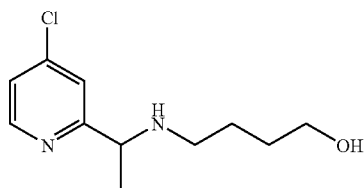

Method 6

4-Amino-1-butanol (0.13 ml, 0.0014 mol) was added at room temperature to a mixture of 1-(4-chloro-2-pyridinyl)-ethanone (200 mg, 0.0013 mol), para-toluene sulfonic acid (123 mg, 0.00065 mol), and 3 Å molecular sieves in MeOH (4 ml). The mixture was stirred 6 hours at room temperature, cooled down to 0° C., and sodium borohydride (98 mg, 0.0026 mol) was slowly added. The mixture was stirred at room temperature for 18 hours. Molecular sieves were filtered off, and the mixture was poured out into water and the solvent was evaporated. The aqueous layer was basified with a saturated solution of sodium hydrogen carbonate, and extracted 3 times with DCM. The organic layer was separated, washed with brine, dried (MgSO₄), filtered, and the solvent was evaporated. The residue was purified by column chromatography over silica gel (40-63 μm) (eluent: DCM/ MeOH 95/5). The pure fractions were collected and the solvent was evaporated, yielding 269 mg (91%) of intermediate 20 as a yellow oil.

Example A14

Preparation of Intermediate 21

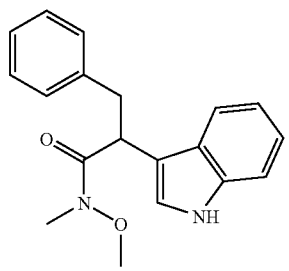

A mixture of x-(phenylmethyl)-1H-indole-3-acetic acid (94 mg, 0.00035 mol) and 1,1 carbonyldiimidazole (59 mg, 0.00036 mol, added portionwise) in DCM (1 ml) was stirred 3 hours at room temperature under argon. N,O-dimethylhydroxylamine hydrochloride (36 mg, 0.00037 mol) was added, and the mixture was stirred 3 more hours at room temperature, cooled down to 0° C., then poured out into water. pH was adjusted to 10 with a 4N solution of sodium hydroxide, and aqueous layer was extracted with EtOAc. The organic layer was separated, washed with a 3N solution of hydrochloric acid, dried (MgSO₄), filtered, and the solvent was evaporated. The residue was purified by column chromatography over silica gel (40-63 μm) (eluent: EtOAc/cyclohexane 50/50). The pure fractions were collected and the solvent was evaporated, yielding 52 mg (47%) of intermediate 21.

Example A15 a) Preparation of Intermediate 22

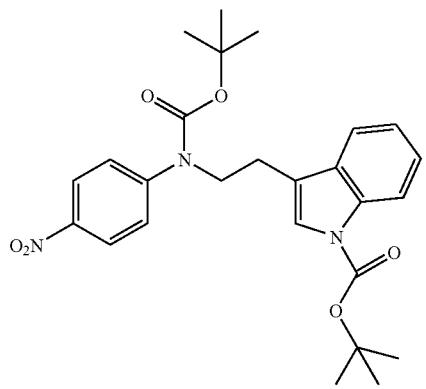

To a solution of intermediate 1 (3.0 g, 0.011 mol) in DCM (130 ml), was added 4-dimethylaminopyridine (261 mg, 0.0021 mol) and di-tert-butyldicarbonate (14.0 g, 0.064 mol). The mixture was stirred at room temperature for 5 hours. The reaction was quenched by addition of water and extracted twice with DCM. The organic layer was washed successively with a saturated solution of sodium bicarbonate and with brine, dried (MgSO₄), filtered, and the solvent was evaporated. The residue was purified by column chromatography over silica gel (40-63 μm) (eluent: EtOAc/cyclohexane 10/90 to 20/80). The pure fractions were collected and the solvent was evaporated, yielding 4.65 g (90%) of intermediate 22 as a yellow solid.

b) Preparation of Intermediate 23

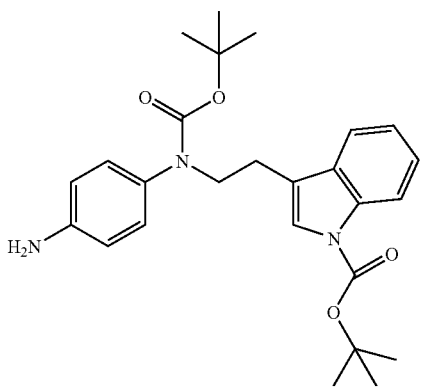

Raney nickel (3 g) was added to a solution of intermediate 22 (4.7 g, 0.0097 mol) in ethanol (15 ml) and THF (15 ml). The reaction mixture was stirred under 1 atmosphere of hydrogen for 16 hours. To complete the reaction, raney nickel (1 g) was added and the mixture was stirred under 1 atmosphere of hydrogen for 4 more hours. The mixture was filtered through a celite pad and the solvent was evaporated. The residue was purified by column chromatography over silica gel (40-63 μm) (eluent: EtOAc/cyclohexane 10/90 to 20/80). The pure fractions were collected and the solvent was evaporated, yielding 4.0 g (92%) of intermediate 23 as a yellow foam.

Example A16 a) Preparation of Intermediate 24

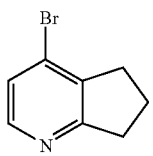

Bromine (0.0104 mol) then a solution of sodium nitrite (0.0362 mol) in water (3 ml) were added drop wise at −10° C. to a mixture of 6,7-dihydro-5H-1-pyridin-4-amine (0.0112 mol) in aqueous hydrogen bromide (48%) (5 ml). The mixture was brought back to 20° C. Ice was added. The mixture was basified with concentrated sodium hydroxide and extracted with EtOAc. The organic layer was separated, dried (MgSO$_4$), filtered, and the solvent was evaporated, yielding: 2 g (90%) of intermediate 24.

b) Preparation of Intermediate 25

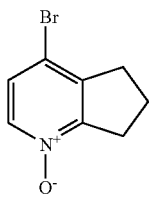

Meta-chloroperbenzoic acid (0.012 mol) was added to a mixture of intermediate 24 (0.01 mol) in DCM (15 ml). The mixture was stirred at room temperature for 12 hours. Sodium hydroxide 3N and water were added. The mixture was extracted three times with DCM. The organic layer was washed with water, dried (MgSO$_4$), filtered, and the solvent was evaporated, yielding 1.85 g (86%) of intermediate 25.

c) Preparation of Intermediate 26

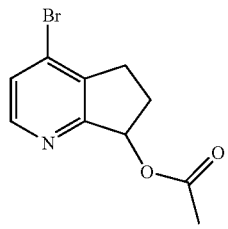

A mixture of intermediate 25 (0.0086 mol) in acetic anhydride (18 ml) was stirred at 100° C. for 30 minutes, then cooled to room temperature and evaporated. The residue was taken up in NaHCO$_3$ and EtOAc and filtered over celite. Celite was washed with EtOAc. The organic layer was separated, dried (MgSO$_4$), filtered, and the solvent was evaporated, yielding 1.63 g (73%) of intermediate 26.

d) Preparation of Intermediate 27

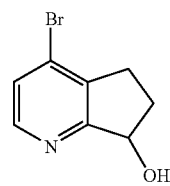

A mixture of intermediate 26 (0.0074 mol) in MeOH (10 ml) and sodium hydroxide 3N (80 ml) was stirred at room temperature for 30 minutes, then stirred at 80° C. for 10 minutes then brought back to room temperature. MeOH was evaporated. The mixture was extracted twice with DCM then washed with saturated NaCl. The organic layer was separated, dried (MgSO$_4$), filtered, and the solvent was evaporated, yielding 1.02 g (64%) of intermediate 27.

Example A17 a) Preparation of Intermediate 28

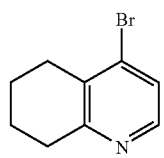

Bromine (1.3 ml) then a solution of sodium nitrite (3.3 g) in water (4 ml) were added drop wise at −10° C. to a solution of 5,6,7,8-tetrahydro-4-quinolinamine (0.0135 mol) in aqueous hydrogen bromide (48%) (6.7 ml). The mixture was brought back to 20° C., poured out on ice, basified with concentrated sodium hydroxide and extracted with EtOAc. The organic layer was separated, dried (MgSO$_4$), filtered, and the solvent was evaporated, yielding 2.2 g (77%) of intermediate 28.

b) Preparation of Intermediate 29

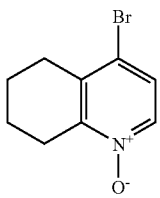

Meta-chloroperbenzoic acid (0.0125 mol) was added to a mixture of intermediate 28 (0.0104 mol) in DCM (20 ml). The mixture was stirred at room temperature for 12 hours. Sodium hydroxide 3N and ice were added. The mixture was extracted twice with DCM. The organic layer was dried (MgSO$_4$), filtered, and the solvent was evaporated, yielding 3 g (100%) of intermediate 29.

c) Preparation of Intermediate 30

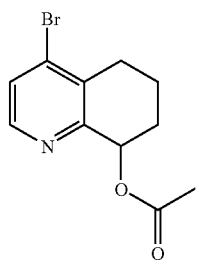

A mixture of intermediate 29 (0.0086 mol) in acetic anhydride (22 ml) was stirred at 100° C. for 30 minutes, then cooled to room temperature and evaporated. The residue was taken up in saturated NaHCO$_3$ and EtOAc. The mixture was stirred for 30 minutes. The organic layer was separated, dried (MgSO$_4$), filtered, and the solvent was evaporated, yielding 3.4 g (100%) of intermediate 30.

d) Preparation of Intermediate 3

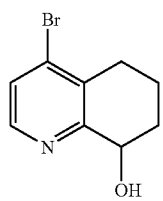

A mixture of intermediate 30 (0.0104 mol) in MeOH (18 ml) and sodium hydroxide 3N (150 ml) was stirred at room temperature for 30 minutes, then stirred at 80° C. for 10 minutes. MeOH was evaporated. The mixture was extracted twice with DCM. The organic layer was washed with saturated NaCl, dried (MgSO$_4$), filtered and the solvent was evaporated, yielding 1.84 g (77%) of intermediate 31.

Example A18 a) Preparation of Intermediate 32

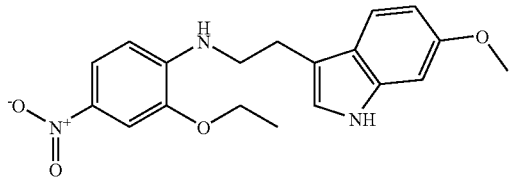

A mixture of 2-ethoxy-4-nitroanisole (0.0107 mol), 6-methoxytryptamine (0.0107 mol) and diisopropylethylamine (0.0268 mol) was stirred at 210° C. for 5 hours then poured out on ice and extracted with DCM. The organic layer was separated, dried (MgSO$_4$), filtered, and the solvent was evaporated. The residue was purified by column chromatography over silica gel (15-40 µm) (eluent: DCM 100%). The pure fractions were collected and the solvent was evaporated, yielding 0.85 g (22%) of intermediate 32.

b) Preparation of Intermediate 33

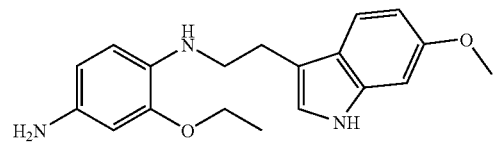

A mixture of intermediate 32 (0.0023 mol) and Raney Nickel (0.85 g) in MeOH (42 ml) and THF (42 ml) was hydrogenated at room temperature for 2 hours under a 3 bar pressure, then filtered over celite. The filtrate was evaporated, yielding 0.74 g (95%) of intermediate 33.

Example A19 a) Preparation of Intermediate 34

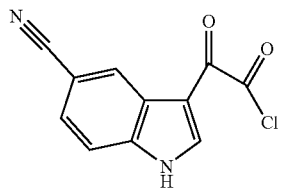

Oxalyl chloride (0.012 mol) was added drop wise at 0° C. to a solution of 5-cyanoindole (0.007 mol) in diethyl ether (21 ml). The mixture was stirred at 0° C. for 5 hours, then stirred at room temperature overnight. The precipitate was filtered, washed with diethyl ether and dried, yielding 1.454 g of (73%) of intermediate 34.

b) Preparation of Intermediate 35

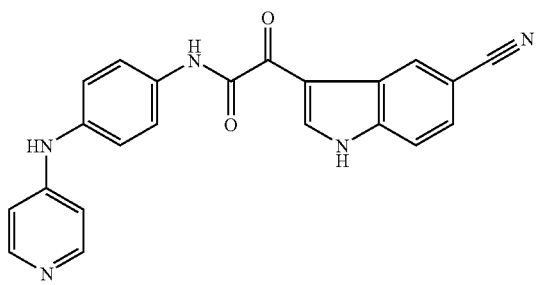

A solution of intermediate 34 (0.0027 mol) in DCM (12 ml) was added drop wise at 5° C. to a solution of N-Pyridin-4-yl-benzene-1,4-diamine (0.022 mol) and N,N-diisopropylethylamine (0.0034 mol) in DCM (4 ml). The mixture was stirred and refluxed for a weekend, then cooled to room temperature. The precipitate was filtered off and dried. The residue was crystallized from iPrOH. The precipitate was filtered off and dried, yielding 0.756 g of crude product. This fraction was purified by column chromatography over kromasil (5 µm) (eluent: DCM/MeOH/NH$_4$OH 97/3/0.3 to 87/13/1.3). The pure fractions were collected and the solvent was evaporated. The residue was purified by column chromatography over silica gel (15-40 µm) (eluent: DCM/MeOH/NH$_4$OH 90/10/0.1 to 87/13/0.1). The pure fractions were collected and the solvent was evaporated, yielding 0.098 g (20%) of intermediate 35, melting point>264° C.

Example A20 a) Preparation of Intermediate 36

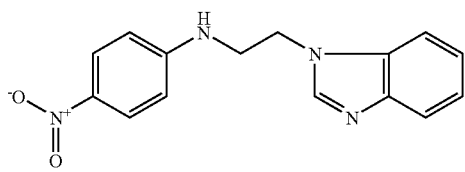

A mixture of 1H-benzimidazole-1-ethanamine (0.011 mol), 1-fluoro-4-nitrobenzene (0.011 mol) and diisopropylethylamine (0.034 mol) was stirred at 210° C. for 30 minutes. Diisopropylethylamine was evaporated. The precipitate was dissolved in DCM/MeOH. The organic layer was washed with potassium carbonate 10%, dried (MgSO$_4$), filtered and the solvent was evaporated. The residue (3.2 g) was purified by column chromatography over silica gel (15-40 cm) (eluent: DCM/MeOH/NH$_4$OH 98/2/0.5). The pure fractions were collected and the solvent was evaporated. The residue (2.1 g, 77%) was crystallized from acetonitrile. The precipitate was filtered off and dried, yielding 1.3 g (47%) of intermediate 36, melting point 144° C.

b) Preparation of Intermediate 37

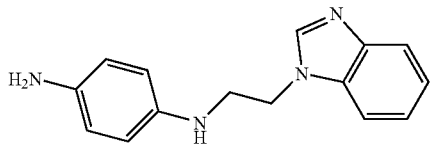

A mixture of intermediate 36 (0.006 mol) and Raney Nickel (2 g) in MeOH (20 ml) was hydrogenated at room temperature under a 3 bar pressure, then filtered over celite. Celite was washed with DCM/MeOH. The filtrate was evaporated, yielding 1.7 g (100%) of intermediate 37.

Example A21 a) Preparation of Intermediate 38

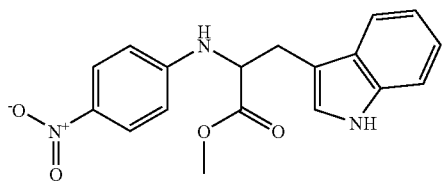

A mixture of DL-Tryptophan, methyl ester (0.0078 mol), 1-fluoro-4-nitrobenzene (0.0078 mol) and diisopropylethylamine (0.0353 mol) was stirred at 210° C. for 4 hours, and then taken up in DCM/MeOH. HCl 3N was added. The mixture was stirred for 15 minutes. The organic layer was washed with saturated NaHCO$_3$, dried (MgSO$_4$), filtered and the solvent was evaporated. The residue was purified by column chromatography over silica gel (35-70 µm) (eluent: DCM 100% then DCM/MeOH 99/1). The pure fractions were collected and the solvent was evaporated, yielding 0.75 g (28%) of intermediate 38.

b) Preparation of Intermediate 39

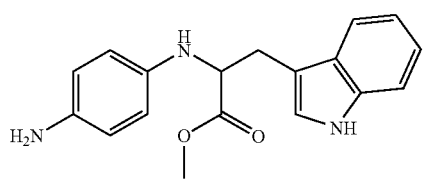

A mixture of intermediate 38 (0.0022 mol) and Raney nickel (0.75 g) in MeOH (100 ml) was hydrogenated at room temperature for 1 hour under a 3 bar pressure, then filtered over celite. The filtrate was evaporated, yielding 0.65 g (96%) of intermediate 39.

c) Preparation of Intermediate 40

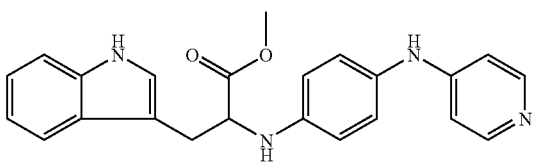

A mixture of intermediate 39 (0.139 mol) and 4-bromopyridine hydrochloride (0.139 mol) in acetic acid (450 ml) was stirred at 120° C. for 3 hours, poured out on ice, basified with concentrated sodium hydroxide and extracted with DCM/MeOH (few). The organic layer was separated, dried (MgSO₄), filtered, and the solvent was evaporated. The residue (62.7 g) was purified by column chromatography over kromasil (20-45 μm) (eluent: DCM/MeOH/NH₄OH 93/7/0.5). The pure fractions were collected and the solvent was evaporated, yielding 22 g (41%) of intermediate 40.

d) Preparation of Intermediate 41

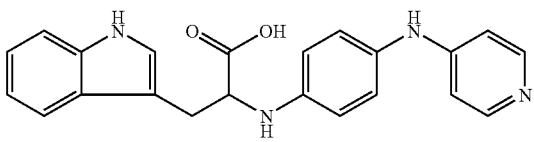

Lithium hydroxide, monohydrate (0.112 mol) was added portion wise at 0° C. to a solution of intermediate 40 (0.056 mol) in MeOH (86 ml) and water (34.4 ml) under N₂ flow. The mixture was stirred at room temperature overnight, then evaporated till dryness, yielding: 22 g (quantitive yield) of intermediate 41.

Example A22

1) Preparation of Intermediate 42

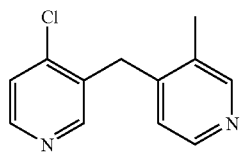

A 2.5N solution of butyl lithium in hexane (3.4 ml, 0.0081 mol) was added to a solution of diisopropylamine (0.85 ml, 0.0088 mol) in THF (6 ml) at −78° C. under Argon. The mixture was stirred 30 minutes at −78° C. 4-Chloro-3-methylpyridine hydrochloride (630 mg, 0.0038 mol) was added portionwise and the mixture was stirred 1 hour at −78° C. Diethyl carbonate (1.0 ml, 0.0096 mol) was added dropwise and the mixture was stirred 1 more hour at −78° C., then warmed up to room temperature and let stirred for 2.5 hours. The reaction was quenched by slow addition of water, and extracted twice with EtOAc. The organic layer was separated, washed with brine, dried (MgSO₄), filtered, and the solvent was evaporated. The residue was purified by column chromatography over silica gel (40-63 μm) (eluent: EtOAc/MeOH 100/0 then 90/10). The pure fractions were collected and the solvent was evaporated, yielding 74 mg (9%) of intermediate 42.

2) Preparation of Intermediate 43

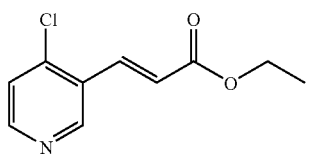

Triethyl phosphonoacetate (0.075 ml, 0.00038 mol) was added dropwise to a mixture of sodium hydride (10.6 mg, 0.00044 mol) in THF (5 ml) at room temperature under argon. The mixture was stirred at room temperature for 20 minutes, then a solution of 4-chloro-3-pyridinecarboxaldehyde (50 mg, 0.00035 mol) in THF (3 ml) was added dropwise. The mixture was stirred at room temperature for 16 hours, then poured out into water and extracted twice with EtOAc. The organic layer was separated, washed with brine, dried (MgSO₄), filtered, and the solvent was evaporated, yielding 77 mg (88%) of intermediate 43.

3) Preparation of Intermediate 44

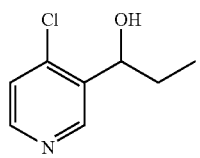

A 2.5N solution of butyl lithium in hexane (0.80 ml, 0.0020 mol) was added to a solution of diisopropylamine (0.28 ml, 0.0020 mol) in THF (2 ml) at −78° C. under Argon. The mixture was stirred 10 minutes at −78° C., then a solution of 4-chloropyridine (219 mg, 0.0019 mol) in THF (1 ml) was added dropwise. The mixture was stirred 1.25 hour at −78° C., then propionaldehyde (0.14 ml, 0.0019 mol) was added dropwise. The mixture was stirred 30 minutes at −78° C., and finally 4 hours at room temperature, poured out into water, and extracted with EtOAc. The organic layer was separated, washed with brine, dried (MgSO₄), filtered, and the solvent was evaporated. The residue was purified by column chromatography over silica gel (40-63 μm) (eluent: EtOAc/cyclohexane 90/10). The pure fractions were collected and the solvent was evaporated, yielding 147 mg (44%) of intermediate 44.

4) Preparation of Intermediate 45

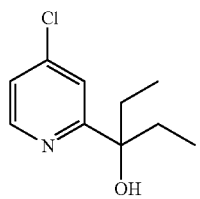

Method 2

A 3M ethyl magnesium bromide solution in diethyl ether (1.1 ml, 0.0032 mol) was added to a 4-chloro-2-pyridinecarboxylic acid, methyl ester solution (200 mg, 0.0012 mol) in THF (4 ml) at −30° C. under Argon. The mixture was heated at 75° C. for 2 h30, cooled down to 0° C. and quenched with water. The resulting mixture was made alkaline with a saturated solution of sodium hydrogen carbonate and extracted twice with EtOAc. The organic layer was washed with brine, dried (MgSO$_4$), filtered and the solvent was evaporated. The residue was purified by column chromatography over silica gel (40-63 µm) (eluent: EtOAc/cyclohexane 10/90). The pure fractions were collected and the solvent was evaporated, yielding 54 mg (23%) of intermediate 45 as a brown oil.

5) Preparation of Intermediate 46

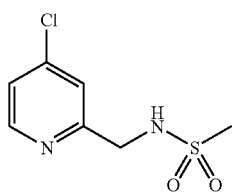

Methane sulfonyl chloride (98 µl, 0.0013 mol) was added dropwise to a solution of 4-chloro-2-pyridinemethanamine (150 mg, 0.0011 mol) and triethylamine (177 µl, 0.0013 mol) in DCM (4 ml) at 0° C. under argon. The mixture was stirred at room temperature for 30 minutes. The reaction was quenched with a saturated solution of sodium bicarbonate and extracted twice with DCM. The organic phase was dried (MgSO$_4$), filtered, and the solvent was evaporated. The residue was purified by column chromatography over silica gel (40-63 µm) (eluent: EtOAc). The pure fractions were collected and the solvent was evaporated, yielding 82 mg (35%) of intermediate 46 as an orange oil.

6) Preparation of Intermediate 47

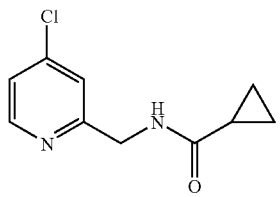

Method 7

Cyclopropanecarbonyl chloride (115 µl, 0.0013 mol) was added dropwise to a solution of 4-chloro-2-pyridinemethanamine (150 mg, 0.0011 mol) and triethylamine (177 µl, 0.0013 mol) in DCM (4 ml) at 0° C. under Argon. The mixture was stirred at room temperature for 15 minutes. The reaction was quenched with a saturated solution of sodium bicarbonate and extracted twice with DCM. The organic phase was dried (MgSO$_4$), filtered, and the solvent was evaporated. The residue was purified by column chromatography over silica gel (40-63 µm) (eluent: EtOAc). The pure fractions were collected and the solvent was evaporated, yielding 85 mg (38%) of intermediate 47 as a white solid.

7) Preparation of Intermediate 48

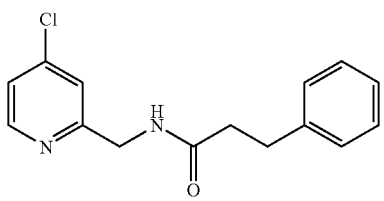

Similar procedure as method 7 (see Example A22/6) was followed, starting from 4-chloro-2-pyridinemethanamine (150 mg, 0.0011 mol) and hydrocinnamoyl chloride (187 µl, 0.0013 mol). After workup, the residue was purified by column chromatography over silica gel (40-63 µm) (eluent: EtOAc). The pure fractions were collected and the solvent was evaporated, yielding 191 mg (66%) of intermediate 48 as a yellow solid.

8) Preparation of Intermediate 49

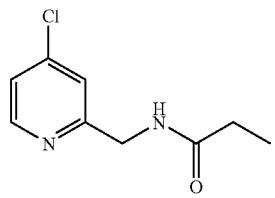

Similar procedure as method 7 (see Example A22/6) was followed, starting from 4-chloro-2-pyridinemethanamine (200 mg, 0.0014 mol) and propionyl chloride (146 µl, 0.0017 mol). After workup, the residue was purified by column chromatography over silica gel (40-63 µm) (eluent: EtOAc). The pure fractions were collected and the solvent was evaporated, yielding 126 mg (45%) of intermediate 49 as a colorless oil.

9) Preparation of Intermediate 50

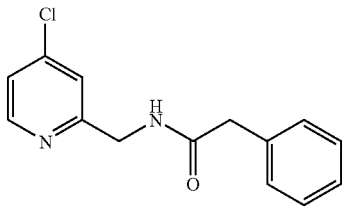

Similar procedure as method 7 (see Example A22/6) was followed, starting from 4-chloro-2-pyridinemethanamine (150 mg, 0.0011 mol) and phenylacetyl chloride (168 µl, 0.0013 mol). After workup, the residue was purified by column chromatography over silica gel (40-63 µm) (eluent:

EtOAc). The pure fractions were collected and the solvent was evaporated, yielding 124 mg (45%) of intermediate 50 as a white solid.

10) Preparation of Intermediates 5 and 52

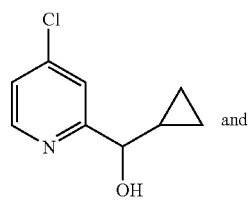
intermediate 51 and

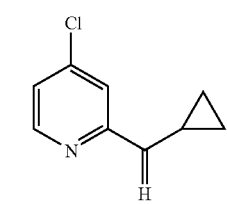
intermediate 52

Method 1

To a solution of 4-chloro-2-pyridinecarboxaldehyde (377 mg, 0.0027 mol) in THF (4 ml) at 0° C. under Argon was added dropwise a 1.4M cyclopropylmagnesium bromide solution in toluene/THF (75/25). The reaction mixture was stirred at 0° C. for 1 hour, the dry ice bath was removed and the mixture was stirred at room temperature for 1 hour. The reaction mixture was quenched by addition of water and extracted twice with EtOAc. The organic layer was washed with brine, dried ($MgSO_4$), filtered, and the solvent was evaporated. The residue was purified by column chromatography over silica gel (40-63 µm) (eluent: cyclohexane/EtOAc 80/20). The pure fractions were collected and the solvent was evaporated, yielding 193 mg (39%) of intermediate 51 and 29 mg of intermediate 52.

11) Preparation of Intermediate 53

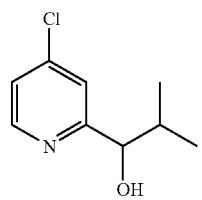

Similar procedure as method 1 (see Example A22/10) was followed, starting from 4-chloro-2-pyridinecarboxaldehyde (300 mg, 0.0021 mol) and a 2.0M isopropylmagnesium chloride solution in THF (2.12 ml, 0.0042 mol). After workup, the residue was purified by column chromatography over silica gel (40-63 µm) (eluent: cyclohexane/EtOAc 80/20). The pure fractions were collected and the solvent was evaporated, yielding 165 mg (42%) of intermediate 53 as a brown oil.

12) Preparation of Intermediate 54

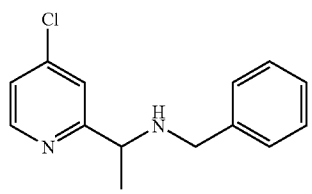

Similar procedure as method 6 (see Example A13) was followed, starting from 1-(4-chloro-2-pyridinyl)-ethanone (298 mg, 0.0019 mol). After workup, the residue was purified by column chromatography over silica gel (40-63 µm) (eluent: cyclohexane/EtOAc 90/10). The pure fractions were collected and the solvent was evaporated, yielding 293 mg (62%) of intermediate 54 as a yellow oil.

13) Preparation of Intermediate 55

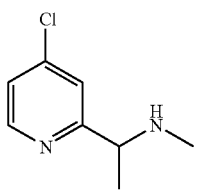

Similar procedure as method 6 (see Example A13) was followed, starting from 1-(4-chloro-2-pyridinyl)-ethanone (100 mg, 0.00064 mol). After workup, the residue was purified by column chromatography over silica gel (40-63 µm) (eluent: DCM/MeOH 85/15). The pure fractions were collected and the solvent was evaporated, yielding 50 mg (45%) of intermediate 55 as a yellow oil.

14) Preparation of Intermediate 56

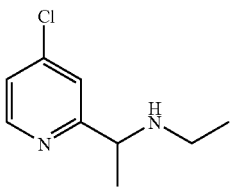

Similar procedure as method 6 (see Example A13) was followed, starting from 1-(4-chloro-2-pyridinyl)-ethanone (100 mg, 0.00064 mol). After workup, the residue was purified by column chromatography over silica gel (40-63 µm) (eluent: DCM/MeOH 90/10). The pure fractions were collected and the solvent was evaporated, yielding 30 mg (25%) of intermediate 56 as a yellow oil.

15) Preparation of Intermediate 57

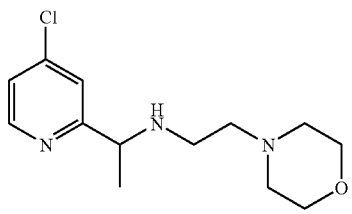

Similar procedure as method 6 (see Example A13) was followed, starting from 1-(4-chloro-2-pyridinyl)-ethanone (157 mg, 0.0010 mol). After workup, the residue was purified by column chromatography over silica gel (40-63 µm) (eluent: DCM/MeOH 95/5). The pure fractions were collected and the solvent was evaporated, yielding 134 mg (49%) of intermediate 57 as a yellow oil.

16) Preparation of Intermediate 58

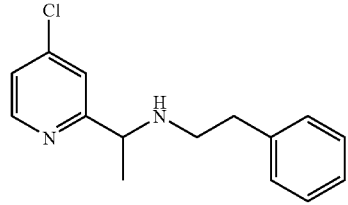

Similar procedure as method 6 (see Example A13) was followed, starting from 1-(4-chloro-2-pyridinyl)-ethanone (200 mg, 0.0013 mol). After workup, the residue was purified by column chromatography over silica gel (40-63 µm) (eluent: DCM/MeOH 95/5). The pure fractions were collected and the solvent was evaporated, yielding 281 mg (66%) of intermediate 58 as a yellow oil.

17) Preparation of Intermediate 59

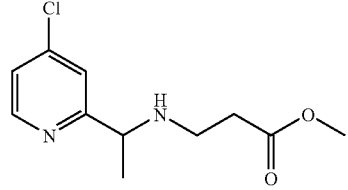

Similar procedure as method 6 (see Example A13) was followed, starting from 1-(4-chloro-2-pyridinyl)-ethanone (200 mg, 0.0013 mol) and with addition of triethylamine (0.2 ml). After workup, the residue was purified by column chromatography over silica gel (40-63 µm) (eluent: EtOAc). The pure fractions were collected and the solvent was evaporated, yielding 80 mg (25%) of intermediate 59 as a yellow oil.

18) Preparation of Intermediate 60

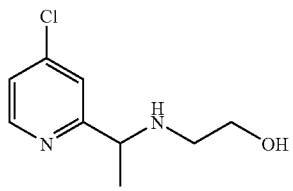

Similar procedure as method 6 (see Example A13) was followed, starting from 1-(4-chloro-2-pyridinyl)-ethanone (200 mg, 0.0013 mol). After workup, the residue was purified by column chromatography over silica gel (40-63 µm) (eluent: DCM/MeOH 95/5). The pure fractions were collected and the solvent was evaporated, yielding 176 mg (68%) of intermediate 60 as a pale yellow oil.

19) Preparation of Intermediate 61

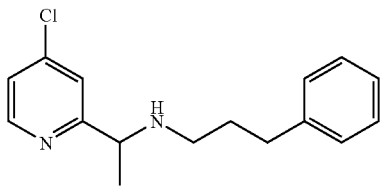

Similar procedure as method 6 (see Example A13) was followed, starting from 1-(4-chloro-2-pyridinyl)-ethanone (200 mg, 0.0013 mol). After workup, the residue was purified by column chromatography over silica gel (40-63 µm) (eluent: EtOAc). The pure fractions were collected and the solvent was evaporated, yielding 274 mg (77%) of intermediate 61 as a yellow oil.

20) Preparation of Intermediate 62

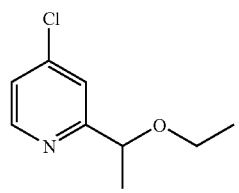

Method 3
A solution of 4-chloro-a-methyl-2-pyridinemethanol (200 mg, 0.0013 mol) in THF (3 ml) was added dropwise to a mixture of sodium hydride (60% weight in mineral oil) (56 mg, 0.0014 mol) in THF (1 ml) at 0° C. under argon. The mixture was heated up to 70° C. and stirred 3 hours, then cooled down to 0° C., and iodoethane (0.102 ml, 0.0013 mol) was added drop wise. The mixture was heated up to 70° C. for 2 hours, cooled down to 0° C., poured out into iced water, and extracted twice with DCM, and once with EtOAc. The organic layer was separated, dried (MgSO$_4$), filtered, and the solvent was evaporated. The residue was purified by column chromatography over silica gel (40-63 µm) (eluent: cyclohexane/EtOAc 90/10). The pure fractions were collected and the solvent was evaporated, yielding 106 mg (45%) of intermediate 62 as a brown oil.

21) Preparation of Intermediate 63

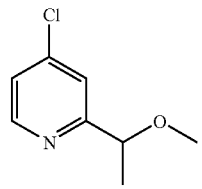

Similar procedure as method 3 (see Example A22/20) was followed, starting from 4-chloro-α-methyl-2-pyridinemethanol (200 mg, 0.0013 mol). After workup, the residue was purified by column chromatography over silica gel (40-63 µm) (eluent: cyclohexane/EtOAc 90/10). The pure fractions were collected and the solvent was evaporated, yielding 85 mg (39%) of intermediate 63 as a pale yellow oil.

22) Preparation of Intermediate 64

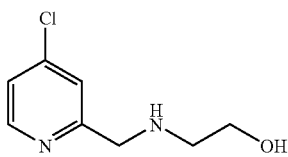

Method 4

4-Chloro-2-pyridinemethanol (400 mg, 0.0028 mol) was dissolved in chloroform (24 ml). Thionyl chloride (0.40 ml, 0.0056 mol) and DMF (2 drops) were added. The mixture was stirred 4 hours at 80° C. The solvent was evaporated. The residue was taken back in MeOH (18 ml) and ethanolamine (1.38 ml, 0.014 mol) was added. The mixture was stirred 4 hours at 80° C. The solvent was evaporated. The residue was poured out onto water and extracted with EtOAc. The organic layer was separated, washed with a saturated solution of sodium hydrogen carbonate, dried (MgSO$_4$), filtered, and the solvent was evaporated. The residue was purified by column chromatography over silica gel (40-63 µm) (eluent: DCM/MeOH 85/15). The pure fractions were collected and the solvent was evaporated, yielding 310 mg (60%) of intermediate 64 as an orange oil.

23) Preparation of Intermediate 65

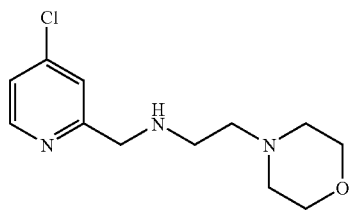

Similar procedure as method 4 (see Example A22/22) was followed, starting from 2-morpholin-4-yl-ethylamine (0.45 ml, 0.0034 mol) and 4-chloro-2-pyridinemethanol (200 mg, 0.0014 mol). After workup, the residue was purified by column chromatography over silica gel (40-63 µm) (eluent: DCM/MeOH 95/5). The pure fractions were collected and the solvent was evaporated, yielding 39 mg (23%) of intermediate 65 as a yellow oil.

24) Preparation of Intermediate 66

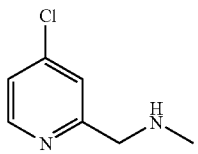

Similar procedure as method 4 (see Example A22/22) was followed, starting from a 33% methyl amine solution in EtOH (10 ml) and 4-chloro-2-pyridinemethanol (300 mg, 0.0021 mol). After workup, the residue was purified by column chromatography over silica gel (40-63 µm) (eluent: DCM/MeOH/ NH$_4$OH 85/15/1). The pure fractions were collected and the solvent was evaporated, yielding 130 mg (40%) of intermediate 66 as an orange oil.

25) Preparation of Intermediate 67

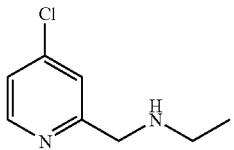

Similar procedure as method 4 (see Example A22/22) was followed, starting from a 2.0M ethyl amine solution in THF (3.5 ml, 0.0069 mol) and 4-chloro-2-pyridinemethanol (200 mg, 0.0014 mol). After workup, the residue was purified by column chromatography over silica gel (40-63 µm) (eluent: DCM/MeOH 85/15). The pure fractions were collected and the solvent was evaporated, yielding 45 mg (19%) of intermediate 67 as an orange oil.

26) Preparation of Intermediate 68

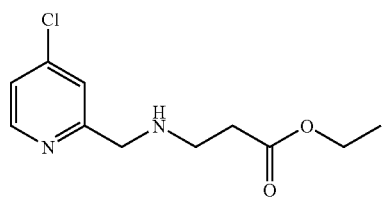

Similar procedure as method 4 (see Example A22/22) was followed, starting from 3-amino-propionic acid ethyl ester (2.45 g, 0.020 mol) and 4-chloro-2-pyridinemethanol (600 mg, 0.0042 mol). After workup, the residue was purified by column chromatography over silica gel (40-63 µm) (eluent:

DCM/MeOH 85/15). The pure fractions were collected and the solvent was evaporated, yielding 730 mg (71%) of intermediate 68 as an orange liquid.

27) Preparation of Intermediate 69

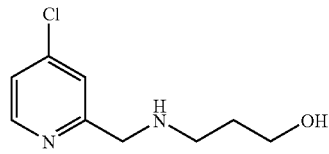

Intermediate 68 (350 mg, 0.0015 mol) was dissolved in MeOH (5 ml) and cooled down at 0° C. Sodium borohydride (300 mg, 0.0078 mol) was slowly added. The mixture was stirred at 80° C. for 9 hours. The reaction was quenched with water and the solvent was evaporated. The residue was extracted with EtOAc. The organic layer was separated, washed with a saturated solution of sodium hydrogen carbonate, dried (MgSO$_4$), filtered, and the solvent was evaporated. The residue was purified by column chromatography over silica gel (40-63 µm) (eluent: DCM/MeOH 85/15). The pure fractions were collected and the solvent was evaporated, yielding 70 mg (23%) of intermediate 69 as a colorless oil.

28) Preparation of Intermediate 70

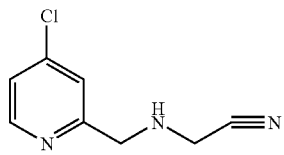

Similar procedure as method 4 (see Example A22/22) was followed, starting from amino-acetonitrile (1.2 g, 0.013 mol) and 4-chloro-2-pyridinemethanol (500 mg, 0.0034 mol). After workup, the residue was purified by column chromatography over silica gel (40-63 µm) (eluent: DCM/MeOH 95/5). The pure fractions were collected and the solvent was evaporated, yielding 160 mg (25%) of intermediate 70 as an orange liquid.

29) Preparation of Intermediate 71

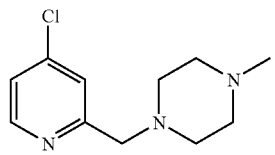

Similar procedure as method 4 (see Example A22/22) was followed, starting from N-methylpiperazine (1.16 ml, 0.010 mol) and 4-chloro-2-pyridinemethanol (300 mg, 0.0021 mol). After workup, the residue was purified by column chromatography over silica gel (40-63 µm) (eluent: DCM/MeOH 95/5). The pure fractions were collected and the solvent was evaporated, yielding 325 mg (69%) of intermediate 71 as a yellow oil.

30) Preparation of Intermediate 72

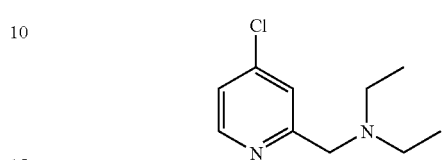

Similar procedure as method 4 (see Example A22/22) was followed, starting from diethylamine (1.45 ml, 0.014 mol) and 4-chloro-2-pyridinemethanol (300 mg, 0.0021 mol). After workup, the residue was purified by column chromatography over silica gel (40-63 µm) (eluent: DCM/MeOH 95/5). The pure fractions were collected and the solvent was evaporated, yielding 300 mg (43%) of intermediate 72 as a yellow liquid.

31) Preparation of Intermediate 73

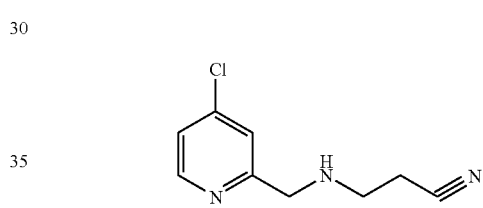

Similar procedure as method 4 (see Example A22/22) was followed, starting from 3-aminopropionitrile (1.02 ml, 0.014 mol) and 4-chloro-2-pyridinemethanol (500 mg, 0.0034 mol). After workup, the residue was purified by column chromatography over silica gel (40-63 µm) (eluent: DCM/MeOH 95/5). The pure fractions were collected and the solvent was evaporated, yielding 180 mg (27%) of intermediate 73 as a yellow oil.

32) Preparation of Intermediate 74

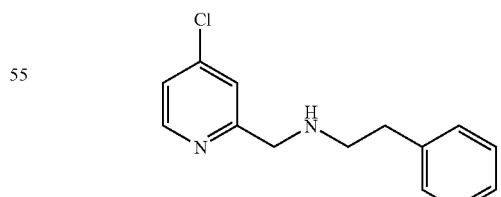

Similar procedure as method 4 (see Example A22/22) was followed, starting from phenethylamine (0.52 ml, 0.0042 mol) and 4-chloro-2-pyridinemethanol (300 mg, 0.0021 mol). After workup, the residue was purified by column chromatography over silica gel (40-63 µm) (eluent: EtOAc). The pure fractions were collected and the solvent was evaporated, yielding 110 mg (22%) of intermediate 74 as a colorless oil.

33) Preparation of Intermediate 75

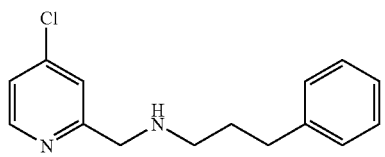

Similar procedure as method 4 (see Example A22/22) was followed, starting from 3-phenyl-propylamine (470 mg, 0.0035 mol) and 4-chloro-2-pyridinemethanol (300 mg, 0.0021 mol). After workup, the residue was purified by column chromatography over silica gel (40-63 µm) (eluent: DCM/MeOH 85/15). The pure fractions were collected and the solvent was evaporated, yielding 90 mg (17%) of intermediate 75 as an orange oil.

34) Preparation of Intermediate 76

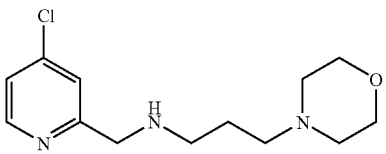

Method 5

A mixture of 4-chloro-2-pyridinecarboxaldehyde (200 mg, 0.0014 mol), N-(3-aminopropyl)morpholine (224 mg, 0.0015 mol), para-toluene sulfonic acid (134 mg, 0.00070 mol) and 3 Å molecular sieves was stirred at room temperature under Argon for 7 hours. Molecular sieves were filtered off, the reaction mixture was cooled down to 0° C., and sodium borohydride (107 mg, 0.0028 mol) was slowly added. The mixture was stirred at room temperature for 17 hours, poured out into water and extracted with DCM. The organic layer was separated, washed with a saturated solution of hydrogen carbonate, dried (MgSO₄), filtered, and the solvent was evaporated. The residue was purified by column chromatography over silica gel (40-63 µm) (eluent: DCM/MeOH/NH₃ 85/15/3). The pure fractions were collected and the solvent was evaporated, yielding 230 mg (60%) of intermediate 76 as a yellow oil.

35) Preparation of Intermediate 77

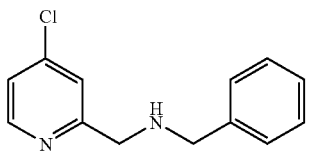

Similar procedure as method 4 (see Example A22/22) was followed, starting from benzylamine (0.46 ml, 0.0042 mol) and 4-chloro-2-pyridinemethanol (300 mg, 0.0021 mol). After workup, the residue was purified by column chromatography over silica gel (40-63 µm) (eluent: EtOAc/cyclohexane 50/50). The pure fractions were collected and the solvent was evaporated, yielding 240 mg (50%) of intermediate 77 as a colorless oil.

36) Preparation of Intermediate 78

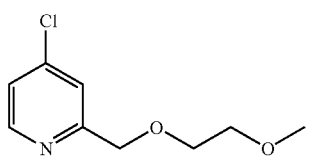

Similar procedure as method 3 (see Example A22/20) was followed, starting from bromoethyl methyl ether (0.13 ml, 0.0014 mol) and 4-chloro-2-pyridinemethanol (200 mg, 0.0014 mol). After workup, the residue was purified by column chromatography over silica gel (40-63 µm) (eluent: AcOEt/cyclohexene 30/70). The pure fractions were collected and the solvent was evaporated, yielding 67 mg (24%) of intermediate 78 as a yellow oil.

37) Preparation of Intermediate 79

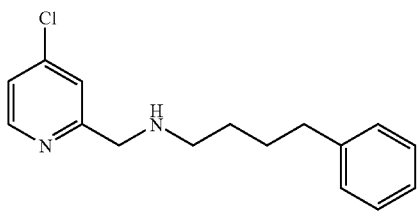

Similar procedure as method 4 (see Example A22/22) was followed, starting from 4-phenyl-butylamine (0.55 ml, 0.0035 mol) and 4-chloro-2-pyridinemethanol (250 mg, 0.0017 mol). After workup, the residue was purified by column chromatography over silica gel (40-63 µm) (eluent: DCM/MeOH 95/5). The pure fractions were collected and the solvent was evaporated, yielding 260 mg (55%) of intermediate 79 as a yellow oil.

38) Preparation of Intermediate 80

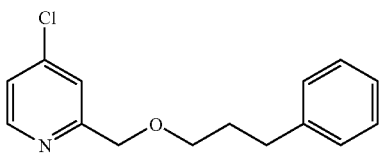

Similar procedure as method 3 (see Example A22/20) was followed, starting from (3-bromo-propyl)-benzene (0.27 ml, 0.0018 mol) and 4-chloro-2-pyridinemethanol (200 mg, 0.0014 mol). After workup, the residue was purified by column chromatography over silica gel (40-63 µm) (eluent: AcOEt/cyclohexane 10/90). The pure fractions were collected and the solvent was evaporated, yielding 57 mg (16%) of intermediate 80 as colorless oil.

39) Preparation of Intermediate 81

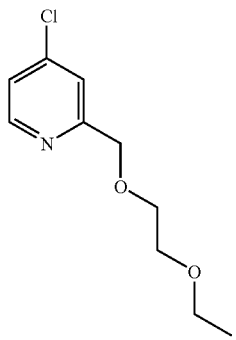

Similar procedure as method 3 (cA22/20) was followed, starting from 1-Bromo-2-ethoxy-ethane (589 mg, 0.0052 mol) and 4-chloro-2-pyridinemethanol (500 mg, 0.0034 mol). After workup, the residue was purified by column chromatography over silica gel (40-63 μm) (eluent: EtOAc/cyclohexane 10/90). The pure fractions were collected and the solvent was evaporated, yielding 270 mg (36%) of intermediate 81 as a colorless oil.

40) Preparation of Intermediate 82

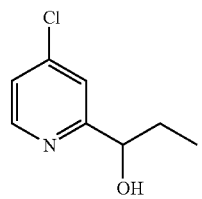

Similar procedure as for method 1 (see Example A22/10) was followed, starting from 4-chloro-2-pyridinecarboxaldehyde (500 mg, 0.0035 mol). After workup, the residue was purified by column chromatography over silica gel (40-63 μm) (eluent: EtOAc/cyclohexane 50/50). The pure fractions were collected and the solvent was evaporated, yielding 136 mg (22%) of intermediate 82 as a yellow oil.

Example A23 a) Preparation of Intermediate 83

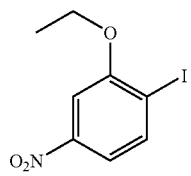

37% Hydrochloric acid solution (14.3 ml) was added to a solution of 2-ethoxy-4-nitro-benzenamine (10.5 g, 0.0577 mol) in acetic acid (210 ml) and the mixture was stirred at room temperature for 30 minutes. Then a solution of sodium nitrite (4.4 g, 0.0635 mol) in water (15 ml) was added drop wise and the mixture was stirred at 0° C. for 30 minutes. A cooled solution of potassium iodide (19.2 g, 0.1157 mol) and iodine (7.3 g, 0.0288 mol) in water (70 ml) was added drop wise at 0° C. The mixture was stirred 30 minutes at 0° C. and 16 hours at room temperature. The resulting precipitate was filtered off, washed with water and then dissolved in DCM. The organic solution was washed with a saturated solution of sodium hydrogen carbonate, dried (MgSO$_4$), filtered and the solvent was evaporated, yielding 13.7 g (81%) of intermediate 83 as a yellow solid.

b) Preparation of Intermediate 84

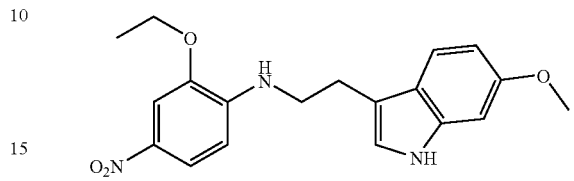

A mixture of intermediate 83 (700 mg, 0.0024 mol), 6-methoxytryptamine (505 mg, 0.0026 mol), dichloro[1,1'-bis(diphenylphosphino)ferrocene]palladium (II) dichloromethane adduct (78 mg, 0.00011 mol), 1,1'Bis(diphenylphosphino)ferrocene (177 mg, 0.00032 mol) and sodium tert-butoxide (255 mg, 0.0026 mol) in THF (95 ml) was heated at 100° C. for 3 hours and at 120° C. for 1.5 hour. After filtration through a celite pad, the solvent was evaporated and the residue was purified by column chromatography over silica gel (40-63 μm) (eluent: DCM). The pure fractions were collected and the solvent was evaporated, yielding 464 mg (55%) of intermediate 84 as a yellow solid.

c) Preparation of Intermediate 85

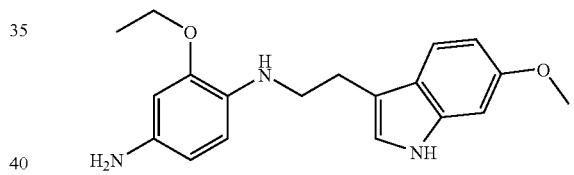

A mixture of intermediate 84 (see Example A23/b) (773 mg, 0.0022 mol) and Raney Nickel (50% slurry in water) in ethanol (8.5 ml) and THF (6.8 ml) was stirred at room temperature under 1 atmosphere of hydrogen for 24 hours. After filtration through celite, the solvent was evaporated, yielding 697 mg (98%) of intermediate 85 as a violet foam.

Example A24

Preparation of Intermediates 86 and 87

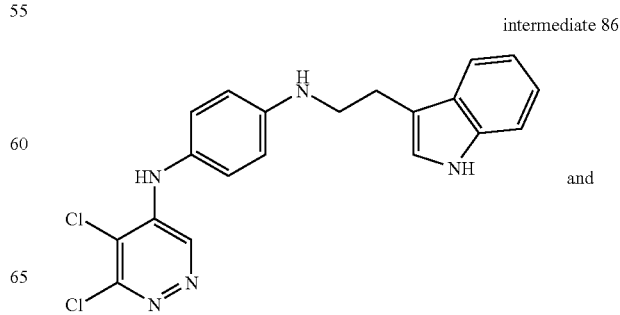

intermediate 86 and

-continued intermediate 87

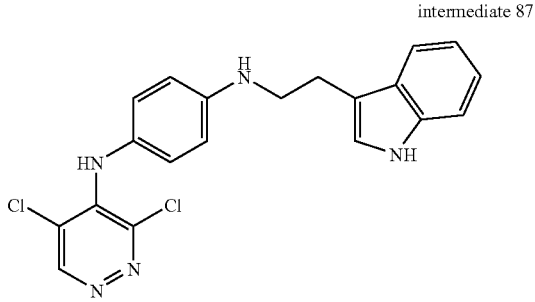

A mixture of 3,4,5-trichloro-pyridazine (200 mg, 0.0011 mol), intermediate 2 (see Example A1/b) (273 mg, 0.0011 mol) and diisopropylamine (0.38 ml, 0.0011 mol) was stirred in 2-propanol (4.0 ml) at 80° C. for 1 hour. The solvent was evaporated, and the crude mixture was taken back in EtOAc. The organic layer was washed with a saturated solution of sodium bicarbonate and with brine, dried (MgSO$_4$), filtered, and the solvent was evaporated. The residue was purified by column chromatography over silica gel (40-63 µm) (eluent: EtOAc/cyclohexane 50/50). The pure fractions were collected and the solvent was evaporated, yielding 179 mg (41%) of intermediate 86 and intermediate 87 as a 1/1 mixture of two pyridazine compounds.

Example A25 a) Preparation of Intermediate 88

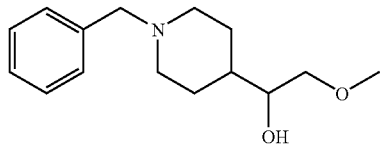

A mixture of 4-oxiranyl-1-(phenylmethyl)-piperidine (0.069 mol) in MeOH (300 ml) and NaOCH$_3$ (0.069 mol) was stirred and refluxed for 6 hours. The solvent was evaporated, then the residue was taken up in water and extracted with DCM. The organic layer was separated, dried, filtered and the solvent was evaporated. The residue was purified by column chromatography over silica gel (eluent: DCM/MeOH 98/2, 90/10, 85/15). The product fractions were collected and the solvent was evaporated, yielding 5.0 g (29%) of intermediate 88.

b) Preparation of Intermediate 89

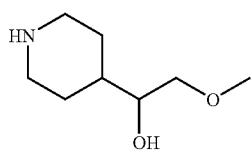

A mixture of intermediate 88 (see Example A25/a) (0.02 mol) in MeOH (100 ml) was hydrogenated with Pd/C 10% (1 g) as a catalyst. After uptake of H$_2$ (1 equiv.), the catalyst was filtered off and the filtrate was evaporated, yield 3.18 g (100%) of intermediate 89.

Example A26 a) Preparation of Intermediate 90

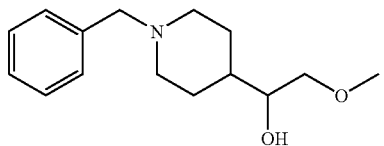

Similar procedure as for method 5 (see Example A22/34) was followed, starting from benzyl N-(2-aminoethyl)carbamate hydrochloride (475 ml, 0.0020 mol) and 4-chloro-2-pyridinecarboxaldehyde (265 mg, 0.0019 mol) and with addition of triethylamine (0.29 ml, 0.0021 mol). After workup, the residue was purified by column chromatography over silica gel (40-63 µm) (eluent: DCM/MeOH 95/5). The pure fractions were collected and the solvent was evaporated, yielding 150 mg (25%) of intermediate 90 as a colorless oil.

B. Preparation of the Final Compounds

Example B1

Preparation of Compound 1

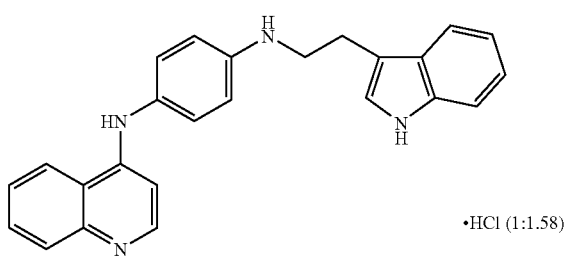

•HCl (1:1.58)

A mixture of 4-chloro-quinoline (0.0009 mol) and intermediate 2 (0.001 mol) in 2-propanol (5 ml) was stirred and refluxed for 6 hours, then brought to room temperature. The solvent was evaporated. The residue was basified with potassium carbonate 10% and extracted with DCM. The organic layer was separated, dried (MgSO$_4$), filtered, and the solvent was evaporated. The residue (0.38 g) was purified by column chromatography over silica gel (10 µm) (eluent: DCM/MeOH/NH$_4$OH 97/3/0.5). The pure fractions were collected and the solvent was evaporated. 2-Propanol and HCl/2-propanol were added. The mixture was stirred for 30 minutes, then brought to room temperature. The precipitate was filtered off and dried with diethyl ether, yielding 0.09 g (23%) of compound 1, melting point 170° C.

Example B2

Preparation of Compound 2

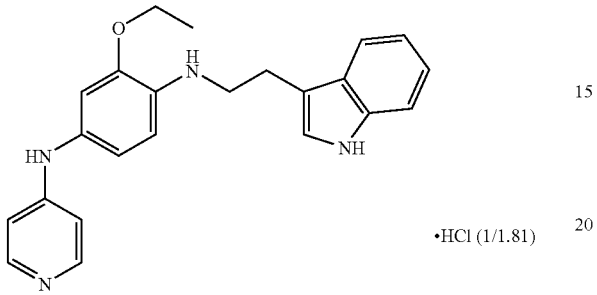

•HCl (1/1.81)

A mixture of 4-bromo-pyridine, hydrochloride (0.0044 mol) and intermediate 4 (0.0044 mol) in acetic acid (13 ml) was stirred at 110° C. for 45 minutes, then cooled to room temperature, poured out into ice water, basified with potassium carbonate and extracted with DCM. The organic layer was separated, dried ($MgSO_4$), filtered, and the solvent was evaporated. The residue (1.4 g) was purified by column chromatography over silica gel (15-40 μm) (eluent: DCM/MeOH/$NH_4OH$ 93/7/0.5). The pure fractions were collected and the solvent was evaporated. The residue (0.38 g) was dissolved in 2-propanol/diethyl ether and converted into the hydrochloric acid salt. The precipitate was filtered off and dried, yielding 0.385 g (20%) of compound 2, melting point 150° C.

Example B3

Preparation of Compounds 3

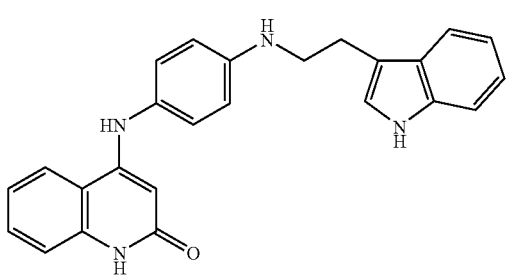

A mixture of 4-chloro-2(1H)-quinolinone (0.0011 mol) and intermediate 2 (0.0016 mol) was stirred at 130° C. for 5 hours, then stirred at 160° C. overnight and brought to room temperature. The residue was purified by column chromatography over silica gel (35-70 μm) (eluent: DCM/MeOH/$NH_4OH$ 95/5/0.1). The pure fractions were collected and the solvent was evaporated. The residue (0.12 g) was taken up in acetonitrile. The precipitate was filtered off and dried, yielding 0.045 g (10%) of compound 3, melting point 238° C.

Example B4

Preparation of Compound 4

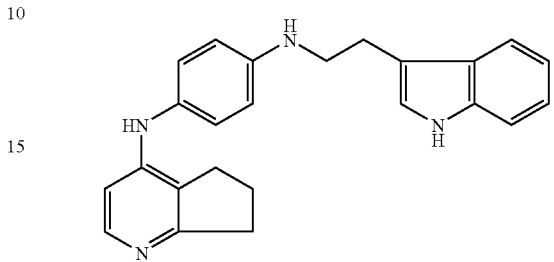

A mixture of 4-chloro-6,7-dihydro-5H-cyclopenta[b]pyridine (0.0006 mol) and intermediate 2 (0.0006 mol) in acetic acid (2 ml) was stirred at 100° C. for 30 minutes and brought to room temperature. Water and then sodium hydroxide (3N) were added and the resulting mixture was extracted with DCM. The organic layer was separated, dried ($MgSO_4$), filtered, and the solvent was evaporated. The obtained residue (0.233 g) was purified by column chromatography over silica gel (10 μm) (DCM/MeOH/$NH_4OH$ 97/3/0.3). The pure fractions were collected and the solvent was evaporated, yielding 0.025 g (11%) of compound 4.

Example B5

Preparation of Compound 5

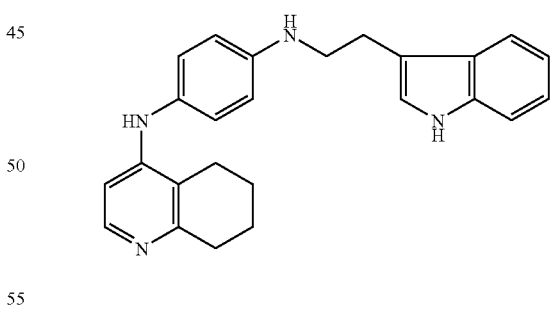

A mixture of 4-chloro-5,6,7,8-tetrahydro-quinoline (0.0009 mol) and intermediate 2 (0.0009 mol) in DMF (3 ml) was stirred at 100° C. for 3 hours and then brought to room temperature. The mixture was poured out into ice water and sodium hydroxide (3N) and was then extracted with DCM. The organic layer was separated, dried ($MgSO_4$), filtered and the solvent was evaporated. The obtained residue (0.49 g) was purified by column chromatography over silica gel (5 μm) (DCM/MeOH/$NH_4OH$ 99/1/0.05 to 80/20/0.5). The pure fractions were collected and the solvent was evaporated, yielding 0.054 g (16%) of compound 5.

Example B6

Preparation of Compound 6

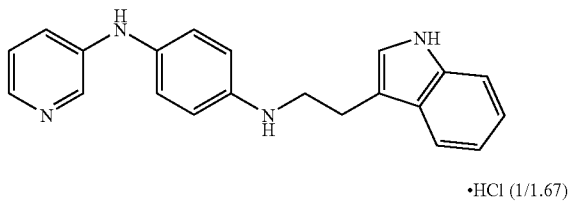

·HCl (1/1.67)

Lithium aluminum hydride (0.0032 mol) was added portionwise at 0° C. to a mixture of N-methoxy-N-methyl-1H-indole-3-acetamide (0.0032 mol) in THF (5 ml) under $N_2$ flow. The mixture was stirred for 1 hour. Potassium hydrogen sulfate (5%) was added. The mixture was extracted with diethyl ether. The organic layer was separated, dried ($MgSO_4$), filtered, and the solvent was evaporated. This mixture has to be used immediately. Intermediate 7 (0.0016 mol), cyanoborohydride (0.0022 mol) on polymer support (Amberlite IRA-300 $BH_3CN$ form-capacity $BH_3CN$-=2.5/4.5 mmol/g resin) and acetic acid (few drops) in MeOH (5 ml) were added to the mixture obtained. The mixture was stirred for 12 hours. The precipitate was filtered off and dried. The residue was purified by column chromatography over silica gel (15-40 μm) (eluent: DCM/MeOH/$NH_4OH$ 97/3/0.3). The pure fractions were collected and the solvent was evaporated. The residue (0.14 g) was taken up in HCl/2-propanol. The precipitate was filtered off and dried, yielding 0.125 g (29%) of compound 6, melting point 160° C.

Example B7

Preparation of Compound 7

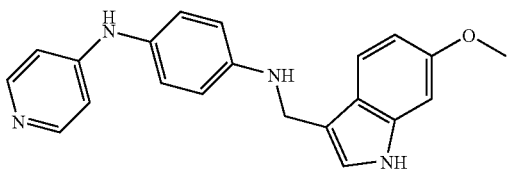

A mixture of N-4-pyridinyl-1,4-benzenediamine (0.0016 mol) and 6-methoxy-1H-indole-3-carboxaldehyde (0.0016 mol) in MeOH (20 ml) was stirred and refluxed overnight. Sodium tetrahydroborate (0.0016 mol) was added. The mixture was stirred at room temperature for 4 hours, poured out on ice and extracted with DCM. The organic layer was separated, dried ($MgSO_4$), filtered, and the solvent was evaporated. The residue was purified twice by column chromatography over kromasil (10 μm) (eluent: DCM/MeOH/$NH_4OH$ 92/8/0.5 then toluene/2-propanol/$NH_4OH$ 85/15/1). The pure fractions were collected and the solvent was evaporated. The residue was crystallized from acetonitrile. The precipitate was filtered off and dried, yielding 0.131 g (23%) of compound 7, melting point 145° C.

Example B8

Preparation of Compound 8

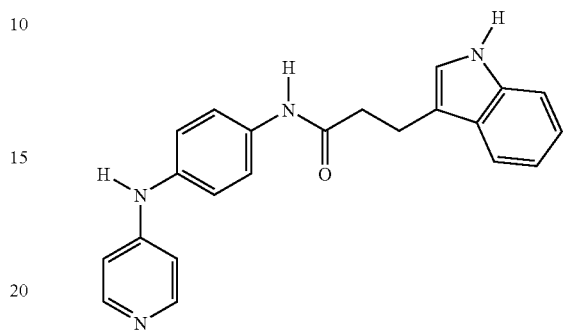

A mixture of 4-bromo-pyridine, hydrochloride (0.0069 mol) and intermediate 8 (0.008 mol) in acetic acid (7 ml) was stirred at 120° C. for 1 hour, then brought to room temperature. Water was added. The mixture was basified with potassium carbonate and extracted twice with DCM/MeOH (95/5). The organic layer was separated, dried ($MgSO_4$), filtered, and the solvent was evaporated. The residue was purified by flash column chromatography over silica gel (35-70 μm) (eluent: DCM/MeOH/$NH_4OH$ 92/8/0.5). The pure fractions were collected and the solvent was evaporated, yielding 1.6 g (65%) of compound 8, melting point 208° C.

Example B9

Preparation of Compound 9

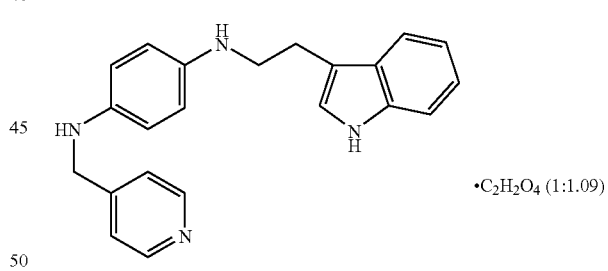

·$C_2H_2O_4$ (1:1.09)

4-Pyridinecarboxaldehyde (0.0005 mol) then cyanoborohydride (0.0004 mol) on polymer support (Amberlite IRA-300 $BH_3CN$ form-capacity $BH_3CN$-=2.5/4.5 mmol/g resin then acetic acid (3 drops) were added to a mixture of intermediate 2 (0.0004 mol) in MeOH (10 ml). The mixture was stirred at room temperature for 3 hours. The precipitate was filtered off and washed with MeOH. The filtrate was evaporated. The residue (0.17 g), which is a mixture of the targeted compound 9 and of the corresponding not reduced intermediate imine, was dissolved in MeOH (20 ml). Sodium tetrahydroborate (0.02 g) was added portionwise. The mixture was stirred for 30 minutes. Water was added. MeOH was partly evaporated. The mixture was extracted with EtOAc. The organic layer was washed with water, dried ($MgSO_4$), filtered and the solvent was evaporated. The residue (0.05 g) was purified by column chromatography over silica gel (10 μm)

(eluent: DCM/MeOH/NH4OH 98/2/0.4). The pure fractions were collected and the solvent was evaporated. The residue (0.034 g) was dissolved in 2-propanone and converted into the ethanedioic acid salt. The precipitate was filtered off and dried, yielding 0.036 g (16%) of compound 9, melting point 132° C.

Example B10

Preparation of Compound 10

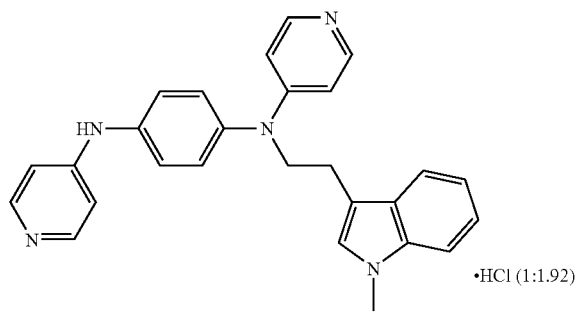

A mixture of 4-bromo-pyridine, hydrochloride (0.001 mol) and intermediate 10 (0.0005 mol) in acetic acid (2 ml) was stirred at 120° C. for 1 hour, then brought to room temperature. Ice then sodium hydroxide 3N were added. The mixture was extracted twice with DCM. The organic layer was separated, dried (MgSO4), filtered, and the solvent was evaporated. The residue was purified by column chromatography over silica gel (10 µm) (eluent: DCM/MeOH/NH4OH 96/4/0.5). The pure fractions were collected and the solvent was evaporated. The residue (0.064 g, 29%) was dissolved in 2-propanol/diethyl ether and converted into the hydrochloric acid salt. The precipitate was filtered off and dried, yielding 0.082 g (29%) of compound 10, melting point>250° C.

Example B11

Preparation of Compound 11

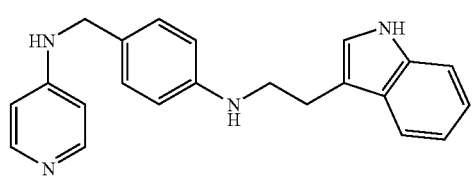

Lithium aluminum hydride (0.0145 mol) was added to a mixture of intermediate 13 (0.0036 mol) in THF (100 ml). The mixture was stirred and refluxed for 3 hours, then brought to room temperature. EtOAc was added. A minimum of water was added. The mixture was filtered over celite. Celite was washed with EtOAc. The organic layer was separated, dried (MgSO4), filtered, and the solvent was evaporated. The residue (1.1 g) was purified by column chromatography over silica gel (15-40 µm) (eluent: DCM/MeOH/NH4OH 93/7/0.5). The pure fractions were collected and the solvent was evaporated. The residue (0.25 g) was crystallized from acetonitrile/diethyl ether. The precipitate was filtered off and dried, yielding 0.11 g (12%) of compound 11, melting point 122° C.

Example B12

Preparation of Compound 86

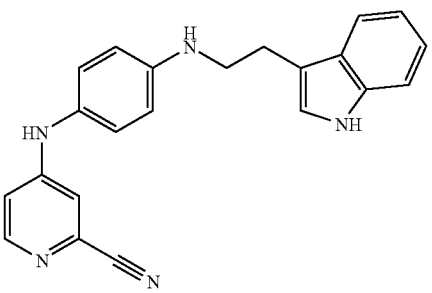

A mixture of 4-chloro-2-pyridinecarbonitrile (154 mg, 0.0011 mol), intermediate 2 ((280 mg, 0.0011 mol) and a 5N hydrochloride solution in 2-propanol (0.19 ml, 0.0011 mol) in DMF (2 ml) was stirred under argon at 100° C. for 24 hours, then cooled down to room temperature and poured out into water. The resulting mixture was made alkaline with a saturated sodium bicarbonate solution and extracted twice with EtOAc. The organic layer was washed successively with a saturated solution of sodium bicarbonate and with brine, dried (MgSO4), filtered, and the solvent was evaporated. The residue was purified by column chromatography over silica gel (40-63 µm) (eluent: EtOAc/cyclohexane 50/50). The pure fractions were collected and the solvent was evaporated, yielding 130 mg (33%) of compound 86 as a beige foam.

Example B13

Preparation of Compound 87

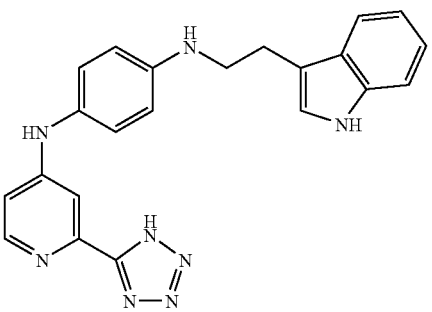

A mixture of compound 86 (110 mg, 0.00031 mol), sodium azide (22 mg, 0.00034 mol) and zinc bromide (70 mg, 0.00031 mol) in water (1 ml) and 2-propanol (0.25 ml) was stirred at 105° C. for 22 hours and was then cooled down to room temperature. A 0.25N solution of sodium hydroxide (3 ml) was added and the mixture was stirred at room temperature for 1 hour. The precipitate was filtered off, washed with MeOH, THF and 1-butanol. The organic layer was evaporated and the resulting solid was washed with MeOH and dried, yielding 26 mg (21%) of compound 87 as a beige solid, melting point 210° C.

Example B14

Preparation of Compound 88

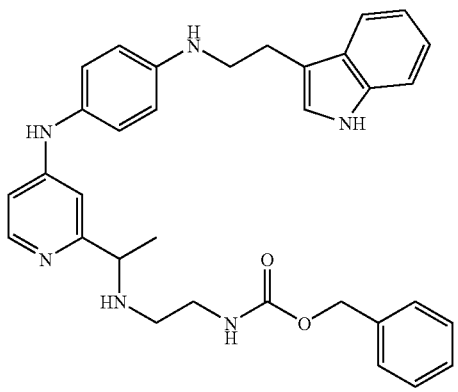

Similar procedure as for compound 86 (method B12) was followed, starting from intermediate 14 (254 mg, 0.00076 mol) and intermediate 2 (191 mg, 0.00076 mol). After workup, the residue was purified by column chromatography over silica gel (40-63 μm) (eluent: DCM/MeOH/NH$_4$OH 95/5/0.2). The pure fractions were collected and the solvent was evaporated, yielding 139 mg (30%) of compound 88 as a grey foam.

Example B15

Preparation of Compound 89

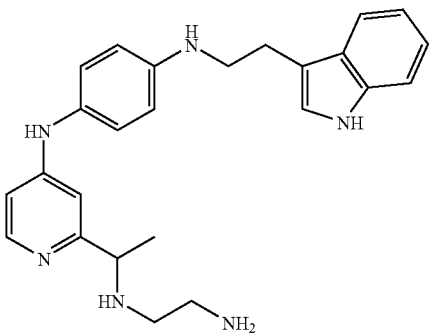

A mixture of compound 88 (112 mg, 0.00020 mol) and palladium on carbon (10% wt) (43 mg, 0.000040 mol) in MeOH (1 ml) and EtOH (4 ml) was stirred at room temperature under 1 atmosphere of hydrogen for 26 hours. After filtration through celite, the solvent was evaporated and the residue was purified by SCX column chromatography. The pure fractions were collected and the solvent was evaporated, yielding 27 mg (33%) of compound 89 as a grey foam.

Example B16

Preparation of Compound 90

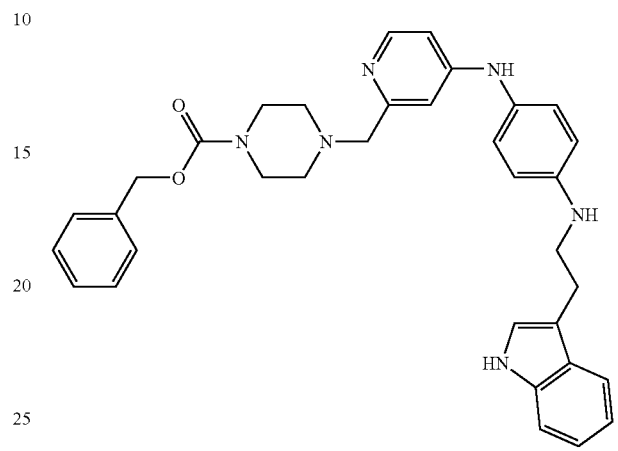

Similar procedure as for compound 86 (method B12) was followed, starting from intermediate 15 (850 mg, 0.0024 mol) and intermediate 2 (561 mg, 0.0022 mol), heating the mixture at 120° C. for 2 hours in a Biotage Initiator microwave apparatus. After workup, the residue was purified by column chromatography over silica gel (40-63 μm) (eluent: DCM/MeOH 95/5). The pure fractions were collected and the solvent was evaporated, yielding 680 mg (56%) of compound 90 as a brown foam.

Example B17

Preparation of Compound 91

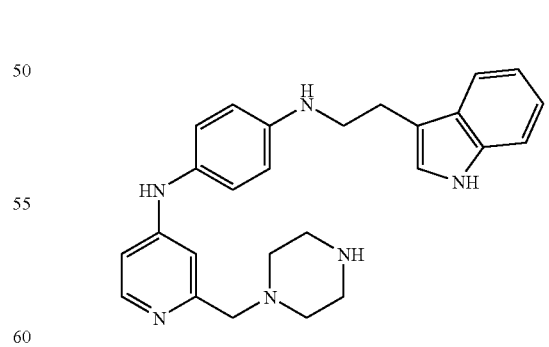

Compound 90 (200 mg, 0.00036 mol) was dissolved in EtOH (10 ml) and MeOH (10 ml). Palladium on carbon (10% wt) (100 mg) was added. The mixture was stirred at room temperature under hydrogen for 24 hours. The mixture was filtrated on celite and washed with MeOH. The solvent was evaporated, yielding 140 mg (92%) of compound 91 as a green oil.

Example B18

Preparation of Compound 92

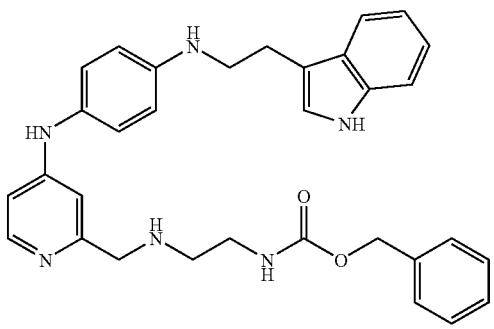

Similar procedure as for compound 86 was followed, starting from intermediate 90 (150 mg, 0.00047 mol) and intermediate 2 (107 mg, 0.00042 mol), heating the mixture at 120° C. for 80 minutes in a Biotage Initiator microwave apparatus. After workup, the residue was purified by column chromatography over silica gel (40-63 μm) (eluent: DCM/MeOH 95/5). The pure fractions were collected and the solvent was evaporated, yielding 30 mg (14%) of intermediate 90 as a green oil.

Example B19

Preparation of Compound 93

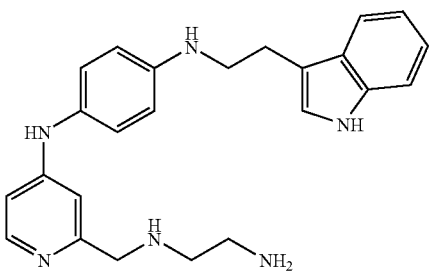

Compound 92 (23 mg, 0.000043 mol) was dissolved in EtOH (1 ml) and MeOH (1 ml). Palladium on carbon (10% wt) (10 mg) was added. The mixture was stirred at room temperature under hydrogen for 20 hours. The mixture was filtrated on celite and washed with MeOH. The solvent was evaporated. The residue was purified by SCX column chromatography, yielding 18 mg (100%) of compound 93 as a green oil.

Example B20

Preparation of Compound 94

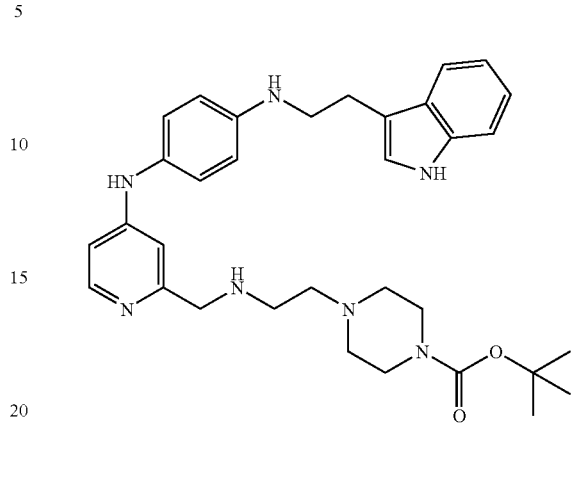

Similar procedure as for compound 86 was followed, starting from intermediate 17 (200 mg, 0.00056 mol) and intermediate 2 (142 mg, 0.00056 mol), heating the mixture at 120° C. for 50 minutes in a Biotage Initiator microwave apparatus. After workup, the residue was purified by column chromatography over silica gel (40-63 μm) (eluent: DCM/MeOH/NH$_4$OH 85/15/1). The pure fractions were collected and the solvent was evaporated, yielding 35 mg (11%) of compound 94 as a red oil.

Example B21

Preparation of Compound 95

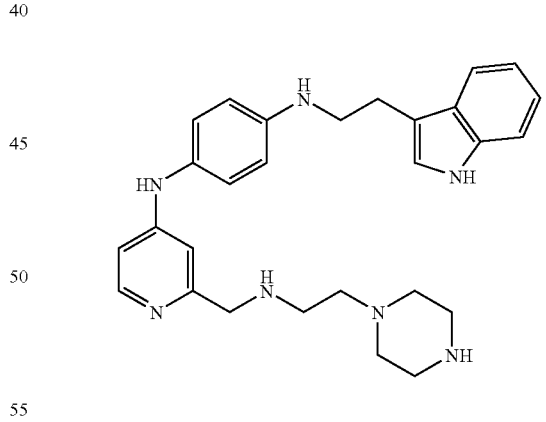

Compound 94 (50 mg, 0.000088 mol) was dissolved in MeOH (3 ml). A 5N hydrochloride solution in 2-propanol (5 ml) was added. The mixture was stirred at room temperature for 17 hours. The solvent was evaporated. The residue was poured out onto water and extracted with EtOAc. The organic layer was separated, washed with a saturated solution of sodium hydrogenocarbonate, dried (MgSO$_4$), filtered, and the solvent was evaporated, yielding 15 mg (36%) of compound 95 as a yellow oil.

Example B22

Preparation of Compound 96

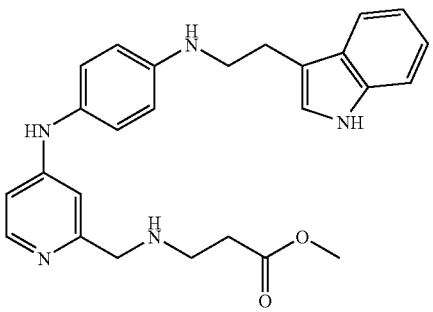

Similar procedure as for compound 86 was followed, starting from intermediate 18 (160 mg, 0.00070 mol) and intermediate 2 (160 mg, 0.00064 mol), heating the mixture at 120° C. for 1 hour in a Biotage Initiator microwave apparatus. After workup, the residue was purified by column chromatography over silica gel (40-63 µm) (eluent: DCM/MeOH/NH$_4$OH 85/15/1). The pure fractions were collected and the solvent was evaporated, yielding 100 mg (35%) of compound 96 as a green oil.

Example B23

Preparation of Compound 97

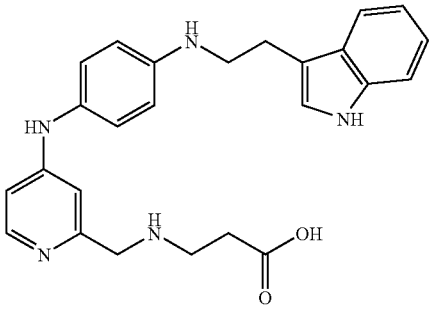

Compound 96 (50 mg, 0.00011 mol) was dissolved in THF (3 ml). Lithium hydroxyde (33 mg, 0.00079 mol) and water (1 drop) were added. The mixture was stirred at room temperature for 24 hours. The residue was poured out onto water and extracted with EtOAc. The organic layer was separated, washed with a 4N sodium hydroxide solution. The organic layer was separated, washed with a 3N hydrochloride solution, dried (MgSO$_4$), filtered, and the solvent was evaporated. The residue was purified by SCX column chromatography, yielding 20 mg (41%) of compound 97 as a green oil.

Example B24

Preparation of Compound 98

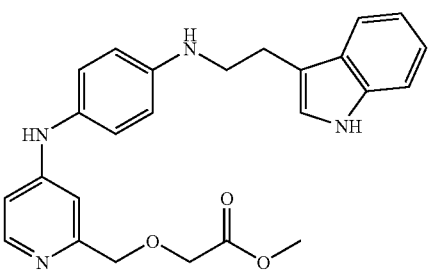

Similar procedure as for compound 86 was followed, starting from intermediate 19 (170 mg, 0.00079 mol) and intermediate 2 (180 mg, 0.00071 mol), heating the mixture at 120° C. for 80 minutes in a Biotage Initiator microwave apparatus. After workup, the residue was purified by column chromatography over silica gel (40-63 µm) (eluent: DCM/MeOH 85/15). The pure fractions were collected and the solvent was evaporated, yielding 224 mg (73%) of compound 98 as a brown oil.

Example B25

Preparation of Compound 99

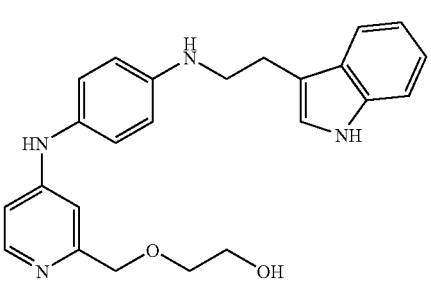

Compound 98 (100 mg, 0.00023 mol) was dissolved in MeOH (5 ml) and cooled at 0° C. Sodium borohydride (27 mg, 0.00069 mol) was added slowly. The mixture was stirred at 80° C. for 4 hours. The reaction was quenched with water and the solvent was evaporated. The residue was extracted with EtOAc. The organic layer was separated, washed with a saturated solution of sodium hydrogenocarbonate, dried (MgSO$_4$), filtered, and the solvent was evaporated. The residue was purified by column chromatography over silica gel (40-63 cm) (eluent: DCM/MeOH 85/15). The pure fractions were collected and the solvent was evaporated, yielding 40 mg (43%) of compound 99 as a colorless oil.

Example B26

Preparation of Compound 100

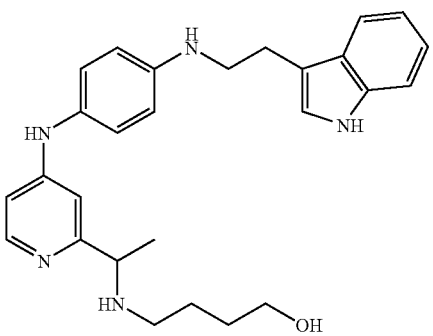

A mixture of intermediate 20 (107 mg, 0.00047 mol), intermediate 2 (118 mg, 0.00047 mol) and a 5N hydrochloride solution in 2-propanol (0.12 ml, 0.00072 mol) in 1-methyl-2-pyrrolidinone (2.3 ml) was stirred under argon at 120° C. for 2 hours, then cooled down to room temperature and poured out into water. The resulting mixture was basified with a saturated sodium hydrogen carbonate solution and extracted 3 times with EtOAc. The organic layer was isolated, washed with water and brine, dried ($MgSO_4$), filtered, and the solvent was evaporated. The residue was purified by column chromatography over silica gel (40-63 µm) (eluent: DCM/MeOH/NH4OH 90/10/0.5). The pure fractions were collected and the solvent was evaporated, yielding 61 mg (26%) of compound 100 as a beige foam.

Example B27

Preparation of Compound 101

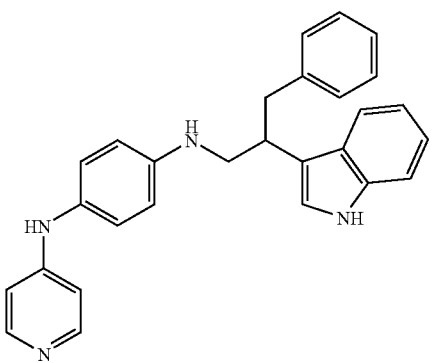

Lithium aluminium hydride (6.5 mg, 0.00017 mol) was added to a mixture of intermediate 21 (53 mg, 0.00017 mol) in THF (1 ml) at 0° C. under argon. The mixture was stirred 1 hour at 0° C., quenched with a 5% solution of potassium hydrogen sulfate, and extracted with EtOAc. The organic layer was separated, dried ($MgSO_4$), filtered, and the solvent was evaporated. The residue was solubilized in MeOH (1 ml) and added dropwise to a mixture of N-4-pyridinyl-1,4-benzenediamine (32 mg, 0.00017 mol), sodium cyanoborohydride (16 mg, 0.0025 mol), and acetic acid (1 drop) in MeOH (0.5 ml). The mixture was stirred 20 hours at room temperature, poured out onto water and extracted twice with EtOAc. The organic layer was separated, washed with a saturated solution of sodium hydrogen carbonate and with brine, dried ($MgSO_4$), filtered, and the solvent was evaporated. The residue was purified by column chromatography over silica gel (40-63 µm) (eluent: EtOAc/MeOH/$NH_4OH$ 90/10/0.3). The pure fractions were collected and the solvent was evaporated, yielding 25 mg (34%) of compound 101 as a beige foam.

Example B28

Preparation of Compound 102

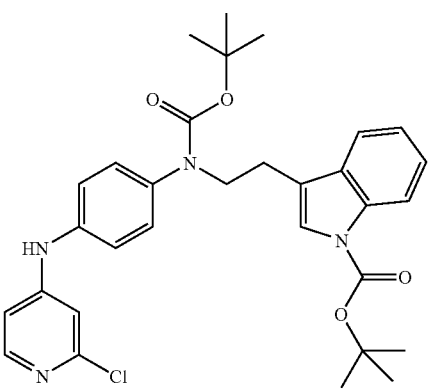

A mixture of intermediate 23 (500 mg, 0.0011 mol), 2-chloro-4-bromopyridine (213 mg, 0.0011 mol), 4,5-bis(diphenylphosphino)-9,9-dimethylxanthene (83 mg, 0.00014 mol), sodium tert-butoxide (264 mg, 0.0028 mol) in toluene (7.5 ml) was degassed under argon for 15 minutes. Tris(dibenzylideneacetone)dipalladium(0)-chloroform adduct (46 mg, 0.000044 mol) was added. The mixture was heated at 100° C. for 90 seconds in a Biotage Initiator microwave apparatus. The mixture was cooled down to room temperature then poured out into water and extracted twice with EtOAc. The organic layer was washed twice with water, once with brine, dried ($MgSO_4$), filtered and the solvent was evaporated. The residue was purified by column chromatography over silica gel (40-63 µm) (eluent: EtOAc/cyclohexane 30/70). The pure fractions were collected and the solvent was evaporated, yielding 254 mg (41%) of compound 102 as a beige foam.

Example B29

Preparation of Compound 103

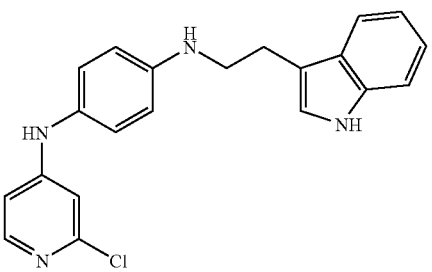

Compound 102 (70 mg, 0.00012 mol) was dissolved in a 5N hydrochloride solution in 2-propanol (1.5 ml). Water (2 drops) was added. The reaction mixture was stirred at room temperature for 5 hours. The reaction was quenched and basified with a saturated sodium bicarbonate solution and extracted 3 times with EtOAc. The organic layer was dried (MgSO$_4$), filtered, and the solvent was evaporated. The residue was purified by column chromatography over silica gel (40-63 μm) (eluent: EtOAc/cyclohexane 50/50). The pure fractions were collected and the solvent was evaporated, yielding 33 mg (76%) of compound 103 as a white foam.

Example B30

Preparation of Compound 104

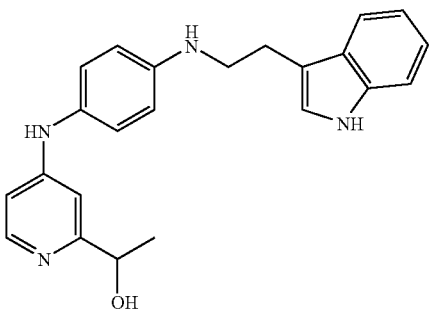

A mixture of 4-chloro-α-methyl-2-pyridinemethanol (170 mg, 0.0011 mol) and intermediate 2 (271 mg, 0.0011 mol) in acetic acid (2 ml) was stirred under Argon at 120° C. for 1 hour, then cooled down to room temperature and poured out into water. The resulting mixture was basified with a 4N sodium hydroxide solution and extracted twice with EtOAc. The organic layer was washed successively with a saturated solution of sodium bicarbonate and with brine, dried (MgSO$_4$), filtered, and the solvent was evaporated. The residue was purified by column chromatography over silica gel (40-63 cm) (eluent: EtOAc/MeOH 80/20). The pure fractions were collected and the solvent was evaporated, yielding 190 mg (47%) of compound 104 as a beige foam.

Example B31

Preparation of Compound 105

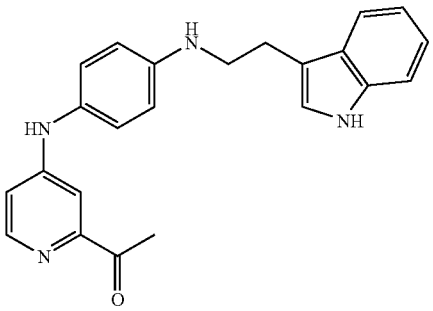

A mixture of compound 104 (106 mg, 0.00029 mol) and activated manganese oxide (148 mg, 0.0017 mol) in chloroform (4 ml) was stirred at room temperature for 6 hours. After filtration through a celite pad, the solvent was evaporated and the residue was purified by column chromatography over silica gel (40-63 μm) (eluent: EtOAc). The pure fractions were collected and the solvent was evaporated, yielding 4 mg (3%) of compound 105 as an orange solid.

Example B32

Preparation of Compound 106

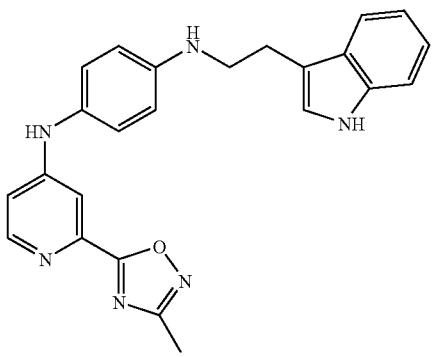

Acetamide oxime (11 mg, 0.00016 mol) was added at room temperature under argon to a mixture of activated 4 Å molecular sieves and sodium hydride (3.72 mg, 0.00016 mol) in THF (0.6 ml). The reaction mixture was stirred at 70° C. for 1.5 hour then cooled down to room temperature. A solution of compound 200 (50 mg, 0.00013 mol) in THF (0.6 ml) was added. The reaction mixture was stirred at 70° C. for 1 hour. The reaction was quenched by addition of water and extracted twice with EtOAc. The organic layer was dried (MgSO$_4$), filtered, and the solvent was evaporated. The residue was purified by column chromatography over silica gel (40-63 μm) (eluent: EtOAc/cyclohexane 70/30). The pure fractions were collected and the solvent was evaporated, yielding 16 mg (30%) of compound 106 as a yellow oil.

Example B33

Preparation of Compound 107

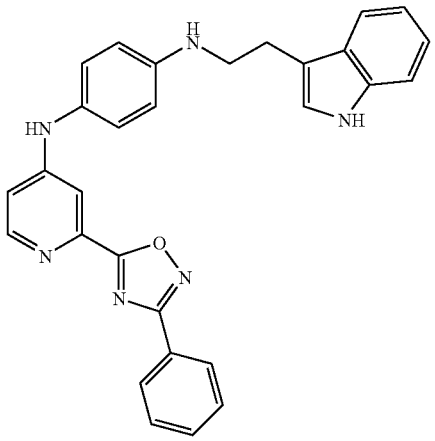

Similar procedure as for compound 106 was followed, starting from benzamidoxime (38 mg, 0.00028 mol) and compound 200 (90 mg, 0.00023 mol). After workup, the residue was purified by column chromatography over silica gel (40-63 μm) (eluent: DCM/EtOAc 90/10). The pure fractions were collected and the solvent was evaporated, yielding 13 mg (12%) of compound 107 as a yellow solid, melting point 170° C.-174° C.

Example B34

Preparation of Compound 108

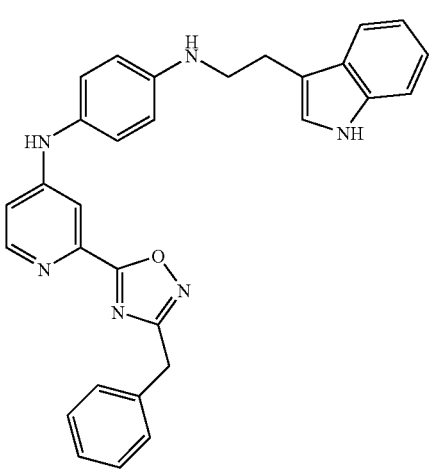

Similar procedure as for compound 106 was followed, starting from N'-Hydroxy-2-phenylethanimidamide (42 mg, 0.00028 mol) and compound 200 (90 mg, 0.00023 mol). After workup, the residue was purified by column chromatography over silica gel (40-63 μm) (eluent: EtOAc/cyclohexane 50/50). The pure fractions were collected and the solvent was evaporated, yielding 50 mg (45%) of compound 108 as a yellow solid, melting point 159° C.-161° C.

Example B35

Preparation of Compound 109

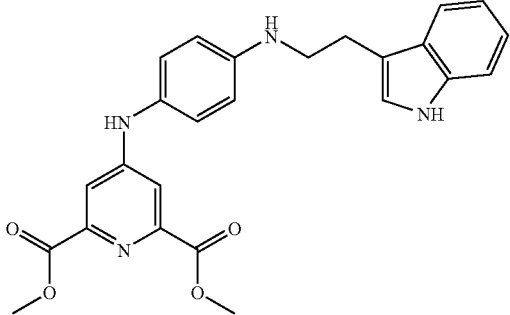

Similar procedure as for compound 86 was followed, starting from 4-chloro-2,6-pyridinedicarboxylic acid, dimethyl ester (228 mg, 0.00099 mol) and intermediate 2 (250 mg, 0.00099 mol), heating the mixture at 120° C. for 2 hours in a Biotage Initiator microwave apparatus. After workup, the residue was purified by column chromatography over silica gel (40-63 μm) (eluent: acetone/cyclohexane 30/70 to 60/40). The pure fractions were collected and the solvent was evaporated, yielding 30 mg (7%) of compound 109 as a yellow foam.

Example B36

Preparation of Compound 110

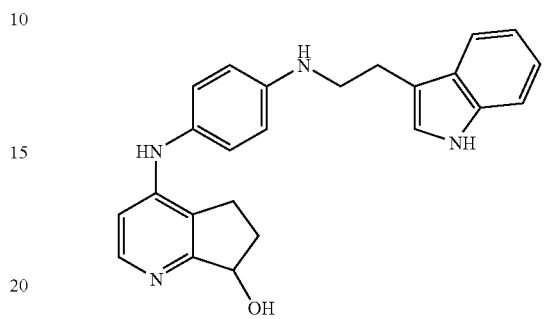

A mixture of intermediate 27 (0.0016 mol) and intermediate 2 (0.0018 mol) in acetic acid (35 ml) was stirred at 120° C. in a CEM Discover microwave oven (P=300 W) for 5 minutes, then brought back to room temperature. Ice and sodium hydroxide were added. The mixture was filtered over celite. Celite was washed with DCM/MeOH (95/5). The organic layer was separated, dried (MgSO$_4$), filtered, and the solvent was evaporated. The residue (1 g) was purified by column chromatography over kromasil (15-40 μm) (eluent: DCM/MeOH/NH$_4$OH 95/5/0.5). The pure fractions were collected and the solvent was evaporated. The residue (0.3 g) was crystallized from CH$_3$CN/MeOH. The precipitate was filtered off and dried, yielding 0.182 g (29%) of compound 110, melting point 136° C.

Example B37

Preparation of Compound 111

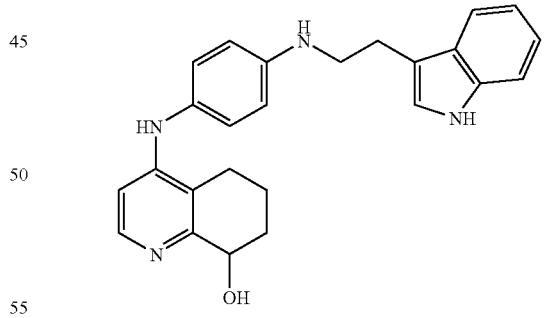

A mixture of intermediate 31 (0.0016 mol) and intermediate 2 (0.0018 mol) in acetic acid (3.5 ml) was stirred in a CEM Discover microwave oven (P=300 W) at 120° C. for 5 minutes, then cooled back to room temperature. Ice and concentrated NaOH were added. The mixture was extracted twice with DCM. The organic layer was separated, dried (MgSO$_4$), filtered, and the solvent was evaporated. The residue (0.9 g) was purified by column chromatography over kromasil (10 μm) (eluent: DCM/MeOH/NH$_4$OH 93/7/0.5). The pure fractions were collected and the solvent was evaporated. The residue (0.2 g) was crystallized from CH$_3$CN/MeOH/acetone. The precipitate was filtered off and dried, yielding 0.137 g (21%) of compound 111, melting point 104° C.

Example B38

Preparation of Compound 112

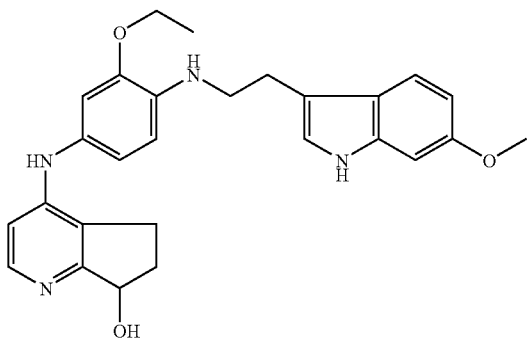

A mixture of intermediate 33 (0.0025 mol) and intermediate 27 (0.0025 mol) in acetic acid (2.7 ml) was stirred in a CEM Discover microwave oven (P=300 W) at 118° C. for 10 minutes, then brought to room temperature. Water and 3N sodium hydroxide were added. The mixture was extracted with DCM. The organic layer was separated, dried (MgSO$_4$), filtered and the solvent was evaporated. The residue (1.42 g) was purified by column chromatography over silica gel (10 μm) (eluent: DCM/MeOH/NH$_4$OH 95/5/0.5). The pure fractions were collected and the solvent was evaporated. The residue (0.56 g) was taken up in 2-propanone/CH$_3$CN. The precipitate was filtered off and dried, yielding 0.506 g (35%) of compound 112, melting point 194° C.

Example B39

Preparation of Compound 113

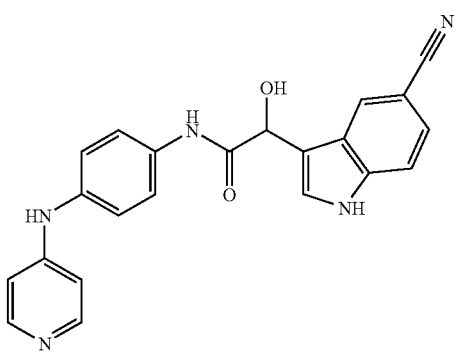

Lithium borohydride (0.0026 mol) then MeOH (1 ml) were added portion wise at 0° C. to a solution of intermediate 35 (0.0002 mol) in THF (15 ml) under N$_2$ flow. The mixture was stirred at 0° C. for 4 hours. Lithium borohydride (15 eq) was added. The mixture was stirred at room temperature overnight. Lithium borohydride (10 eq) was added. The mixture was stirred at room temperature for 4 hours and 30 minutes. Lithium borohydride (15 eq) was added. The mixture was stirred at room temperature for 24 hours and poured out into water. MeOH and THF were evaporated. DCM was added.

The mixture was filtered, yielding 0.01 g of a first batch of crude product. The filtrate was extracted with DCM. The organic layer was separated, dried (MgSO$_4$), filtered and the solvent was evaporated, yielding 0.035 g of a second batch of crude product. Both fractions were purified by column chromatography over kromasil (5 μm) (eluent: DCM/MeOH/NH$_4$OH 95/5/0.5 to 85/15/1.5). The pure fractions were collected and the solvent was evaporated, yielding 0.056 g (28%) of compound 113, melting point 154° C.

Example B41

Preparation of Compound 36

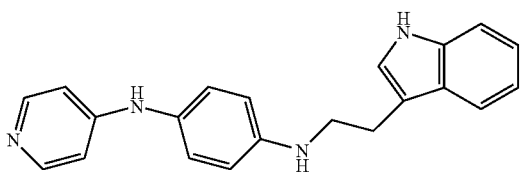

A mixture of 4-bromo-pyridine, hydrochloride (0.034 mol) and intermediate 2 (0.0374 mol) in acetic acid (13 ml) was stirred at 110° C. for 40 minutes, then cooled to room temperature, poured out into ice water and basified with potassium carbonate. DCM was added. The mixture was stirred for 30 minutes, then filtered over celite. The filtrate was decanted. Celite was taken up in DCM/MeOH (95/5). The mixture was stirred for 30 minutes, then filtered. Both filtrates were combined, dried (MgSO$_4$), filtered and the solvent was evaporated. The residue (16.8 g) was purified by column chromatography over silica gel (20-45 μm) (eluent: DCM/MeOH/NH$_4$OH 92/8/0.5). The pure fractions were collected and the solvent was evaporated. The residue (4.2 g) was taken up in 2-propanone. The precipitate was filtered off and dried, yielding 3.6 g (32%) of compound 36, melting point 236° C.

Example B42

Preparation of Compound 115

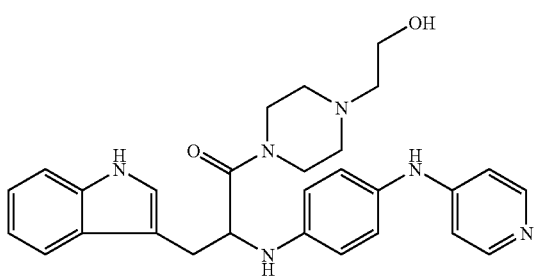

N-(2-hydroxyethyl)piperazine (0.0019 mol), EDC (0.0019 mol), HOBT (0.0019 mol) and triethylamine (0.0019 mol) were added to a solution of intermediate 41 (0.0013 mol) in DCM/DMF 75/25 (20 ml). The mixture was stirred at room temperature overnight. Potassium carbonate 10% was added. The mixture was extracted with DCM. The organic layer was separated, dried (MgSO$_4$), filtered, and the solvent was evaporated. The residue (0.32 g) was purified by column chromatography over kromasil (10 μm) (eluent: DCM/

MeOH/NH$_4$OH 90/10/1). The pure fractions were collected and the solvent was evaporated, yielding 0.027 g (4%) of compound 115.

Example B43

Preparation of Compound 116

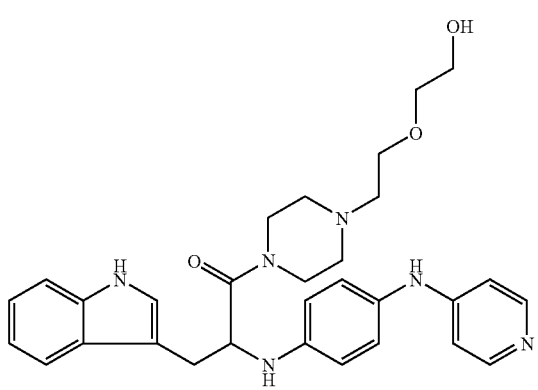

1-[2-(2-hydroxyethoxy)ethyl]piperazine (0.0019 mol), EDCI (0.0019 mol), HOBT (0.0019 mol), and triethylamine (0.0019 mol) were added to a solution of intermediate 41 (0.0013 mol) in DCM/DMF 75/25 (20 ml). The mixture was stirred at room temperature overnight. Potassium carbonate 10% was added. The mixture was extracted with DCM. The organic layer was separated, dried (MgSO$_4$), filtered, and the solvent was evaporated. The residue (0.38 g) was purified by column chromatography over kromasil (10 µm) (eluent: DCM/MeOH/NH$_4$OH 90/10/1). The pure fractions were collected and the solvent was evaporated, yielding 0.108 g (16%) of compound 116.

Example B44

Preparation of Compound 117

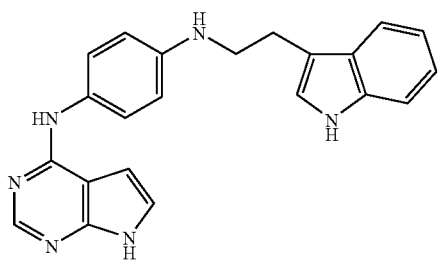

A mixture of intermediate 2 (0.002 mol) and 4-chloro-1H-pyrrolo[2,3-d]pyrimidine (0.002 mol) in acetic acid (5 ml) was stirred in a CEM Discover microwave oven at 140° C. for 15 minutes. Acetic acid was evaporated. The crude product was dissolved in DCM. The organic layer was separated, dried (MgSO$_4$), filtered and the solvent was evaporated. The residue (1 g) was purified by column chromatography over silica gel (15-40 µm) (eluent: DCM/MeOH/NH$_4$OH 93/7/0.5). The pure fractions were collected and the solvent was evaporated. The residue (0.27 g) was crystallized from aceto- nitrile. The precipitate was filtered off and dried, yielding 0.233 g (31%) of compound 117, melting point 211° C.

Example B45

Preparation of Compound 118

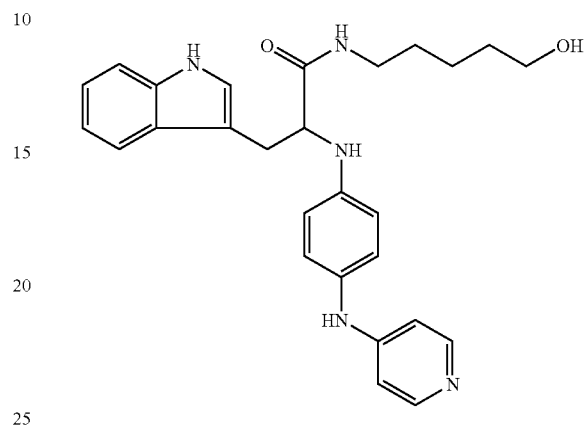

5-amino-1-pentanol (0.0019 mol), EDC (0.0019 mol), HOBT (0.0019 mol), and triethylamine (0.0019 mol) were added to a solution of intermediate 41 (0.0013 mol) in DCM/DMF 75/25 (10 ml). The mixture was stirred at room temperature overnight. potassium carbonate 10% was added. The mixture was extracted with DCM. The organic layer was separated, dried (MgSO$_4$), filtered, and the solvent was evaporated. The residue (0.38 g) was purified by column chromatography over kromasil (10 µm) (eluent: DCM/MeOH/NH$_4$OH 90/10/1 to 80/20/2). The pure fractions were collected and the solvent was evaporated, yielding 0.128 g of compound 118.

Example B46

Preparation of Compound 119

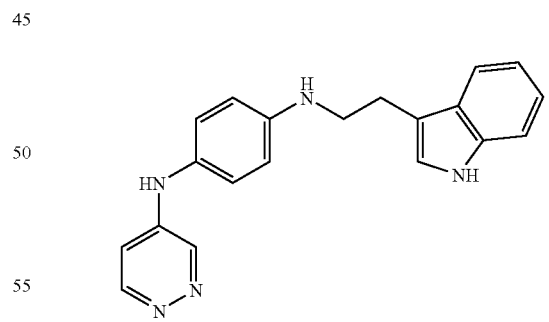

A mixture of intermediates 86 and 87 (179 mg, 0.00045 mol) and 10% palladium over carbon (20 mg) in EtOH was stirred at room temperature under 1 atmosphere of hydrogen for 16 hours. After filtration trough a celite pad, the solvent was evaporated. The residue was purified by column chromatography over silica gel (40-63 µm) (eluent: DCM/MeOH 9/1). The pure fractions were collected and the solvent was evaporated, yielding 70 mg (47%) of compound 119 as a yellow foam.

Example B47

Preparation of Compound 120

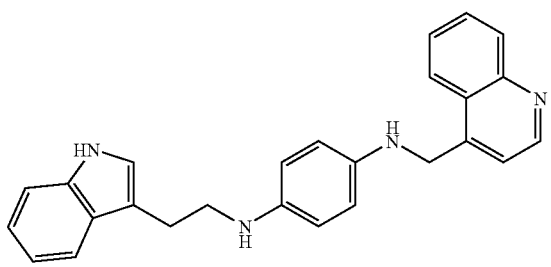

A mixture of intermediate 2 (0.050 mg, 0.000199 mol), 4-quinolinecarboxaldehyde (31 mg, 0.000199 mol) in MeOH were stirred and refluxed overnight, then cooled to room temperature. Sodium borohydride was added portionwise and the mixture was stirred at room temperature for 1 hour, hydrolyzed with water, extracted with DCM, dried over $MgSO_4$ and concentrated. The residue was purified by column chromatography over kromasil (10 μm) (eluent: DCM/MeOH/$NH_4OH$ 90/10/1 to 80/20/2). The pure fractions were collected and the solvent was evaporated, yielding 0.045 g (45%) of compound 120.

Example B48

Preparation of Compound 121

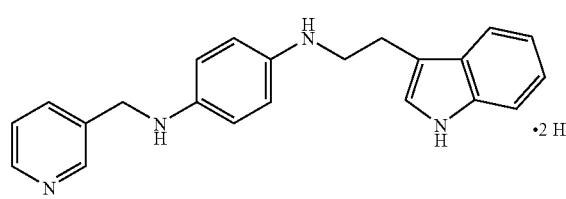

A mixture of 3-pyridinecarboxaldehyde (0.0028 mol) and intermediate 2 (0.0028 mol) in MeOH (20 ml) was stirred and refluxed overnight, then brought to room temperature. Sodium tetrahydroborate (0.0028 mol) was added portionwise. The mixture was stirred at room temperature for 5 hours. Ice and water were added. The mixture was extracted with DCM. The organic layer was separated, dried ($MgSO_4$), filtered, and the solvent was evaporated. The residue was purified by column chromatography over silica gel (15-40 μm) (eluent: DCM/MeOH/$NH_4OH$ 97/3/0.2). The pure fractions were collected and the solvent was evaporated. The residue (0.4 g) was taken up in HCl/isopropanol/diethyl ether. The precipitate was filtered off and dried. Ice and water were added. The mixture was basified with sodium hydroxide 3N. The mixture was extracted with DCM. The residue (0.3 g) was purified by column chromatography over silica gel (15-40 μm) (eluent: toluene/isopropanol/$NH_4OH$ 90/10/0.5). The pure fractions were collected and the solvent was evaporated. The residue (0.24 g) was taken up in isopropanol/HCl/isopropanol/diethyl ether. The precipitate was filtered off and dried, yielding 0.23 g (20%) of compound 121, isolated as a hydrochloric acid salt, melting point 130° C.

Table F-1 lists the compounds that were prepared according to one of the above Examples. The following abbreviations were used in the tables: .$C_2HF_3O_2$ stands for the trifluoroacetate salt, int. stands for intermediate, comp. stands for compound, .HCl stands for hydrochloric acid salt, mp. stands for melting point, ms. stands for MASS spectrum.

TABLE F-1

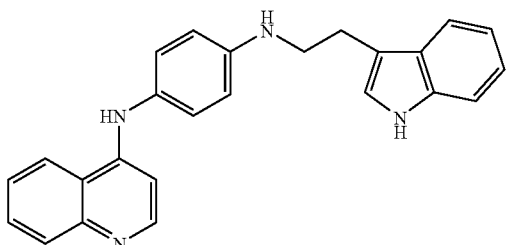

•1.58 HCl; Co. No. 1; mp. 170° C.
Ex. [B1]

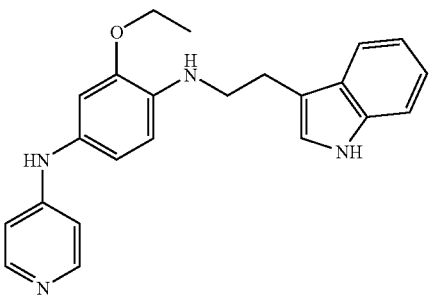

•1.81 HCl; Co. No. 2; mp. 150° C.
Ex. [B2]

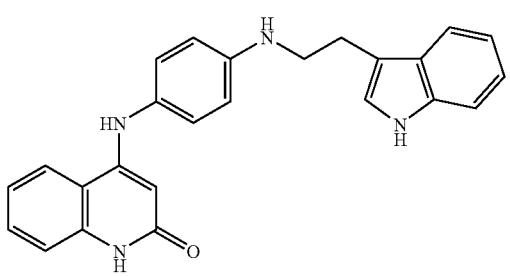

Co. No. 3; mp. 238° C.
Ex. [B3]

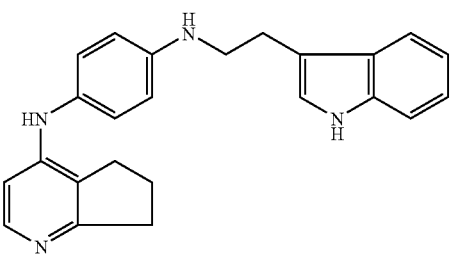

Co. No. 4; mp. 369
Ex. [B4]

TABLE F-1-continued
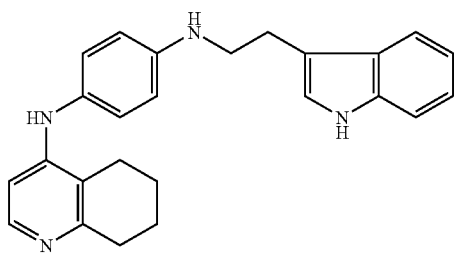
Co. No. 5; mp. 383
Ex. [B5]
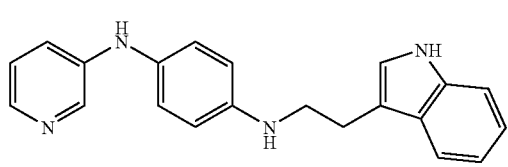
•1.67 HCl; Co. No. 6; mp. 160° C.
Ex. [B6]
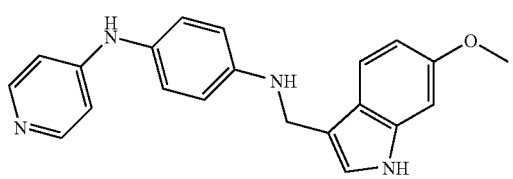
Co. No. 7; mp. 145° C.
Ex. [B7]
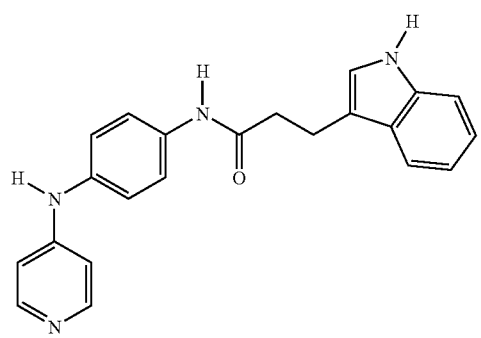
Co. No. 8; mp. 208° C.
Ex. [B8]
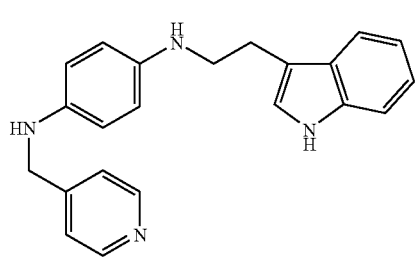
Co. No. 9; mp. 132° C.
Ex. [B9]
TABLE F-1-continued
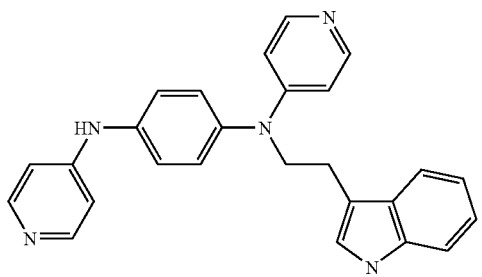
•1.92 HCl; Co. No. 10; mp. >250° C.
Ex. [B10]
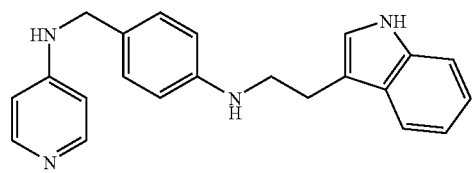
Co. No. 11; mp. 122° C.
Ex. [B11]
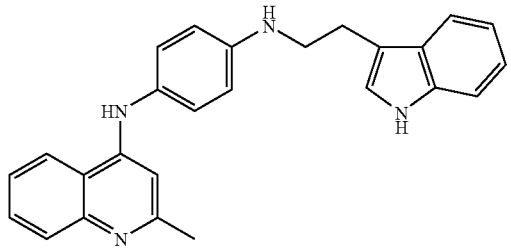
•0.93 HCl; Co. No. 12; mp. 240° C.
Ex. [B1]
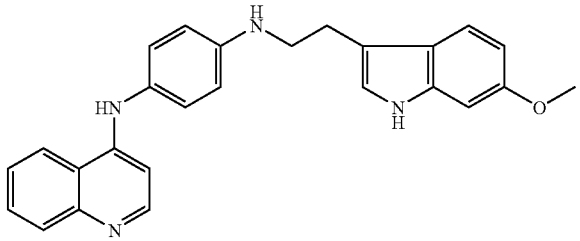
Co. No. 13; mp. 107° C.
Ex. [B1]
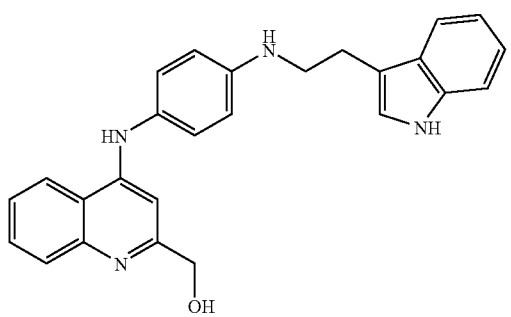
Co. No. 14; mp. 107° C.
Ex. [B1]

TABLE F-1-continued
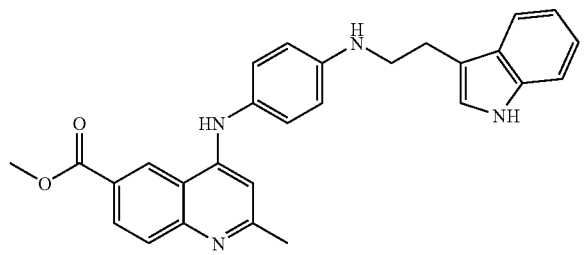
•0.81 HCl; Co. No. 15; mp. 168° C.
Ex. [B1]
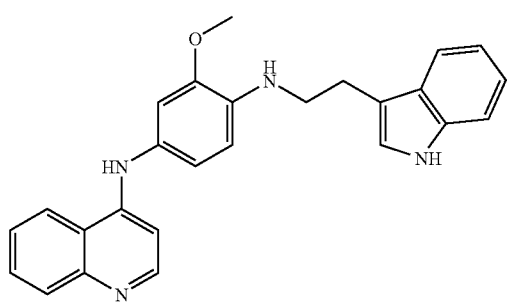
Co. No. 16; mp. 100° C.
Ex. [B1]
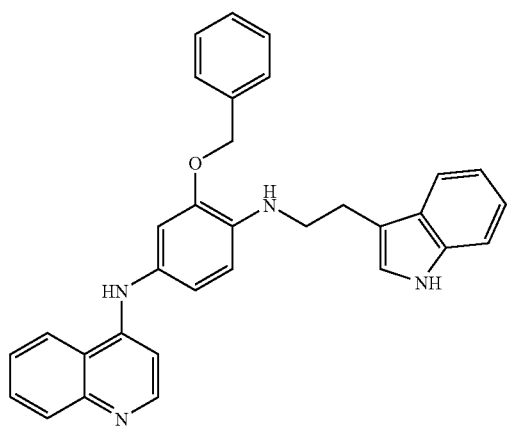
Co. No. 17; mp. 99° C.
Ex. [B1]
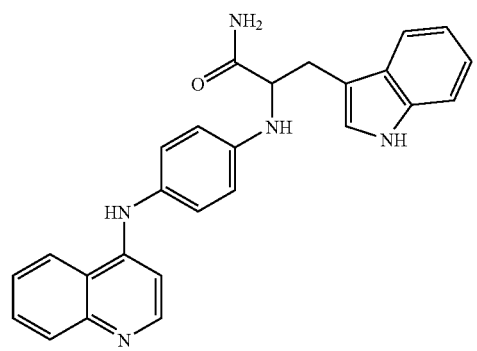
•HCl•0.5 C₃H₈O; Co. No. 18; mp. 189° C.
Ex. [B1]
TABLE F-1-continued
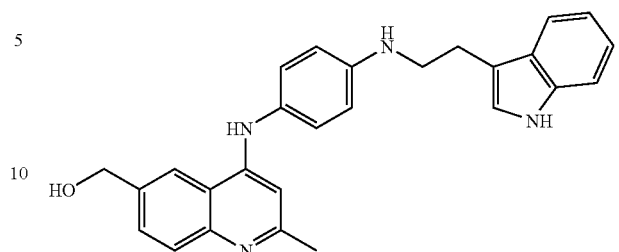
Co. No. 19; mp. 127° C.
Ex. [B1]
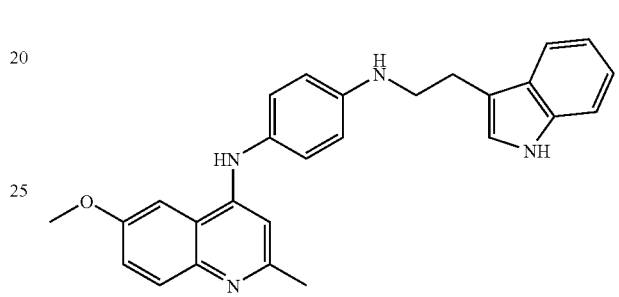
•1.94 HCl; Co. No. 20; mp. 213° C.
Ex. [B1]
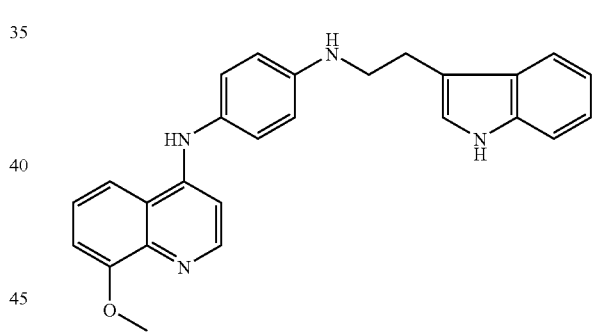
Co. No. 21; mp. 220° C.
Ex. [B1]
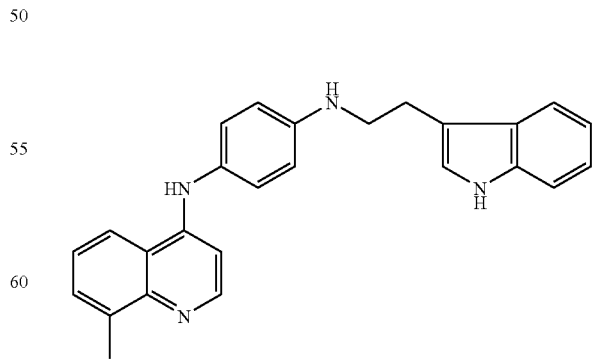
•0.76 HCl; Co. No. 22; mp. >250° C.
Ex. [B1]

TABLE F-1-continued
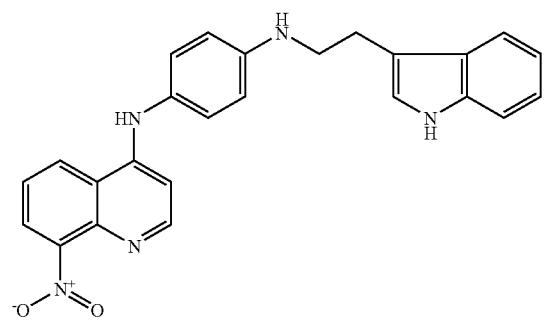
Co. No. 23; mp. 107° C.
Ex. [B1]
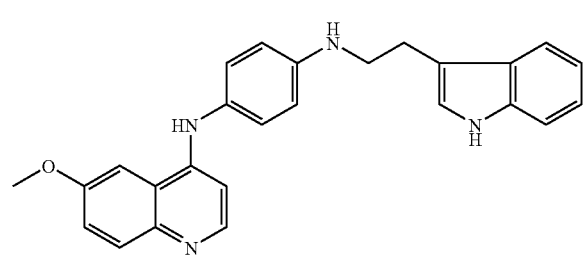
Co. No. 24; mp. 125° C.
Ex. [B1]
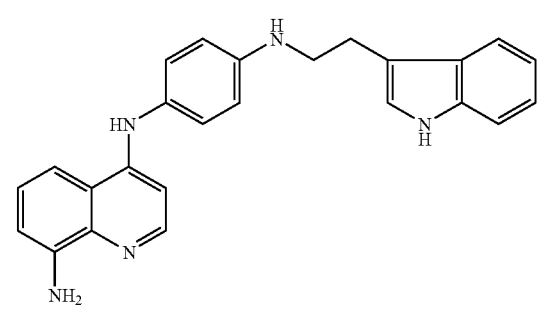
•1.95 HCl; Co. No. 25; mp. 186° C.
Ex. [B1]
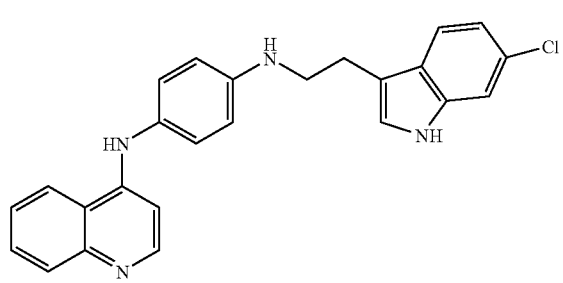
Co. No. 26; mp. 102° C.
Ex. [B1]
TABLE F-1-continued
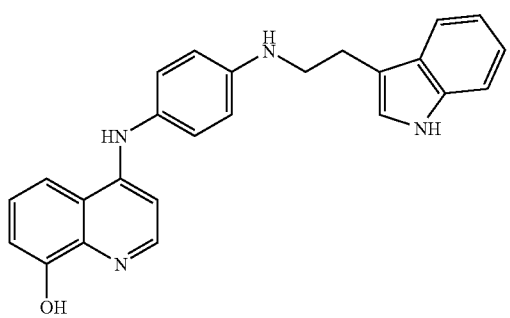
Co. No. 27; mp. 200° C.
Ex. [B1]
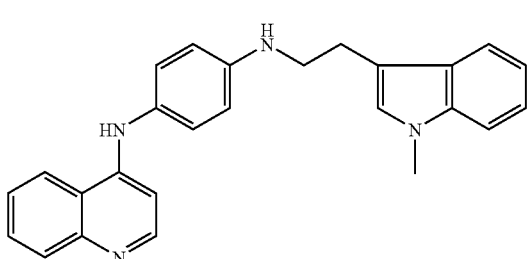
•1.79 HCl; Co. No. 28; mp. 184° C.
Ex. [B1]
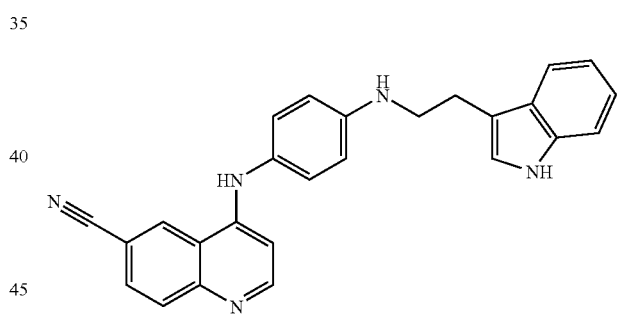
Co. No. 29; mp. 206° C.
Ex. [B1]
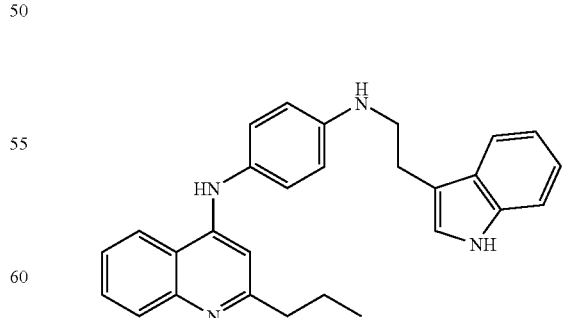
•1.87 HCl; Co. No. 30; mp. 208° C.
Ex. [B1]

TABLE F-1-continued
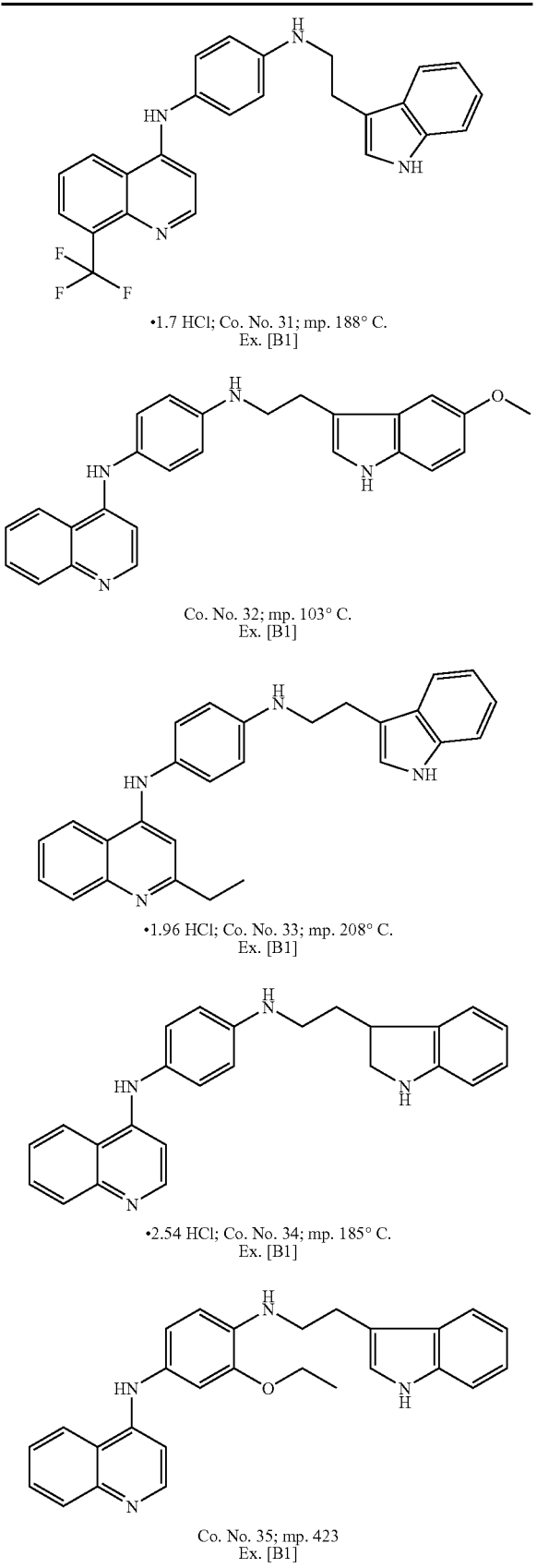
•1.7 HCl; Co. No. 31; mp. 188° C.
Ex. [B1]
Co. No. 32; mp. 103° C.
Ex. [B1]
•1.96 HCl; Co. No. 33; mp. 208° C.
Ex. [B1]
•2.54 HCl; Co. No. 34; mp. 185° C.
Ex. [B1]
Co. No. 35; mp. 423
Ex. [B1]
TABLE F-1-continued
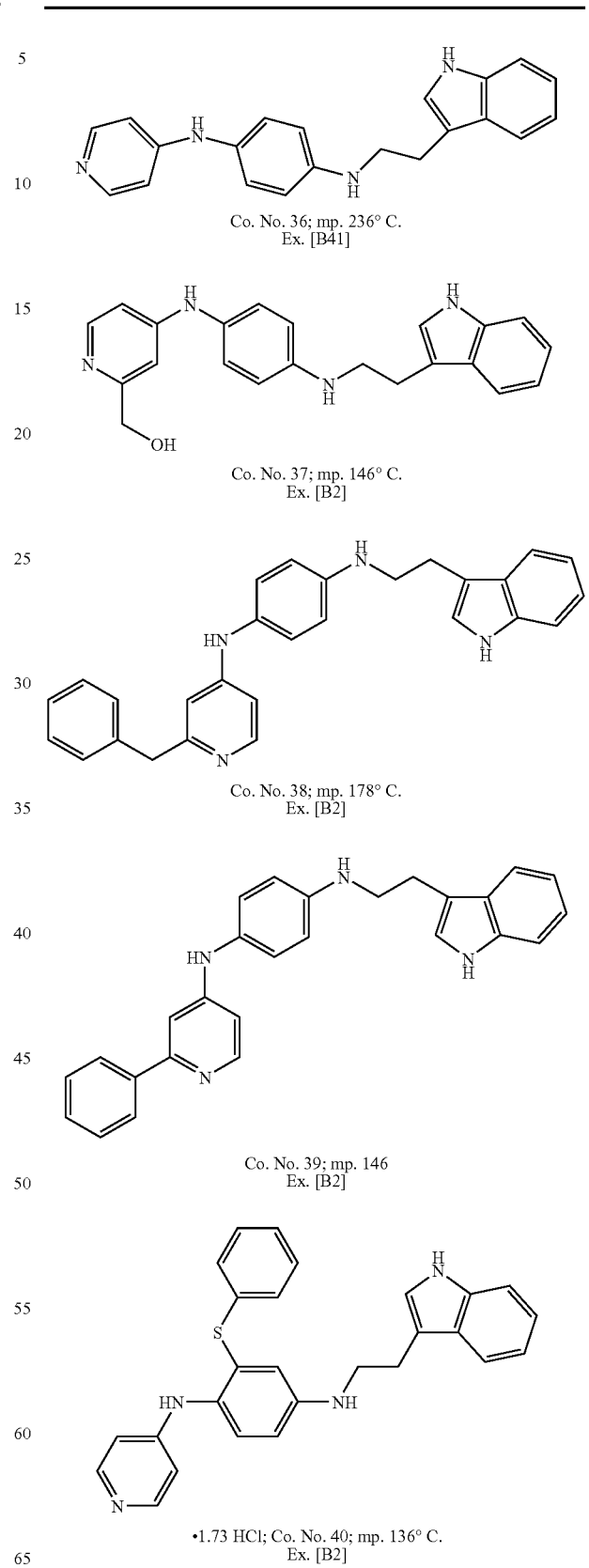
Co. No. 36; mp. 236° C.
Ex. [B41]
Co. No. 37; mp. 146° C.
Ex. [B2]
Co. No. 38; mp. 178° C.
Ex. [B2]
Co. No. 39; mp. 146
Ex. [B2]
•1.73 HCl; Co. No. 40; mp. 136° C.
Ex. [B2]

TABLE F-1-continued
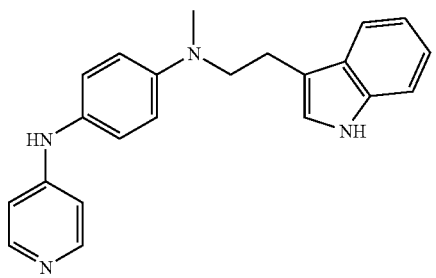
Co. No. 41; mp. 188° C.
Ex. [B2]
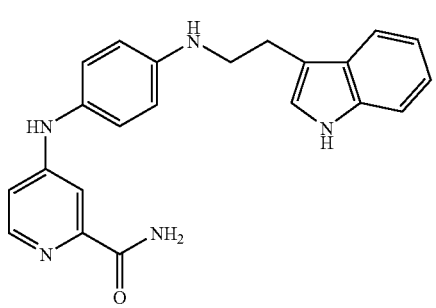
•1.94 HCl•1.76 H₂O; Co. No. 42
mp. 167° C.
Ex. [B2]
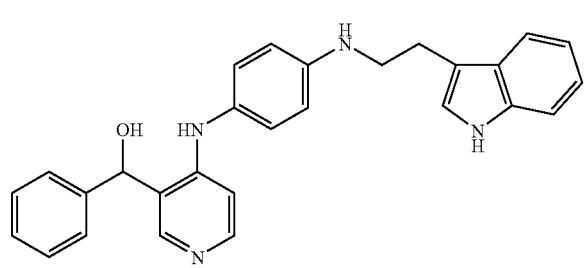
Co. No. 43; mp. 192° C.
Ex. [B2]
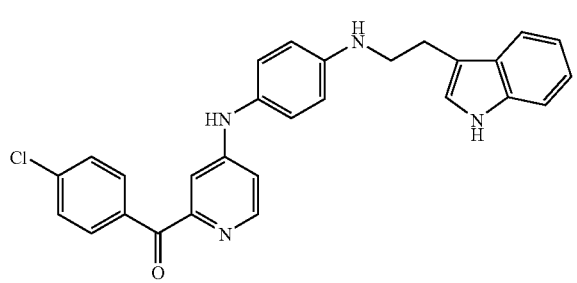
Co. No. 44; mp. 90° C.
Ex. [B2]
TABLE F-1-continued
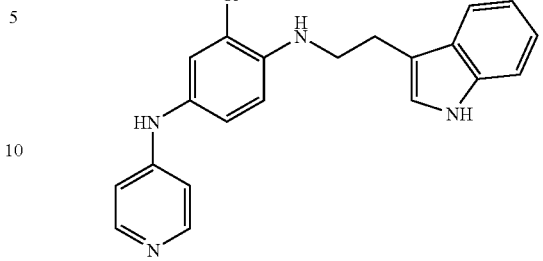
Co. No. 45; mp. 144° C.
Ex. [B2]
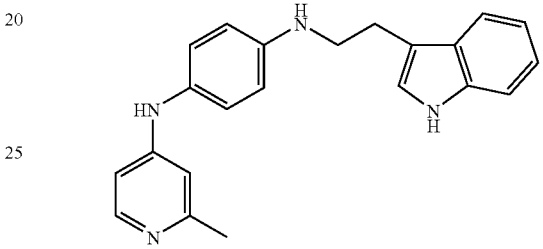
•1.5 H₂O•1.99 C₂H₂O₄; Co. No. 46;
mp. 119° C.
Ex. [B2]
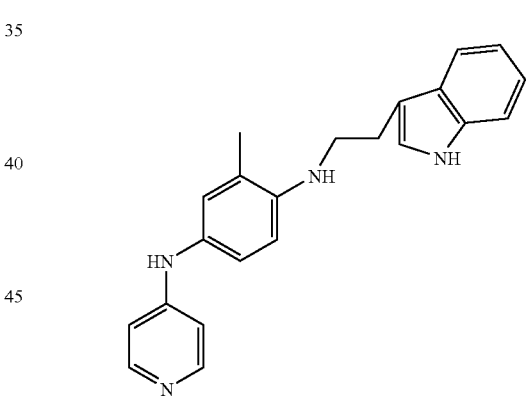
Co. No. 47; mp. 184° C.
Ex. [B2]
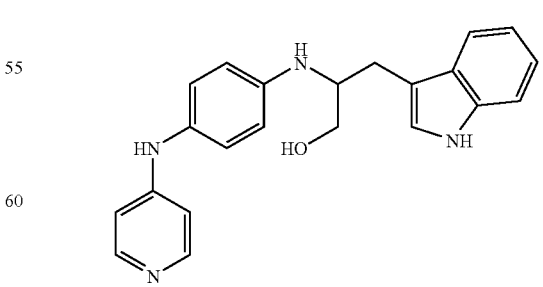
Co. No. 48; mp. 93° C.
Ex. [B2]

TABLE F-1-continued
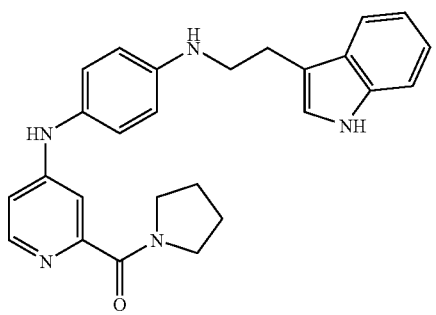
Co. No. 49; mp. 118° C.
Ex. [B2]
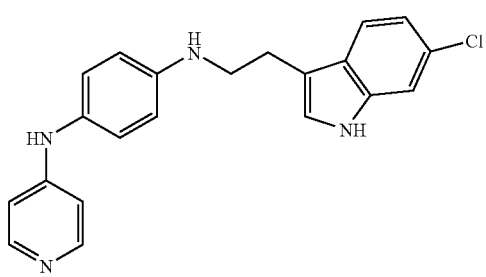
Co. No. 50; mp. 162° C.
Ex. [B2]
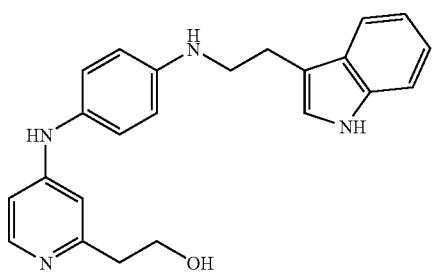
•1.74 HCl; Co. No. 51; mp. 145° C.
Ex. [B2]
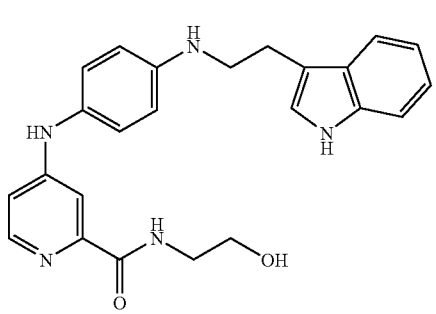
Co. No. 52; mp. 108° C.
Ex. [B2]
TABLE F-1-continued
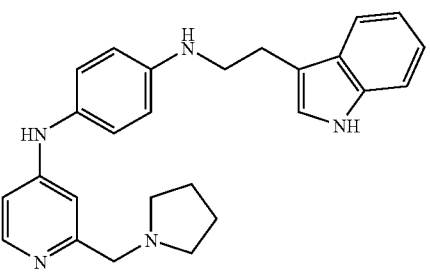
Co. No. 53; mp. 190° C.
Ex. [B2]
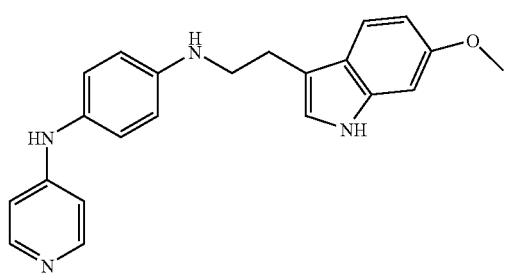
Co. No. 54; mp. 58° C.
Ex. [B2]
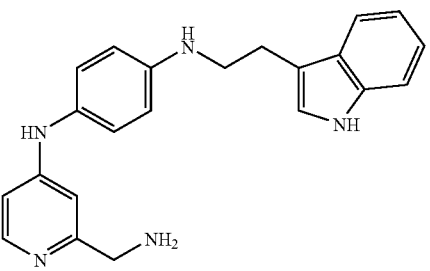
Co. No. 55; mp. 164° C.
Ex. [B2]
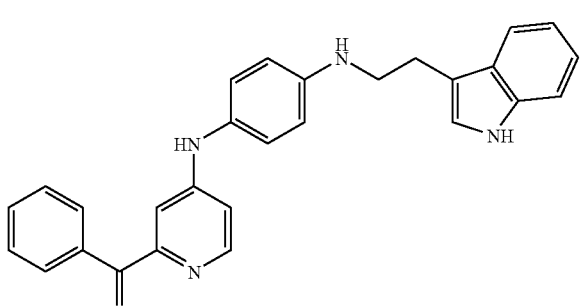
Co. No. 56; mp. 128° C.
Ex. [B2]

TABLE F-1-continued
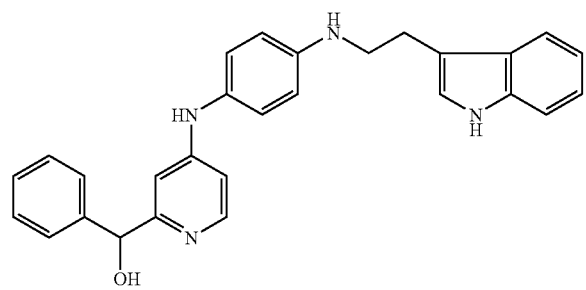
Co. No. 57; mp. 124° C.
Ex. [B2]
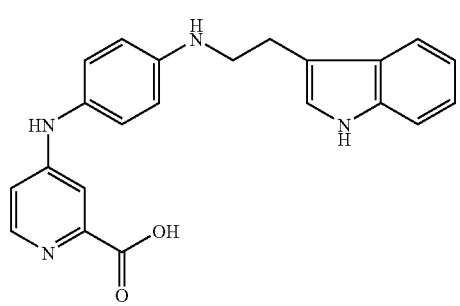
Co. No. 58; mp. 190° C.
Ex. [B2]
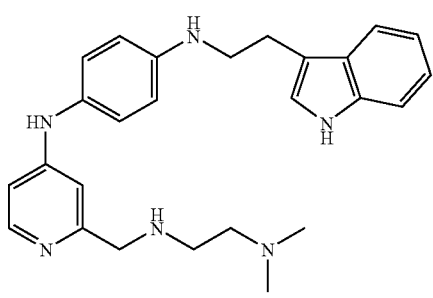
Co. No. 59; mp. 70° C.
Ex. [B2]
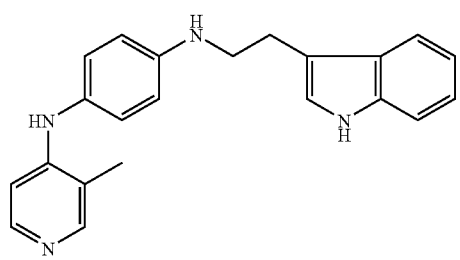
Co. No. 60; mp. 76° C.
Ex. [B2]
TABLE F-1-continued
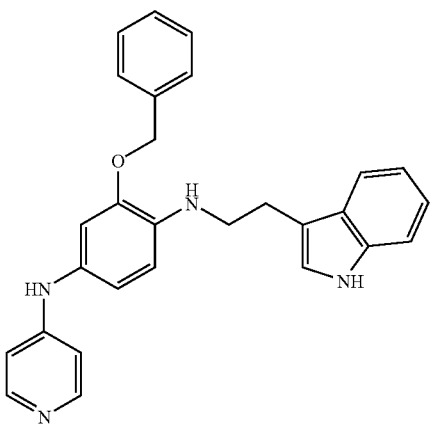
Co. No. 61; mp. 130° C.
Ex. [B2]
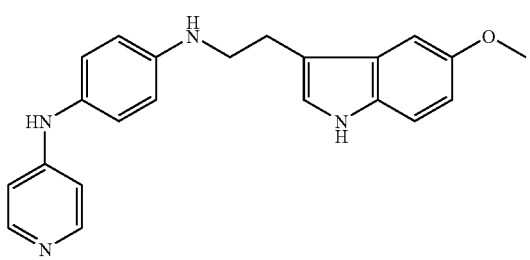
Co. No. 62; mp. 84° C.
Ex. [B2]
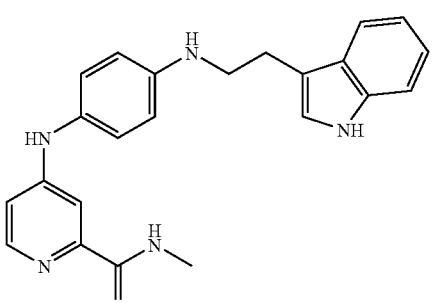
Co. No. 63; mp. 207° C.
Ex. [B2]
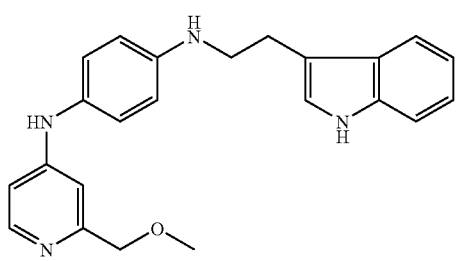
•2.03 HCl; Co. No. 64; mp. 240° C.
Ex. [B2]

TABLE F-1-continued
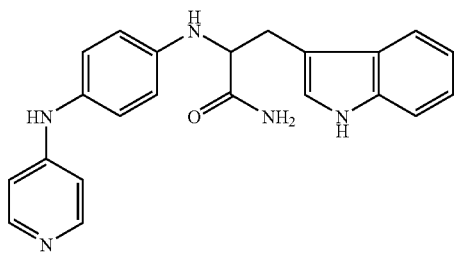
Co. No. 65; mp. 105° C.
Ex. [B2]
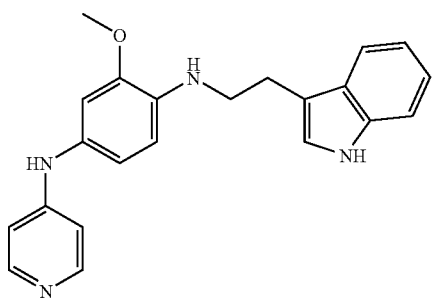
•1.79 HCl; Co. No. 66; mp. 162° C.
Ex. [B2]
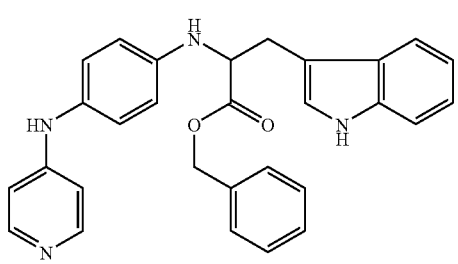
•1.61 C$_2$H$_2$O$_4$; Co. No. 67; mp. 115° C.
Ex. [B2]
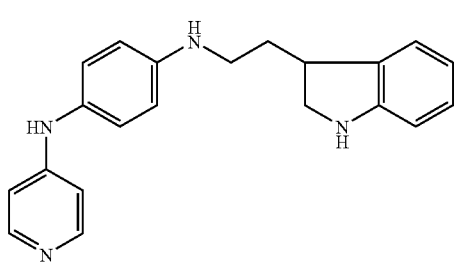
•3HCl•3 H$_2$O; Co. No. 68; mp. 198° C.
Ex. [B2]
TABLE F-1-continued
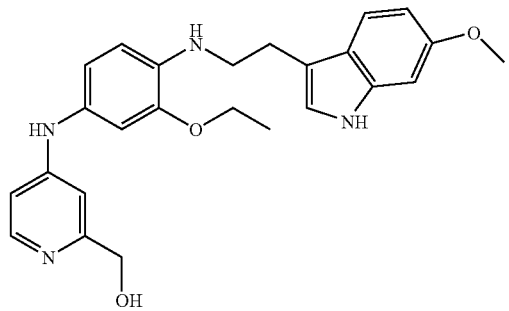
Co. No. 69; mp. 432
Ex. [B2]
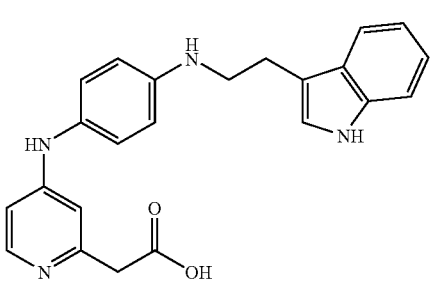
Co. No. 70; mp. 149° C.
Ex. [B2]
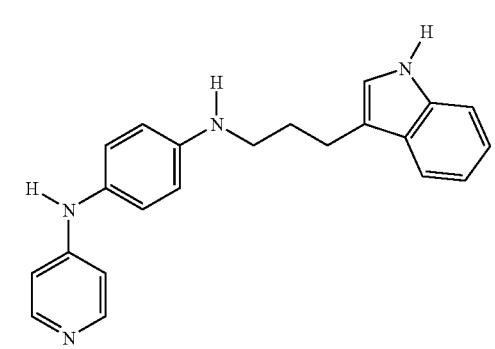
Co. No. 71; mp. 170° C.
Ex. [B6]
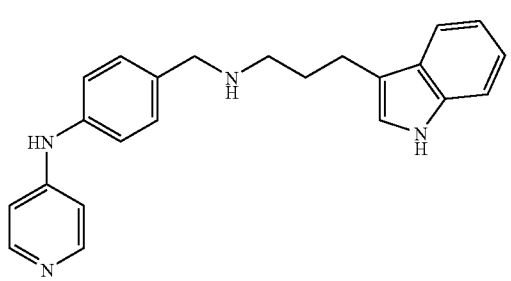
Co. No. 72; mp. 102° C.
Ex. [B6]

TABLE F-1-continued
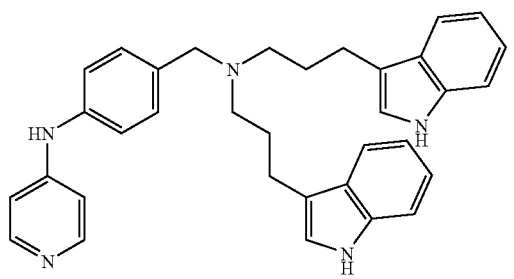
Co. No. 73; mp. 80° C.
Ex. [B6]
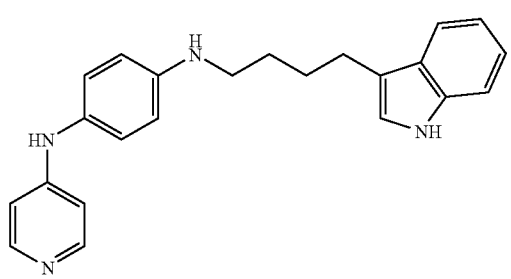
Co. No. 74; mp. 119° C.
Ex. [B6]
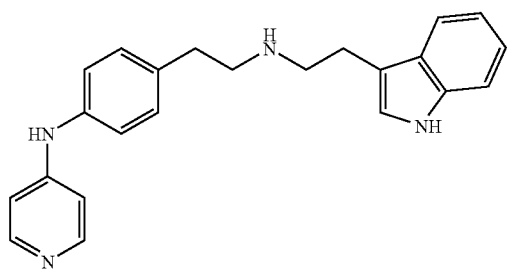
Co. No. 75; mp. 110° C.
Ex. [B6]
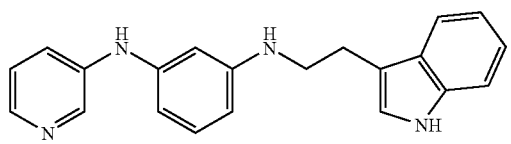
•1.54 HCl; Co. No. 76; mp. 130° C.
Ex. [B6]
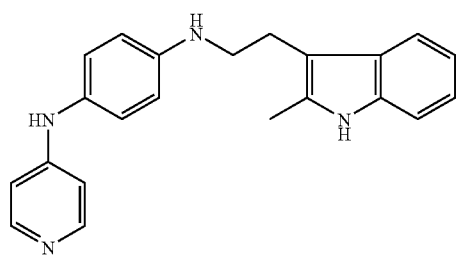
Co. No. 77; mp. 174° C.
Ex. [B6]
TABLE F-1-continued
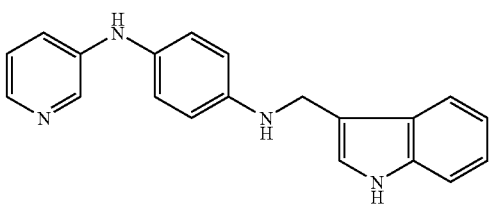
Co. No. 78;
Ex. [B7]
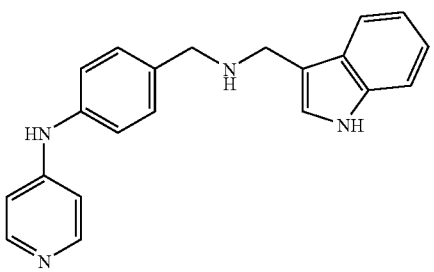
Co. No. 79; mp. 75° C.
Ex. [B7]
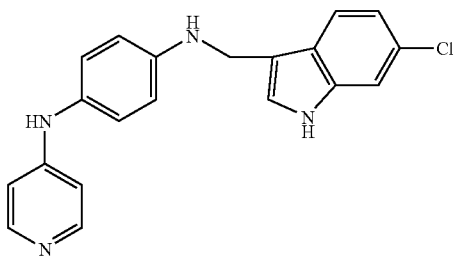
Co. No. 80; mp. 98° C.
Ex. [B7]
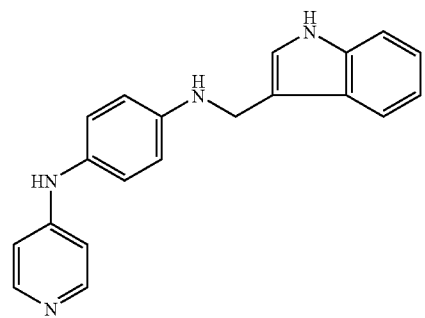
Co. No. 81; mp. 165° C.
Ex. [B7]
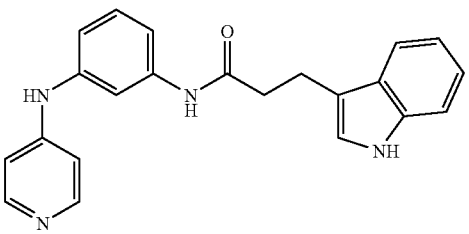
Co. No. 82; mp. 225° C.
Ex. [B8]

TABLE F-1-continued
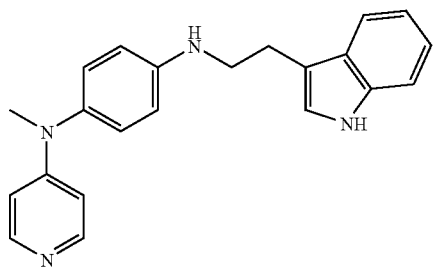
Co. No. 83; mp. 162° C.
Ex. [B8]
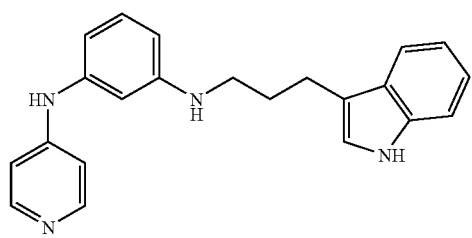
•1.85 HCl; Co. No. 84; mp. 210° C.
Ex. [B8]
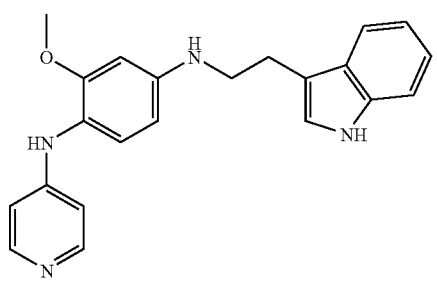
Co. No. 85; mp. 110° C.
Ex. [B8]
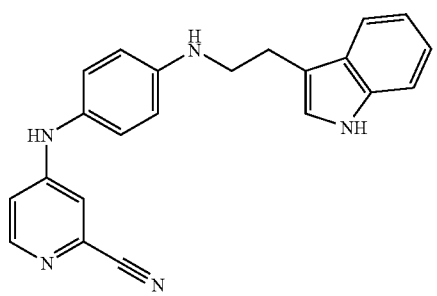
Co. No. 86; mp. 354
Ex. [B12]
TABLE F-1-continued
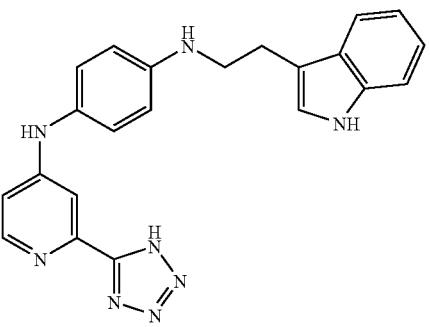
Co. No. 87; mp. 210° C.
Ex. [B13]
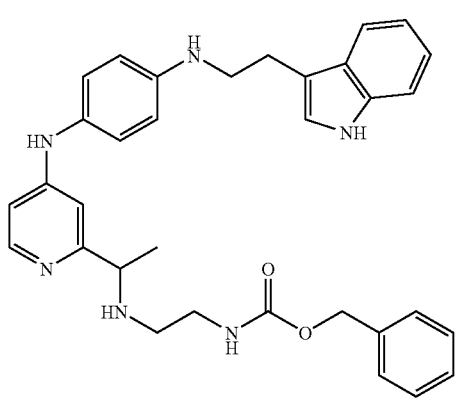
Co. No. 88; ms. 549
Ex. [B14]
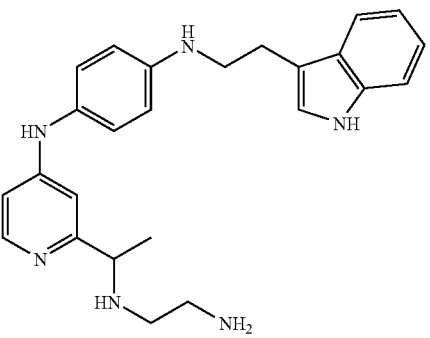
Co. No. 89; ms. 415
Ex. [B15]

TABLE F-1-continued
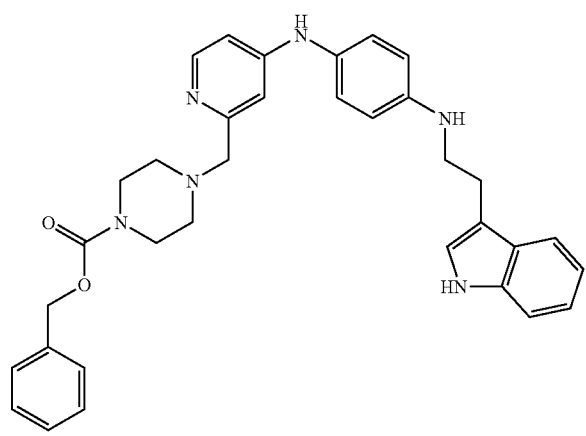
Co. No. 90; ms. 561
Ex. [B16]
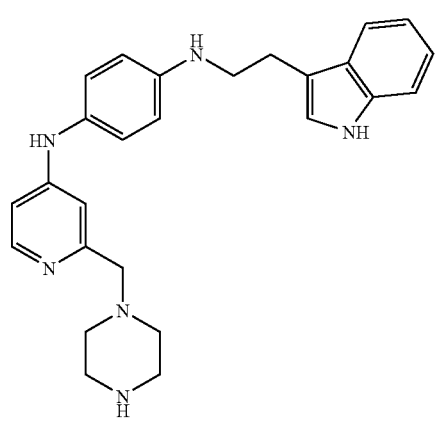
Co. No. 91; ms. 427
Ex. [B17]
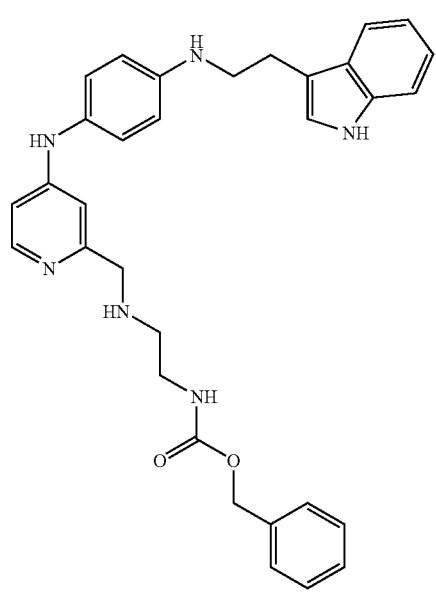
Co. No. 92; ms. 535
Ex. [B18]
TABLE F-1-continued
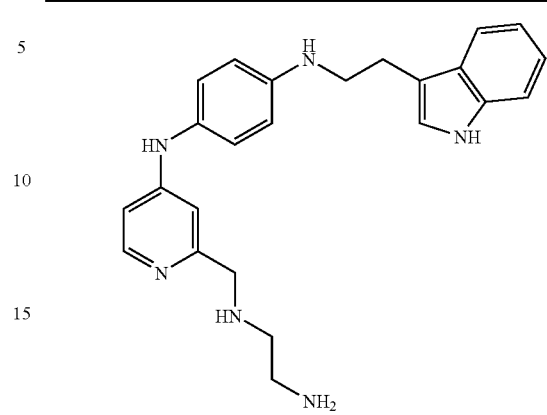
Co. No. 93; ms. 401
Ex. [B19]
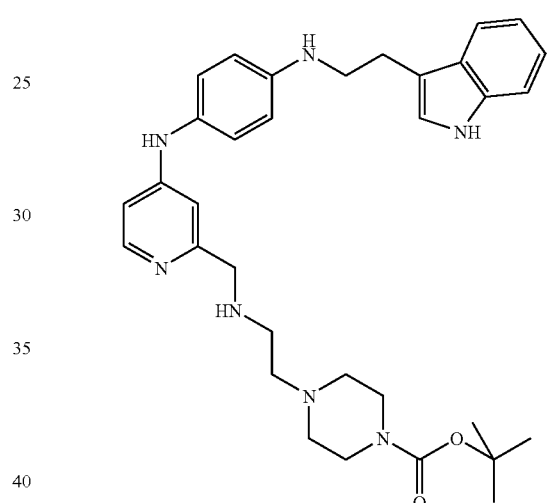
Co. No. 94; ms. 570
Ex. [B20]
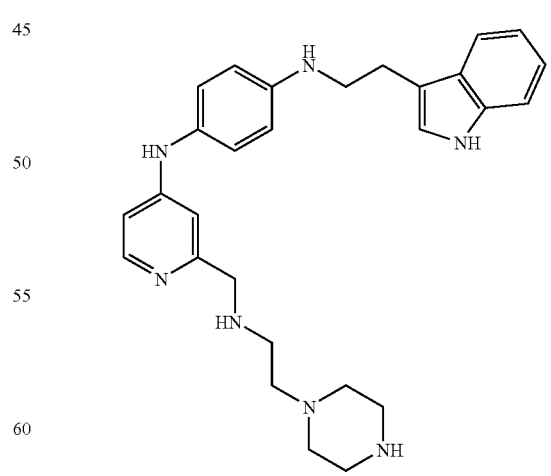
Co. No. 95; ms. 470
Ex. [B21]

TABLE F-1-continued
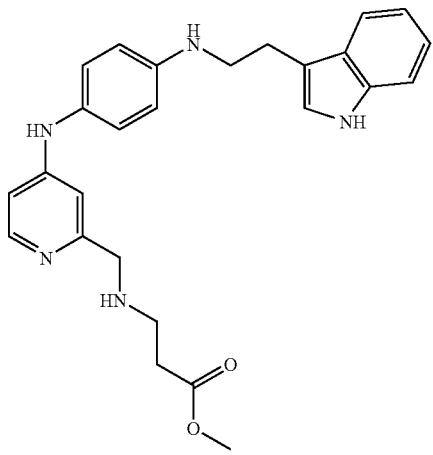
Co. No. 96; ms. 444
Ex. [B22]
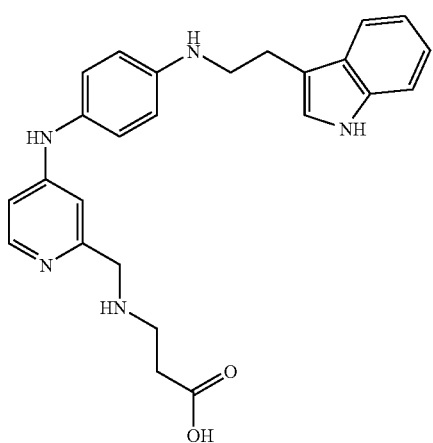
Co. No. 97; ms. 430
Ex. [B23]
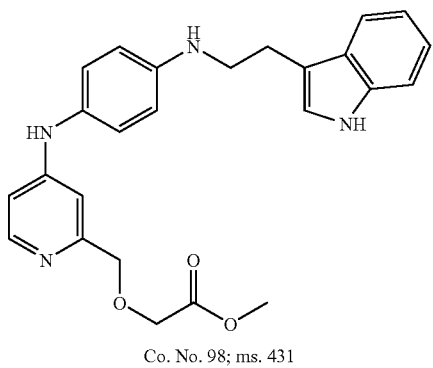
Co. No. 98; ms. 431
Ex. [B24]
TABLE F-1-continued
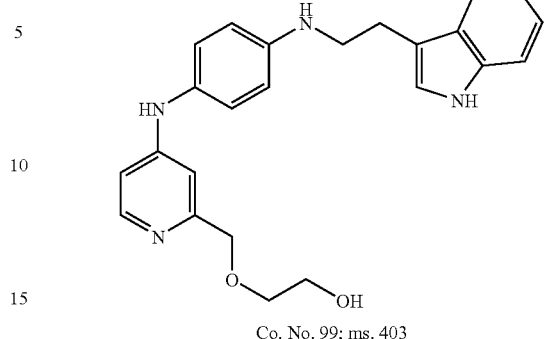
Co. No. 99; ms. 403
Ex. [B25]
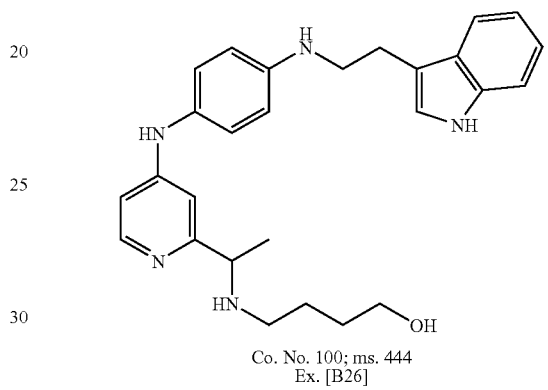
Co. No. 100; ms. 444
Ex. [B26]
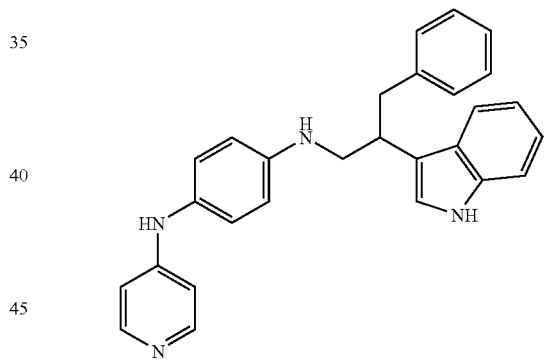
Co. No. 101; ms. 419
Ex. [B27]
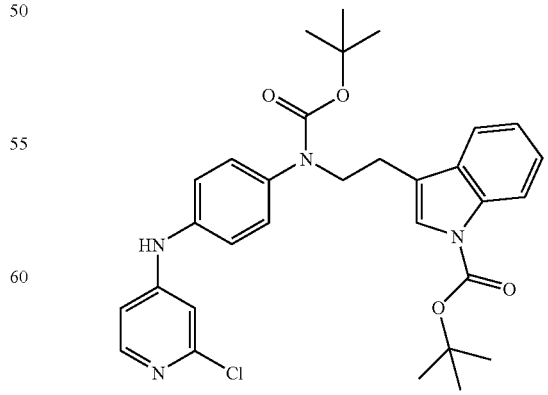
Co. No. 102; ms. 563
Ex. [B28]

TABLE F-1-continued
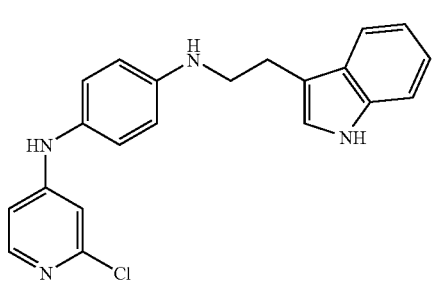
Co. No. 103; ms. 363
Ex. [B29]
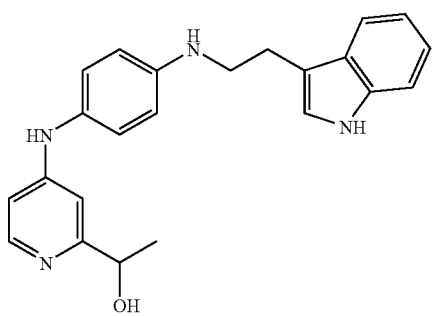
Co. No. 104; ms. 373
Ex. [B30]
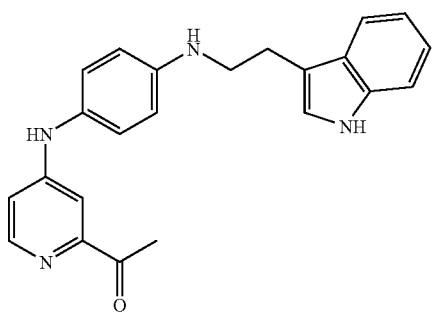
Co. No. 105; ms. 371
Ex. [B31]
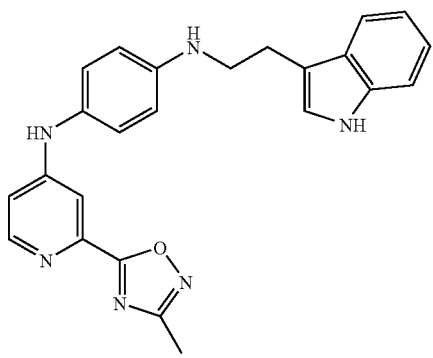
Co. No. 106; ms. 411
Ex. [B32]
TABLE F-1-continued
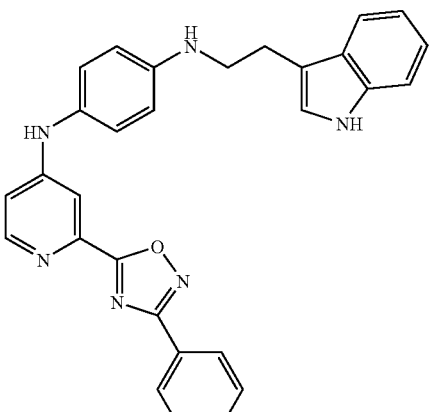
Co. No. 107; mp. 170-174° C.
Ex. [B33]
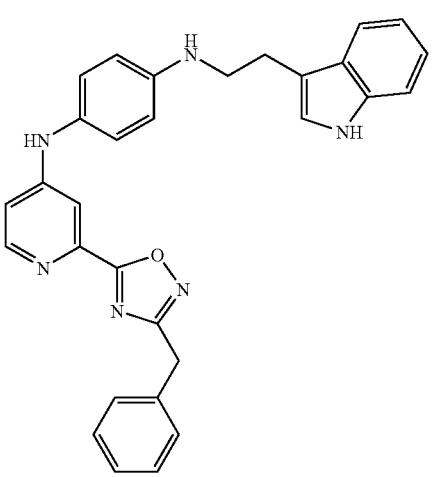
Co. No. 108; mp. 169-161° C.
Ex. [B34]
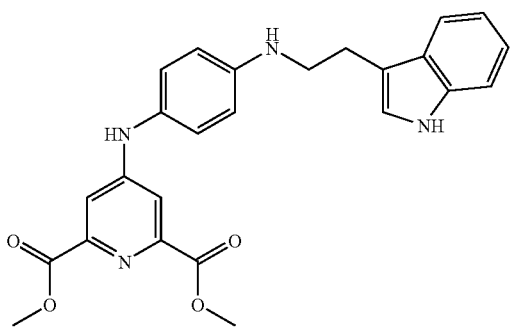
Co. No. 109; ms. 445
Ex. [B35]

TABLE F-1-continued
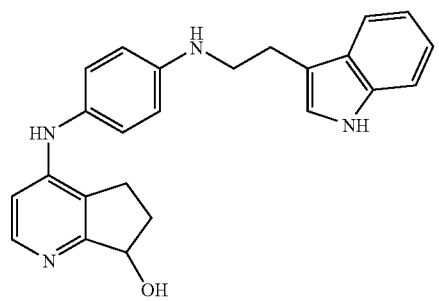
Co. No. 110; mp. 136° C.
Ex. [B36]
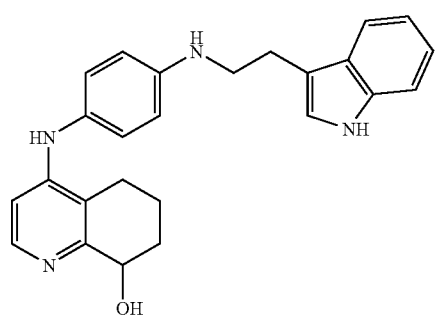
Co. No. 111; mp. 104° C.
Ex. [B37]
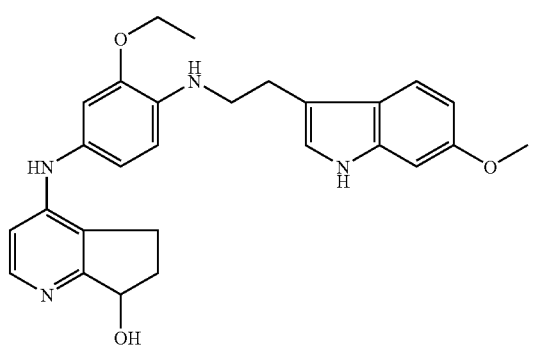
Co. No. 112; mp. 194° C.
Ex. [B38]
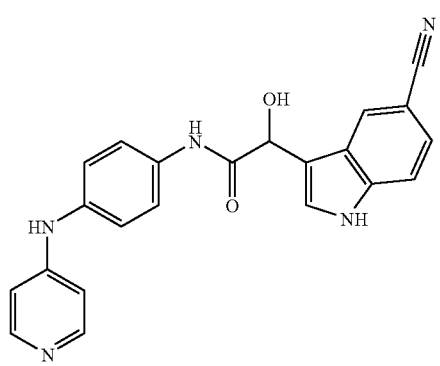
Co. No. 113; mp. 154° C.
Ex. [B39]
TABLE F-1-continued
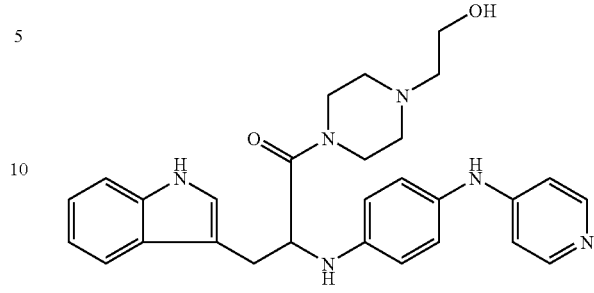
Co. No. 115; ms. 485
Ex. [B42]
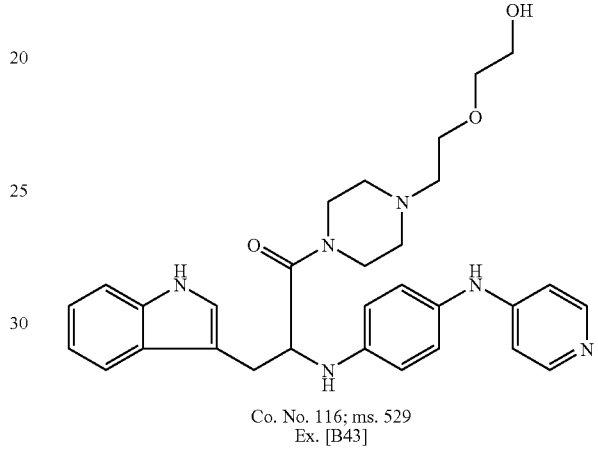
Co. No. 116; ms. 529
Ex. [B43]
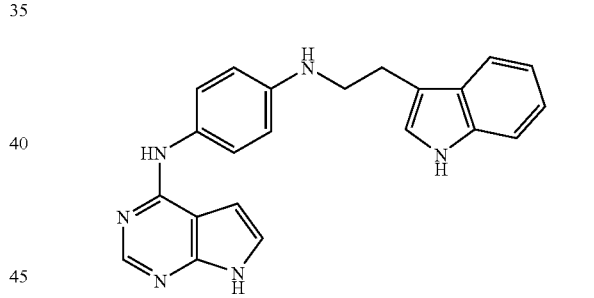
Co. No. 117; mp. 211° C.
Ex. [B44]
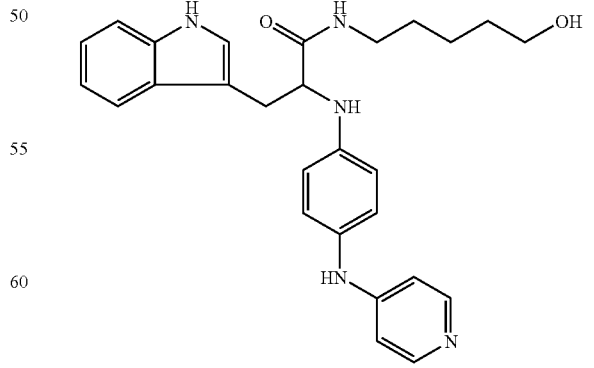
Co. No. 118; ms. 457
Ex. [B45]

TABLE F-1-continued
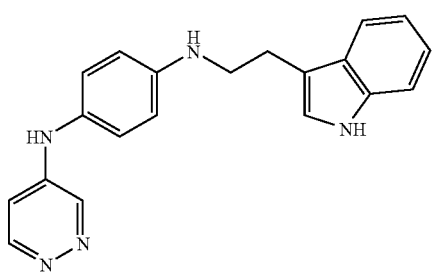
Co. No. 119;
Ex. [B46]
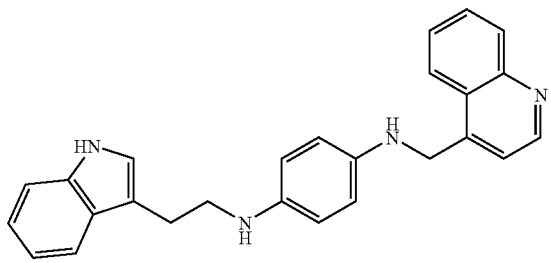
Co. No. 120; ms. 393
Ex. [B47]
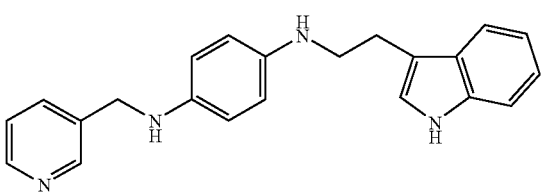
•2 HCl; Co. No. 121; mp. 130° C.
Ex. [B48]
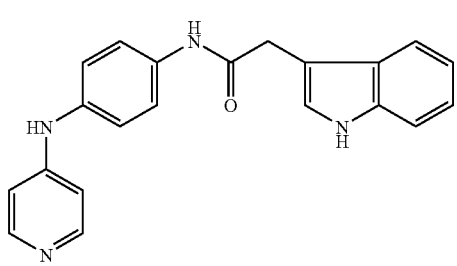
Co. No. 114; mp. 230° C.
Ex. [B8]
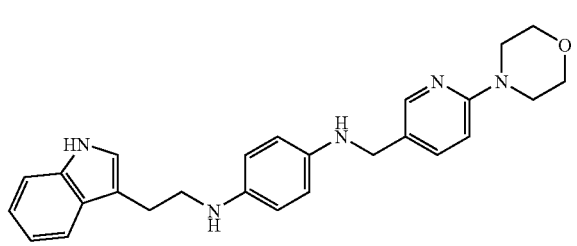
Co. No. 122; ms. 427
Ex. [B9]
TABLE F-1-continued
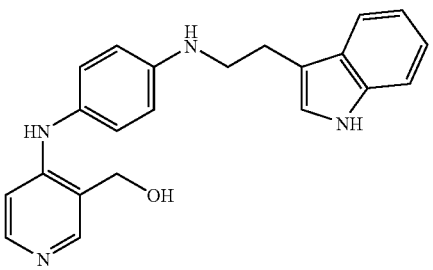
Co. No. 123; ms. 359
Ex. [B12]
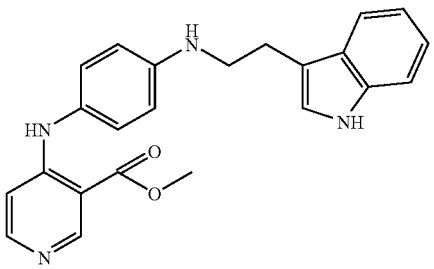
Co. No. 124; mp. 149° C.
Ex. [B12]
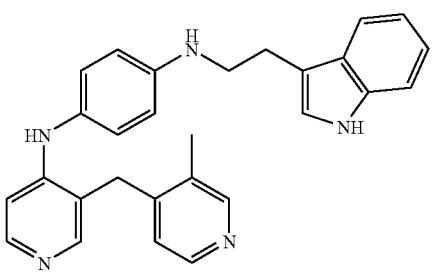
Co. No. 125; ms. 434
Ex. [B12]; from int. 42
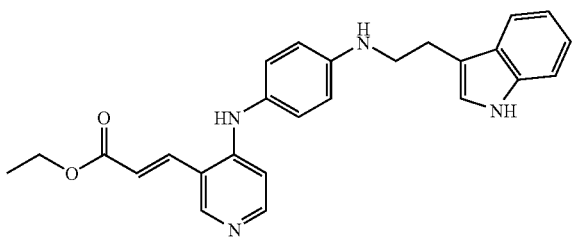
Co. No. 126; mp. 86° C.
Ex. [B12]; from int. 43
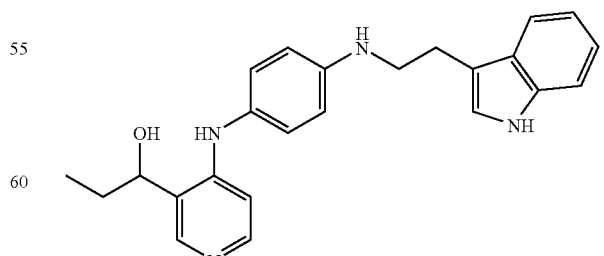
Co. No. 127; mp. 78° C.
Ex. [B12]; from int. 44

TABLE F-1-continued
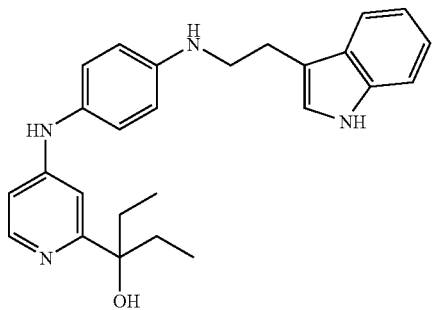
Co. No. 128; ms. 415
Ex. [B12]; from int. 45
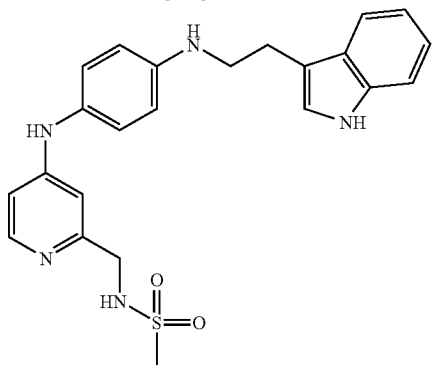
Co. No. 129; ms. 436
Ex. [B12]; from int. 46
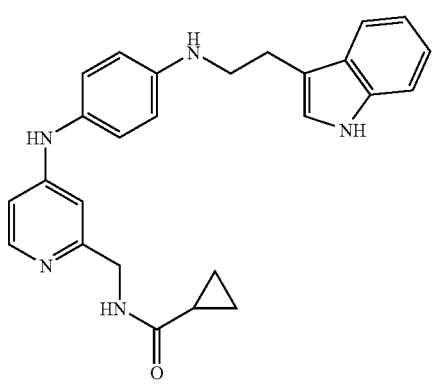
Co. No. 130; ms. 426
Ex. [B12]; from int. 47
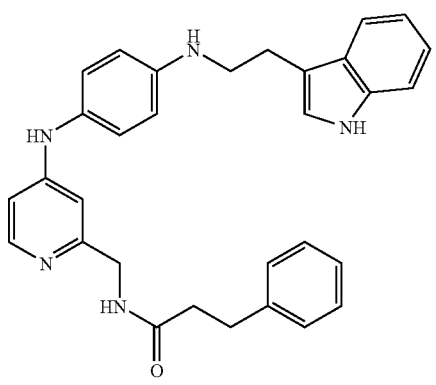
Co. No. 131; ms. 490
Ex. [B12]; from int. 48
TABLE F-1-continued
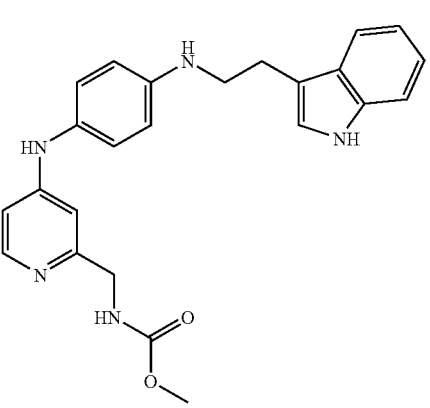
Co. No. 132; ms. 414
Ex. [B12]; from int. 49
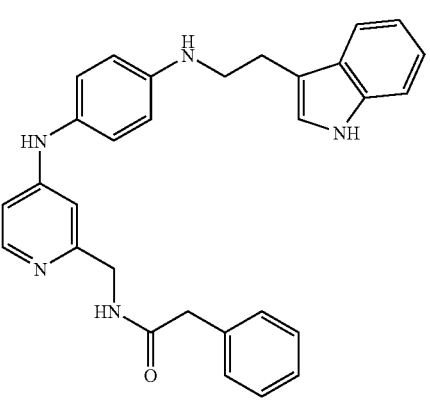
Co. No. 133; ms. 476
Ex. [B12]; from int. 50
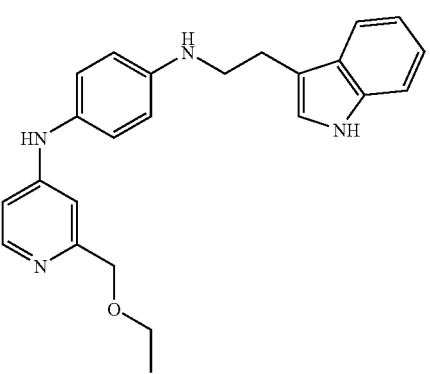
Co. No. 134; ms. 387
Ex. [B12]

TABLE F-1-continued
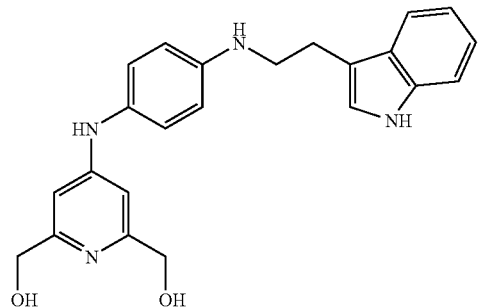
Co. No. 135; mp. 174-176° C.
Ex. [B12]
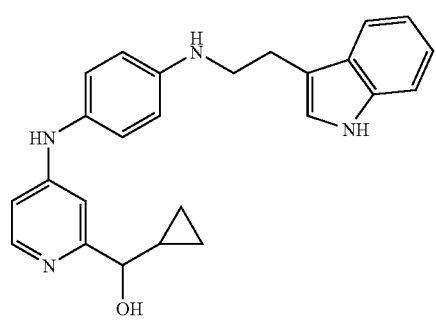
Co. No. 136; mp. 178-185° C.
Ex. [B12]; from int. 51
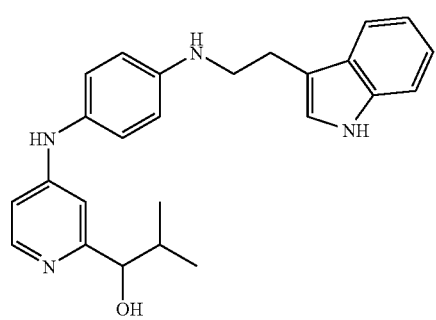
Co. No. 137; ms. 401
Ex. [B12]; from int. 53
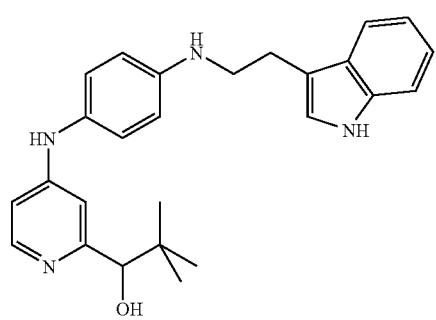
Co. No. 138; ms. 415
Ex. [B12]
TABLE F-1-continued
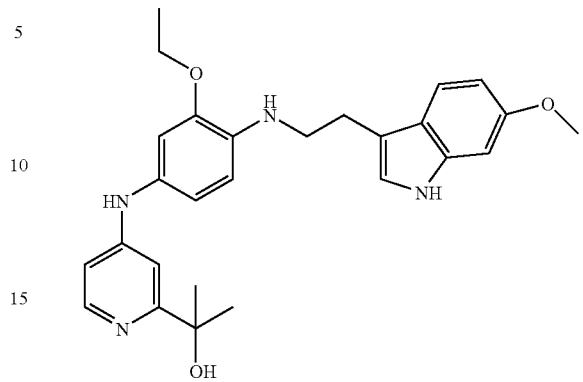
Co. No. 139; ms. 461
Ex. [B12]
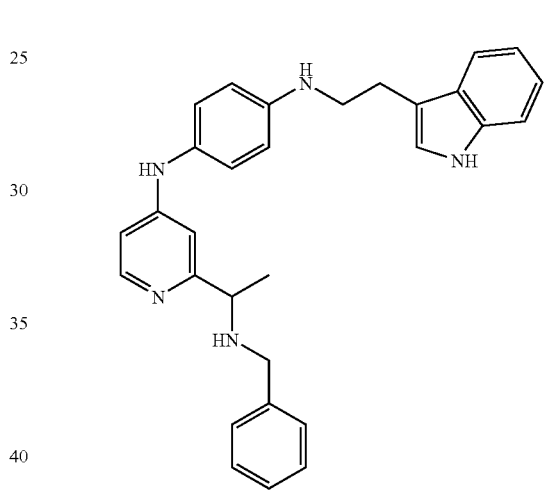
Co. No. 140; ms. 462
Ex. [B12]; from int. 54
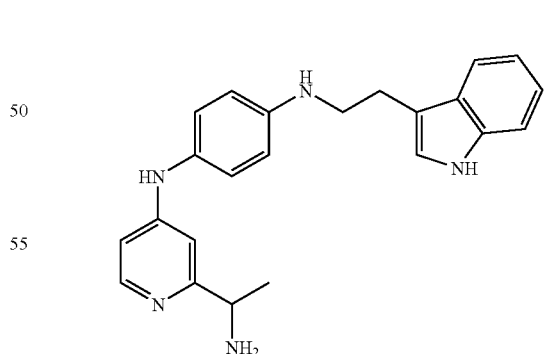
Co. No. 141; ms. 372
Ex. [B12]

TABLE F-1-continued
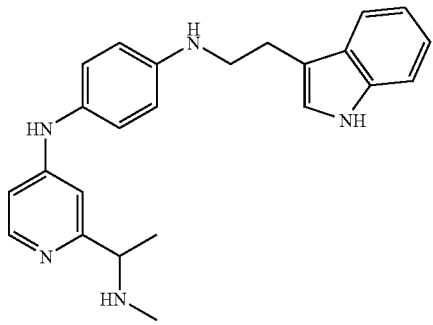
Co. No. 142; ms. 386
Ex. [B12]; from int. 55
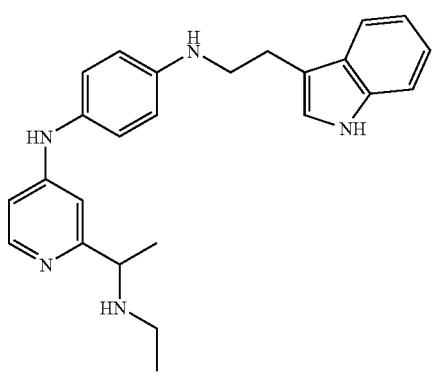
Co. No. 143; ms. 400
Ex. [B12]; from int. 56
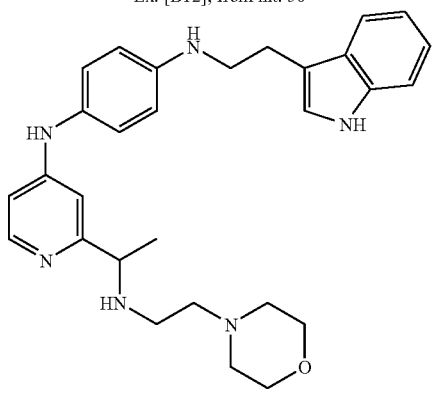
Co. No. 144; ms. 485
Ex. [B12]; from int. 57
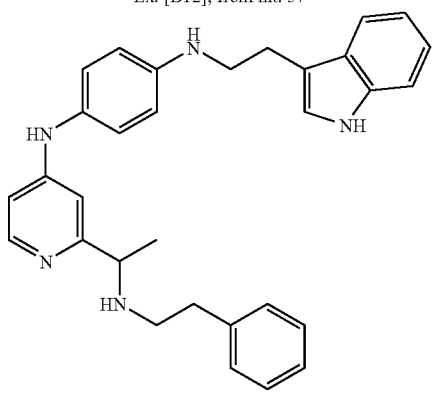
Co. No. 145; ms. 476
Ex. [B12]; from int. 58
TABLE F-1-continued
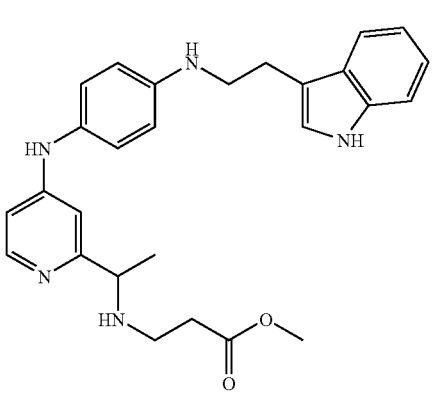
Co. No. 146; ms. 458
Ex. [B12]; from int. 58
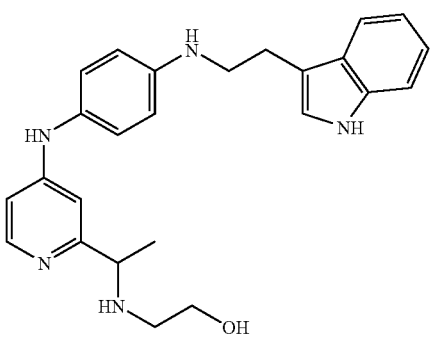
Co. No. 147; ms. 416
Ex. [B12]; from int. 60
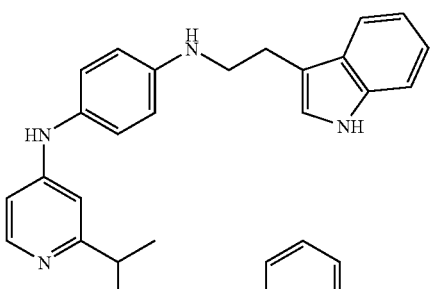
Co. No. 148; ms. 490
Ex. [B12]; from int. 61
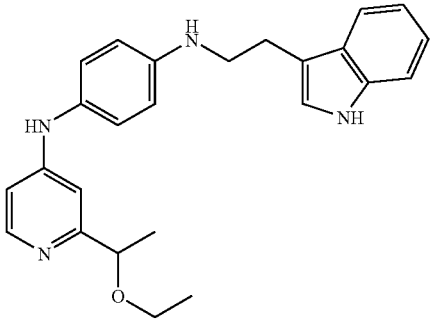
Co. No. 149; ms. 401
Ex. [B12]; from int. 62

TABLE F-1-continued
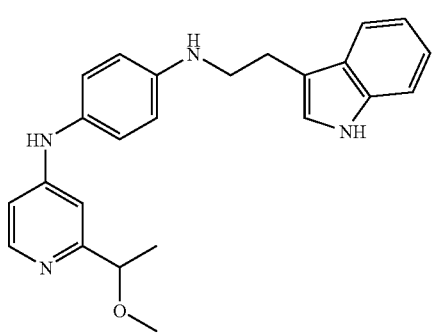
Co. No. 150; ms. 387
Ex. [B12]; from int. 63
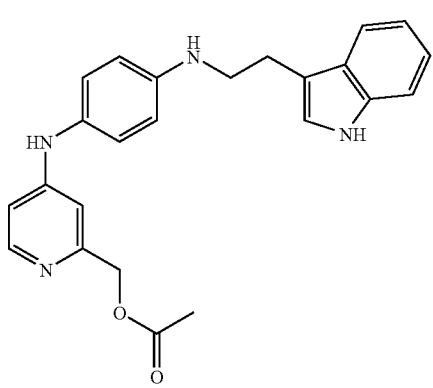
Co. No. 151; ms. 401
Ex. [B12]
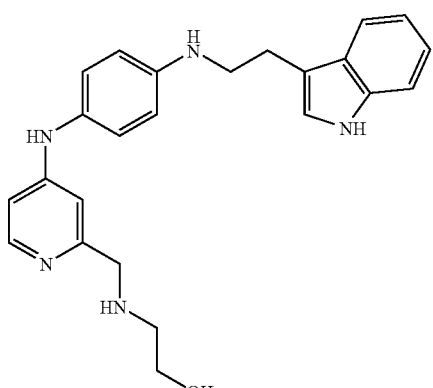
Co. No. 152; ms. 402
Ex. [B12]; from int. 64
TABLE F-1-continued
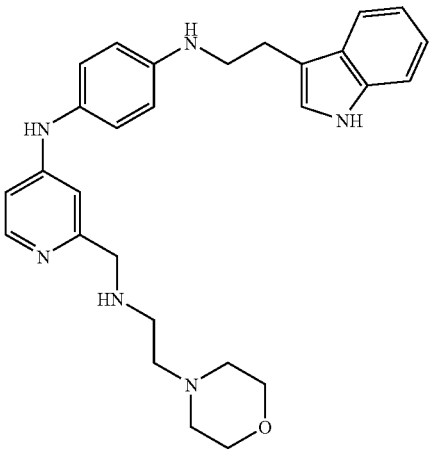
Co. No. 153; ms. 471
Ex. [B12]; from int. 65
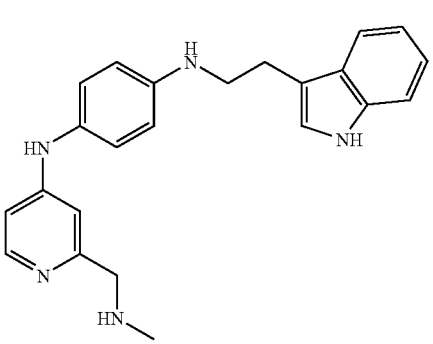
Co. No. 154; ms. 372
Ex. [B12]; from int. 66
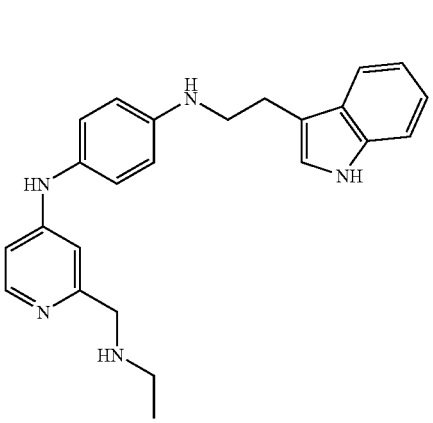
Co. No. 155; ms. 386
Ex. [B12]; from int. 67

TABLE F-1-continued
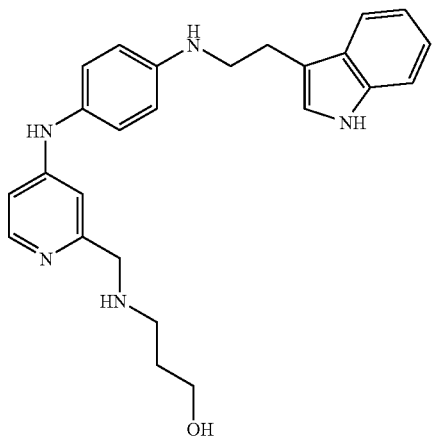
Co. No. 156; ms. 416
Ex. [B12]; from int. 69
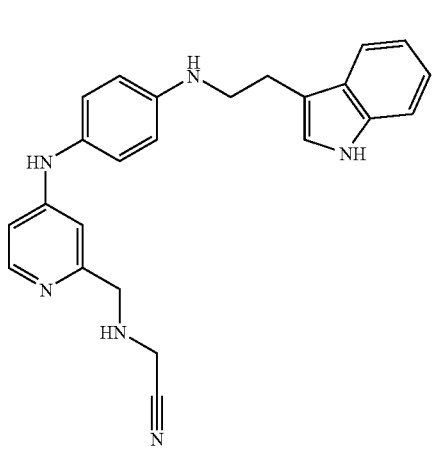
Co. No. 157; ms. 397
Ex. [B12]; from int. 70
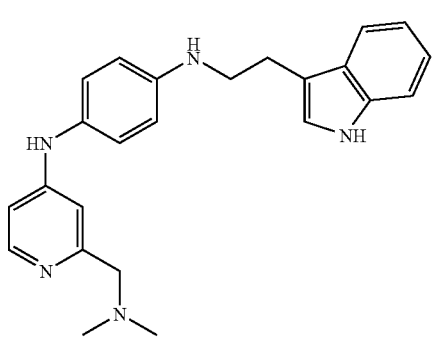
Co. No. 158; ms. 386
Ex. [B12]
TABLE F-1-continued
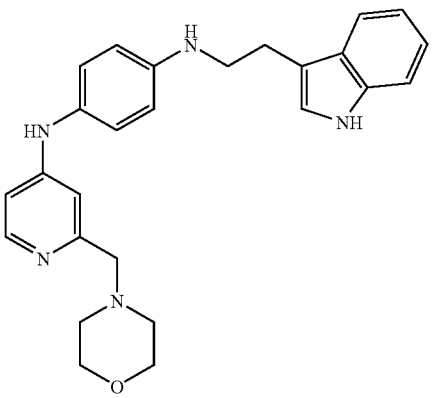
Co. No. 159; ms. 429
Ex. [B12]
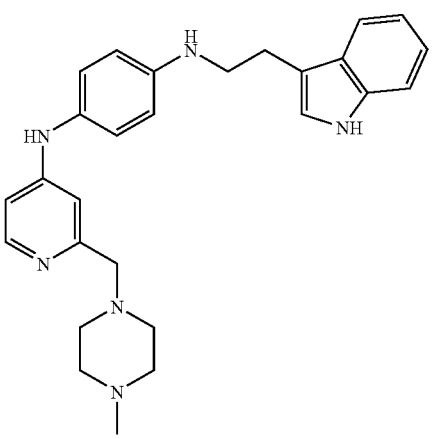
Co. No. 160; ms. 441
Ex. [B12]; from int. 71
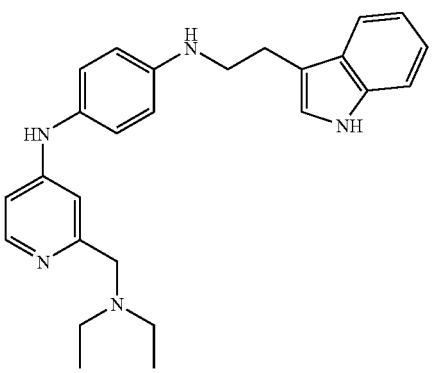
Co. No. 161; ms. 414
Ex. [B12]; from int. 72

TABLE F-1-continued
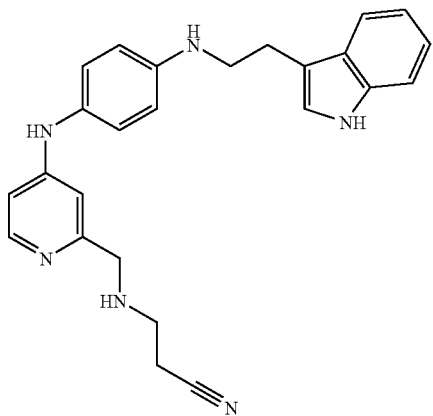
Co. No. 162; ms. 411
Ex. [B12]; from int. 73
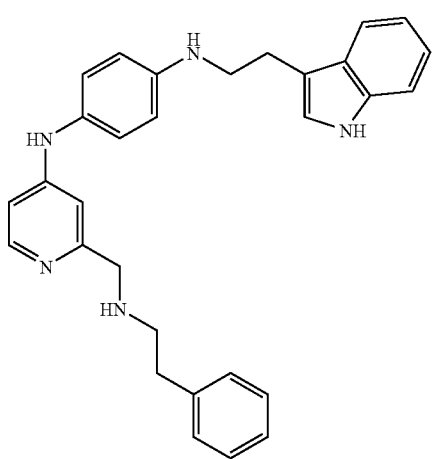
Co. No. 163; ms. 462
Ex. [B12]; from int. 74
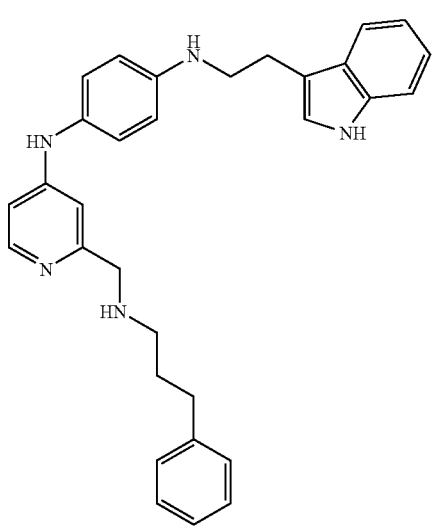
Co. No. 164; ms. 476
Ex. [B12]; from int. 75
TABLE F-1-continued
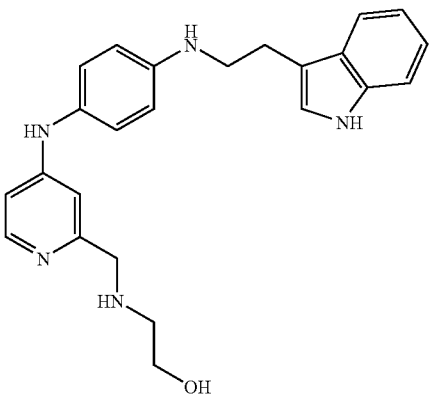
Co. No. 165; ms. 430
Ex. [B12]
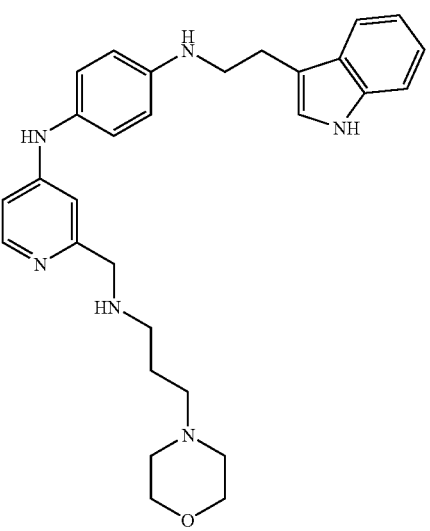
Co. No. 166; ms. 485
Ex. [B12]; from int. 76
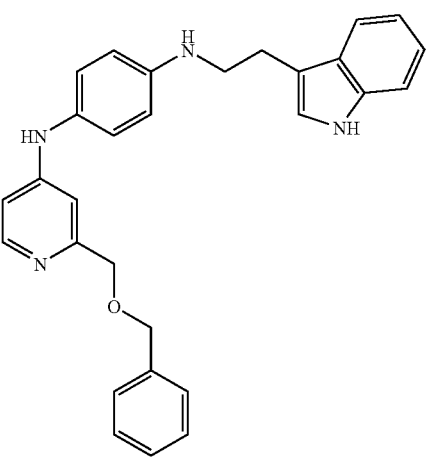
Co. No. 167; ms. 449
Ex. [B12]

TABLE F-1-continued
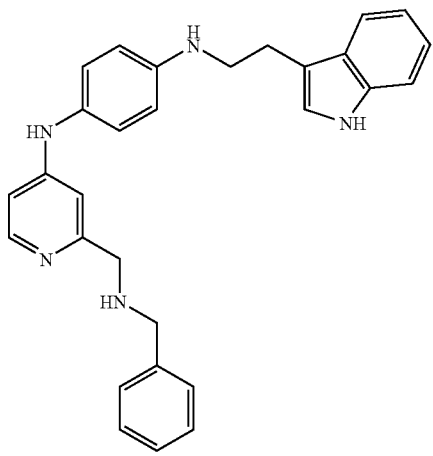
Co. No. 168; ms. 448
Ex. [B12]; from int. 77
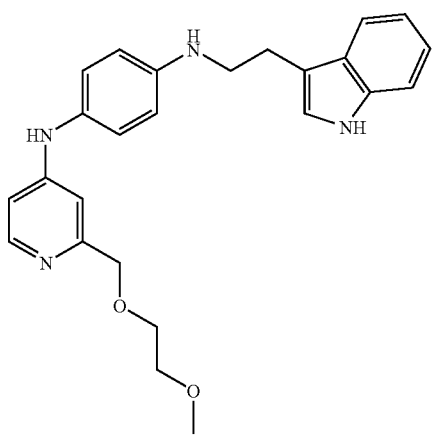
Co. No. 169; ms. 417
Ex. [B12]; from int. 78
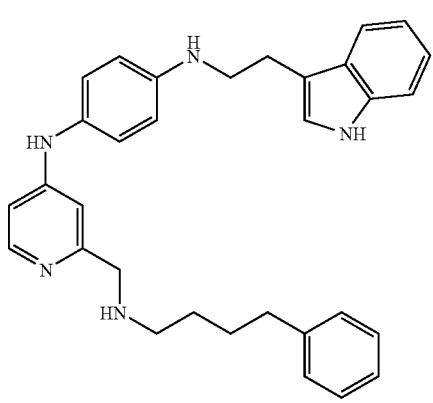
Co. No. 170; ms. 490
Ex. [B12]; from int. 79
TABLE F-1-continued
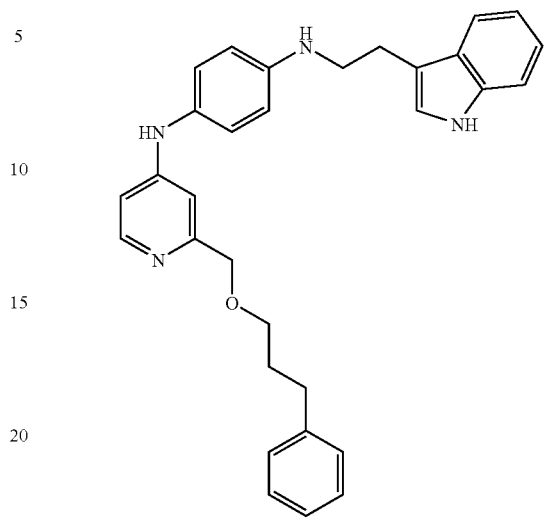
Co. No. 171; ms. 477
Ex. [B12]; from int. 80
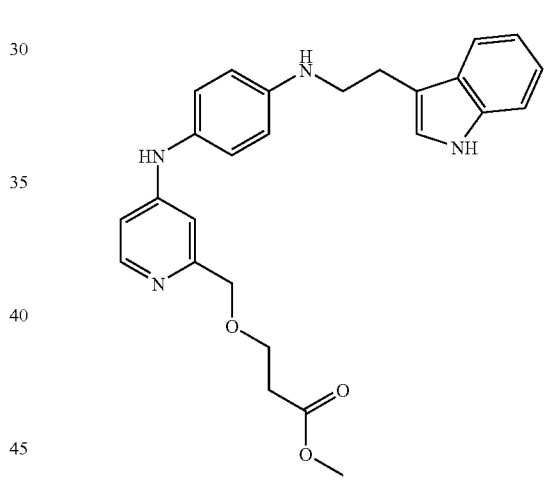
Co. No. 172; ms. 445
Ex. [B12]
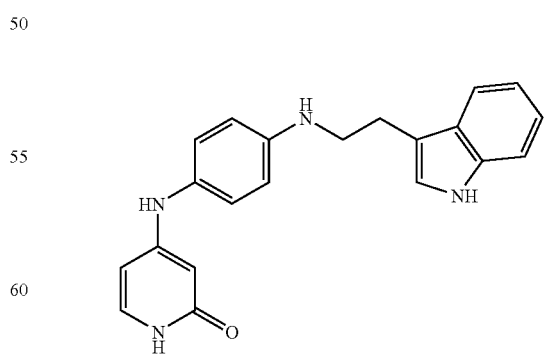
Co. No. 173; ms. 345
Ex. [B12]

TABLE F-1-continued
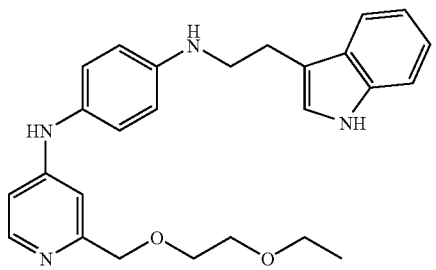
Co. No. 174; ms. 431
Ex. [B12]; from int. 81
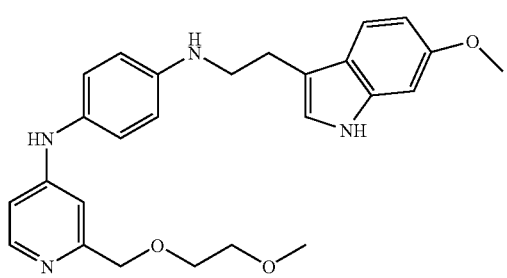
Co. No. 175; ms. 447
Ex. [B12]; from int. 78
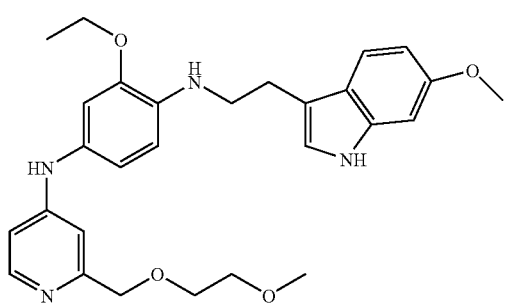
Co. No. 176; ms. 491
Ex. [B12]
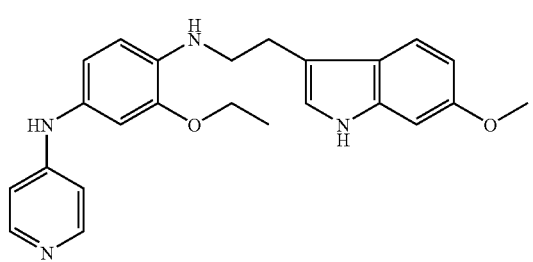
Co. No. 177; ms. 402
Ex. [B2]
TABLE F-1-continued
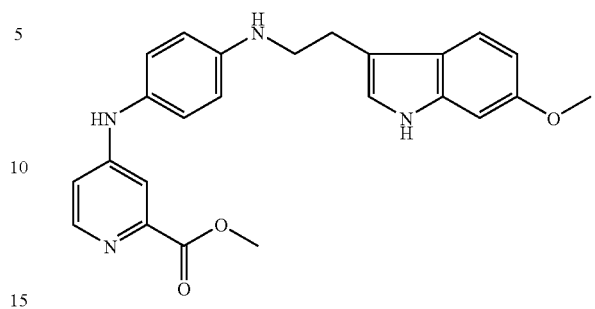
Co. No. 178; ms. 416
Ex. [B2]
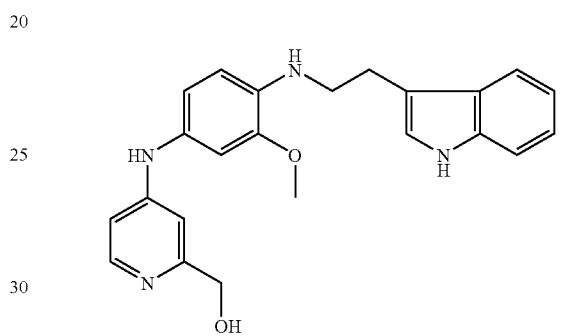
Co. No. 179; ms. 388
Ex. [B2]
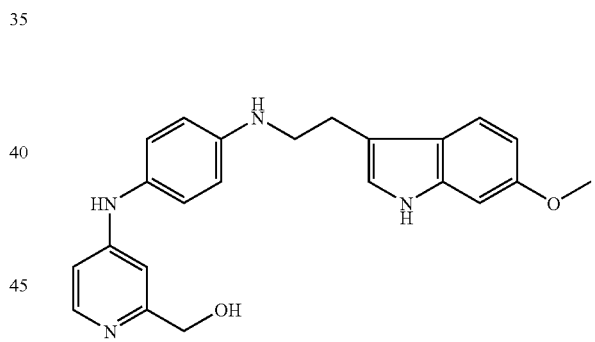
Co. No. 180; mp. 190° C.
Ex. [B2]
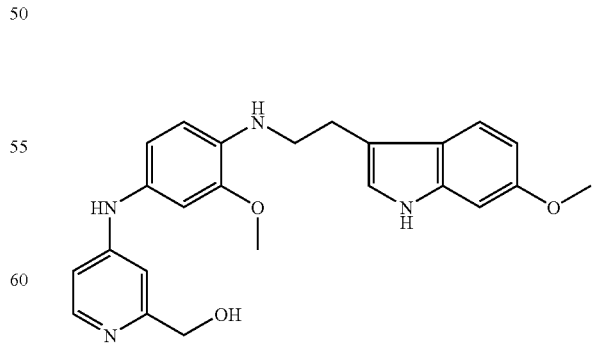
Co. No. 181; mp. 200° C.
Ex. [B2]

TABLE F-1-continued
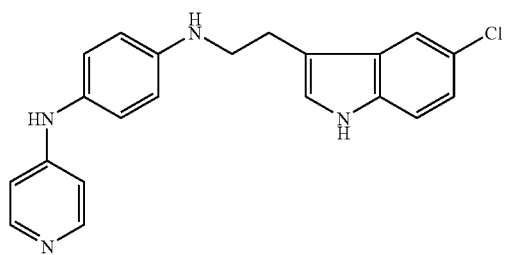
•041 HCl; Co. No. 182; mp. 114° C.
Ex. [B2]
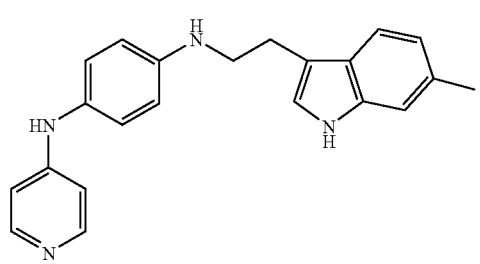
Co. No. 183; mp. 171° C.
Ex. [B2]
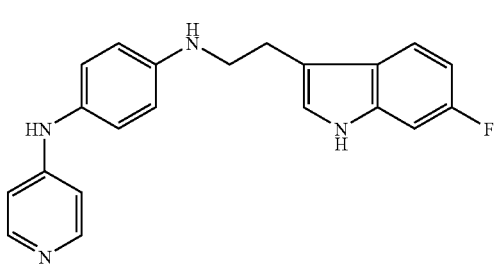
Co. No. 184; mp. 82° C.
Ex. [B2]
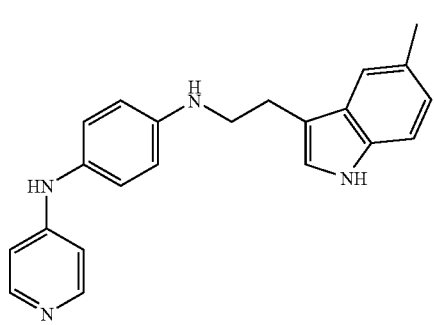
Co. No. 185; mp. 64° C.
Ex. [B2]
TABLE F-1-continued
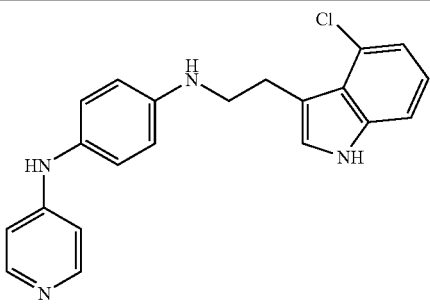
Co. No. 186; mp. 169° C.
Ex. [B2]
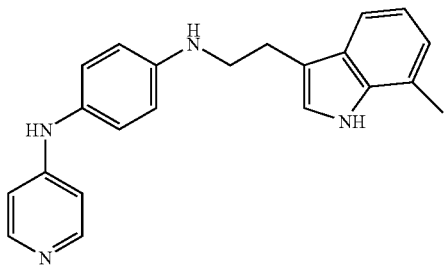
Co. No. 187; mp. 76° C.
Ex. [B2]
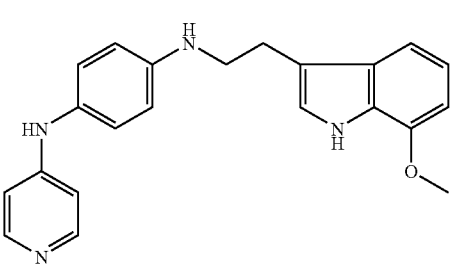
Co. No. 188; mp. 64° C.
Ex. [B2]
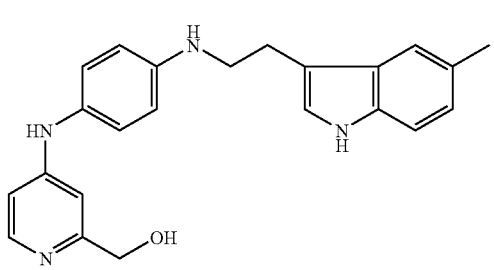
Co. No. 189; mp. 82° C.
Ex. [B2]
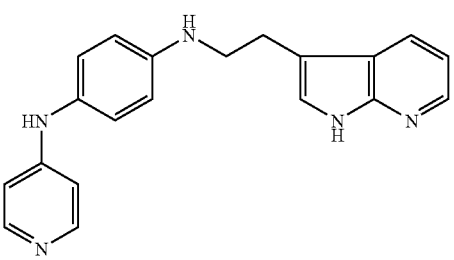
Co. No. 190; mp. 182° C.
Ex. [B2]

TABLE F-1-continued
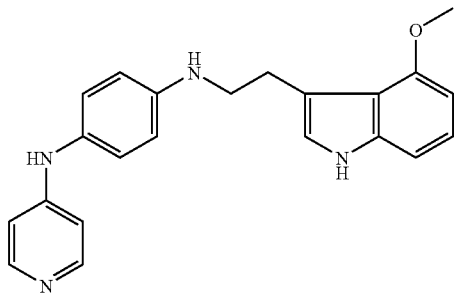
Co. No. 191; mp. 88° C.
Ex. [B2]
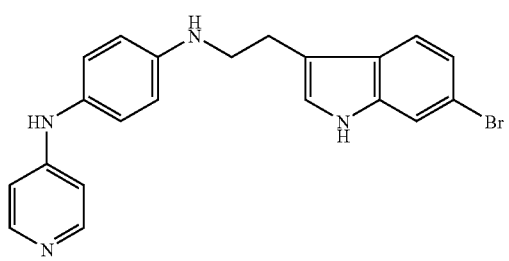
Co. No. 192; mp. 89° C.
Ex. [B2]
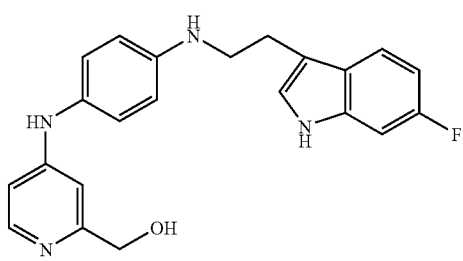
Co. No. 193; mp. 146° C.
Ex. [B2]
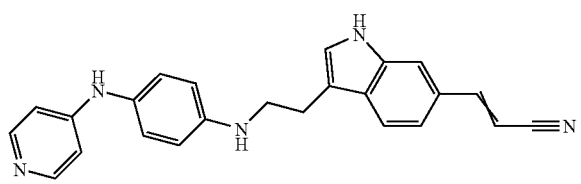
Co. No. 194; E/Z mixture (80/20)
Ex. [B2]
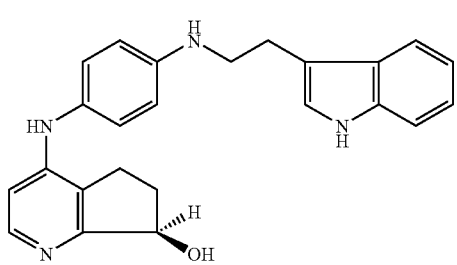
Co. No. 195; (A); mp. 112° C.
Ex. [B4]
TABLE F-1-continued
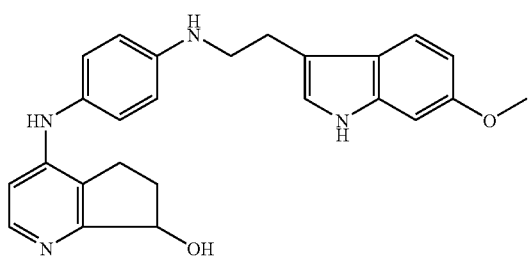
Co. No. 196; mp. 118° C.
Ex. [B4]
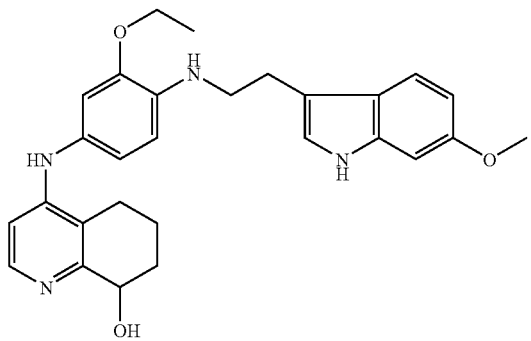
Co. No. 197; mp. 110° C.
Ex. [B5]
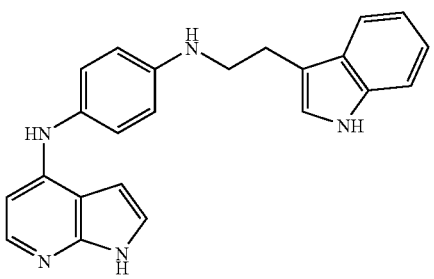
Co. No. 198; ms. 368
Ex. [B26]
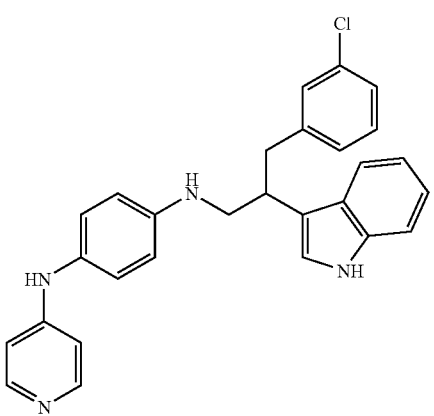
Co. No. 199; ms. 453
Ex. [B27]

TABLE F-1-continued
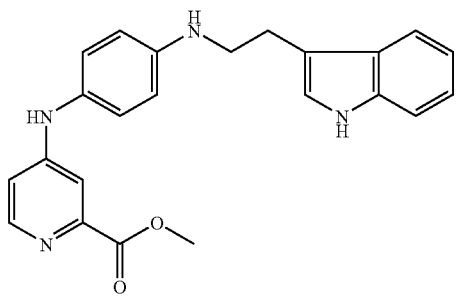
Co. No. 200; mp. 100-104° C.
Ex. [B30]
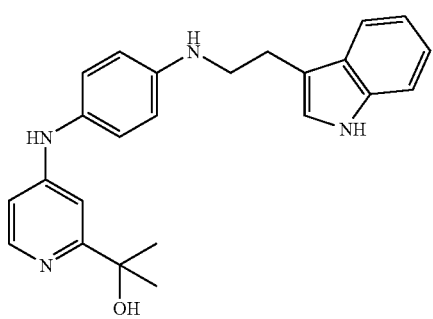
Co. No. 201; ms. 387
Ex. [B30]
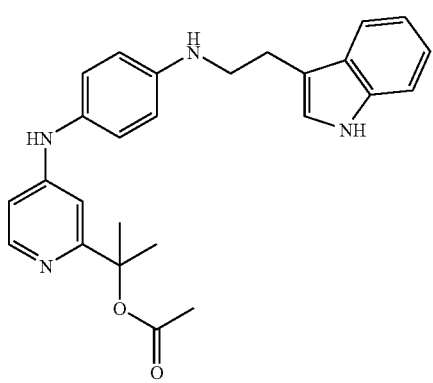
Co. No. 202; ms. 429
Ex. [B30]
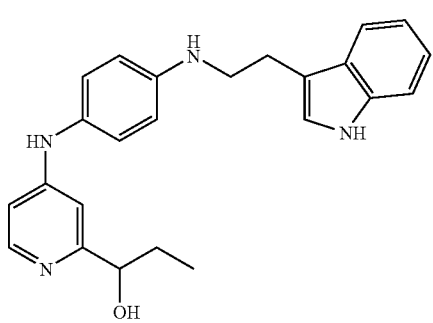
Co. No. 203; ms. 387
Ex. [B30]; from int. 82
TABLE F-1-continued
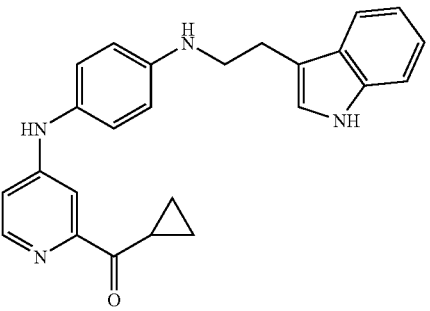
Co. No. 204; ms. 397
Ex. [B30]; from int. 52
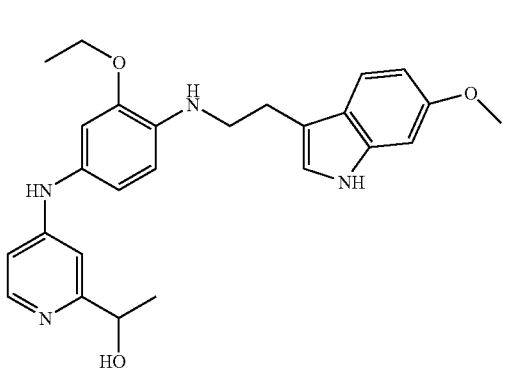
Co. No. 205; mp. 80-90° C.
Ex. [B30]; from int. 85
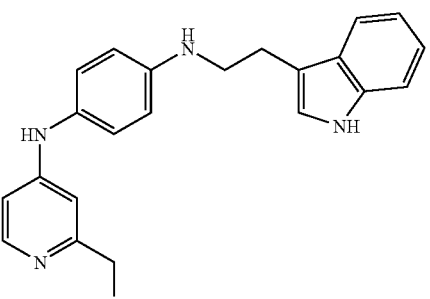
Co. No. 206; ms. 400
Ex. [B30]

TABLE F-1-continued
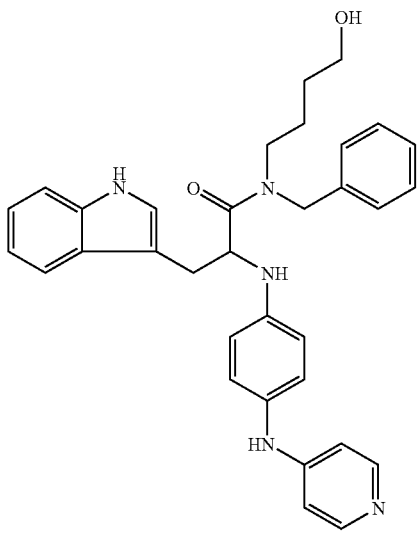
Co. No. 207; ms. 533
Ex. [B45]
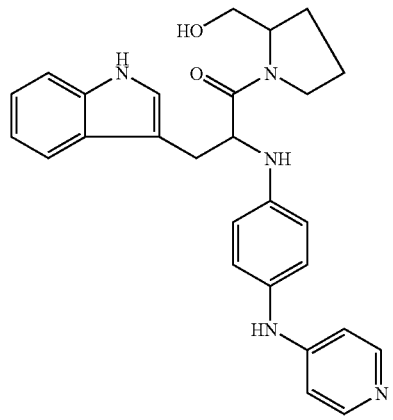
Co. No. 208; ms. 455
Ex. [B45]
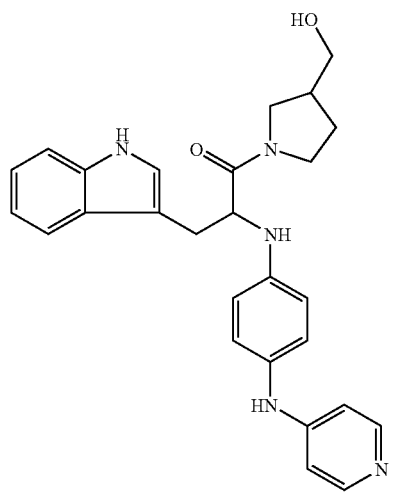
Co. No. 209; ms. 455
Ex. [B45]
TABLE F-1-continued
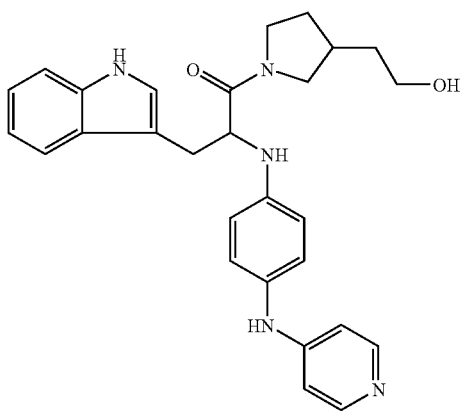
Co. No. 210; ms. 469
Ex. [B45]
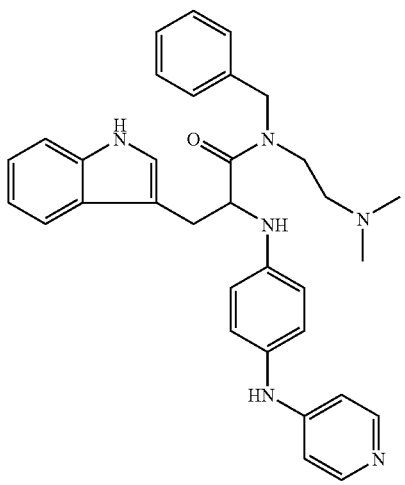
Co. No. 211; ms. 532
Ex. [B45]
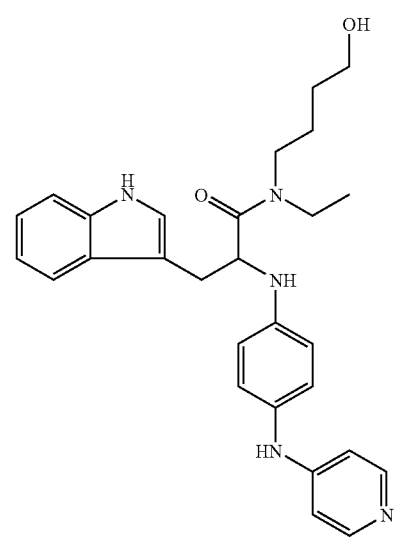
Co. No. 212; ms. 471
Ex. [B45]

TABLE F-1-continued
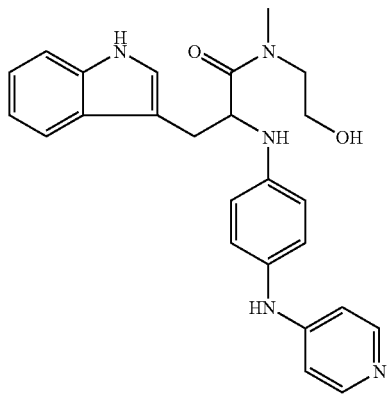
Co. No. 213; ms. 429
Ex. [B45]
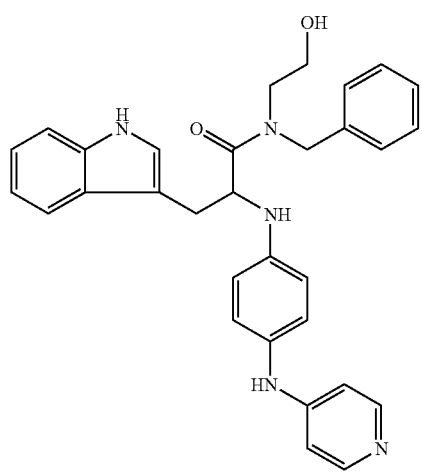
Co. No. 214; ms. 505
Ex. [B45]
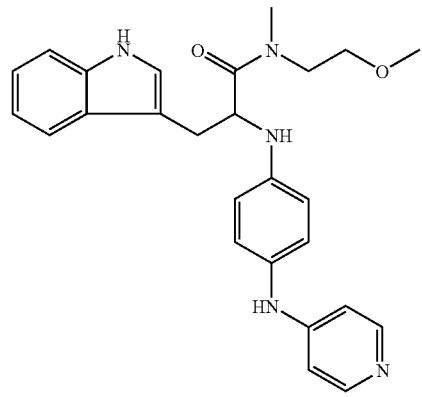
Co. No. 215; ms. 443
Ex. [B45]
TABLE F-1-continued
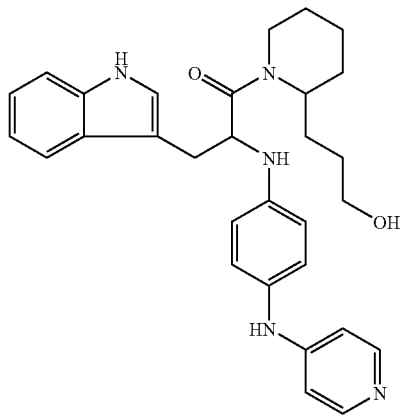
Co. No. 216; ms. 497
Ex. [B45]
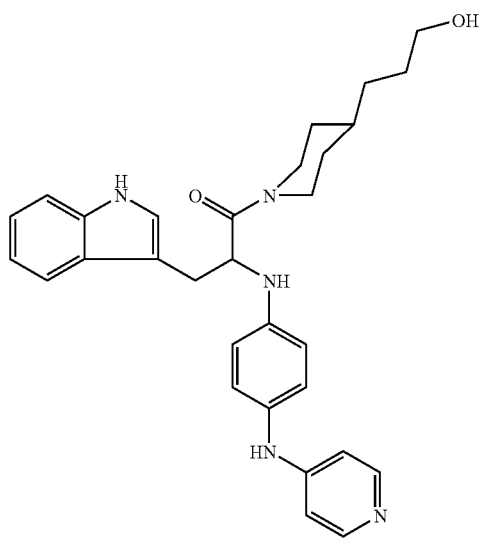
Co. No. 217; ms. 497
Ex. [B45]
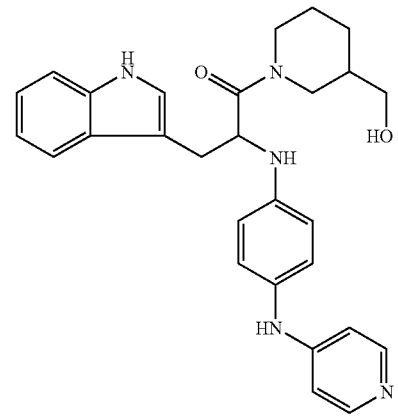
Co. No. 218; ms. 469
Ex. [B45]

TABLE F-1-continued
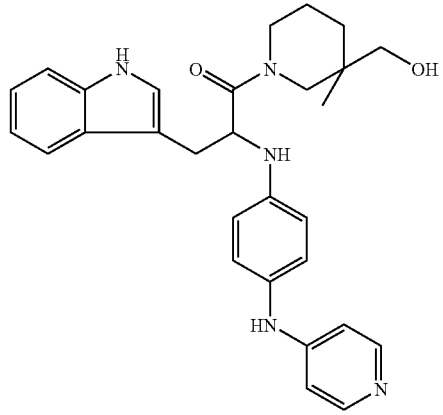
Co. No. 219; ms. 483
Ex. [B45]
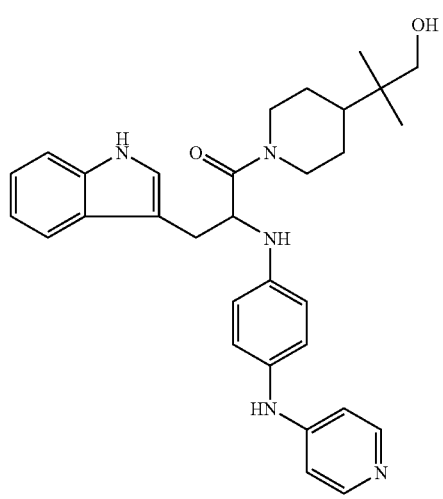
Co. No. 220; ms. 511
Ex. [B45]
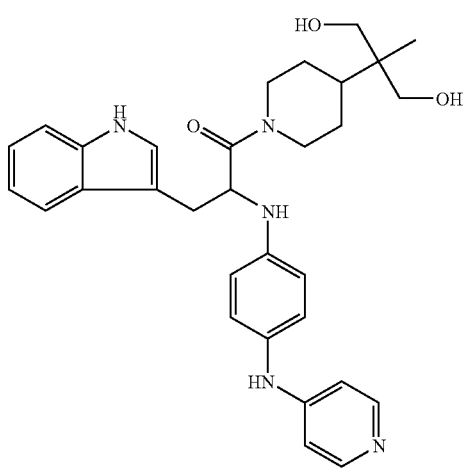
Co. No. 221; ms. 527
Ex. [B45]
TABLE F-1-continued
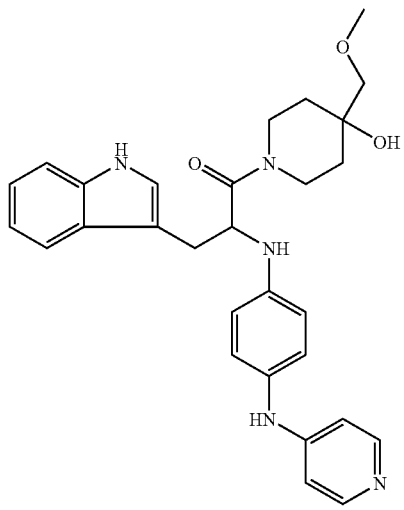
Co. No. 222; ms. 499
Ex. [B45]
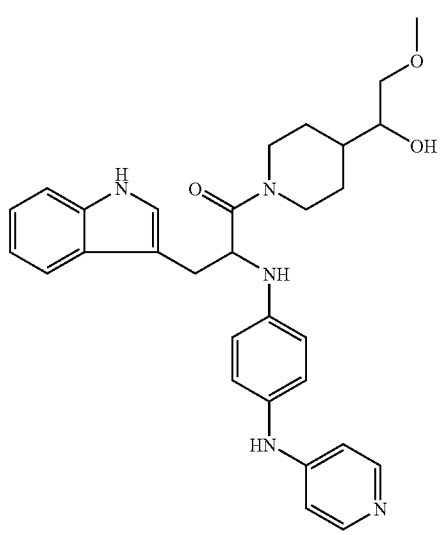
Co. No. 223; ms. 513
Ex. [B45]
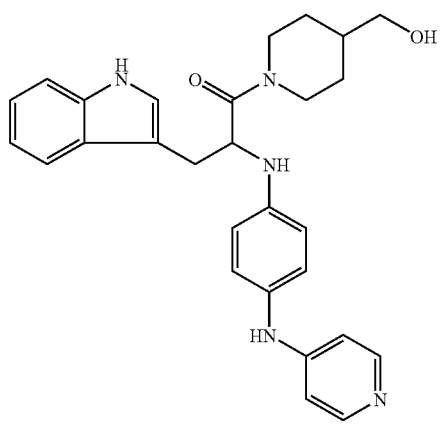
Co. No. 224; ms. 469
Ex. [B45]

TABLE F-1-continued

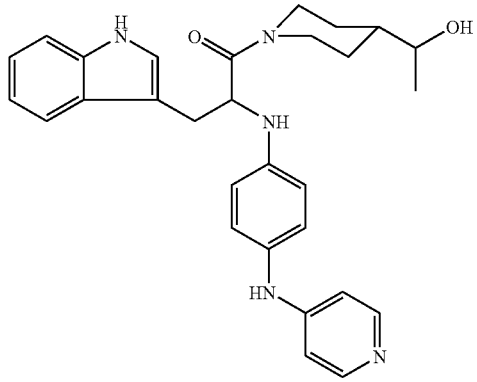

Co. No. 225; ms. 483
Ex. [B45]

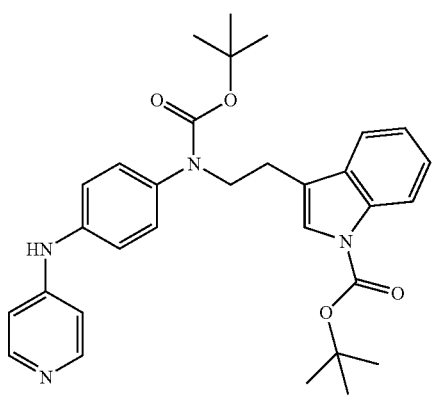

Co. No. 226; ms. 529
Ex. [B28]; from int. 23

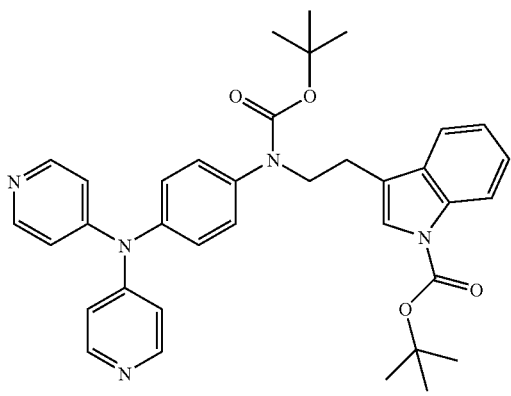

Co. No. 227; ms. 606
Ex. [B28]; from int. 23

TABLE F-1-continued

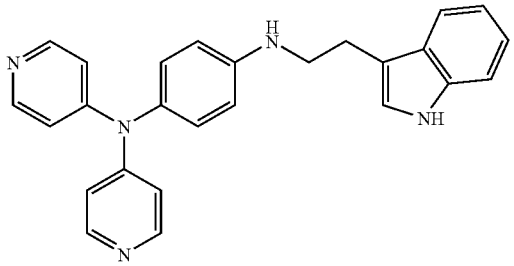

Co. No. 228; mp. 131-134° C.
Ex. [B29]; from comp. 227

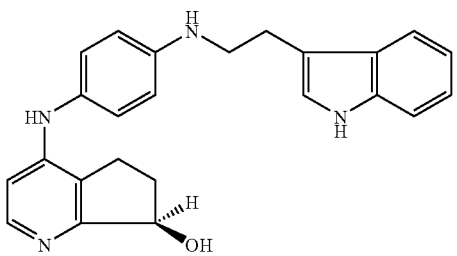

Co. No. 228; (B)
Ex. [B4]

C. Pharmacological Example

U87MG cells are human glioblastoma cells with wild type p53. In this cell line MDM2 tightly controls p53 expression.

The capacity of the compounds to preserve p53 in U87MG cells was measured with the p53 enzyme linked immunosorbent assay. The p53 assay is a "sandwich" enzyme immunoassay employing two polyclonal antibodies. A polyclonal antibody, specific for the p53 protein, has been immobilized onto the surface of the plastic wells. Any p53 present in the sample to be assayed will bind to the capture antibody. The biotinylated detector polyclonal antibody also recognizes p53 protein, and will bind to any p53, which has been retained by the capture antibody. The detector antibody, in turn, is bond by horseradish peroxidase-conjugated streptavidin. The horseradish peroxidase catalyses the conversion of the chromogenic substrate o-phenylene diamine, the intensity of which is proportional to the amount of p53 protein bond to the plate. The colored reaction product is quantified using a spectrophotometer. Quantitation is achieved by the construction of a standard curve using known concentrations of purified recombinant HIS tagged p53 protein (see example C.1.).

Cellular activity of the compounds of formula (I) was determined on U87MG tumour cells using a colorimetric assay for cell toxicity or survival (see example C.2).

C.1. p53 ELISA

U87MG cells (ATCC) were cultivated in Dulbecco's minimal essential medium (DMEM) supplemented with 10% foetal calf serum (FCS), 2 mM L-glutamine, 1 mM sodium pyruvate, 1.5 g/l sodium bicarbonate and gentamycin at 37° C. in a humidified incubator with 5% $CO_2$.

U87MG cells were seeded at 30.000 cells per well in a 96 well plate, cultured for 24 hours and treated with compound for 16 hours at 37° C. in a humidified incubator. After incubation, the cells were washed once with phosphate-buffered saline and 30 µl, per well, low salt RIPA buffer (20 mM tris, pH7.0, 0.5 mM EDTA, 1% Nonidet P40, 0.5% DOC, 0.05%

SDS, 1 mM PMSF, 1 µg/ml aprotinin and 0.5µ/ml leupeptin) was added. Plates were placed on ice for 30 minutes to complete the lysis. p53 protein was detected in de lysates by using the sandwich ELISA, described below.

High binding polystyrene EIA/RIA 96 well plates (Costar 9018) were coated with the capture antibody pAb122 (Roche 1413147) at a concentration of 2 µg/ml in coating buffer (0.1 M NaHCO$_3$ pH8.2), 50 µl per well. The antibody was allowed to adhere overnight at 4° C. Coated plates were washed once with phosphate-buffered saline (PBS)/0.05% Tween 20 and 300 µl of blocking buffer (PBS, 1% bovine serum albumins (BSA)) was added, for an incubation period of 2 hours at room temperature. Dilutions of purified recombinant HIS tagged p53 protein, ranging from 3-200 ng/ml, were made in blocking buffer and used as standards.

Plates were washed twice with PBS/0.05% Tween 20 and blocking buffer or standards were added at 80 µl/well. To the standards, 20 µl of lysis buffer was added. The samples were added to the other wells at 20 µl lysate/well. After an overnight incubation at 4° C., plates were washed twice with PBS/0.05% Tween 20. Aliquots of 100 µl secondary polyclonal antibody p53(FL-393) (Tebubio, sc-6243) at a concentration of 1 µg/ml in blocking buffer were added to each well and allowed to adhere for 2 hours at room temperature. Plates were washed three times with PBS/0.05% Tween 20. Detection antibody anti-rabbit HRP (sc-2004, Tebubio) at 0.04 µg/ml in PBS/1% BSA was added and incubated for 1 hour at room temperature. Plates were washed three times with PBS/0.05% Tween 20 and 100 µl of substrate buffer was added (substrate buffer was prepared shortly before use by adding 1 tablet of 10 mg o-phenylene diamine (OPD) from Sigma and 125 µl 3% H$_2$O$_2$ to 25 ml OPD buffer: 35 mM citric acid, 132 mM Na$_2$HPO$_4$, pH5.6). After 5 to 10 minutes, colour reaction was stopped by adding 50 µl stop buffer (1 M H$_2$SO$_4$) per well. The absorbance at dual wavelengths of 450/655 nm was measured using a Biorad micro plate reader and the results were then analyzed.

For each experiment, controls (containing no drug) and a blank incubation (containing no cells or drugs) were run in parallel. The blank value was subtracted from all control and sample values. For each sample, the value of p53 (in absorbance units) was expressed as the percentage of the value for p53 present in the control. Percentage preservation higher than 130% was defined as significant. Herein the effects of test compounds are expressed as the lowest dose giving at least 130% of the value for p53 present in the control (LAD) (see table F-2).

C.2. Proliferation Assay

All compounds tested were dissolved in DMSO and further dilutions were made in culture medium. Final DMSO concentrations never exceeded 0.1% (v/v) in cell proliferation assays. Controls contained U87MG cells and DMSO without compound and blanks contained DMSO but no cells.

U87MG cells were seeded in 96-well cell culture plates at 3000 cells/well/100 µl. 24 hours later, medium was changed and compound and/or solvent were added to a final volume of 200 µl. Following 4 days of incubation, medium was replaced by 200 µl fresh medium and cell growth was assessed using a MTT-based assay. Therefore, 25 µl of MTT solution (0.5% MTT research grade from Serva in phosphate-buffered saline) was added to each well and the cells were further incubated for 2 hours at 37° C. The medium was then carefully aspirated and the blue MTT-formazan product was dissolved by adding to each well 25 µl 0.1M glycin and 100 µl DMSO. The plates were shaken for another 10 min on a micro plate shaker before reading absorbance at 540 nm by a Biorad micro plate reader.

Within an experiment, the results for each experimental condition are the mean of 3 replicate wells. For initial screening purposes, compounds were tested at a single fixed concentration of $10^{-5}$ M. For active compounds, the experiments were repeated to establish full concentration-response curves. For each experiment, controls (containing no drug) and a black incubation (containing no cells or drugs) were run in parallel. The blank value was subtracted from all control and sample values. For each sample, the mean value for cell growth (in absorbance units) was expressed as a percentage of the mean value for cell growth of the control. When appropriate, $IC_{50}$-values (concentration of the drug, needed to reduce cell growth to 50% of the control) were computed using probit analysis for graded data (Finney, D. J., Probit Analyses, $2^{nd}$ Ed. Chapter 10, Graded Responses, Cambridge University Press, Cambridge 1962). Herein the effects of test compounds are expressed as $pIC_{50}$ (the negative log value of the $IC_{50}$-value) (see table F-2).

TABLE F-2

Table F-2 lists the results of the compounds that were tested according to example C.1 and C.2.

| Co No | p53-elisa LAD | cell proliferation $pIC_{50}$ |
|---|---|---|
| 1 | 3.0E−08 | >8.0 |
| 2 | 3.0E−07 | 7.2 |
| 3 | >1.0E−05 | 5.3 |
| 4 | 3.0E−08 | 8.0 |
| 5 | 3.0E−08 | |
| 6 | >1.0E−05 | 5.5 |
| 7 | 1.0E−05 | 5.7 |
| 8 | >1.0E−05 | 5.3 |
| 9 | >1.0E−05 | |
| 10 | >1.0E−05 | 5.9 |
| 11 | >1.0E−05 | 5.3 |
| 12 | 3.0E−07 | 7.9 |
| 13 | 1.0E−07 | 7.6 |
| 14 | 3.0E−07 | 7.4 |
| 15 | >1.0E−05 | 7.3 |
| 16 | >1.0E−05 | 7.4 |
| 17 | >1.0E−05 | 6.2 |
| 18 | 1.0E−07 | 6.3 |
| 19 | 3.0E−07 | 6.7 |
| 20 | 3.0E−07 | 7.0 |
| 21 | 3.0E−08 | 8.0 |
| 22 | 1.0E−07 | 7.7 |
| 23 | 1.0E−06 | 6.4 |
| 24 | 1.0E−07 | >8.0 |
| 25 | >1.0E−05 | 7.4 |
| 26 | 3.0E−06 | 7.0 |
| 27 | 3.0E−06 | 7.1 |
| 28 | >1.0E−05 | 6.7 |
| 29 | 3.0E−06 | 6.6 |
| 30 | >1.0E−05 | 6.5 |
| 31 | >1.0E−05 | 5.9 |
| 32 | 3.0E−06 | 6.8 |
| 33 | >1.0E−05 | 7.2 |
| 34 | >1.0E−05 | 7.3 |
| 35 | 1.0E−06 | 7.4 |
| 36 | 1.0E−06 | 6.7 |
| 37 | 3.0E−07 | 6.8 |
| 38 | >1.0E−05 | |
| 39 | 1.0E−05 | 6.2 |
| 40 | >1.0E−05 | |
| 41 | >1.0E−05 | |
| 42 | >1.0E−05 | |
| 43 | >1.0E−05 | |
| 44 | >1.0E−05 | |
| 45 | >1.0E−05 | 6.0 |

TABLE F-2-continued

Table F-2 lists the results of the compounds that were tested according to example C.1 and C.2.

| Co No | p53-elisa LAD | cell proliferation $pIC_{50}$ |
|---|---|---|
| 46 | 1.0E−06 | 6.6 |
| 47 | 1.0E−05 | 6.8 |
| 48 | 1.0E−05 | 6.8 |
| 49 | >1.0E−05 | <5.0 |
| 50 | 3.0E−06 | 7.0 |
| 51 | >1.0E−05 | 6.5 |
| 52 | >1.0E−05 | 6.3 |
| 53 | >1.0E−05 | 6.2 |
| 54 | 1.0E−06 | 6.9 |
| 55 | 3.0E−07 | 6.3 |
| 56 | >1.0E−05 | 5.6 |
| 57 | >1.0E−05 | 6.1 |
| 58 | >1.0E−05 | <5.0 |
| 59 | 1.0E−06 | 6.4 |
| 60 | >1.0E−05 | 7.0 |
| 61 | >1.0E−05 | 6.5 |
| 62 | >1.0E−05 | 5.6 |
| 63 | >1.0E−05 | 5.8 |
| 64 | 1.0E−06 | 6.4 |
| 65 | >1.0E−05 | <5.0 |
| 66 | 3.0E−07 | 7.2 |
| 67 | >1.0E−05 | 5.9 |
| 68 | >1.0E−05 | 5.6 |
| 69 | 1.0E−07 | 7.0 |
| 70 | >1.0E−05 | 6.6 |
| 71 | >1.0E−05 | 6.1 |
| 72 | >1.0E−05 | 5.7 |
| 73 | >1.0E−05 | 6.3 |
| 74 | >1.0E−05 | 5.8 |
| 75 | >1.0E−05 | 5.5 |
| 76 | >1.0E−05 | <5.0 |
| 77 | >1.0E−05 | 5.5 |
| 78 | >1.0E−05 | 5.0 |
| 79 | >1.0E−05 | 5.6 |
| 82 | >1.0E−05 | <5.0 |
| 83 | >1.0E−05 | 5.5 |
| 84 | >1.0E−05 | 5.8 |
| 85 | >1.0E−05 | 6.8 |
| 86 | >1.00E−05 | <5.0 |
| 87 | >1.00E−05 | <5.0 |
| 88 | >1.00E−05 | 5.5 |
| 89 | 3.00E−06 | 5.4 |
| 90 | >1.00E−05 | 5.6 |
| 91 | >1.00E−05 | 5.6 |
| 92 | >1.00E−05 | 5.5 |
| 93 | >1.00E−05 | <5.0 |
| 95 | >1.00E−05 | 5.1 |
| 96 | >1.00E−05 | <5.0 |
| 97 | 1.00E−06 | <5.0 |
| 98 | >1.00E−05 | 5.4 |
| 99 | 1.00E−05 | 5.6 |
| 100 | >1.00E−05 | 5.4 |
| 101 | >1.00E−05 | 5.6 |
| 102 | >1.00E−05 | <5.0 |
| 103 | 1.00E−05 | 5.4 |
| 104 | 3.00E−06 | 5.5 |
| 105 | >1.00E−05 | 5.1 |
| 106 | >1.00E−05 | 5.8 |
| 107 | >1.00E−05 | |
| 108 | >1.00E−05 | |
| 109 | 1.00E−06 | <5.0 |
| 110 | 1.00E−07 | 8.0 |
| 111 | 1.00E−07 | 7.1 |
| 112 | 1.00E−07 | 7.5 |
| 113 | >1.00E−05 | <5.0 |
| 114 | >1.00E−05 | <5.0 |
| 114 | >1.00E−05 | <5.0 |
| 115 | >1.00E−05 | <5.0 |
| 116 | >1.00E−05 | <5.0 |
| 117 | >1.00E−05 | <5.0 |
| 118 | >1.00E−05 | <5.0 |
| 119 | >1.00E−05 | <5.0 |
| 120 | >1.00E−05 | 5.3 |
| 121 | >1.00E−05 | <5.0 |
| 123 | | 5.3 |
| 124 | | 5.3 |
| 125 | >1.00E−05 | 5.4 |
| 126 | >1.00E−05 | <5.0 |
| 127 | >1.00E−05 | 5.1 |
| 128 | >1.00E−05 | 5.5 |
| 129 | 3.00E−06 | 5.7 |
| 130 | >1.00E−05 | 5.8 |
| 131 | >1.00E−05 | 5.6 |
| 132 | >1.00E−05 | <5.0 |
| 134 | >1.00E−05 | 5.9 |
| 135 | 1.00E−06 | 6.0 |
| 136 | >1.00E−05 | 5.7 |
| 137 | >1.00E−05 | 5.5 |
| 138 | >1.00E−05 | 5.8 |
| 139 | >1.00E−05 | 5.7 |
| 140 | >1.00E−05 | 5.6 |
| 141 | 1.00E−05 | 5.4 |
| 142 | 3.00E−06 | 5.5 |
| 143 | >1.00E−05 | 5.5 |
| 144 | | 5.5 |
| 145 | | 5.6 |
| 146 | >1.00E−05 | 5.1 |
| 147 | >1.00E−05 | 5.3 |
| 148 | 3.00E−07 | 5.5 |
| 149 | >1.00E−05 | 5.7 |
| 150 | 1.00E−06 | 5.5 |
| 151 | 1.00E−06 | <5.0 |
| 152 | >1.00E−05 | 5.0 |
| 153 | >1.00E−05 | 5.6 |
| 154 | >1.00E−05 | 5.5 |
| 155 | >1.00E−05 | 5.7 |
| 156 | >3.00E−06 | 5.5 |
| 157 | >1.00E−05 | 5.8 |
| 158 | >1.00E−05 | <5.0 |
| 159 | >1.00E−05 | 5.5 |
| 160 | >1.00E−05 | 6.4 |
| 161 | >1.00E−05 | 6.0 |
| 162 | >1.00E−05 | 5.5 |
| 163 | >1.00E−05 | 5.5 |
| 164 | >1.00E−05 | 5.6 |
| 165 | 3.00E−06 | 5.3 |
| 166 | >1.00E−05 | <5.0 |
| 167 | >1.00E−05 | 5.4 |
| 168 | >1.00E−05 | 5.7 |
| 169 | >1.00E−05 | 6.4 |
| 170 | 3.00E−07 | 5.5 |
| 171 | >1.00E−05 | <5.0 |
| 172 | >1.00E−05 | <5.0 |
| 173 | >1.00E−05 | <5.0 |
| 174 | >1.00E−05 | |
| 175 | >1.00E−05 | |
| 176 | 3.00E−06 | |
| 177 | 3.00E−07 | 7.3 |
| 178 | >1.00E−05 | 5.8 |
| 179 | 3.00E−06 | 6.6 |
| 180 | >1.00E−05 | 6.2 |
| 181 | 3.00E−07 | 6.6 |
| 182 | >1.00E−05 | 5.8 |
| 183 | 1.00E−05 | 6.3 |
| 184 | >1.00E−05 | 6.0 |
| 185 | 3.00E−06 | 5.7 |
| 186 | 1.00E−06 | 6.0 |
| 187 | 1.00E−06 | 6.4 |
| 188 | 1.00E−06 | 6.1 |
| 189 | >1.00E−05 | 5.5 |
| 190 | >1.00E−05 | 5.4 |
| 191 | >1.00E−05 | 5.5 |
| 192 | 1.00E−06 | <5.0 |
| 193 | 3.00E−06 | 6.0 |

TABLE F-2-continued

Table F-2 lists the results of the compounds that were tested according to example C.1 and C.2.

| Co No | p53-elisa LAD | cell proliferation pIC$_{50}$ |
|---|---|---|
| 194 | >1.00E−05 | 5.2 |
| 195 | 1.00E−06 | 7.1 |
| 196 | >1.00E−05 | 6.7 |
| 197 | 1.00E−07 | 6.6 |
| 198 | 1.00E−06 | 5.9 |
| 199 | >1.00E−05 | 5.7 |
| 201 | >1.00E−05 | 5.5 |
| 202 | >1.00E−05 | 5.5 |
| 203 | >1.00E−05 | 5.5 |
| 204 | >1.00E−05 | 5.1 |
| 205 | 3.00E−06 | 6.1 |
| 206 | >1.00E−05 | 5.5 |
| 207 | >1.00E−05 | 6.1 |
| 208 | 3.00E−06 | <5.0 |
| 209 | >1.00E−05 | <5.0 |
| 210 | >1.00E−05 | <5.0 |
| 211 | 3.00E−07 | 7.2 |
| 212 | >1.00E−05 | 5.8 |
| 213 | 3.00E−06 | <5.0 |
| 214 | 1.00E−06 | <5.0 |
| 215 | >1.00E−05 | 5.5 |
| 216 | 1.00E−06 | 5.6 |
| 217 | >1.00E−05 | 5.4 |
| 218 | >1.00E−05 | <5.0 |
| 219 | >1.00E−05 | 5.4 |
| 220 | 3.00E−06 | 5.2 |
| 221 | >1.00E−05 | 5.4 |
| 222 | >1.00E−05 | 5.4 |
| 223 | >1.00E−05 | 6.1 |
| 224 | >1.00E−05 | 5.4 |
| 225 | >1.00E−05 | 6.8 |
| 226 | 3.00E−06 | 5.5 |
| 227 | >1.00E−05 | 5.1 |
| 228 | 1.00E−06 | 5.1 |
| 229 | 1.00E−07 | 7.0 |

D. Composition Example: Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I),

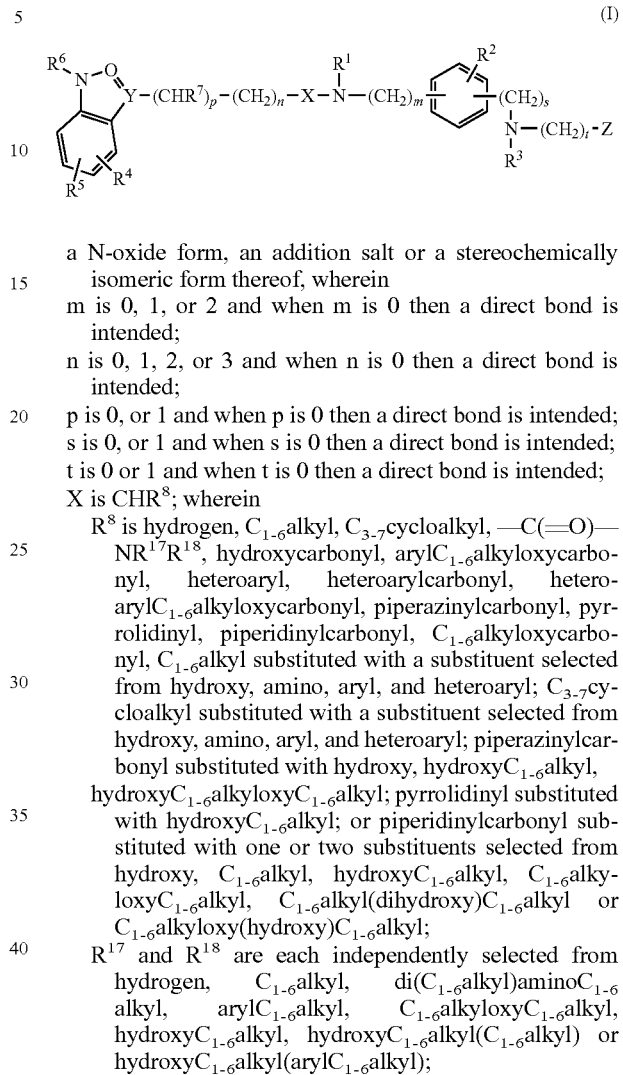

a N-oxide form, an addition salt or a stereochemically isomeric form thereof, wherein m is 0, 1, or 2 and when m is 0 then a direct bond is intended;

n is 0, 1, 2, or 3 and when n is 0 then a direct bond is intended;

p is 0, or 1 and when p is 0 then a direct bond is intended;

s is 0, or 1 and when s is 0 then a direct bond is intended;

t is 0 or 1 and when t is 0 then a direct bond is intended;

X is CHR$^8$; wherein

R$^8$ is hydrogen, C$_{1-6}$alkyl, C$_{3-7}$cycloalkyl, —C(=O)—NR$^{17}$R$^{18}$, hydroxycarbonyl, arylC$_{1-6}$alkyloxycarbonyl, heteroaryl, heteroarylcarbonyl, heteroarylC$_{1-6}$alkyloxycarbonyl, piperazinylcarbonyl, pyrrolidinyl, piperidinylcarbonyl, C$_{1-6}$alkyloxycarbonyl, C$_{1-6}$alkyl substituted with a substituent selected from hydroxy, amino, aryl, and heteroaryl; C$_{3-7}$cycloalkyl substituted with a substituent selected from hydroxy, amino, aryl, and heteroaryl; piperazinylcarbonyl substituted with hydroxy, hydroxyC$_{1-6}$alkyl, hydroxyC$_{1-6}$alkyloxyC$_{1-6}$alkyl; pyrrolidinyl substituted with hydroxyC$_{1-6}$alkyl; or piperidinylcarbonyl substituted with one or two substituents selected from hydroxy, C$_{1-6}$alkyl, hydroxyC$_{1-6}$alkyl, C$_{1-6}$alkyloxyC$_{1-6}$alkyl, C$_{1-6}$alkyl(dihydroxy)C$_{1-6}$alkyl or C$_{1-6}$alkyloxy(hydroxy)C$_{1-6}$alkyl;

R$^{17}$ and R$^{18}$ are each independently selected from hydrogen, C$_{1-6}$alkyl, di(C$_{1-6}$alkyl)aminoC$_{1-6}$alkyl, arylC$_{1-6}$alkyl, C$_{1-6}$alkyloxyC$_{1-6}$alkyl, hydroxyC$_{1-6}$alkyl, hydroxyC$_{1-6}$alkyl(C$_{1-6}$alkyl) or hydroxyC$_{1-6}$alkyl(arylC$_{1-6}$alkyl);

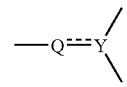

s is —CR$^9$=C< and then the dotted line is a bond, —C(=O)—CH<, —CHR$^9$—CH<or —CHR$^9$—N<; wherein each R$^9$ is independently hydrogen or C$_{1-6}$alkyl;

R$^1$ is hydrogen, aryl, heteroaryl, C$_{1-6}$alkyloxycarbonyl, C$_{1-12}$alkyl, or C$_{1-12}$alkyl substituted with one or two substituents independently selected from hydroxy, aryl, heteroaryl, amino, C$_{1-6}$alkyloxy, mono- or di(C$_{1-6}$alkyl)amino, morpholinyl, piperidinyl, pyrrolidinyl, piperazinyl, C$_{1-6}$alkylpiperazinyl, arylC$_{1-6}$alkylpiperazinyl, heteroarylC$_{1-6}$alkylpiperazinyl, C$_{3-7}$cycloalkylpiperazinyl and C$_{3-7}$cycloalkylC$_{1-6}$alkylpiperazinyl;

R$^2$ is hydrogen, halo, C$_{1-6}$alkyl, C$_{1-6}$alkyloxy, arylC$_{1-6}$alkyloxy, heteroarylC$_{1-6}$alkyloxy, phenylthio, hydroxyC$_{1-6}$alkylcarbonyl, C$_{1-6}$alkyl substituted with a substituent selected from amino, aryl and heteroaryl; or $C_{3-7}$cycloalkyl substituted with a substituent selected from amino, aryl and heteroaryl;

$R^3$ is hydrogen, $C_{1-6}$alkyl, heteroaryl, $C_{3-7}$cycloalkyl, $C_{1-6}$alkyl substituted with a substituent selected from hydroxy, amino, aryl and heteroaryl; or $C_{3-7}$cycloalkyl substituted with a substituent selected from hydroxy, amino, aryl and heteroaryl;

$R^4$ and $R^5$ are each independently hydrogen, halo, $C_{1-6}$alkyl, polyhalo$C_{1-6}$alkyl, cyano, cyano$C_{1-6}$alkyl, hydroxy, amino or $C_{1-6}$alkyloxy; or $R^4$ and $R^5$ together can optionally form a bivalent radical selected from methylenedioxy or ethylenedioxy;

$R^6$ is hydrogen, $C_{1-6}$alkyloxycarbonyl or $C_{1-6}$alkyl;

when p is 1 then $R^7$ is hydrogen, aryl$C_{1-6}$alkyl, hydroxy or heteroaryl$C_{1-6}$alkyl;

Z is a radical selected from

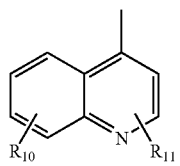
(a-1)

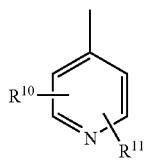
(a-2)

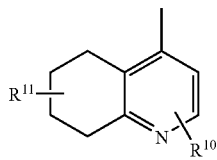
(a-3)

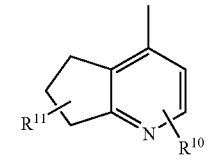
(a-4)

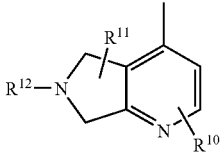
(a-5)

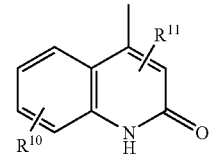
(a-6)

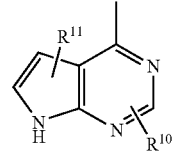
(a-7)

-continued

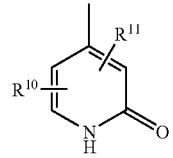
(a-8)

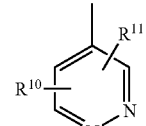
(a-9)

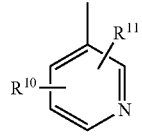
(a-10)

(a-11)

wherein each $R^{10}$ or $R^{11}$ are each independently selected from hydrogen, halo, hydroxy, amino, $C_{1-6}$alkyl, nitro, polyhalo$C_{1-6}$alkyl, cyano, cyano$C_{1-6}$alkyl, tetrazolo$C_{1-6}$alkyl, aryl, heteroaryl, aryl$C_{1-6}$alkyl, heteroaryl$C_{1-6}$alkyl, aryl(hydroxy)$C_{1-6}$alkyl, heteroaryl(hydroxy)$C_{1-6}$alkyl, arylcarbonyl, heteroarylcarbonyl, $C_{1-6}$alkylcarbonyl, aryl$C_{1-6}$alkylcarbonyl, heteroaryl$C_{1-6}$alkylcarbonyl, $C_{1-6}$alkyloxy, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy$C_{1-6}$alkyl, hydroxy$C_{1-6}$alkyloxy$C_{1-6}$alkyl, $C_{1-6}$alkyloxycarbony$C_{2-6}$alkenyl $C_{1-6}$alkyloxy$C_{1-6}$alkyl, $C_{1-6}$alkyloxycarbonyl, $C_{1-6}$alkylcarbonyloxy, aminocarbonyl, hydroxy$C_{1-6}$alkyl, amino$C_{1-6}$alkyl, hydroxycarbonyl, hydroxycarbonyl$C_{1-6}$alkyl and —$(CH_2)_v$—$(C(=O))_r$—$(CHR^{19})_u$—$NR^{13}R^{14}$; wherein v is 0, 1, 2, 3, 4, 5, or 6 and when v is 0 then a direct bond is intended;

r is 0, or 1 and when r is 0 then a direct bond is intended;

u is 0, 1, 2, 3, 4, 5, or 6 and when u is 0 then a direct bond is intended;

$R^{19}$ is hydrogen or $C_{1-6}$alkyl;

$R^{12}$ is hydrogen, $C_{1-6}$alkyl, $C_{3-7}$cycloalkyl, $C_{1-6}$alkyl substituted with a substituent selected from hydroxy, amino, $C_{1-6}$alkyloxy and aryl; or $C_{3-7}$cycloalkyl substituted with a substituent selected from hydroxy, amino, aryl and $C_{1-6}$alkyloxy;

$R^{13}$ and $R^{14}$ are each independently selected from hydrogen, $C_{1-12}$alkyl, $C_{1-6}$alkylcarbonyl, $C_{1-6}$alkylsulfonyl, aryl$C_{1-6}$alkylcarbonyl, $C_{3-7}$cycloalkyl, $C_{3-7}$cycloalkylcarbonyl, —$(CH_2)_k$—$NR^{15}R^{16}$, $C_{1-12}$alkyl substituted with a substituent selected from hydroxy, hydroxycarbonyl, cyano, $C_{1-6}$alkyloxycarbonyl, $C_{1-6}$alkyloxy, aryl or heteroaryl; or $C_{3-7}$cycloalkyl substituted with a substituent selected from hydroxy, $C_{1-6}$alkyloxy, aryl, amino, aryl$C_{1-6}$alkyl, heteroaryl or heteroaryl$C_{1-6}$alkyl; or $R^{13}$ and $R^{14}$ together with the nitrogen to which they are attached can optionally form a morpholinyl, piperidinyl, pyrrolidinyl, piperazinyl, or piperazinyl substituted with a substituent selected from $C_{1-6}$alkyl, aryl$C_{1-6}$alkyl, aryl$C_{1-6}$alkyloxycarbonyl, heteroaryl$C_{1-6}$alkyl, $C_{3-7}$cycloalkyl and $C_{3-7}$cycloalkyl$C_{1-6}$alkyl; wherein k is 0, 1, 2, 3, 4, 5, or 6 and when k is 0 then a direct bond is intended;

$R^{15}$ and $R^{16}$ are each independently selected from hydrogen, $C_{1-6}$alkyl, aryl$C_{1-6}$alkyloxycarbonyl, $C_{3-7}$cycloalkyl, $C_{1-12}$alkyl substituted with a substituent selected from hydroxy, $C_{1-6}$alkyloxy, aryl, and heteroaryl; and $C_{3-7}$cycloalkyl substituted with a substituent selected from hydroxy, $C_{1-6}$alkyloxy, aryl, aryl$C_{1-6}$alkyl, heteroaryl, and heteroaryl$C_{1-6}$alkyl; or $R^{15}$ and $R^{16}$ together with the nitrogen to which they are attached can optionally form a morpholinyl, a piperazinyl or a piperazinyl substituted with $C_{1-6}$alkyloxycarbonyl;

aryl is phenyl or naphthalenyl;

each phenyl or naphthalenyl can optionally be substituted with one, two or three substituents each independently selected from halo, hydroxy, $C_{1-6}$alkyl, amino, polyhalo$C_{1-6}$alkyl and $C_{1-6}$alkyloxy; and each phenyl or naphthalenyl can optionally be substituted with a bivalent radical selected from methylenedioxy and ethylenedioxy;

heteroaryl is pyridinyl, indolyl, quinolinyl, imidazolyl, furanyl, thienyl, oxadiazolyl, tetrazolyl, benzofuranyl or tetrahydrofuranyl;

each pyridinyl, indolyl, quinolinyl, imidazolyl, furanyl, thienyl, oxadiazolyl, tetrazolyl, benzofuranyl, or tetrahydrofuranyl can optionally be substituted with one, two or three substituents each independently selected from halo, hydroxy, $C_{1-6}$alkyl, amino, polyhalo$C_{1-6}$alkyl, aryl, aryl$C_{1-6}$alkyl or $C_{1-6}$alkyloxy; and each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy;

with the proviso that when m is 1; the substituents on the phenyl ring other than $R^2$ are in the meta position;

s is 0; and t is 0; then

Z is a radical selected from (a-1), (a-3), (a-4), (a-5), (a-6), (a-7), (a-8) or (a-9).

2. A compond according to claim 1 wherein

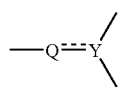

is —CR$^9$=C< and then the dotted line is a bond, —CHR$^9$—CH< or —CHR$^9$—N<.

3. A compound according to claim 2 wherein X is CHR$^8$ wherein R$^8$ is hydrogen, $C_{1-6}$alkyl, $C_{3-7}$cycloalkyl, aminocarbonyl, mono- or di($C_{1-6}$alkyl)aminocarbonyl, hydroxycarbonyl, aryl$C_{1-6}$alkyloxycarbonyl, heteroaryl$C_{1-6}$alkyloxycarbonyl, $C_{1-6}$alkyloxycarbonyl, $C_{1-6}$alkyl substituted with a substituent selected from hydroxy, amino, aryl, and heteroaryl or $C_{3-7}$cycloalkyl substituted with a substituent selected from hydroxy, amino, aryl and heteroaryl; R$^1$ is hydrogen, aryl, heteroaryl, $C_{1-12}$alkyl, or $C_{1-12}$alkyl substituted with one or two substituents independently selected from hydroxy, aryl, heteroaryl, amino, $C_{1-6}$alkyloxy, mono- or di($C_{1-6}$alkyl)amino, morpholinyl, piperidinyl, pyrrolidinyl, piperazinyl, $C_{1-6}$alkylpiperazinyl, aryl$C_{1-6}$alkylpiperazinyl, heteroaryl$C_{1-6}$alkylpiperazinyl, $C_{3-7}$cycloalkylpiperazinyl and $C_{3-7}$cycloalkyl$C_{1-6}$alkylpiperazinyl; R$^3$ is hydrogen, $C_{1-6}$alkyl, $C_{3-7}$cycloalkyl, $C_{1-6}$alkyl substituted with a substituent selected from hydroxy, amino, aryl, and heteroaryl; or $C_{3-7}$cycloalkyl substituted with a substituent selected from hydroxy, amino, aryl and heteroaryl; R$^4$ and R$^5$ are each independently hydrogen, halo, $C_{1-6}$alkyl, polyhalo$C_{1-6}$alkyl, hydroxy, amino or $C_{1-6}$alkyloxy; R$^4$ and R$^5$ together can optionally form a bivalent radical selected from methylenedioxy or ethylenedioxy; R$^6$ is hydrogen or $C_{1-6}$alkyl; when p is 1 then R$^7$ is hydrogen, aryl$C_{1-6}$alkyl or heteroaryl$C_{1-6}$alkyl; Z is a radical selected from (a-1), (a-2), (a-3), (a-4), (a-5) and (a-6); each R$^{10}$ or R$^{11}$ are each independently selected from hydrogen, hydroxy, amino, $C_{1-6}$alkyl, nitro, polyhalo$C_{1-6}$alkyl, cyano, cyano$C_{1-6}$alkyl, tetrazolo$C_{1-6}$alkyl, aryl, heteroaryl, aryl$C_{1-6}$alkyl, heteroaryl$C_{1-6}$alkyl, aryl(hydroxy)$C_{1-6}$alkyl, heteroaryl(hydroxy)$C_{1-6}$alkyl, arylcarbonyl, heteroarylcarbonyl, aryl$C_{1-6}$alkylcarbonyl, heteroaryl$C_{1-6}$alkylcarbonyl, $C_{1-6}$alkyloxy, $C_{1-6}$alkyloxy$C_{1-6}$alkyl, $C_{1-6}$alkyloxycarbonyl, $C_{1-6}$alkylcarbonyloxy, aminocarbonyl, hydroxy$C_{1-6}$alkyl, amino$C_{1-6}$alkyl, hydroxycarbonyl, hydroxycarbonyl$C_{1-6}$alkyl and —(CH$_2$)$_v$—(C(=O)$_r$)—(CH$_2$)$_u$—NR$^{13}$R$^{14}$; R$^{13}$ R and R$^{14}$ are each independently selected from hydrogen, $C_{1-12}$alkyl, $C_{3-7}$cycloalkyl, —(CH$_2$)$_k$—NR$^{15}$R$^{16}$, $C_{1-12}$alkyl substituted with a substituent selected from hydroxy, $C_{1-6}$alkyloxy, aryl, and heteroaryl; or $C_{3-7}$cycloalkyl substituted with a substituent selected from hydroxy, $C_{1-6}$alkyloxy, aryl, aryl$C_{1-6}$alkyl, heteroaryl and heteroaryl$C_{1-6}$alkyl; R$^{13}$ and R$^{14}$ together with the nitrogen to which they are attached can optionally form a morpholinyl, piperidinyl, pyrrolidinyl, piperazinyl, or piperazinyl substituted with a substituent selected from $C_{1-6}$alkyl, aryl$C_{1-6}$alkyl, heteroaryl$C_{1-6}$alkyl, $C_{3-7}$cycloalkyl, and $C_{3-7}$cycloalkyl$C_{1-6}$alkyl; R$^{15}$ and R$^{16}$ are each independently selected from hydrogen, $C_{1-6}$alkyl, $C_{3-7}$cycloalkyl, $C_{1-12}$alkyl substituted with a substituent selected from hydroxy, $C_{1-6}$alkyloxy, aryl, and heteroaryl; and $C_{3-7}$cycloalkyl substituted with a substituent selected from hydroxy, $C_{1-6}$alkyloxy, aryl, aryl$C_{1-6}$alkyl, heteroaryl and heteroaryl$C_{1-6}$alkyl; heteroaryl is pyridinyl, indolyl, quinolinyl, imidazolyl, furanyl, thienyl, benzofuranyl, or tetrahydrofuranyl; and each pyridinyl, indolyl, quinolinyl, imidazolyl, furanyl, thienyl, benzofuranyl, or tetrahydrofuranyl can optionally be substituted with one, two or three substituents each independently selected from halo, hydroxy, $C_{1-6}$alkyl, amino, polyhalo$C_{1-6}$alkyl and $C_{1-6}$alkyloxy, or each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy.

4. A compound according to claim 2 wherein;
R$^8$ is hydrogen, —C(=O)—NR$^{17}$R$^{18}$, aryl$C_{1-6}$alkyloxycarbonyl, $C_{1-6}$alkyl substituted with hydroxy, piperazinylcarbonyl substituted with hydroxy, hydroxy$C_{1-6}$alkyl, hydroxy$C_{1-6}$alkyloxy$C_{1-6}$alkyl, pyrrolidinyl substituted with hydroxy$C_{1-6}$alkyl or piperidinylcarbonyl substituted with one or two substituents selected from hydroxy, $C_{1-6}$alkyl, hydroxy$C_{1-6}$alkyl, C$_{1-6}$alkyloxyC$_{1-6}$alkyl, C$_{1-6}$alkyl(dihydroxy)C$_{1-6}$alkyl or C$_{1-6}$alkyloxy(hydroxy)C$_{1-6}$alkyl; R$^{17}$ and R$^{18}$ are each independently selected from hydrogen, C$_{1-6}$alkyl, di(C$_{1-6}$alkyl)aminoC$_{1-6}$alkyl, arylC$_{1-6}$alkyl, C$_{1-6}$alkyloxyC$_{1-6}$alkyl or hydroxyC$_{1-6}$alkyl;

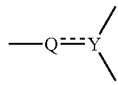

is —CR$^9$=C< and then the dotted line is a bond, —CHR$^9$—CH< or —CHR$^9$—N<; R$^1$ is hydrogen, heteroaryl, C$_{1-6}$alkyloxycarbonyl, C$_{1-12}$alkyl or C$_{1-12}$alkyl substituted with heteroaryl; R$^2$ is hydrogen, halo, C$_{1-6}$alkyl, C$_{1-6}$alkyloxy, arylC$_{1-6}$alkyloxy or phenylthio; R$^3$ is hydrogen, C$_{1-6}$alkyl or heteroaryl; R$^4$ and R$^5$ are each independently hydrogen, halo, C$_{1-6}$alkyl, cyano, cyanoC$_{1-6}$alkyl, hydroxy or C$_{1-6}$alkyloxy; when p is 1 then R$^7$ is arylC$_{1-6}$alkyl or hydroxy; Z is a radical selected from (a-1), (a-2), (a-3), (a-4), (a-5), (a-6), (a-8), (a-9), (a-10) and (a-11); each R$^{10}$ or R$^{11}$ are each independently selected from hydrogen, halo, hydroxy, amino, C$_{1-6}$alkyl, nitro, polyhaloC$_{1-6}$alkyl, cyano, cyanoC$_{1-6}$alkyl, tetrazoloC$_{1-6}$alkyl, aryl, heteroaryl, heteroarylC$_{1-6}$alkyl, aryl(hydroxy)C$_{1-6}$alkyl, arylcarbonyl, C$_{1-6}$alkylcarbonyl, C$_{3-7}$cycloalkylcarbonyl, C$_{3-7}$cycloalkyl(hydroxy)C$_{1-6}$alkyl, arylC$_{1-6}$alkyloxyC$_{1-6}$alkyl, C$_{1-6}$alkyloxyC$_{1-6}$alkyloxyC$_{1-6}$alkyl, C$_{1-6}$alkylcarbonyloxyC$_{1-6}$alkyl, C$_{1-6}$alkyloxycarbonylC$_{1-6}$alkyloxyC$_{1-6}$alkyl, hydroxyC$_{1-6}$alkyloxyC$_{1-6}$alkyl, C$_{1-6}$alkyloxycarbonyC$_{2-6}$alkenyl, C$_{1-6}$alkyloxyC$_{1-6}$alkyl, C$_{1-6}$alkyloxycarbonyl, aminocarbonyl, hydroxyC$_{1-6}$alkyl, aminoC$_{1-6}$alkyl, hydroxycarbonyl, hydroxycarbonylC$_{1-6}$alkyl and —(CH$_2$)$_v$—(C(=O)$_r$)—(CHR$^{19}$)$_u$—NR$^{13}$R$^{14}$; v is 0 or 1; u is 0 or 1; R$^{12}$ is hydrogen or C$_{1-6}$alkyl; R$^{13}$ and R$^{14}$ are each independently selected from hydrogen, C$_{1-12}$alkyl, C$_{1-6}$alkylcarbonyl, C$_{1-6}$alkylsulfonyl, arylC$_{1-6}$alkylcarbonyl, C$_{3-7}$cycloalkylcarbonyl, —(CH$_2$)$_k$—NR$^{15}$R$^{16}$, C$_{1-12}$alkyl substituted with a substituent selected from hydroxy, hydroxycarbonyl, cyano, C$_{1-6}$alkyloxycarbonyl or aryl; R$^{13}$ and R$^{14}$ together with the nitrogen to which they are attached can optionally form a morpholinyl, pyrrolidinyl, piperazinyl or piperazinyl substituted with a substituent selected from C$_{1-6}$alkyl or arylC$_{1-6}$alkyloxycarbonyl; k is 2; R$^{15}$ and R$^{16}$ are each independently selected from hydrogen, C$_{1-6}$alkyl or arylC$_{1-6}$alkyloxycarbonyl; k is 2; R$^{15}$ and R$^{16}$ are each independently selected from hydrogen, C$_{1-6}$alkyl or arylC$_{1-6}$alkyloxycarbonyl;

R$^{15}$ and R$^{16}$ together with the nitrogen to which they are attached can optionally form a morpholinyl or piperazinyl, or a piperazinyl substituted with C$_{1-6}$alkyloxycarbonyl; aryl is phenyl or phenyl substituted with halo; heteroaryl is pyridinyl, indolyl, oxadiazolyl or tetrazolyl; and each pyridinyl, indolyl, oxadiazolyl or tetrazolyl can optionally be substituted with one substituent selected from C$_{1-6}$alkyl, aryl or arylC$_{1-6}$alkyl.

5. A compound according to claim 4 wherein m is 0; n is 1; p is 0; s is 0; t is 0.

6. A compound according to claim 5 wherein X is CHR$^8$ and R$^8$ is hydrogen.

7. A compound according to claim 2 wherein

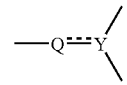

is —CR$^9$=C< and R$^9$ is hydrogen.

8. A compound according to claim 2 wherein R$^1$ is hydrogen; R$^3$ is hydrogen; R$^6$ is hydrogen.

9. A compound according to claim 2 wherein R$^4$ and R$^5$ are each independently hydrogen, C$_{1-6}$alkyl or C$_{1-6}$alkyloxy.

10. A compound according to claim 2 wherein Z is a radical selected from (a-1), (a-2), (a-3) or (a-4).

11. A compound according to claim 2 wherein R$^{10}$ or R$^{11}$ are each independently selected from hydrogen, hydroxy or hydroxyC$_{1-6}$alkyl.

12. A compound according to claim 2 wherein R$^2$ is hydrogen or C$_{1-6}$alkyloxy.

13. A compound according to claim 2 wherein m is 0; n is 1; p is 0; s is 0; t is 0; X is CHR$^8$; R$^8$ is hydrogen;

is —CR$^9$=C<; each R$^9$ is hydrogen; R$^1$ is hydrogen; R$^2$ is hydrogen or C$_{1-6}$alkyloxy; R$^3$ is hydrogen; R$^4$ and R$^5$ are each independently hydrogen, C$_{1-6}$alkyl or C$_{1-6}$alkyloxy; R$^6$ is hydrogen; Z is a radical selected from (a-1), (a-2), (a-3) or (a-4); and R$^{10}$ or R$^{11}$ are each independently selected from hydrogen, hydroxy or hydroxyC$_{1-6}$alkyl.

14. A compound according to claim 1 wherein the compound is selected from the group consisting of:

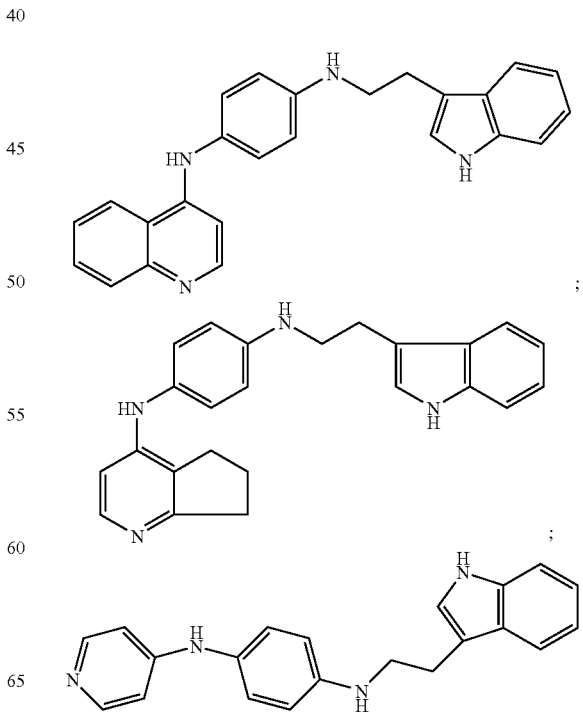

-continued

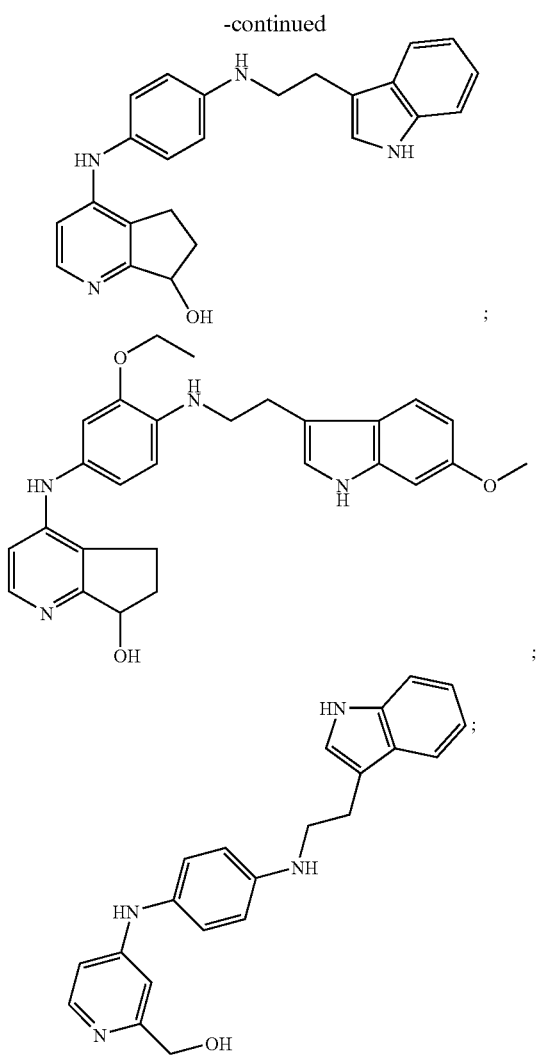

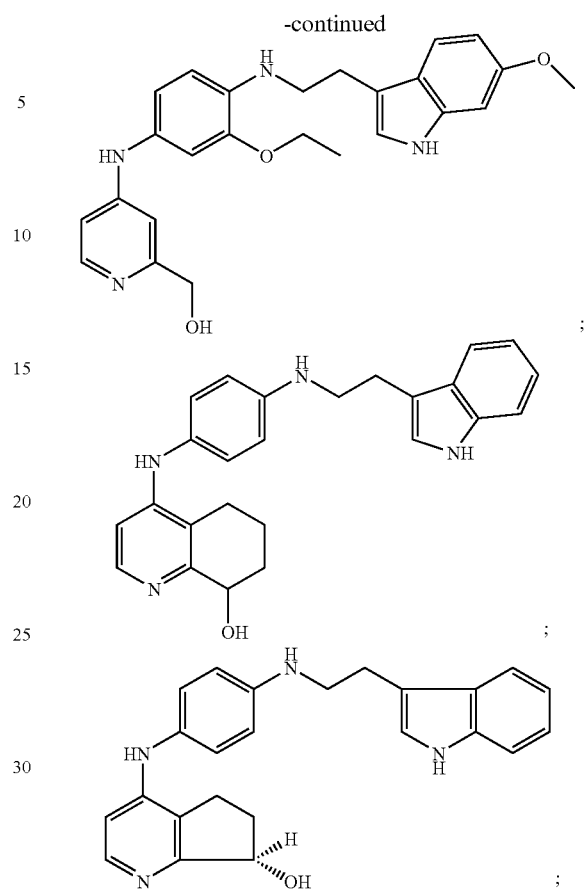

and the N-oxide form, the addition salt or the stereochemically isomeric form thereof.

15. A compound according to claim 13 which is

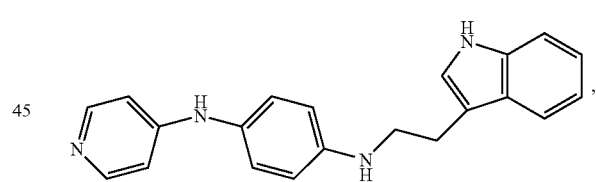

or the pharmaceutically acceptable salt thereof.

16. A compound according to claim 13 which is

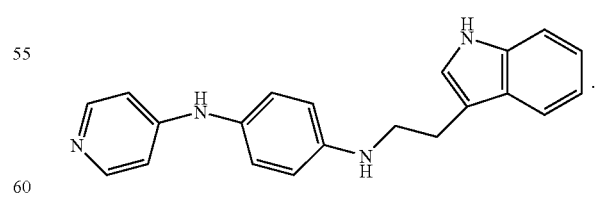

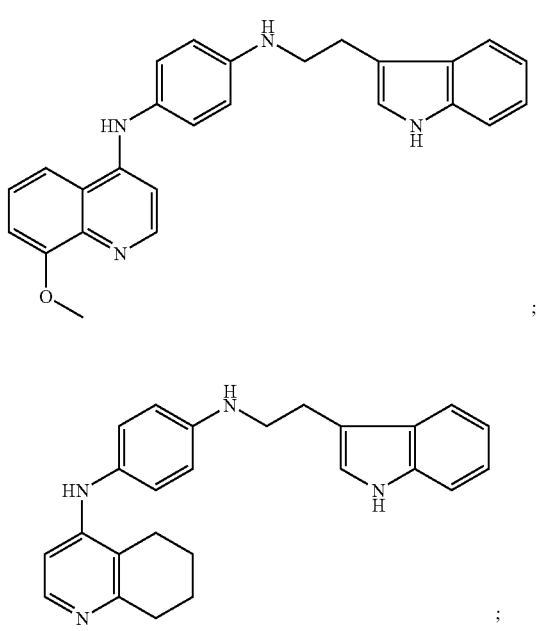

17. A combination of an anti-cancer agent and a compound claimed in claim 1.

18. The combination according to claim 17 wherein the anti-cancer agent is selected from the group consisting of platinum coordination compounds cisplatin, carboplatin or oxalyplatin; taxane compounds paclitaxel or docetaxel;

topoisomerase I inhibitors; camptothecin compounds irinotecan or topotecan; topoisomerase II inhibitors, anti-tumour podophyllotoxin derivatives etoposide or teniposide; anti-tumour vinca alkaloids vinblastine, vincristine or vinorelbine; anti-tumour nucleoside derivatives 5-fluorouracil, gemcitabine or capecitabine; alkylating agents nitrogen mustard or nitrosourea, cyclophosphamide, chlorambucil, carmustine or lomustine; anti-tumour anthracycline derivatives daunorubicin, doxorubicin, idarubicin or mitoxantrone; HER2 antibodies trastuzumab; estrogen receptor antagonists or selective estrogen receptor modulators tamoxifen, toremifene, droloxifene, faslodex or raloxifene; aromatase inhibitors exemestane, anastrozole, letrazole and vorozole; differentiating agents, retinoids, vitamin D and retinoic acid metabolism blocking agents, (RAMBA), accutane; DNA methyl transferase inhibitors, azacytidine; kinase inhibitors flavoperidol, imatinib mesylate or gefitinib; farnesyltransferase inhibitors; HDAC inhibitors; inhibitors of the ubiquitin-proteasome pathway, velcade; and yondelis.

19. A pharmaceutical composition comprising pharmaceutically acceptable carriers and as an active ingredient a therapeutically effective amount of a compound as claimed in claim 1.

20. A pharmaceutical composition comprising pharmaceutically acceptable carriers and as an active ingredient a therapeutically effective amount of a compound as claimed in claim 2.

21. A pharmaceutical composition comprising pharmaceutically acceptable carriers and as an active ingredient a therapeutically effective amount of a compound as claimed in claim 13.

22. A pharmaceutical composition comprising pharmaceutically acceptable carriers and as an active ingredient a therapeutically effective amount of a compound as claimed in claim 16.

23. A method for the treatment of a disorder mediated by a p53-MDM2 interaction in a subject in need of treatment, said method comprising administering to said subject a therapeutically effective amount of a compound as claimed in claim 1.

24. A method for the treatment of a disorder mediated by a p53-MDM2 interaction in a subject in need of treatment, said method comprising administering to said subject a therapeutically effective amount of a compound as claimed in claim 4.

25. A method for the treatment of a disorder mediated by a p53-MDM2 interaction in a subject in need of treatment, said method comprising administering to said subject a therapeutically effective amount of a compound as claimed in claim 13.

26. A method for the treatment of a disorder mediated by a p53-MDM2 interaction in a subject in need of treatment, said method comprising administering to said subject a therapeutically effective amount of a compound as claimed in claim 14.

27. A method for the treatment of cancer in a subject in need of such treatment, said method comprising administering to said subject a therapeutically effective amount of a compound as claimed in claim 1, wherein the cancer is selected from the group consisting of breast cancer, prostate cancer, and colon cancer.

28. The method of claim 27 wherein the cancer is breast cancer.

29. The method of claim 28 wherein the cancer is prostate cancer.

30. A composition which is a combination of an anti-cancer agent and a compound according to claim 1, wherein the anti-cancer agent treats breast cancer, prostate cancer, and colon cancer.

31. A composition of claim 30 as a combined preparation for simultaneous, separate or sequential use in the treatment of patients suffering from cancer, wherein the cancer is elected from the group consisting of breast cancer, prostate cancer, and colon cancer.

32. A process for preparing a compound as claimed in claim 1, said process comprising the steps of:
a) reacting an intermediate of formula (II) with an intermediate of formula (III) wherein W is an appropriate leaving group such as, for example, halo,

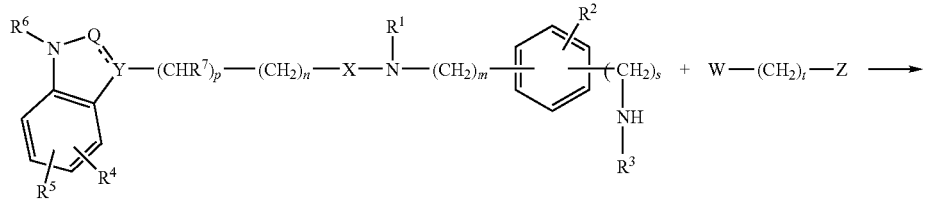

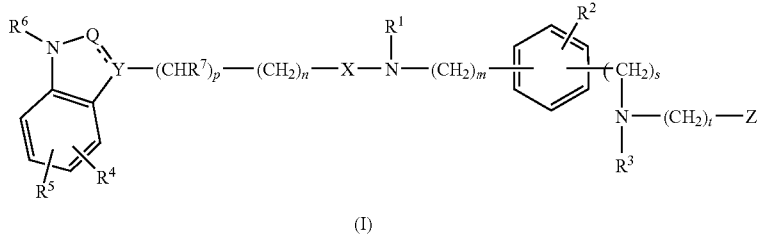

wherein the variables are as defined in claim 1;
b) converting a compound of formula (I) wherein X is C(=O), herein referred to as compounds of formula (I-b), into compounds of formula (I), wherein X is CH$_2$, herein referred to as compounds of formula (I-a), in the presence of lithium aluminium hydride in a suitable solvent,

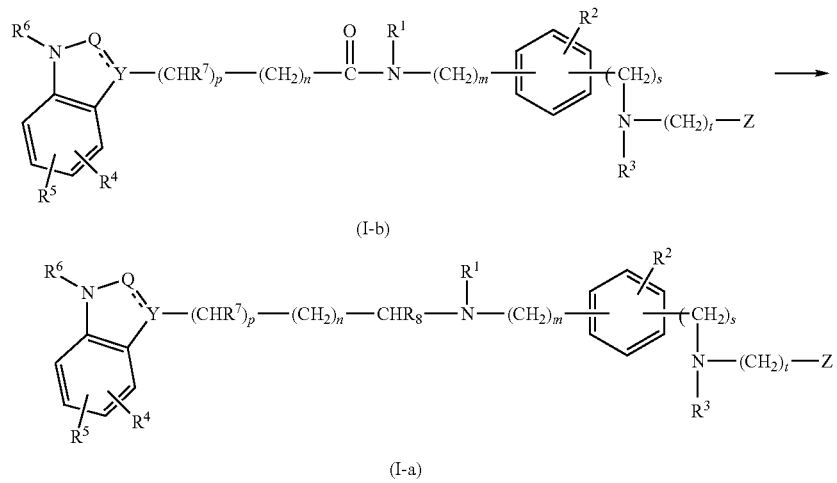

(I-b)

(I-a)

wherein the variables are as defined in claim 1;
  c) reacting an appropriate carboxaldehyde of formula (IV), with an intermediate of formula (V), in the presence of an appropriate reagent, in a suitable solvent,

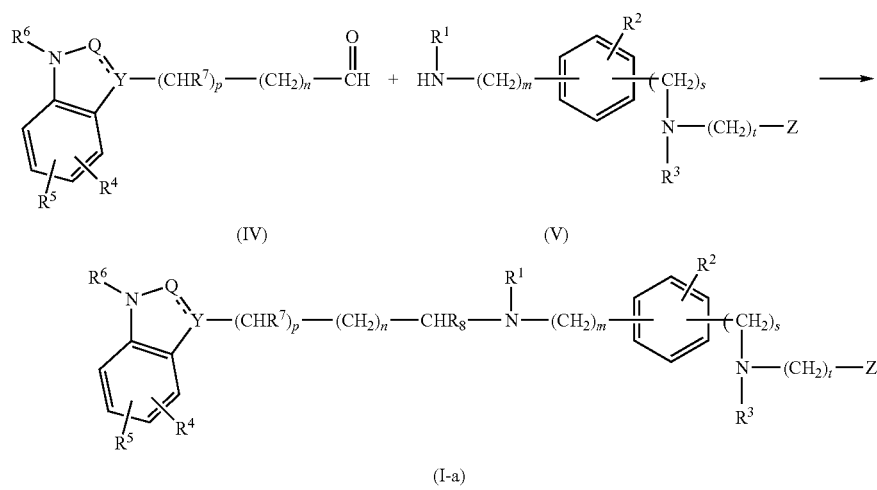

(IV)  (V)

(I-a)

wherein the variables are as defined in claim 1;
  d) reacting an intermediate of formula (II) with an appropriate carboxaldehyde of formula (VI) with the formation of a compound of formula (I), wherein t is 1, herein referred to as compounds of formula (I-c),

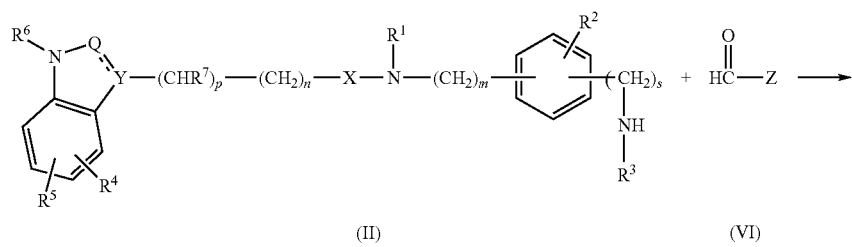

(II)  (VI)

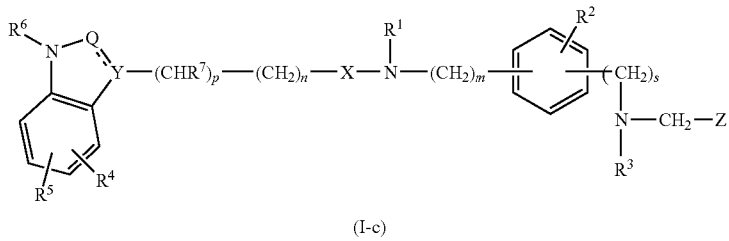

(I-c)

wherein the variables are as defined in claim 1;

e) reacting an intermediate of formula (VII) with lithium aluminium hydride in a suitable solvent, with the formation of a compound of formula (I), wherein s is 1, herein referred to as compounds of formula (I-d)

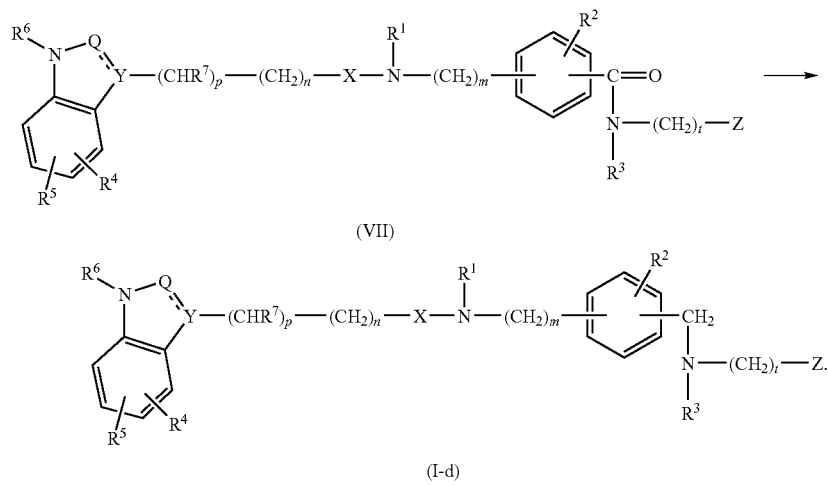

wherein the variables are as defined in claim 1.

33. The method of claim 28 wherein the cancer is colon cancer.

34. The composition of claim 31, wherein the cancer is breast cancer.

35. The composition of claim 31, wherein the cancer is prostate cancer.

36. The composition of claim 31, wherein the cancer is colon cancer.

* * * * *